US010905760B2

(12) United States Patent
Sällberg et al.

(10) Patent No.: US 10,905,760 B2
(45) Date of Patent: Feb. 2, 2021

(54) CHIMERIC HEPATITIS D VIRUS ANTIGEN AND HEPATITIS B VIRUS PRE S1 GENES FOR USE ALONE OR IN VACCINES CONTAINING HEPATITIS B VIRUS GENES

(71) Applicant: Svenska Vaccinfabriken Produktion AB, Stockholm (SE)

(72) Inventors: Matti Sällberg, Stockholm (SE); Lars Frelin, Älvsjö (SE)

(73) Assignee: Svenska Vaccinfabriken Produktion AB, Stockholm (SE)

( * ) Notice: Subject to any disclaimer, the term of this patent is extended or adjusted under 35 U.S.C. 154(b) by 287 days.

(21) Appl. No.: 16/069,372

(22) PCT Filed: Jan. 26, 2017

(86) PCT No.: PCT/US2017/015064
§ 371 (c)(1),
(2) Date: Jul. 11, 2018

(87) PCT Pub. No.: WO2017/132332
PCT Pub. Date: Aug. 3, 2017

(65) Prior Publication Data

US 2019/0083607 A1 Mar. 21, 2019

Related U.S. Application Data

(60) Provisional application No. 62/288,316, filed on Jan. 28, 2016.

(51) Int. Cl.

| | |
|---|---|
| ***C07K 14/02*** | (2006.01) |
| ***C07K 14/005*** | (2006.01) |
| ***A61K 39/29*** | (2006.01) |
| ***A61K 39/39*** | (2006.01) |
| ***A61K 39/12*** | (2006.01) |
| *A61K 39/00* | (2006.01) |

(52) U.S. Cl.
CPC .............. *A61K 39/29* (2013.01); *A61K 39/12* (2013.01); *A61K 39/39* (2013.01); *C07K 14/005* (2013.01); *C07K 14/02* (2013.01); *A61K 2039/55538* (2013.01); *A61K 2039/70* (2013.01); *C07K 2319/00* (2013.01); *C12N 2730/10122* (2013.01); *C12N 2730/10134* (2013.01); *C12N 2760/10122* (2013.01); *C12N 2760/10134* (2013.01)

(58) Field of Classification Search
CPC .. A61K 2039/70; A61K 39/29; C07K 14/005; C07K 2319/00
See application file for complete search history.

(56) References Cited

U.S. PATENT DOCUMENTS

| | | | |
|---|---|---|---|
| 2003/0158149 | A1 | 8/2003 | Casey et al. |
| 2005/0170337 | A1 | 8/2005 | Hogle et al. |

OTHER PUBLICATIONS

Hsu el al., "Immunohistochemical differentiation of hepatitis D virus genotypes. Hepalology", Nov. 2000, vol. 32, No. 5. pp. 1111-1116. Especially p. 1111, col. 2, para 2; p. 11 14, col. 2, para 3.
Search Report and Written Opinion in International application No. PCT/US2017/015064, dated Apr. 4, 2017.

*Primary Examiner* — Bao Q Li
(74) *Attorney, Agent, or Firm* — Knobbe Martens Olson & Bear, LLP

(57) ABSTRACT

Disclosed herein are chimeric genes, compositions of chimeric genes, and compositions of polypeptides that are useful for the generation, enhancement, or improvement of an immune response to a target antigen. Some embodiments of the compositions include chimeric genes encoding hepatitis D antigen (HDAg) protein in combination with one or more self-cleavage 2A polypeptides and a preS 1 polypeptide. In certain embodiments the self-cleavage polypeptide is P2A.

24 Claims, 24 Drawing Sheets

Specification includes a Sequence Listing.

```
                                        20                                      40
                                         |                                       |
HBV preS1 D1  GQNLSTSNPL GFFPDHQLDP AFRANTANPD WDFNPNKDTW PDANKVG 47
HBV preS1 D3  GQNLSTSNPL GFFPDHQLDP AFRANTANPD WDFNPNKDTW PDANKVG 47
 HBV preS1 F  GQNLSVPNPL GFFPDHQLDP LFRANTSSPD WDFNTNKDSW PMANKVG 47
HBV-preS1-A1  GTNLSVPNPL GFFPDHQLDP AFGANSNNPD WDFIPNKDHW PQANQVG 47
 HBV preS1 C  GTNLSVPNPL GFFPDHQLDP AFGANSNNPD WDFNPNKDHW PEANQVG 47
 HBV preS-A2  GTNLSVPNPL GFFPDHQLDP AFGANSNNPD WDFNPIKDHW PTANQVG 47
 HBV preS1 B  GTNLSVPNPL GFFPDHQLDP AFKANSDNPD WDLNPHKDNW PDSNKVG 47
HBV preS1 B2  GTNLSVPNPL GFFPDHQLDP AFKANSENPD WDLNPHKDNW PDANKVG 47
HBV preS1 E1  GKNHSTTNPL GFFPDHQLDP AFRANTRNPD WDHNPNKDHW TEANKVG 47
HBV preS1 E2  GKNHSTTNPL GFFPDHQLDP AFRANTRNPD WDHNPNKDHW TEANKVG 47
   Consensus  GTNLSVPNPL GFFPDHQLDP AFRANXNNPD WDFNPNKDHW PDANKVG
```

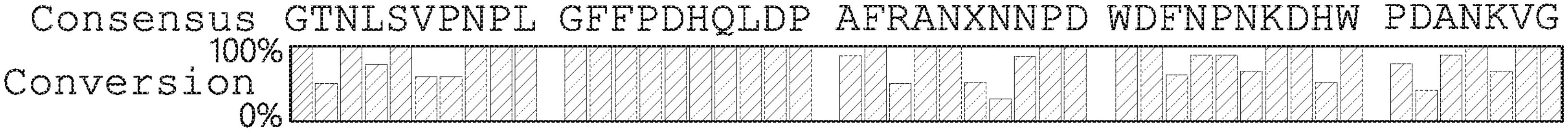

FIG. 1

Delta-7

| HDAg gt1 A/B | PreS1 A/B |

Delta-8

| HDAg gt2 A/B | PreS1 A/B |

Delta-9

| HDAg gt1 A/B |

Delta-10

| HDAg gt2 A/B |

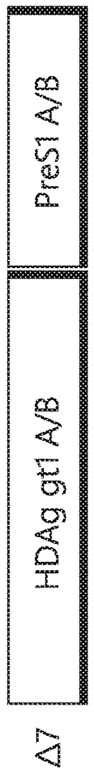
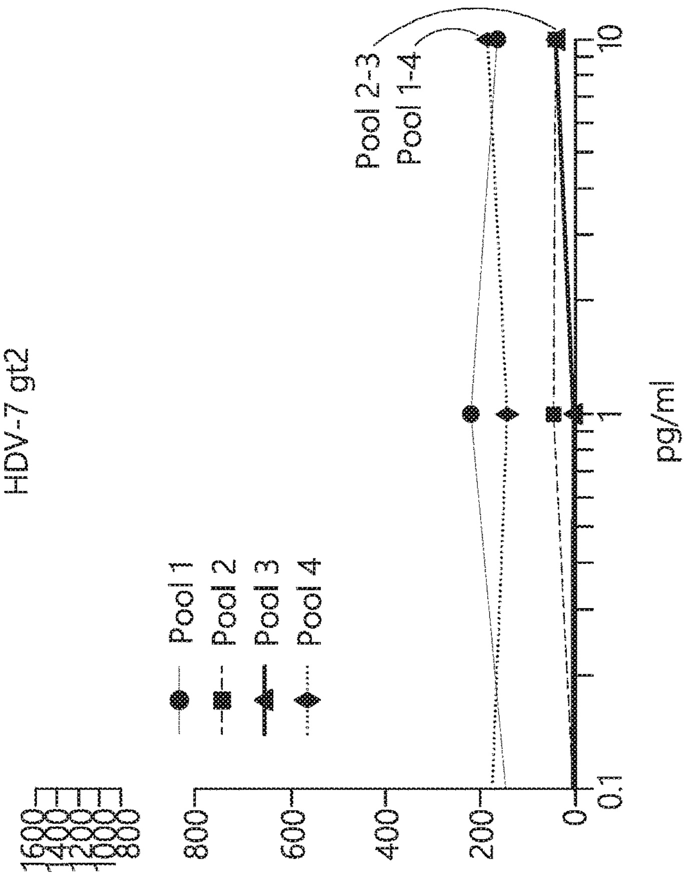
FIG. 4N
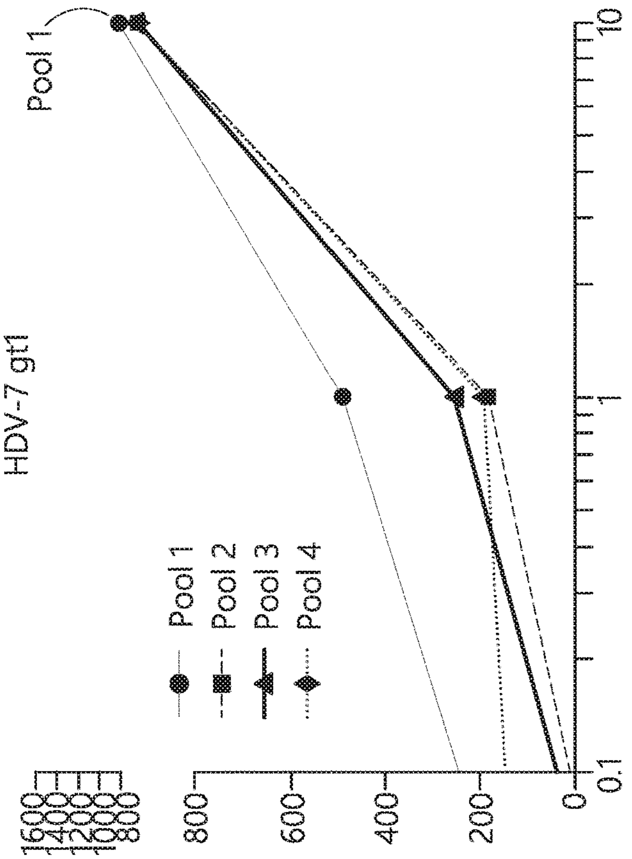
FIG. 4M

Δ9 HDAg gt1 A/B

CHIMERIC HEPATITIS D VIRUS ANTIGEN AND HEPATITIS B VIRUS PRE S1 GENES FOR USE ALONE OR IN VACCINES CONTAINING HEPATITIS B VIRUS GENES

RELATED APPLICATIONS

This application is a U.S. National Phase Application of PCT International Application PCT/US2017/015064, filed Jan. 26, 2017, designating the United States of America and published in the English language, which is an International Application of and claims the benefit of priority to U.S. Provisional Patent Application No. 62/288,316, filed on Jan. 28, 2016. The disclosures of the above-referenced applications are hereby expressly incorporated by reference in their entireties.

REFERENCE TO SEQUENCE LISTING, TABLE, OR COMPUTER PROGRAM LISTING

This incorporates by reference the Sequence Listing is-provided as an ASCII text file entitled SVF-002NP.TXT created Jul. 11, 2018, which is 233 kb in size. The information in the electronic format of the Sequence Listing is incorporated herein by reference in its entirety.

FIELD OF THE INVENTION

Described herein are chimeric genes that overcome genotype variability. Hepatitis D virus (HDV) genotype 1 sequences, which serve as an adjuvant in patients infected by genotype 2 HDV strains, are utilized. Moreover, the HDV genes are linked to a sequence encoding a part of the PreS1 region of the Hepatitis B virus (HBV). By this approach, neutralizing antibodies and T cells to HBV and HDV are generated. These can be used alone or be combined with genes or proteins expressing HBV proteins to raise both HBV and HDV specific immune responses in patients with HBV. These constructs are used as both genetic and protein-based vaccines or immunogenic compositions, which inhibit, ameliorate, treat and/or prevent HDV and/or HBV infections.

BACKGROUND

Hepatitis is a disease resulting in swelling and inflammation of the liver. This disorder is commonly caused by viruses, five types of which are currently known (Hepatitis A, B, C, D and E). The hepatitis D virus (HDV) causes severe liver disease and cancer in patients infected by the hepatitis B virus (HBV). HDV exist in three major genotypes world-wide. Hepatitis D virus (HDV), also referred to as Hepatitis delta virus, is a small, spherical single-stranded circular RNA virus. The entire virus was cloned and sequenced in 1986, and given the genus of *Deltavirus*. HDV is structurally unrelated to the other hepatitis viruses. Since HDV is an incomplete virus, it can only replicate in the presence of Hepatitis B (HBV) virus, which provides structural components for HDV. In particular, HDV has an outer coat that contains large, medium and small hepatitis B surface antigens, and host lipids surrounding an inner nucleocapsid, which contains about 200 molecules of hepatitis D antigen (HDAg) for each genome. The circular genome of HDV is unique to animal viruses because of its high GC content.

HDV produces a single protein, namely hepatitis D antigen (HDAg). HDAg exists in two isoforms: a 27 kDa large-HDAg (HDAg-L), and a 24 kDa small-HDAg (HDAg-S). The two sequences differ in that the C-terminus of the HDAg-L contains an additional 19 amino acids not found in HDAg-S, which are essential to virus assembly. Both isoforms are produced from the same open reading frame (ORF), which contains a UAG stop codon at codon 196, which normally produces only the HDAg-S. However, editing by the cellular enzyme adenosine deaminase-1 changes the stop codon to UCG, allowing HDAg-L to be produced, HDAg-S is produced in the early stages of infection, enters the nucleus and supports viral replication. In contrast, HDAg-L is produced during the later stages of infection, acts as an inhibitor of viral replication, and is required for assembly of viral particles. Both isoforms bind RNA, with a specificity for the rod-like folding of the HDV genome and antigenome (Chao et al., *J. Virol*, 65:4057-4062, 1991; Lee et al., *J. Virol.*, 67:2221-2227, 1993). HDAg contains a coiled-coil dimerization domain, nuclear localization signal, RNA-binding domain, and a putative assembly domain. Various epitopes of HDAg were determined to be exposed by PEPSCAN, immunoprecipitation analysis and ELISA, including those within amino acids 12-60, 58-78, 82-102, 123-143, 156-184, 167-184 and 197-211 (Bichko et al., (1996) *J. Virol.* 70:5807-5811). Epitope mapping of HDAg in patients with chronic Hepatitis D infection exhibited the following potential cytotoxic T-ligand epitopes: amino acids 43 to 51, 50 to 58 and 114 to 122 (Wang et al., *J. Virol*, 81:4438-4444, 2007).

HDV is transmitted through percutaneous or mucosal contact with infected blood. HDV can be acquired by either simultaneous infection with HBV (coinfection), or by super-infection, in, which HDV is superimposed on chronic HBV infection or carrier state. Both types of infection result in more deleterious effects than infection solely with HBV, including enhanced possibility of liver failure and more rapid onset of cirrhosis and potentially liver cancer. The combination of HBV and HDV results in the highest mortality rate of all hepatitis infections at about 20%. There is no current vaccine for HDV, but it can be prevented in individuals who are not already infected with HBV by HBV vaccination.

HDV is structurally unrelated to the other hepatitis viruses. As HDV is an incomplete virus, it can only replicate in the presence of Hepatitis B (HBV) virus, which provides structural components for HDV. HDV is a defect virus, or a viroid, that lacks the ability to productively infect a liver cell on its own. In particular, HDV has an outer coat that contains large, medium and small hepatitis B surface antigens, and host lipids surrounding an inner nucleocapsid, which contains about 200 molecules of hepatitis D antigen (HDAg) for each genome. The circular genome of HDV is unique to animal viruses because of its high GC content. The 1700 base circular positive RNA genome encodes a single protein, the small (S) hepatitis D antigen (S-HDAg) that acts as the viral capsid. However, a posttranscriptional editing of the S-HDAg stop codon in the transcribed genome results in the production of a 19 amino acid longer large (L-HDAg), which acts as a regulator of transcription. The replication of the viral RNA genome takes place in the nucleus through a rolling circle mechanism using host cell RNA polymerases. The use of host RNA polymerase for genome synthesis makes it extremely difficult to develop non-toxic antiviral polymerase inhibitors. The rolling circle replication results in a more than full length genomic RNA than is trimmed to the genomic RNA by hammer-head ribozymes and then circularized. For assembly and release of viral particles HDV will steal the surface protein of HBV, HBsAg. Thus, the HDV virion leaving the cell is encompassed of HDAg enclosing the viral RNA genome with a lipid envelope containing HBsAg.

Since all cells infected by HBV express and secrete high levels of HBsAg particles, and importantly, HBsAg expression can be completely independent of the HBV replication, this means that HDV uses the same entry receptor as HBV, the sodium taurocholate co-transporting polypeptide (NTCP) and can only productively infect cells infected by HBV.

HDV can be prevented by HBV vaccination in a host naïve to both HBV and HDV. However, since the HBV vaccine is based on HBsAg this vaccine is useless in a person already infected with HBV. Thus, there is no strategy currently to prevent HDV infection in HBV carriers. In addition, since the production of HBsAg is independent of the HBV replication, the currently used polymerase inhibitors for HBV cannot be used to prevent or to treat the HDV coinfection.

Potent antiviral drugs inhibit HBV replication without affecting the HDV replication. Thus antiviral drugs affect neither the production of the HBV envelope (HBsAg) required for HDV assembly, nor the replication of the HDV genome mediated by the host cell RNA polymerase II. The latter significantly impairs the possibility to develop antiviral enzyme inhibitors for HDV. HBsAg-based HBV vaccines can prevent a non-infected subject from becoming infected by both HBV and HDV; however, the HBV vaccine cannot protect a subject already infected by HBV against HDV super-infection due to the inherent overproduction of HBsAg during the HBV infection. HDV RNA replication is mediated by host cell RNA polymerase II, which significantly impairs the possibility to develop antiviral enzyme inhibitors. The HBV infection can be treated with a life-long therapy using polymerase inhibitors that blocks HBV replication, but not protein synthesis, and reduces the risk of HBV-induced liver damage. However, HDV replication is completely unaffected by the HBV antivirals since these do not block HBsAg production. The only treatment available for HDV today is an expensive and cumbersome 48-month therapy of pegylated interferon (PEG-IFN), which cures 25% of HDV infections. Thus, new preventive and therapeutic strategies are desperately needed for the increasing problem of HBV-HDV coinfections.

SUMMARY OF THE INVENTION

In a first aspect, a chimeric gene comprising HDAg sequences is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least-two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ) ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof.

In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In a second aspect, a chimeric protein comprising at least two HDAg protein domains, encoded by the chimeric gene of anyone of the alternatives described herein is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59 In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In a third aspect, a composition comprising anyone or more of the chimeric genes of any one of the alternatives is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a fourth aspect, the chimeric gene or composition of any one of the alternatives is for use in generating an immune response in a subject or for DNA vaccination so as to inhibit, ameliorate, treat, or prevent HBV and HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a fifth aspect, the chimeric gene or composition of any one of the alternatives herein, is for use in generating an antibody, T-lymphocyte or CTL-specific response in a subject so as to inhibit, ameliorate, treat, or prevent an HBV and HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one pre S1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a sixth aspect, the chimeric gene or composition of any one of the alternatives described herein is for DNA vaccination against HBV and HDV in a subject that has been identified as having and HDV or HBV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ) ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ) ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set, forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In a seventh aspect, a method of eliciting an immune response is provided, wherein the method comprises administering to a subject having HDV infection and/or HBV infection the nucleic acid or composition of any one of the alternatives herein. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or an antigenic portion thereof comprises a sequence set forth in SEQ ID NO: 60 or 62 or an antigenic portion thereof. In some alternatives, the HBV Core or antigenic portion thereof comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant, comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, said administering comprises injecting said nucleic acid into a patient, such as using an IVIN needle with or without electroporation. In some alternatives, the method further comprising administering a second administration of a nucleic acid or composition of any one of the alternatives described herein. In some alternatives, the method further comprises providing an adjuvant. In some alternatives, said adjuvant is a nucleic acid encoding a polypeptide adjuvant, such as IL-12, IL-15, or IL-21. In some alternatives, said adjuvant is IL-12, IL-15, or IL-21. In some alternatives, said second administration is given after said first time. In some alternatives, said adjuvant is given before, during, or after administration of said nucleic acid or composition of any one of claims 1-45. In some alternatives, said second administration is given one week, two weeks, three weeks, four weeks, five weeks, or six weeks after the first administration of said nucleic acid or composition of any one of claims 1-45. In some alternatives, the subject has been identified as a person at risk of contracting HDV or that has HDV. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

In an eighth aspect, a method of increasing preS1 antibodies in a subject in need, the method comprising administering the compositions of anyone of the alternatives described herein to the subject in need. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least, two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least, one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ) ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof. In some alternatives, the sequences encoding the HBV Core or antigenic portion thereof comprises a sequence set forth in SEQ ID NO: 60 or 62 or an antigenic portion thereof. In some alternatives, the HBV Core comprises an amino acid sequence set forth in SEQ ID NO: 64 or an antigenic portion thereof. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

BRIEF DESCRIPTION OF THE DRAWINGS

FIG. 1 shows the alignment of HBV preS1 peptides.

DEFINITIONS

Figure 2:
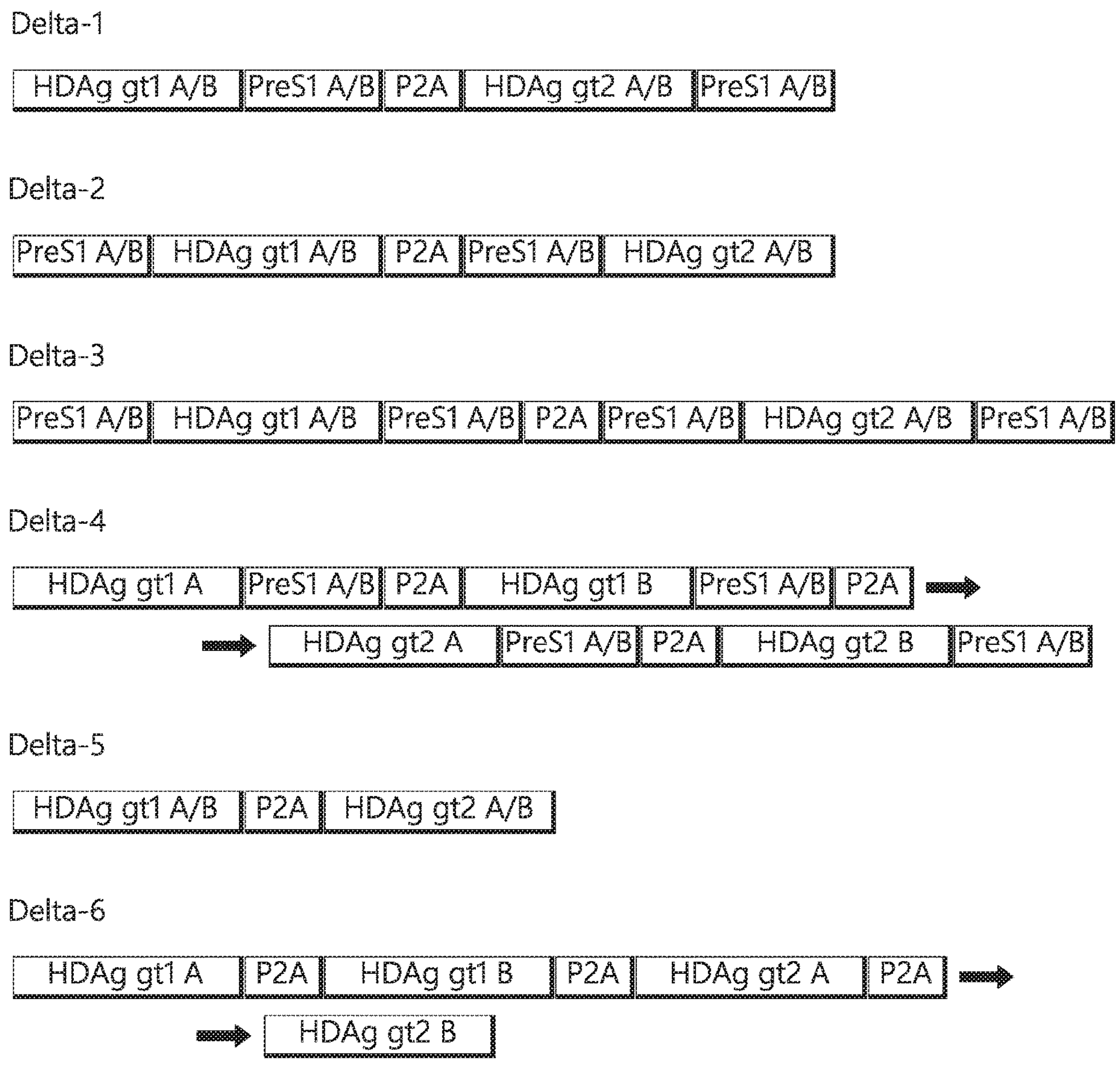
FIG. 2 is a schematic of several primary sequences of combined HDV-PreS1 vaccine design. As shown, the HDV-PreS1's can have domains from HDAg genotype 1 A/B, PreS1 A/B, P2A and HDAg gt2 A/B to make up the vaccines Delta-1, Delta-2, Delta-3, Delta-4, Delta-5, Delta-6, Delta-7, Delta-8, Delta-9 and Delta 10.
Figure 2:
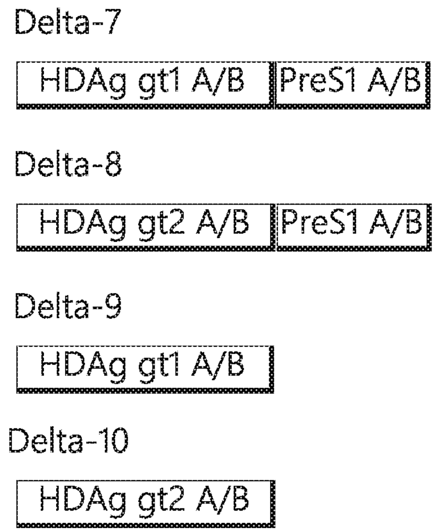

Unless defined otherwise, all technical and scientific terms used herein have the same meaning as commonly understood by one of ordinary skill in the art to which the invention pertains.

"About" as used herein when referring to a measurable value is meant to encompass variations of ±20% or ±10%, more preferably ±5%, even more preferably ±1%, and still more preferably ±0.1% from the specified value.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives described herein, a gene delivery polynucleotide for stable insertion of a nucleic acid into a gene is provided. "Oligonucleotide" can be used interchangeable with nucleic acid and can refer to DNA or RNA, either double stranded or a single stranded piece or DNA or RNA.

The nucleic acids described herein can have natural bases, modified bases and/or synthetic bases. Natural bases can include, for example, cytosine, guanine, adenine, thymine, uracil and pseudouracil. Modified bases can include, but are not limited to, xanthine and 2-deoxypseudoguanosine. Synthetic bases may include methyl-cytosine.

"Chimeric gene" as described herein refers to a combination of portions of one or more coding sequences to produce new genes. These mutations are distinct from fusion genes which merge whole gene sequences into a single reading frame and often retain their original functions. In some alternatives described herein, a chimeric gene comprising HDAg sequences is provided. The chimeric gene can have at least two sequences encoding hepatitis D antigen (HDAg), at least one cleavage sequence and at least one preS1 derived sequence. A chimeric gene can be DNA or RNA.

"Chimeric protein" is a hybrid protein that is encoded by a nucleotide sequence spliced together from two or more complete or partial genes produced by recombinant DNA technology. Methods for creating a chimeric protein through chimeric genes is well known to those skilled in the art and can be performed with basic molecular cloning in which fragments of genes are combined with vector DNA to create the chimeric gene for protein expression.

"HDag" as described herein is hepatitis D antigen. In some alternatives described herein a chimeric gene comprising HDAg sequences is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. A chimeric gene can be DNA or RNA. Shown in FIG. 2 are the combined HDV-PreS1 vaccine designs for Delta-1, Delta-2, Delta-3, Delta-4, Delta-5, Delta-6, Delta-7, Delta-8, Delta-9 and Delta-10 for the chimeric genes described in the alternatives herein. These constructs are used to encode the chimeric proteins described in the alternatives herein and are utilized for nucleic acid-based immunization by approaches described herein.

"Cleavage sequence" as described herein can refer to a self-cleaving 2A peptide. The chimeric genes can further encode at least one self-cleavage polypeptide sequence. Self-cleaving 2A polypeptide sequences, also referred to herein as self-cleavage sequences, sites or domains were first identified in the foot-and-mouth disease virus (Ryan, M D et al. (1991) "Cleavage of foot and mouth disease virus protein is mediated by residues located within a 19 amino acid sequence." J. Gen. Virol. 72(Pt 11):2727-2732). The 'cleavage' of a 2A peptide from its immediate downstream peptide is in fact affected by ribosomal skipping of the synthesis of the glycyl-prolyl peptide bond at the C-terminus of the 2A polypeptide (Lyan Lab Webpage; de Felipe P, Luke G A, Brown J D, Ryan M D (2010) Inhibition of 2A-mediated 'cleavage' of certain artificial polyproteins bearing N-terminal signal sequences. Biotechnol J 5:213-223; Donnelly M L, Luke G, Mehrotra A, Li X, Hughes L E, et al. (2001) Analysis of the aphthovirus 2A/2B polyprotein 'cleavage' mechanism indicates not a proteolytic reaction, but a novel translational effect: a putative ribosomal 'skip'. J Gen Virol 82:1013-1025). Several 2A self-cleavage polypeptides have been isolated (see, e.g., Szymczak A L, Vignali D A (2005) Development of 2A peptide-based strategies in the design of multicistronic vectors. Expert Opin Biol Ther 5: 627-638, the disclosure of which is hereby incorporated by reference in its entirety). Four of the 2A polypeptide sequences identified to date have seen substantial use in biomedical research: picornavirus 2A sequences FMDV 2A (abbreviated herein as F2A); equine rhinitis A virus (ERAV) 2A (E2A); porcine teschovirus-1 2A (P2A), and insect virus *Thosea asigna* virus 2A (T2A), (de Felipe P, Luke G A, Hughes L E, Gani D, Halpin C, et al. (2006) E unum pluribus: multiple proteins from a self-processing polyprotein. Trends Biotechnol 24:68-75).

Self-cleaving 2A sequences are preferred over alternative methods of expressing multiple proteins from a single construct, such as Internal Ribosomal Entry-Sequences (IRES), because of their short length and stoichiometric expression of multiple proteins flanking the 2A polypeptide (de Felipe P, Luke G A, Hughes L E, Gani D, Halpin C, et al. (2006) E unum pluribus: multiple proteins from a self-processing polyprotein. Trends Biotechnol 24:68-75). In the alternatives described herein, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus.

The Pre-S1 derived sequence, as described herein encodes the Pre-S1 domain of the surface antigen of hepatitis B virus. Targeting of preS1 may be used to prevent both infections of HBV and HDV. It has been shown that a 48 amino acid stretch within the preS1 region is effective in generating preS1-specific antibodies. In some alternatives described herein, a chimeric gene comprising HDAg sequences is provided. The chimeric gene can have at least two sequences encoding hepatitis D antigen (HDAg), at least one cleavage sequence and at least one preS1 derived sequence. In some alternatives, the at least one preS1 derived sequence is preS1 A and/or preS1 B.

"Codon optimization" as described herein, refers to a method for maximal protein selection by adaptation of codons of the transcript gene to the typical codon usage of a host. Those skilled in the art will appreciate that gene expression levels are dependent on many factors, such as promoter sequences and regulatory elements. As noted for most bacteria, small subsets of codons are recognized by tRNA species leading to translational selection, which can be an important limit on protein expression. In this aspect, many synthetic genes can be designed to increase their protein expression level. The design process of codon optimization can be to alter rare codons to codons known to increase maximum protein expression efficiency. In some alternatives, codon selection is described, wherein codon selection is performed by using algorithms that are known to those skilled in the art to create synthetic genetic transcripts optimized for higher levels of transcription and protein yield. Programs containing algorithms for codon optimization are known to those skilled in the art. Programs can include, for example, OptimumGene™, GeneGPS® algorithms, etc. Additionally synthetic codon optimized sequences can be obtained commercially for example from Integrated DNA Technologies and other commercially available DNA sequencing services. In some alternatives, the chimeric gene comprises sequences, wherein at least one sequence is codon optimized. In some alternatives, the genes are codon optimized for expression in humans, which can include gene transcripts the core protein, HDAg, or at least one preS1 derived sequence. The 2A and/or P2A sequences may or may not be codon optimized for expression in humans.

"HBV core antigen" (HBcAg) or the nucleocapsid of HBV is an immunogenic particle composed of 180 subunits of a single protein chain. HBcAg has been disclosed as an immunogenic moiety that stimulates the T cell response of an immunized host animal. See, e.g, U.S. Pat. Nos. 4,818,527, and 5,143,726, each of which is hereby incorporated by reference in their entirety. It, can be used as a carrier for several peptidic epitopes covalently linked by genetic engineering as well as for chemically coupled protein antigens. (See Sallberg et al. (1998) Human Gene Therapy 9:1719-29). In addition, HBcAg is non-cytotoxic in humans. Accordingly, it was contemplated that HBcAg is useful in genetic constructs for generating or enhancing an immune response to an accompanied target antigen (e.g., in constructs that encode a TCE derived from a pathogen).

Current listings of exemplary HBcAg sequences are publicly available at the National Center for Biotechnology Information (NCBI) world-wide web site. Several different HBcAg nucleic acid sequences (including novel HBcAg regions) can be utilized (e.g., humans, birds, such as stork or heron, or rodents such as ground squirrel or woodchuck). DNA obtained from a subject infected with HBV (e.g., humans, birds, such as stork or heron, or rodents such as ground squirrel or woodchuck) can also be isolated by PCR or another amplification technique.

For a review of PCR technology, see Molecular Cloning to Genetic Engineering White, B. A. Ed. in *Methods in Molecular Biology* 67: Humana Press, Totowa (1997) and the publication entitled "PCR Methods and Applications" (1991, Cold Spring Harbor Laboratory Press). For amplification of mRNAs, it is within the scope of the invention to reverse transcribe mRNA into cDNA followed by PCR (RT-PCR); or, to use a single enzyme for both steps as described in U.S. Pat. No. 5,322,770. Another technique involves the use of Reverse Transcriptase Asymmetric Gap Ligase Chain Reaction (RT-AGLCR), as described by Marshall R. L. et al. (*PCR Methods and Applications* 4:80-84, 1994).

The source of the HBcAg sequences that are included in the isolated nucleic acids described herein is not particularly limited. Accordingly, alternatives described herein may utilize an isolated nucleic acid that encodes an HBcAg derived from a hepatitis virus capable of infecting animals of any species, including but limited to, humans, non-human primates (e.g., baboons, monkeys, and chimpanzees), rodents, mice, reptiles, birds (e.g., stork and heron), pigs, micro-pigs, goats, dogs and cats. In some alternatives, the HBcAg is selected from a human hepatitis antigen or an avian hepatitis antigen. Particularly preferred are the stork hepatitis antigen and a heron hepatitis antigen.

In certain alternatives, the HBcAg sequences described herein have variations in nucleotide and/or amino acid sequences, compared to native HBcAg sequences and are referred to as HBcAg variants or mutants. As used herein, the term "native" refers to naturally occurring HBV sequences (e.g., available HBV isotypes). Variants may include a substitution, deletion, mutation or insertion of one or more nucleotides, amino acids, or codons encoding the HBcAg sequence, which may result in a change in the amino acid sequence of the HBcAg polypeptide, as compared with the native sequence. Variants or mutants can be engineered, for example, using any of the techniques and guidelines for conservative and non-conservative mutations set forth, for instance, in U.S. Pat. No. 5,364,934, which is hereby incorporated by reference in its entirety.

Accordingly, when the term "consisting essentially of" is used, in some contexts, variants or mutants of an HBcAg sequence or of a particular antigen sequence are intended to be encompassed. That is, in some contexts and in some alternatives, the variants or mutants of the sequences disclosed herein are equivalents because the variation or mutation in sequence does not change or materially affect the basic and novel characteristics of the claimed invention.

A codon-optimized HBcAg can, in some alternatives, be encoded within the isolated nucleic acid or chimeric gene. A codon-optimized sequence may, in some alternatives, be obtained by substituting codons in an existing sequence with codons more frequently used in the intended host subject (e.g., a human).

Some alternatives include, for example, one or more of the HBcAg nucleic acid or protein sequences disclosed in International Patent Application Publication Number WO 20091130588, published Dec. 7, 2011, which designated the United States and was published in English, the disclosure of which is hereby expressly incorporated by reference in its entirety. In some alternatives, a chimeric gene encoding HBV core (HBcAg) is provided. In some alternatives, the chimeric gene comprises a sequence set forth in SEQ ID NO's: 60, 62, 65, 67, 70 or 72.

DETAILED DESCRIPTION

Existing therapies with reversed transcriptase (RT) inhibitors effectively supress HBV replication but fails to induce off-therapy responses, and have no effect on HDV replication. The viroid-like virus HDV is a highly pathogenic virus and can only complete its replication cycle in cells infected by HBV. HDV lacks its own gene for a viral envelope protein and therefore "steals" the envelope of HBV, the hepatitis B surface antigen (HBsAg), when leaving the cell. Hence, the HBV vaccine can protect naive individuals from both HBV and HDV, but cannot protect a person infected by HBV against HDV superinfection due to the inherent overproduction of HBsAg during the HBV infection.

In some alternatives described herein, preS1 antibodies were shown to prevent HBV and HDV infection. Importantly, both HBV and HDV require the same preS1 sequence to enter hepatocytes. Thus, targeting preS1 is an excellent way to prevent both infections. It has been shown that a 48 amino acid stretch within the preS1 region is effective in generating preS1-specific antibodies. In some alternatives described herein, preS1 antibodies can be induced by a chimeric HBV core antigen (HBcAg) protein exposing a preS1 sequence (aa 1-42) on the surface. In addition, HDAg was shown to induce genotype-specific T cell responses in mice. This suggests that multiple genotypes must be contained in an HDAg-based vaccine.

Additionally, it has been discovered that hepatitis B core antigen (HBcAg) is a potent adjuvant that improves the immune response of a subject to a co-administered antigen (See, e.g., PCT Publication No. WO 2010/086743 A2, published Aug. 5, 2010, which is hereby incorporated by reference in its entirety). In the present disclosure, it is contemplated that a nucleic acid encoding HBcAg improves the immune response of a mammal to the second polypeptide antigen.

Accordingly, some alternatives include methods of enhancing or improving an immune response of a subject, wherein a nucleic acid encoding an HBcAg, preferably codon-optimized for expression in humans, is provided to a subject along with another chimeric gene comprises at least two HDAg sequences, which are also preferably codon-optimized for expression in humans. In some alternatives, a chimeric gene encoding a HDV polypeptide with a pre-S1 domain is provided. The pre-S1 domain, as described herein, can allow prevention of HBV and HDV infections. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, preS1 A is encoded by a nucleic acid sequence set forth in SEQ ID NO: 5. In some alternatives, preS1 B is encoded by a nucleic acid sequence set forth in SEQ ID NO: 6.

The HDV infection cannot be prevented in patients infected by HBV using the current HBsAg-based vaccines lacking both preS1 and preS2. Thus, a combined approach with vaccines containing both parts of preS1 that induces neutralising antibodies, and parts or the whole HDAg to induce HDV-specific T cells should be able to inhibit, ameliorate, treat or prevent HDV infection in HBV infected patients.

Several alternatives described herein concern isolated chimeric genes, expression constructs, DNA immunogenic compositions, DNA vaccines or nucleic acid immunogens, preferably, which are codon-optimized for expression in humans, and that encode a peptide that comprises, consists of, or consists essentially of at least two antigenic sequence, which is an HDV sequence. In some alternatives a chimeric gene is also contemplated, which can encode HBcAg, preferably from avian, stork or heron, which is codon optimized for expression in humans.

Chimeric Genes

Chimeric Genes for Expression of HDAg Protein Domains.

Provided herein are chimeric genes comprising HDAg sequences and chimeric genes encoding HBV core antigen (HBcAg). In some alternatives, a chimeric gene comprising HDAg sequences and a sequence encoding a preS1 domain is provided. The chimeric gene can comprise at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, preS1 A comprises an amino acid sequence set forth in SEQ ID NO: 1. In some alternatives, preS1 B comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO: 10. In some alternatives, the chimeric gene comprises a nucleic acid sequence set forth in SEQ ID NO: 12. In some alternatives, the chimeric gene encodes a protein comprises an amino acid sequence set forth in SEQ ID NO: 14. In some alternatives, the chimeric gene comprises a nucleic acid sequence set forth in SEQ ID NO: 15. In some alternatives, the chimeric gene comprises a nucleic acid sequence set forth in SEQ ID NO: 17. In some alternatives, the chimeric gene encodes a protein wherein the protein comprises an amino acid sequence set forth in SEQ ID NO: 19. In some alternatives, the chimeric gene comprises a nucleic acid sequence set forth in SEQ ID NO: 20. In some alternatives, the chimeric gene comprises a nucleic acid sequence set forth in SEQ ID NO: 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO: 25. In some alternatives, the chimeric gene comprises a nucleic acid sequence set forth in SEQ ID NO: 27. In some alternatives, the chimeric gene encodes a protein wherein the protein comprises an amino acid sequence set forth in SEQ ID NO: 21. In some alternatives, the chimeric gene comprises a nucleic acid sequence set forth in SEQ ID NO: 30. In some alternatives, the chimeric gene comprises a nucleic acid sequence set forth in SEQ ID NO: 32. In some alternatives, the chimeric gene encodes a protein wherein the protein comprises an amino acid sequence set forth in SEQ ID NO: 34. In some alternatives, the chimeric gene comprises a nucleic acid sequence set forth in SEQ ID NO: 35. In some alternatives, the chimeric gene comprises a nucleic acid sequence set forth in SEQ ID NO: 37. In some alternatives, the chimeric gene encodes a protein wherein the protein comprises an amino acid sequence set forth in SEQ ID NO: 39. In some alternatives, the chimeric gene comprises a nucleic acid sequence set forth in SEQ ID NO: 40. In some alternatives, the chimeric gene comprises a nucleic acid sequence set forth in SEQ ID NO: 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO: 45. In some alternatives, the chimeric gene comprises a nucleic acid sequence set forth in SEQ ID NO: 47. In some alternatives, the chimeric gene encodes a protein wherein the protein comprises an amino acid sequence set forth in SEQ ID NO: 49. In some alternatives, the chimeric gene comprises a nucleic acid sequence set forth in SEQ ID NO: 50. In some alternatives, the chimeric gene comprises a nucleic acid sequence set forth in SEQ ID NO: 52. In some alternatives, the chimeric gene encodes a protein wherein the protein comprises an amino acid sequence set forth in SEQ ID NO: 54. In some alternatives, the chimeric gene comprises a nucleic acid sequence set forth in SEQ ID NO: 55. In some alternatives, the chimeric gene comprises a nucleic acid sequence set forth in SEQ ID NO: 57. In some alternatives, the chimeric gene encodes a protein wherein the protein comprises an amino acid sequence set forth in SEQ ID NO: 59. In some alternatives, the chimeric gene is codon optimized. Preferably, this sequence is codon optimized for expression in humans.

The preS1 peptides that are used are shown in FIG. 1, which is an alignment of the preS1 peptides of HBV. As shown in FIG. 2 are the combined HDV-PreS1 vaccine designs for Delta-1, Delta-2, Delta-3, Delta-4, Delta-5, Delta-6, Delta-7, Delta-8, Delta-9 and Delta-10 for the chimeric genes described in the alternatives herein. These constructs are used to encode the chimeric proteins described herein.

Chimeric Genes for Expression of HBV Core Protein

Described herein are chimeric genes for the expression of HBV core. In some alternatives, a chimeric gene for expressing HBV core antigen is provided, wherein the chimeric gene comprises a sequence encoding an HBV core antigen. In some alternatives, the chimeric gene comprises a sequence set forth in SEQ ID NO's: 60, 62, 65, 67, 70 or 72. In some alternatives, the chimeric gene is codon optimized for expression in humans. In some alternatives, the chimeric gene encodes a protein, wherein the protein comprises an amino acid sequence set forth in SEQ ID NO's 64, 69 or 74. Preferably, this sequence is codon optimized for expression in humans.

Chimeric Proteins

Chimeric HDAg Proteins

Chimeric proteins encoded by the chimeric genes described herein are provided. In some alternatives a chimeric protein comprising at least two HDAg protein domains, encoded by the chimeric genes of anyone of the alternatives described herein is provided. The chimeric gene can comprise at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, preS1 A comprises an amino acid sequence set forth in SEQ ID NO: 1. In some alternatives, preS1 B comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ) ID NO: 9. In some alternatives, the chimeric gene comprises a nucleic acid sequence set forth in SEQ ID NO: 10. In some alternatives, the chimeric gene comprises a nucleic acid sequence set forth in SEQ ID NO: 12. In some alternatives, the chimeric gene encodes a protein comprises an amino acid sequence set forth in SEQ ED NO: 14. In some alternatives, the chimeric gene comprises a nucleic acid sequence set forth in SEQ ID NO: 15. In some alternatives, the chimeric gene comprises a nucleic acid sequence set forth in SEQ ID NO: 17. In some alternatives, the chimeric gene encodes a protein wherein the protein comprises an amino acid sequence set forth in SEQ ID NO: 19. In some alternatives, the chimeric gene comprises a nucleic acid sequence set forth in SEQ ID NO: 20. In some alternatives, the chimeric gene comprises a nucleic acid sequence set forth in SEQ ID NO: 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO: 25. In some alternatives, the chimeric gene comprises a nucleic acid sequence set forth in SEQ ID NO: 27. In some alternatives, the chimeric gene encodes a protein wherein the protein comprises an amino acid sequence set forth in SEQ ID NO: 21. In some alternatives, the chimeric gene comprises a nucleic acid sequence set forth in SEQ ID NO: 30. In some alternatives, the chimeric gene comprises a nucleic acid sequence set forth in SEQ ID NO: 32. In some alternatives, the chimeric gene encodes a protein wherein the protein comprises an amino acid sequence set forth in SEQ ID NO: 34. In some alternatives, the chimeric gene comprises a nucleic acid sequence set forth in SEQ ID NO: 35. In some alternatives, the chimeric gene comprises a nucleic acid sequence set forth in SEQ ID NO: 37. In some alternatives, the chimeric gene encodes a protein wherein the protein comprises an amino acid sequence set forth in SEQ ID NO: 39. In some alternatives, the chimeric gene comprises a nucleic acid sequence set forth in SEQ ID NO: 40. In some alternatives, the chimeric gene comprises a nucleic acid sequence set forth in SEQ ID NO: 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO: 45. In some alternatives, the chimeric gene comprises a nucleic acid sequence set forth in SEQ ID NO: 47. In some alternatives, the chimeric gene encodes a protein wherein the protein comprises an amino acid sequence set forth in SEQ ID NO: 49. In some alternatives, the chimeric gene comprises a nucleic acid sequence set forth in SEQ ID NO: 50. In some alternatives, the chimeric gene comprises a nucleic acid sequence set forth in SEQ ID NO: 52. In some alternatives, the chimeric gene encodes a protein wherein the protein comprises an amino acid sequence set forth in SEQ ID NO: 54. In some alternatives, the chimeric gene comprises a nucleic acid sequence set forth in SEQ ID NO: 55. In some alternatives, the chimeric gene comprises a nucleic acid sequence set forth in SEQ ID NO: 57. In some alternatives, the chimeric gene encodes a protein wherein the protein comprises an amino acid sequence set forth in SEQ ID NO: 59. In some alternatives, the chimeric gene is codon optimized for expression in humans.

Chimeric HBV Core (HBcAg)

In some alternatives described herein, a chimeric protein comprising HBV core or an antigenic or immunogenic portion thereof (e.g., a portion that improves an immunological response to a co-administered nucleic acid, such as a portion that promotes an adjuvant activity with respect to a co-administered nucleic acid). In some alternatives, the HBV Core or an antigenic or immunogenic portion thereof is a human HBV Core or an antigenic or immunogenic portion thereof, a rodent HBV Core or an antigenic or immunogenic portion thereof, such as a woodchuck or ground squirrel HBV Core or antigenic or immunogenic portion thereof, or an avian HBV Core or an antigenic or immunogenic portion thereof, such as a stork or heron HBV Core or an immunogenic portion thereof is provided. The protein can be encoded by any one of the chimeric genes encoding HBV core or an antigenic portion thereof described herein. In some alternatives, the chimeric gene comprises a sequence encoding an HBV core antigen or an antigenic portion thereof. In some alternatives, the chimeric gene comprises a sequence set forth in SEQ ID NO's: 60, 62, 65, 67, 70 or 72 or an antigenic or immunogenic portion thereof. In some alternatives, the chimeric gene is codon optimized for expression in humans. In some alternatives, the chimeric gene encodes a protein, wherein the protein comprises an amino acid sequence set forth in SEQ ID NO's 64, 69 or 74 or an antigenic or immunogenic portion thereof.

Compositions

Accordingly, several aspects of the invention described herein concern compositions that comprise, consist essentially of, or that consist of chimeric genes that encode an HDAg which may be codon-optimized for expression in humans, and, which can be joined (e.g., in Cis) to a nucleic acid (preferably codon-optimized for expression in an animal or human) that encodes at least one preS1 derived sequence. The sequence can further comprise a self-cleavage sequence or domains (e.g., P2A, T2A, E2A, or F2A) that exist between the nucleic acid encoding the target antigen and the nucleic acid encoding the HDAg, and, which may optionally, exist within the nucleic acid sequence encoding the HDAg polypeptide such that the translated HDAg is self-cleaved into polypeptide fragments. Preferably, one or more or all of these sequences are codon optimized for expression in humans. Methods of using the foregoing immunogenic compositions to generate an immune response (e.g., a T cell and/or antibody specific immune response) or to inhibit, ameliorate, treat, or prevent HBV and HDV infection in a subject, preferably a human and, optionally a chronically infected human, are contemplated alternatives.

Optionally, a subject can be identified as one in need of an immune response to HBV and HDV prior to administration of the composition and/or said subject can be evaluated for the immune response or viral clearance after administration of said compositions and such identification and/or evaluation can be accomplished using readily available diagnostics and/or clinical approaches.

Compositions or mixtures that further comprise, consist essentially of, or that consist of one or more of nucleic acids (e.g., in Trans) that encode polypeptide adjuvants, such as nucleic acids encoding IL-12, IL-15, or IL-21, which may optionally be codon optimized for expression in humans, or that consist of polypeptide adjuvants IL-12, IL-15, or IL-21 or that consist of small molecule adjuvants such as ribavirin or CpG nucleic acids are also alternatives. Preferably, these nucleic acids are codon optimized for expression in humans and these nucleic acids can be used as an immunogen to inhibit, ameliorate, treat, or prevent HBV and HDV infection. Methods of using the aforementioned compositions to improve, enhance, or generate an immune response in a subject or to treat diseases such as HBV and HDV, especially in chronically infected individuals, are also contemplated.

Figure 3:
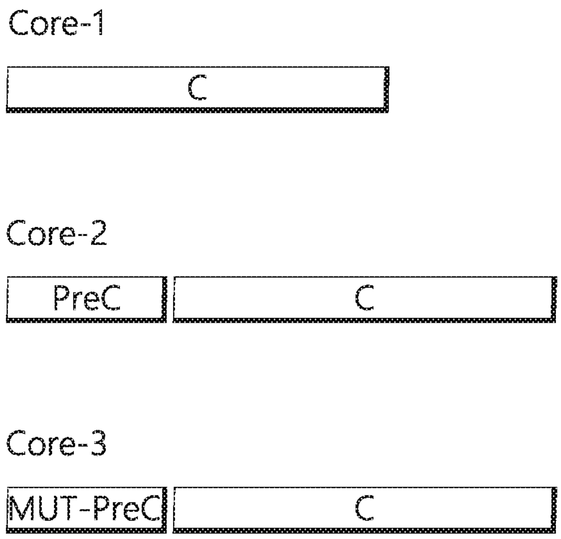
FIG. 3 shows the primary structures of the HBv-PreC/C vaccine designs, Core-1, Core-2 and Core-3.
Figures 4A, 4B:
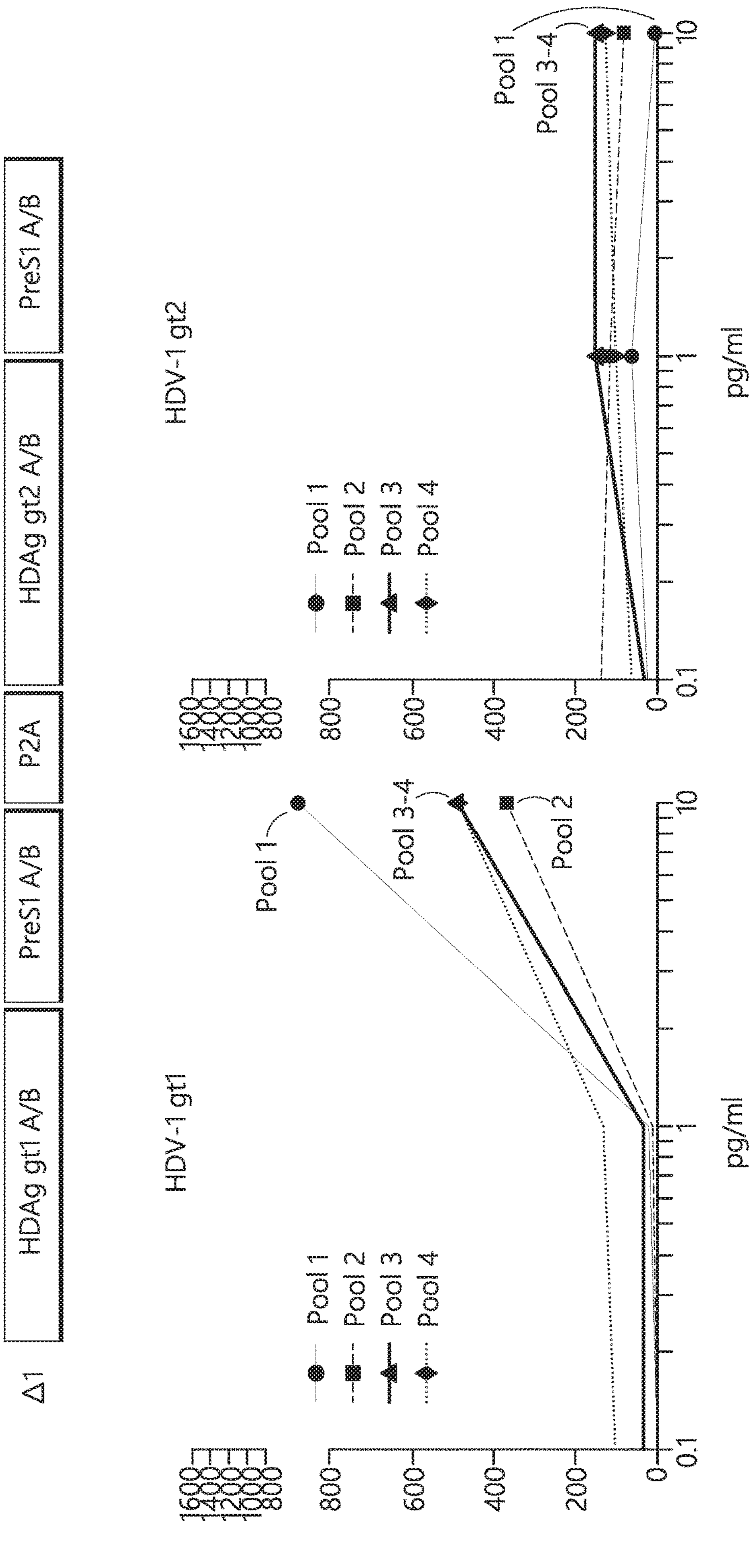
FIG. 4A-4T shows an in vitro recall of T cells primed after a single immunization using HDV constructs 1-10 towards gt1 (right panel) or gt2 (left panel) peptides (Peptides are shown in Table 1). The peptide constructs are also shown above the graphs.
Figures 4C, 4D:
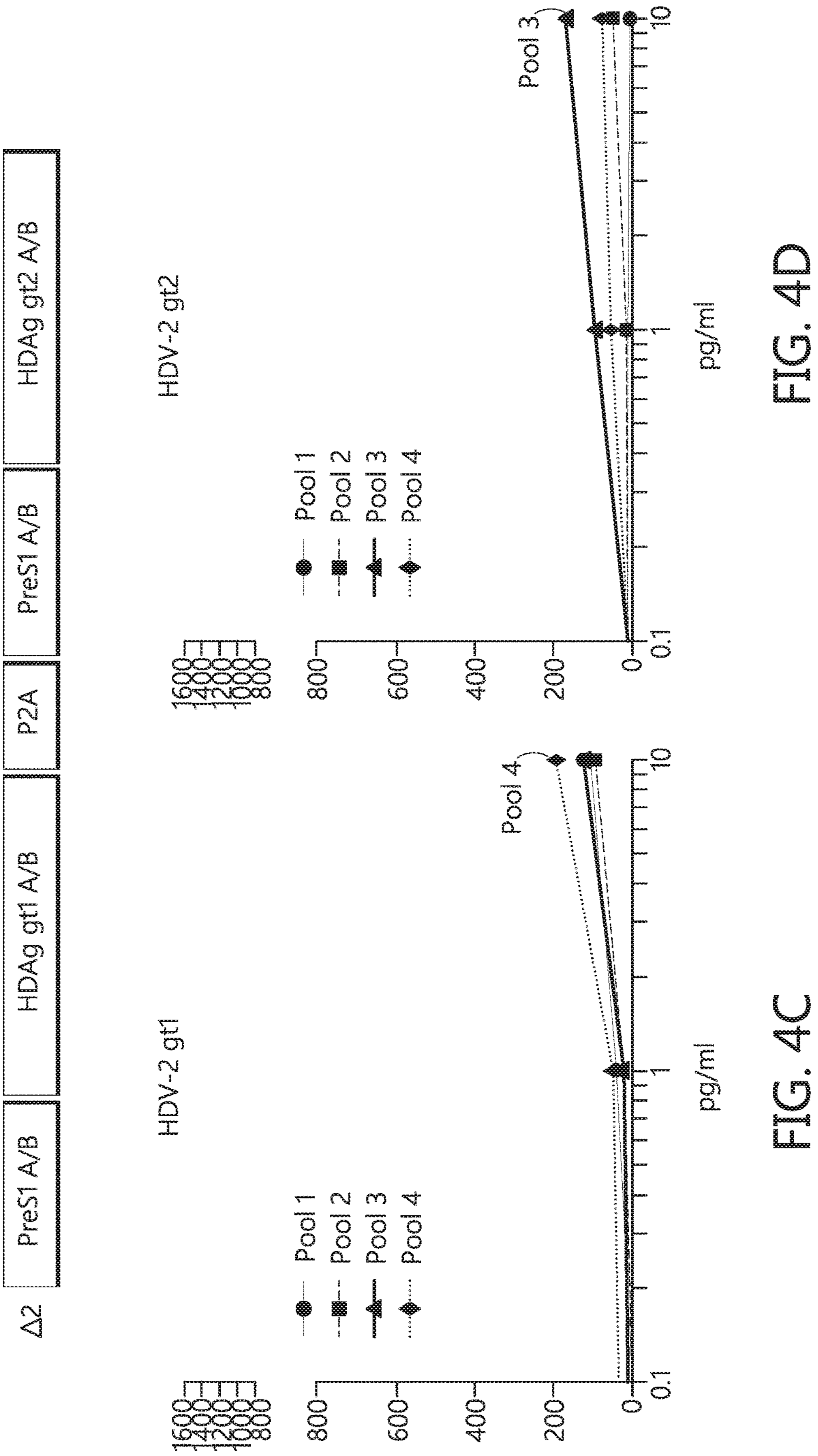
Figures 4E, 4F:
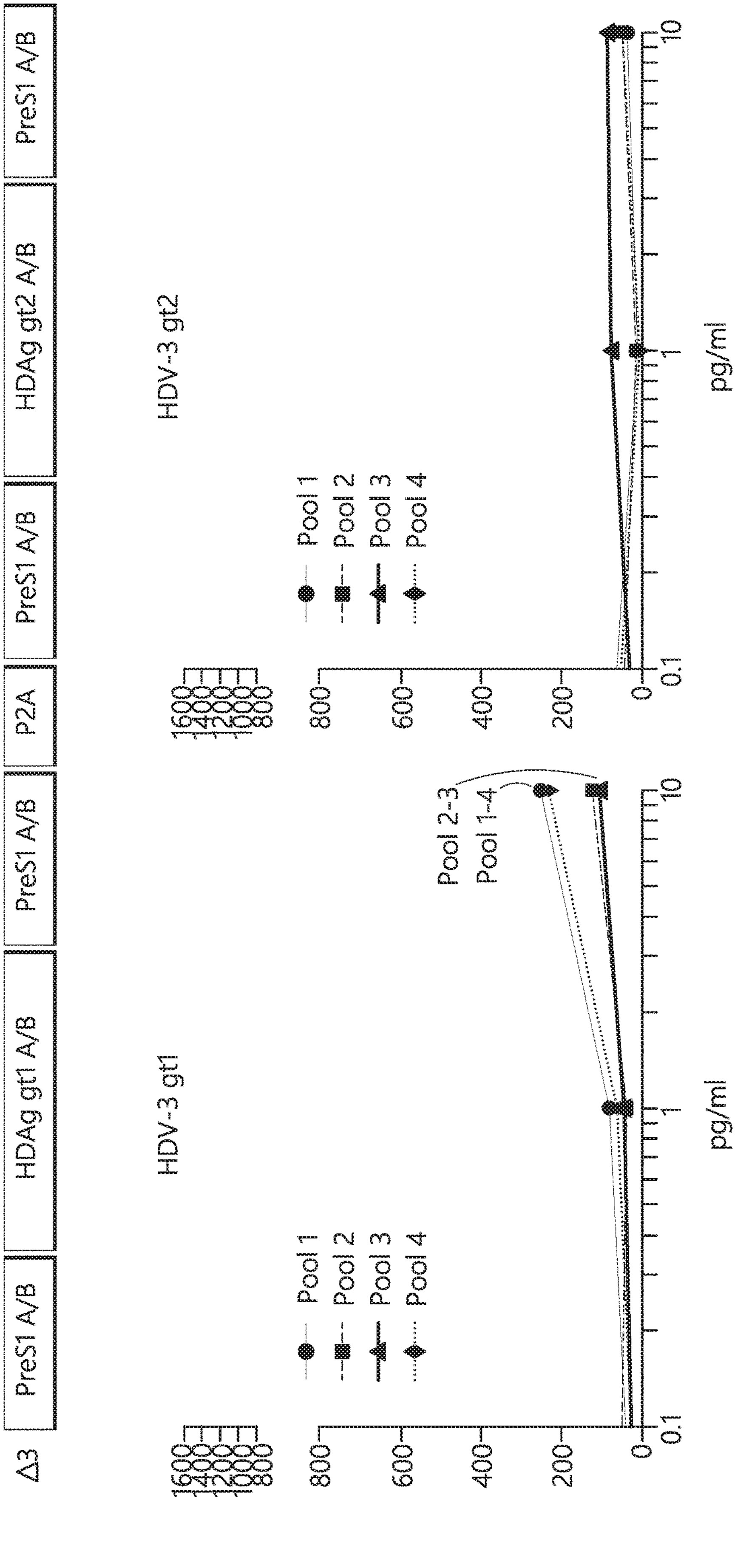
Figures 4G, 4H:
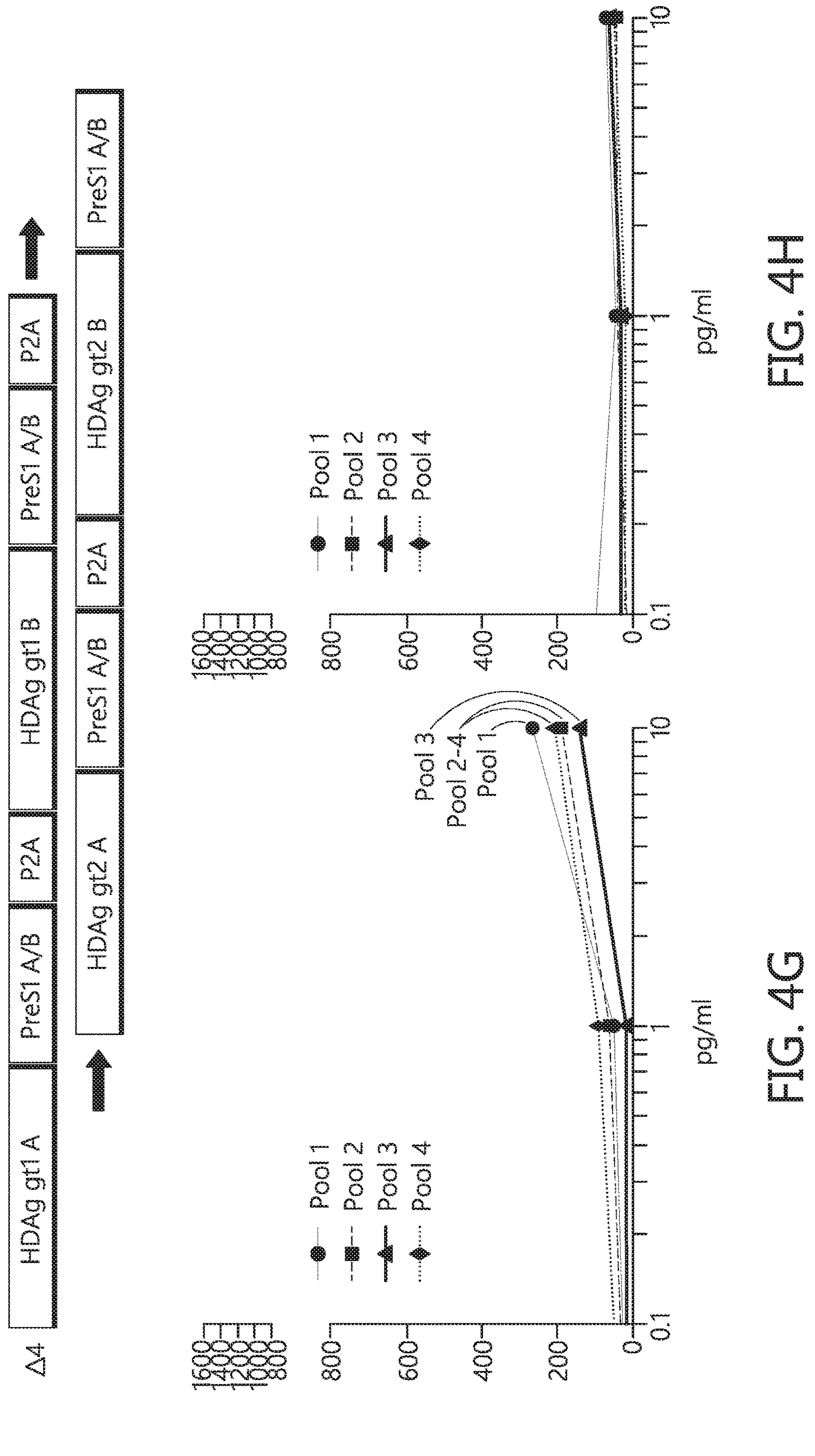
Figures 4I, 4J:
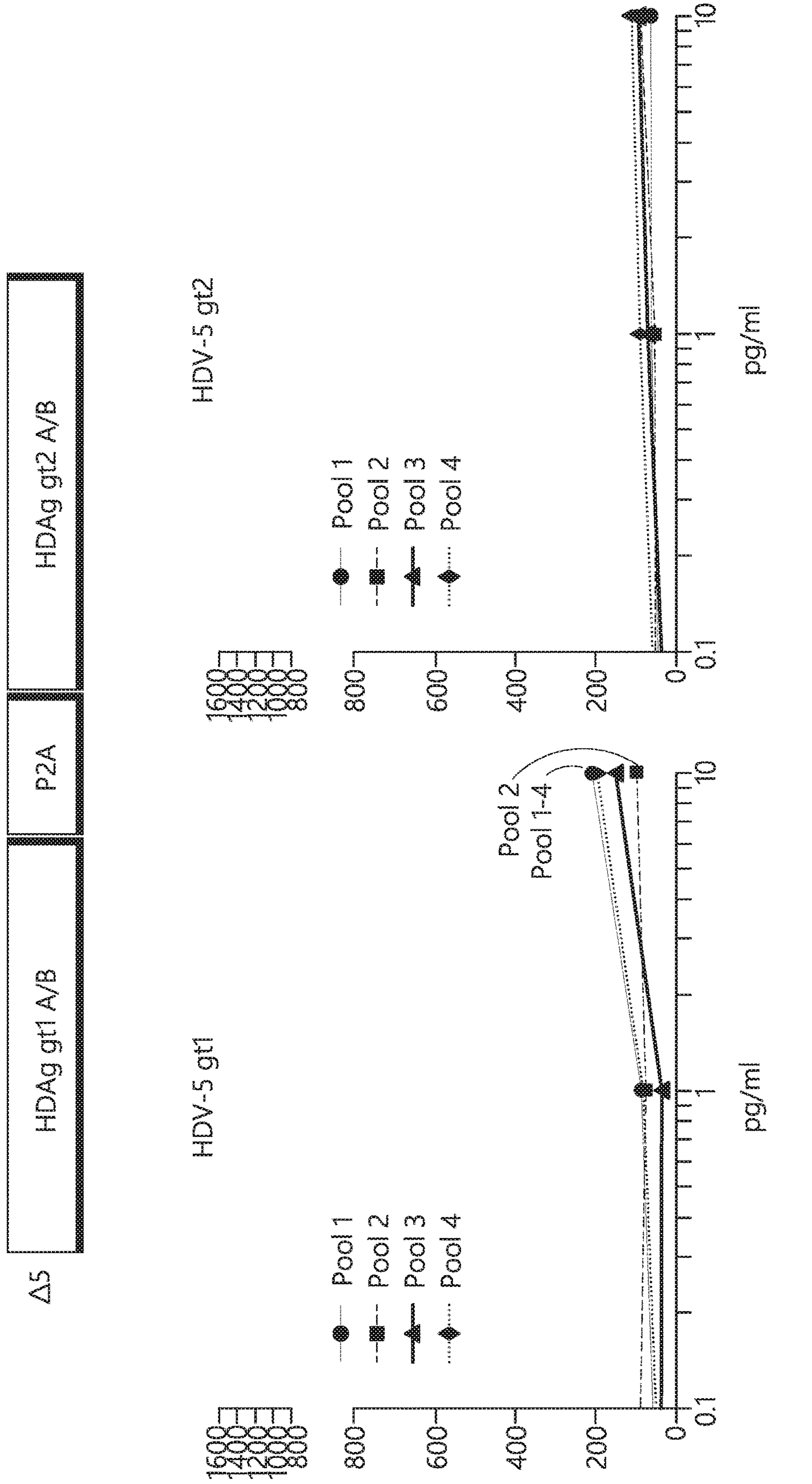
Figures 4K, 4L:
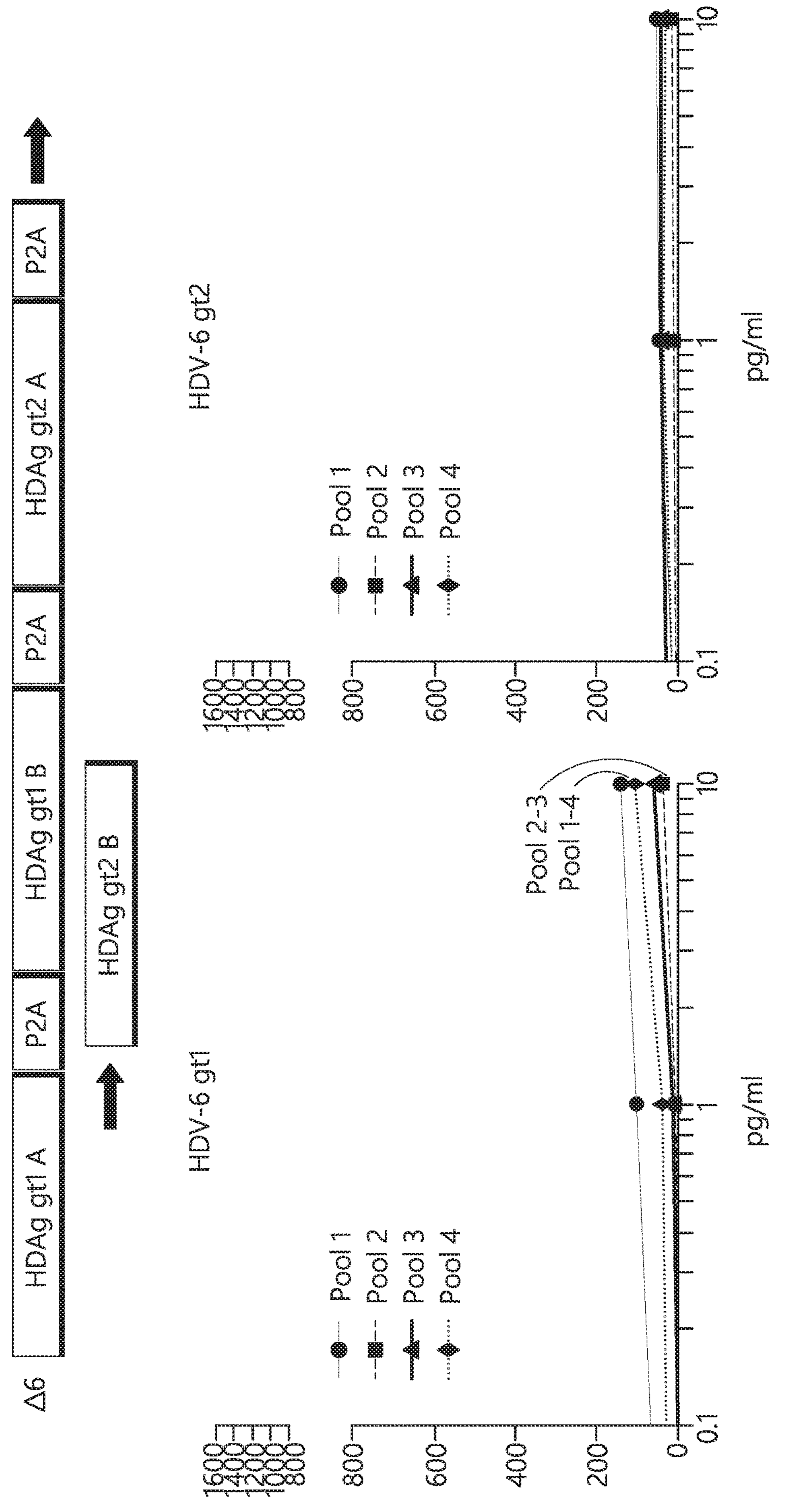
Figures 4O, 4P:
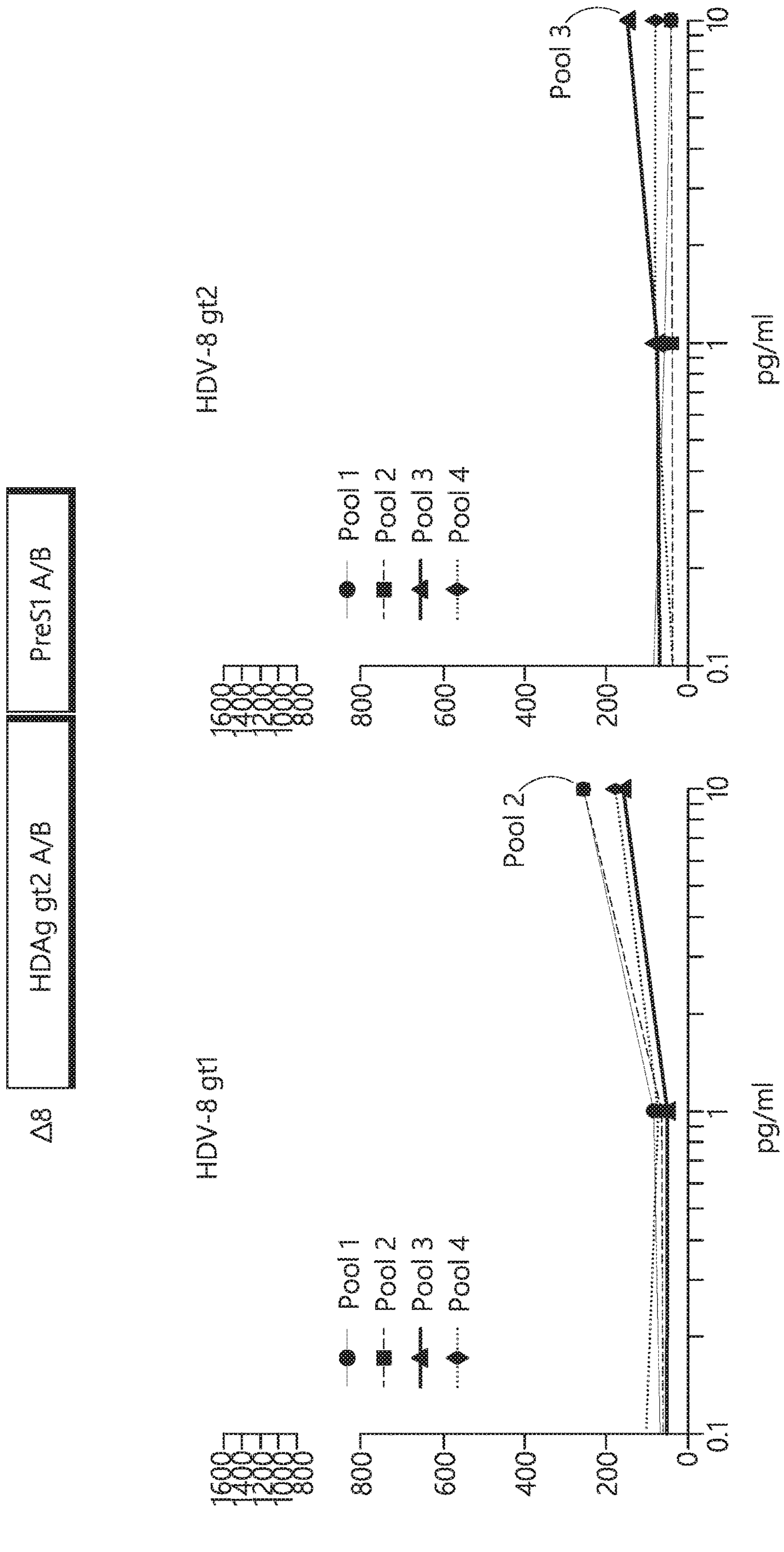
Figures 4Q, 4R:
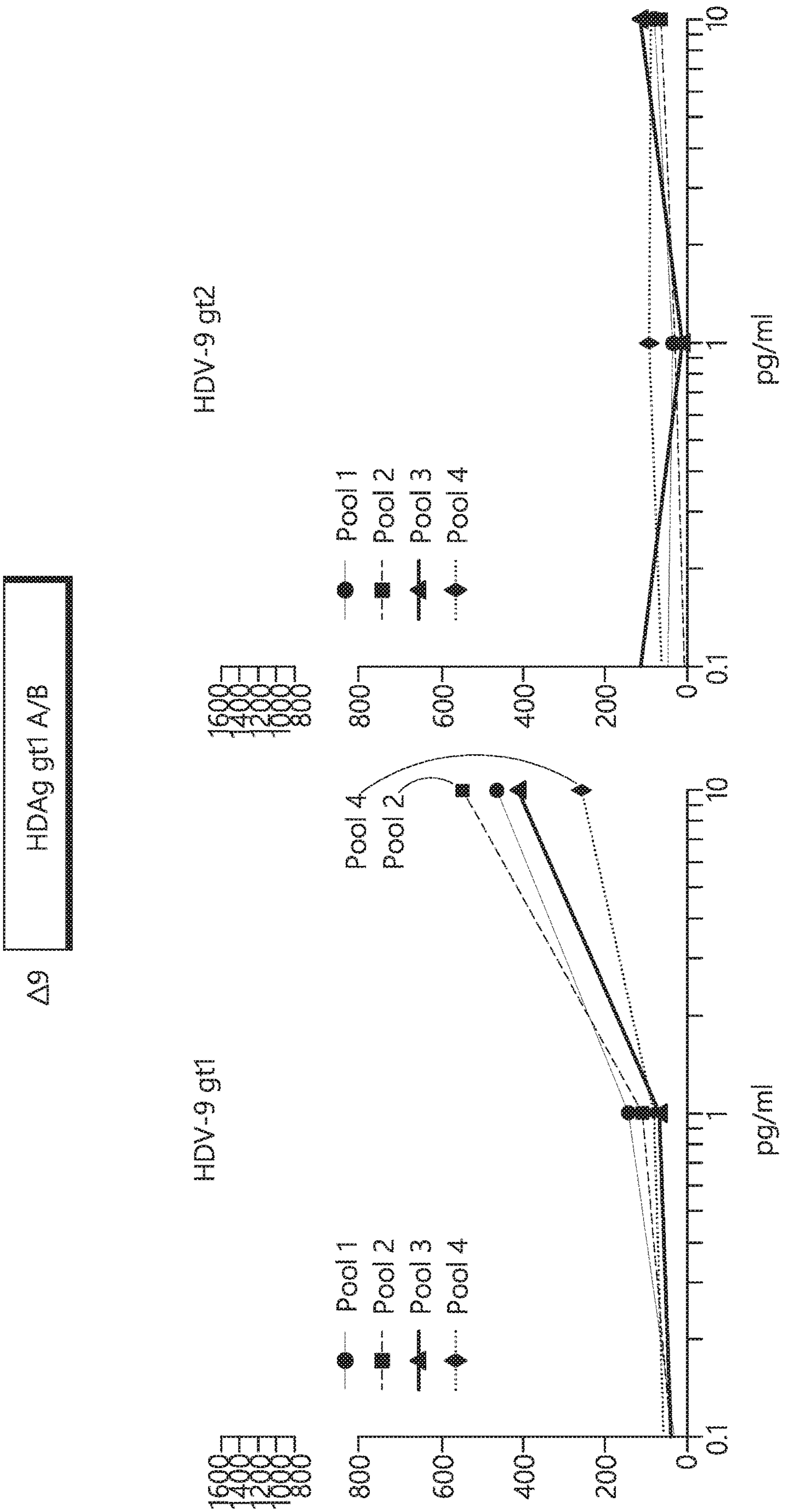
Figures 4S, 4T:
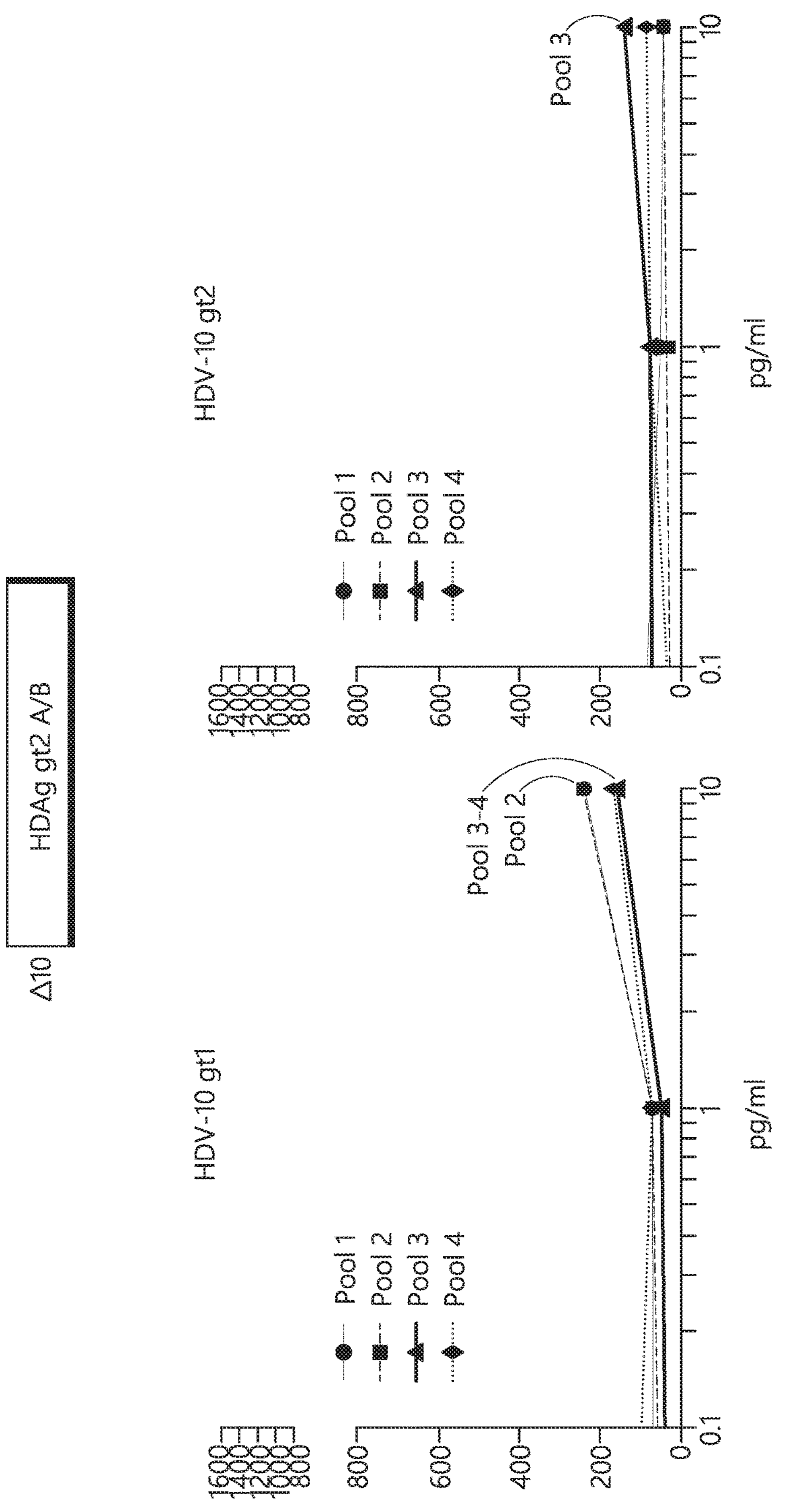
Figures 5A, 5B:
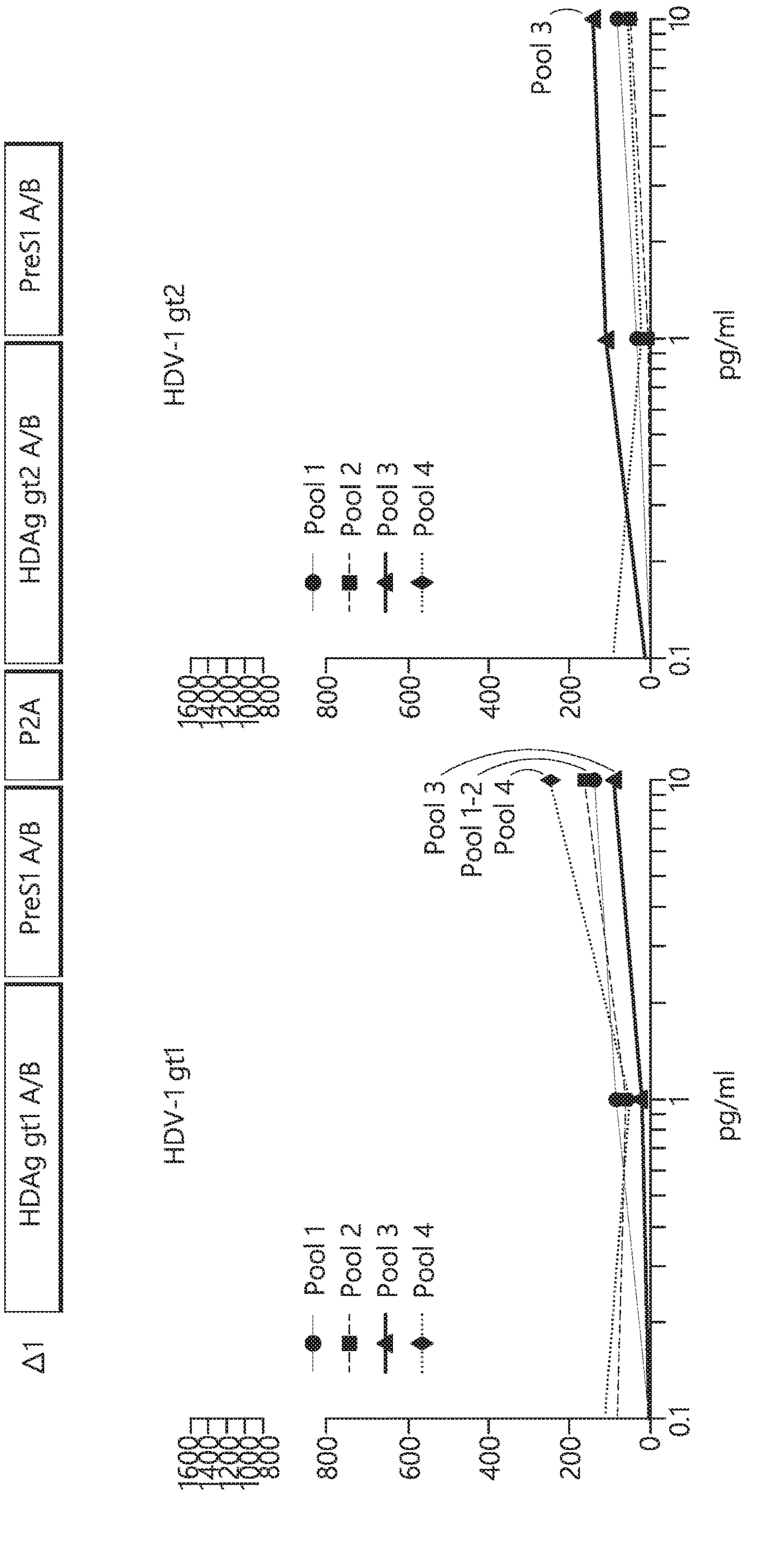
FIG. 5A-5T shows an in vitro recall of T cells primed after two monthly immunizations using HDV constructs 1-10 towards gt1 (right panel) or gt2 (left panel) peptides (Peptides are shown in Table 1).
Figures 5C, 5D:
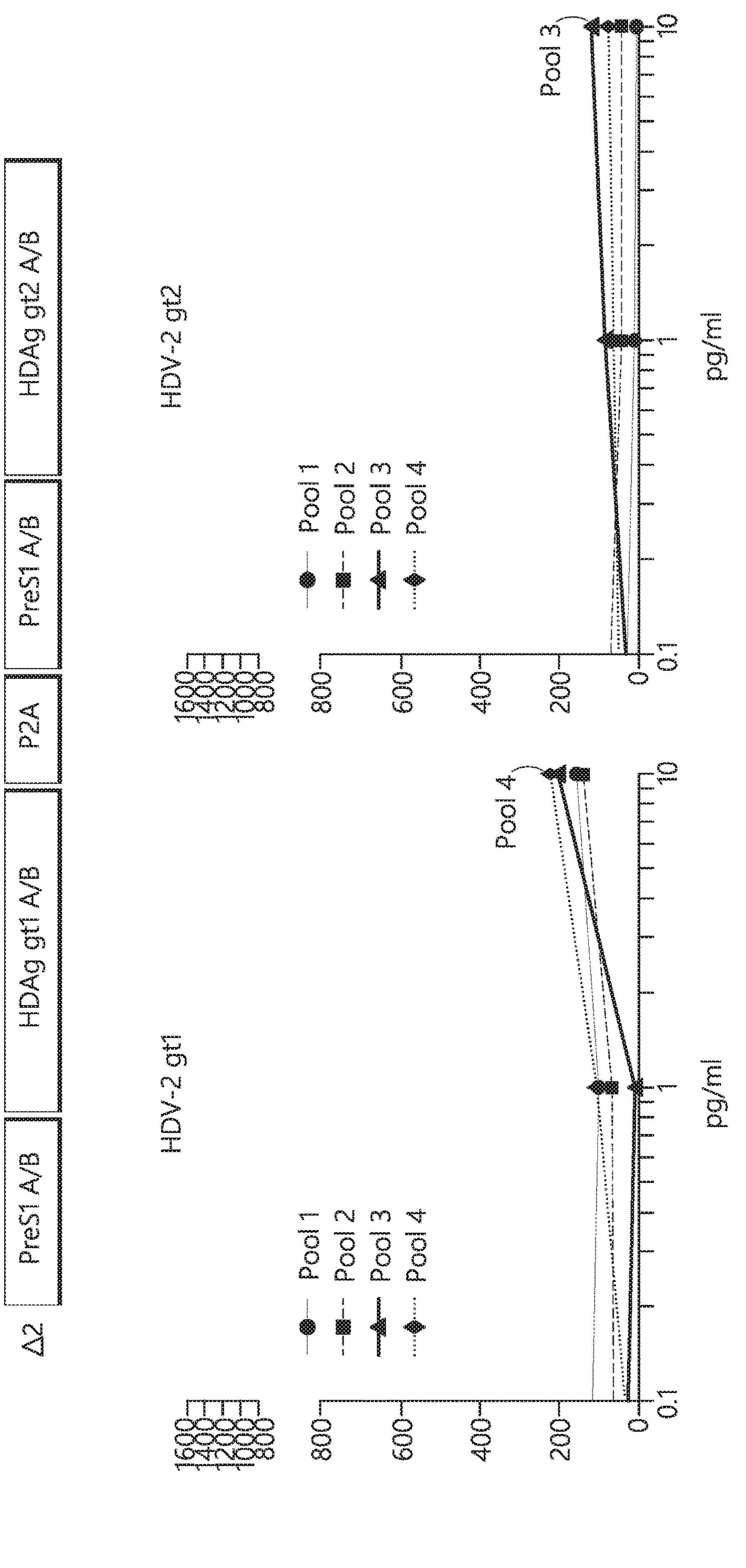
Figures 5E, 5F:
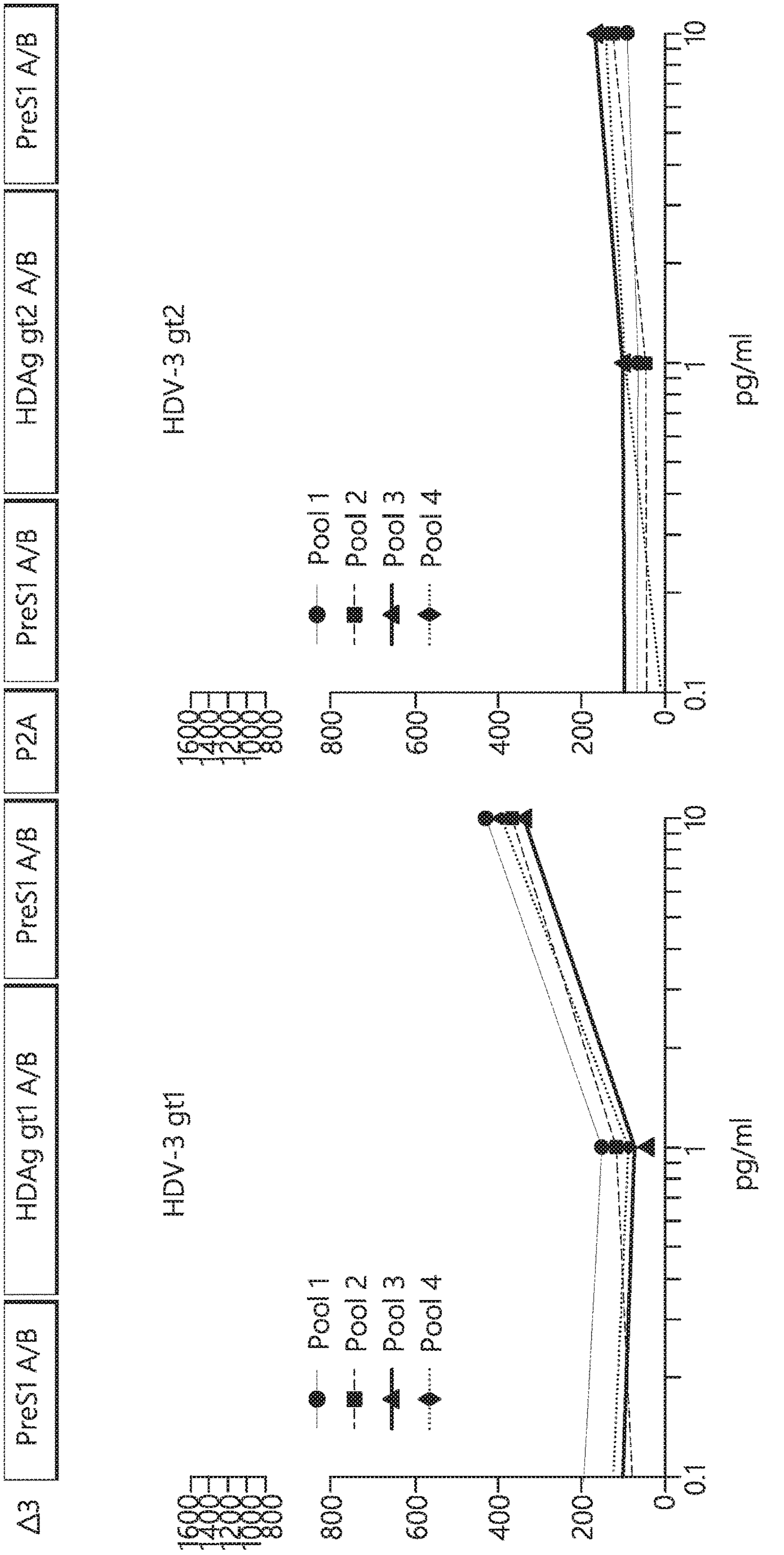
Figures 5G, 5H:
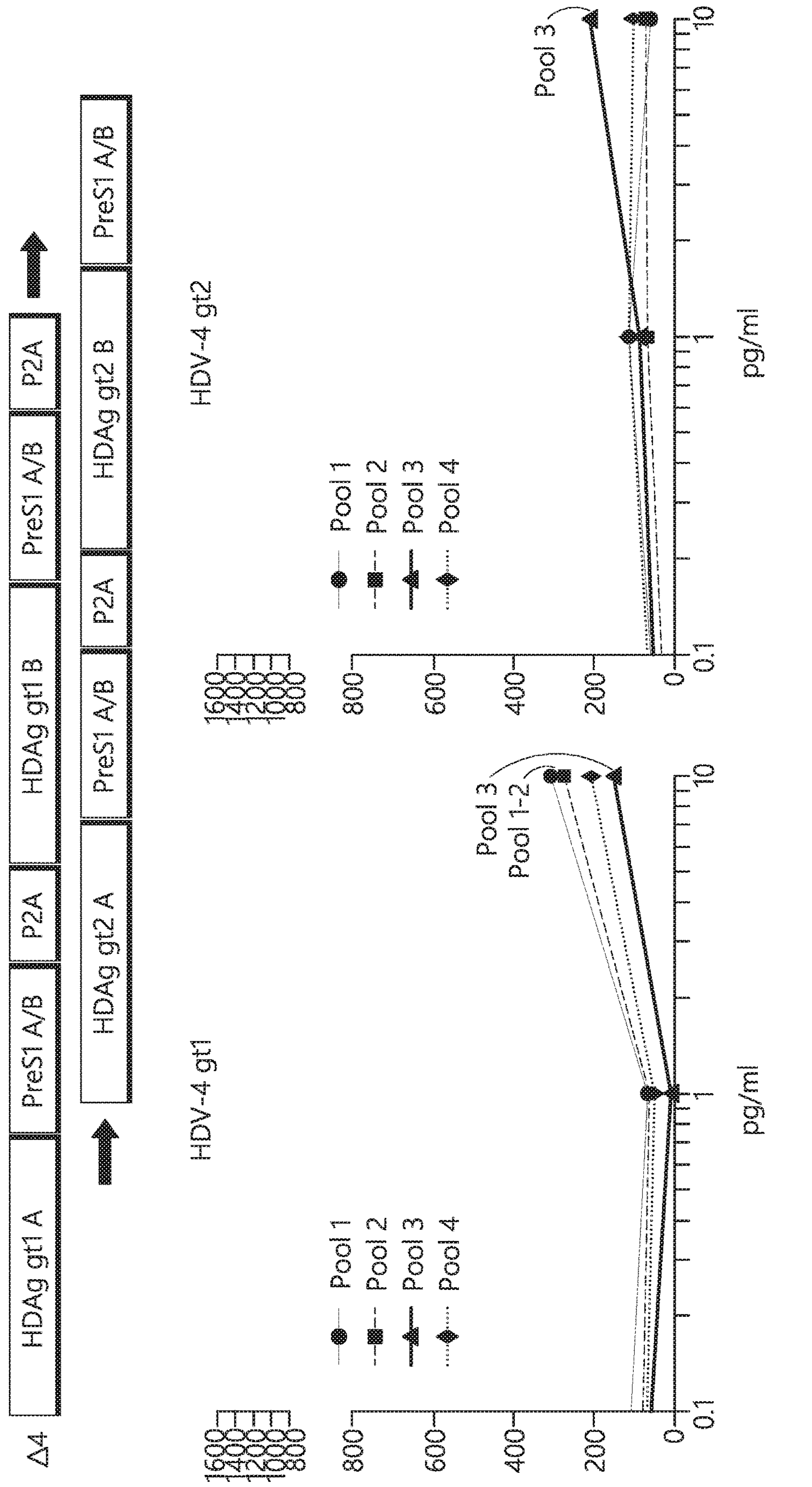
Figures 5I, 5J:
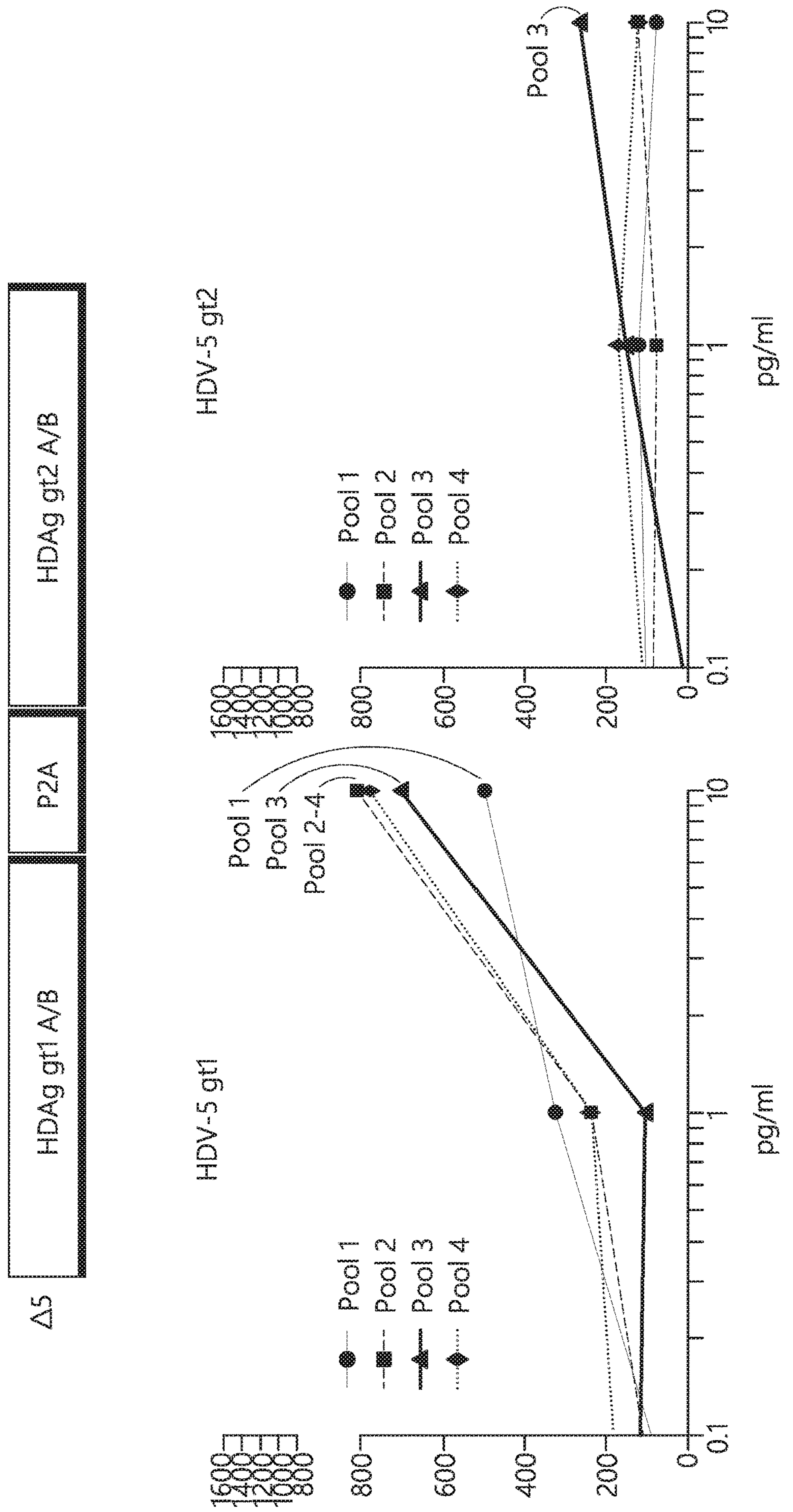
Figures 5K, 5L:
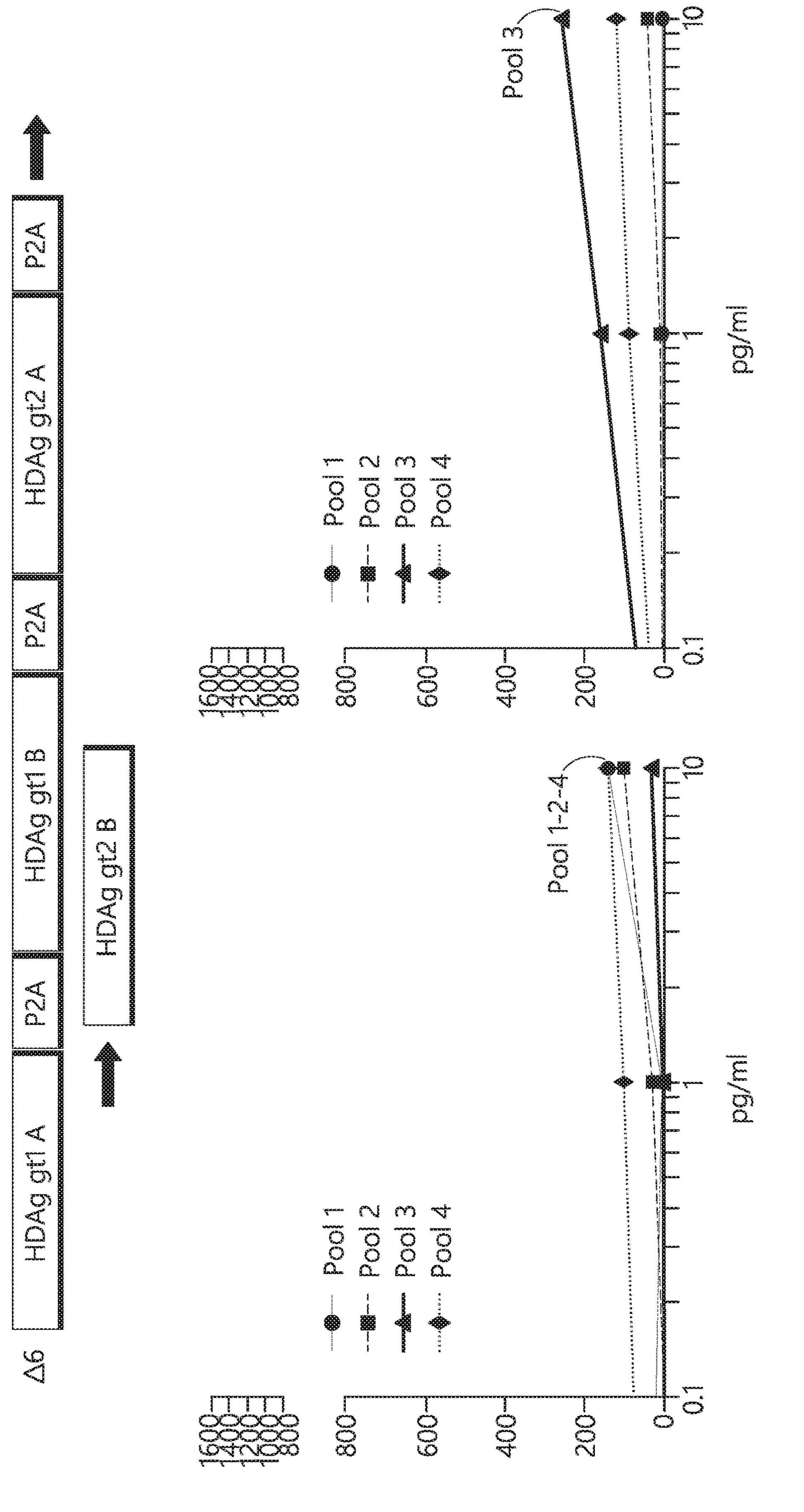
Figures 5M, 5N:
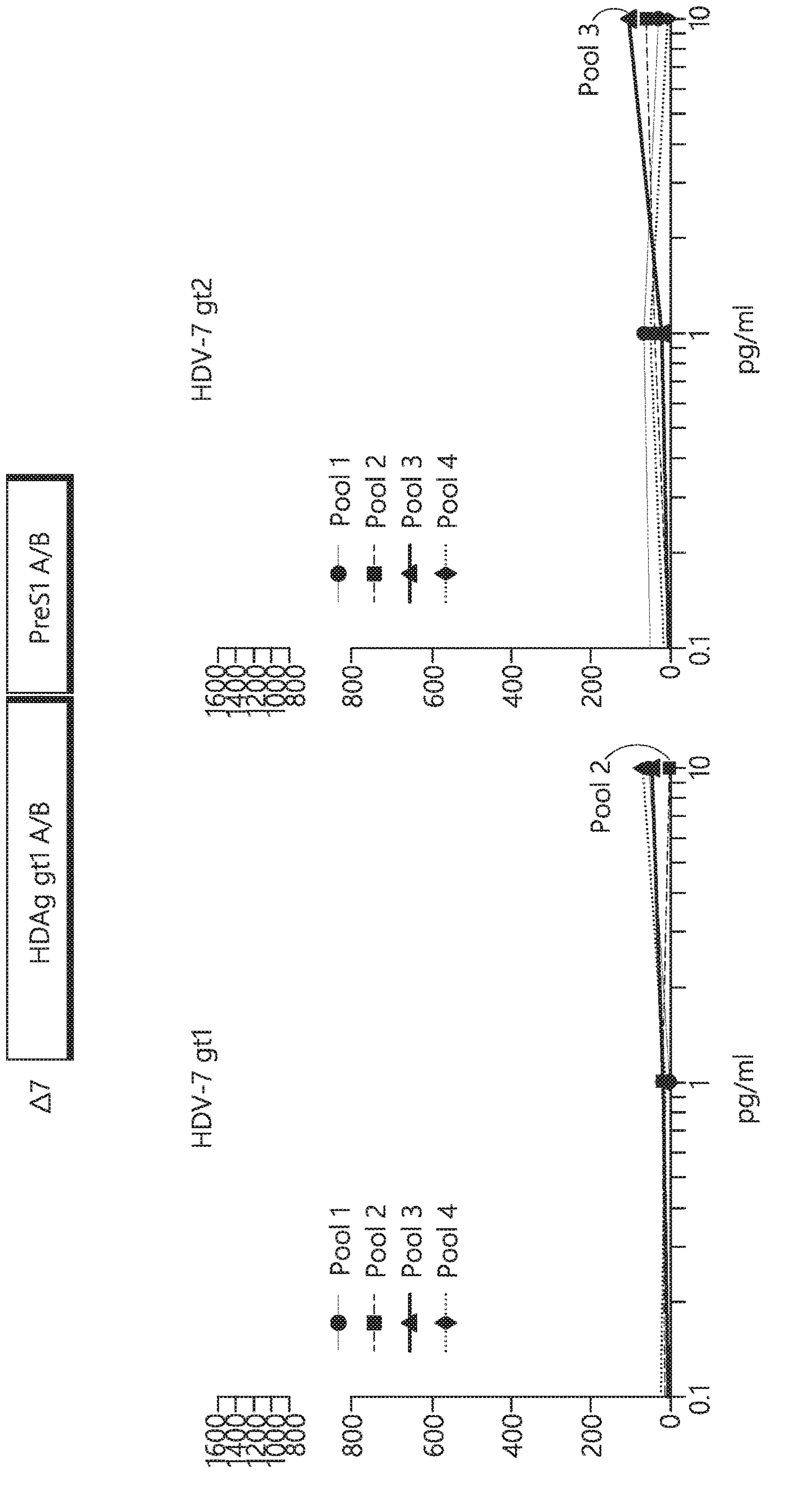
Figures 5O, 5P:
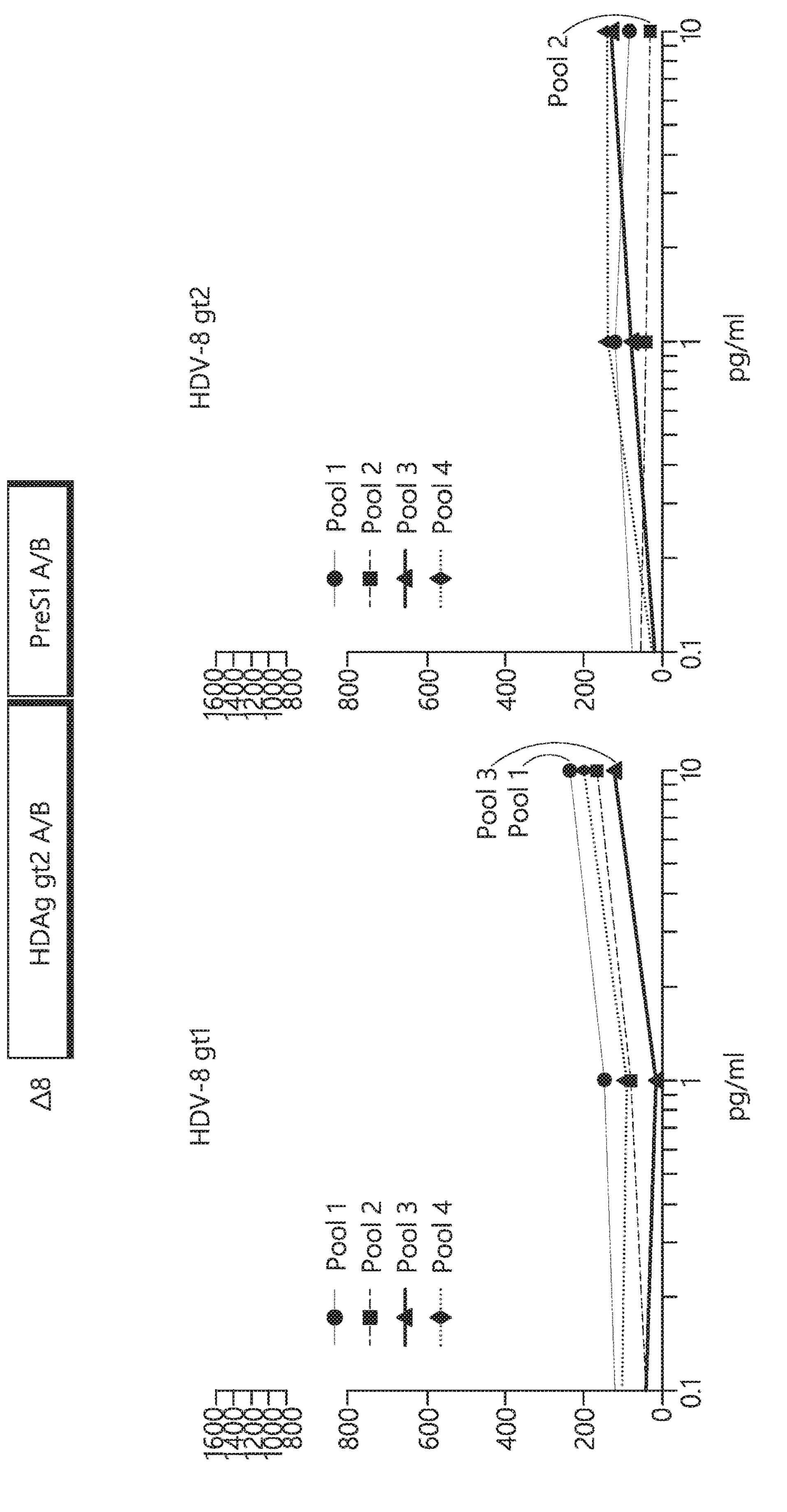
Figure 5Q:
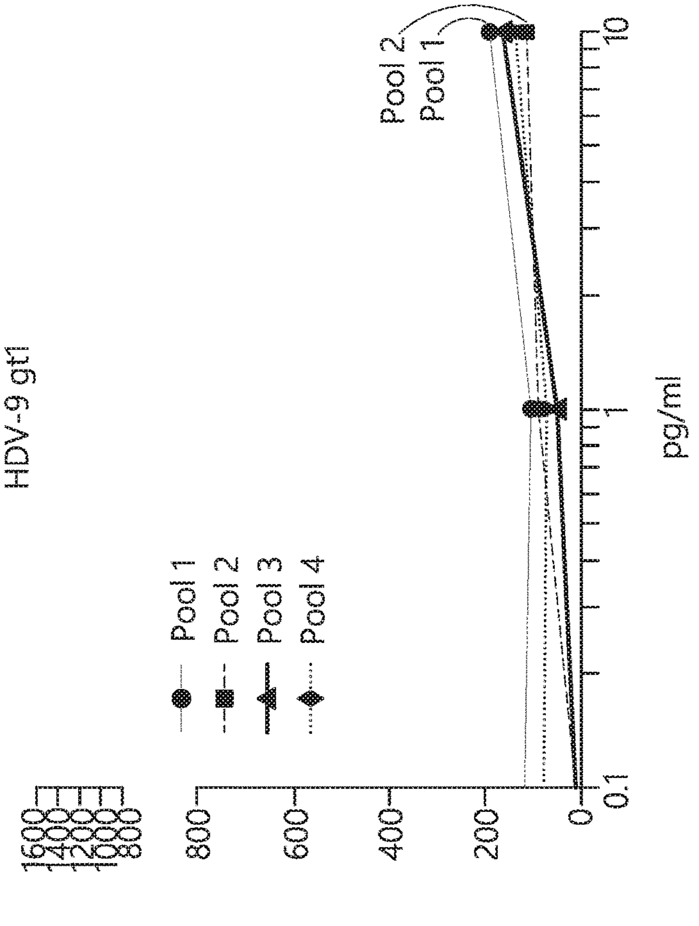
Figure 5R:
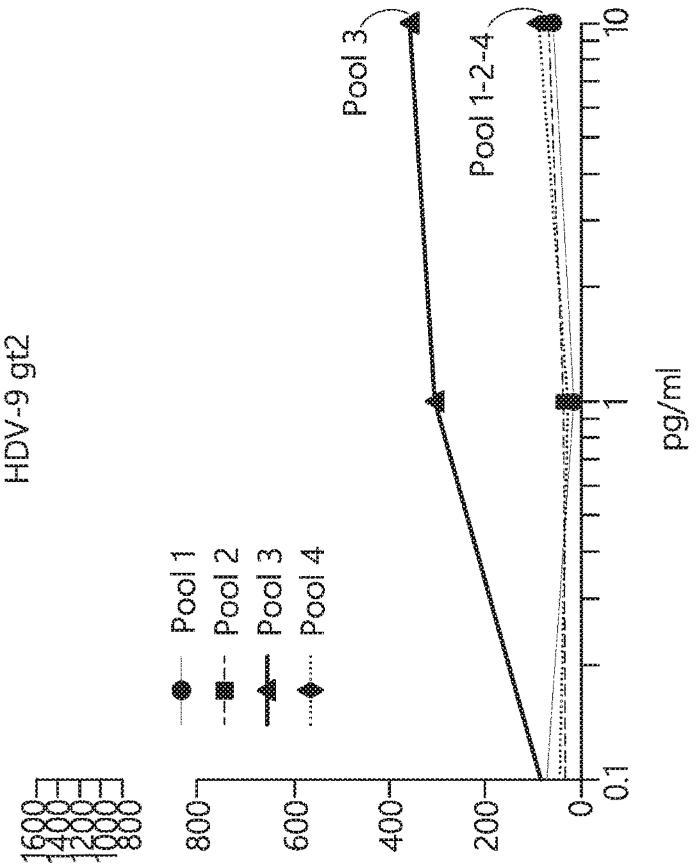
Figures 5S, 5T:
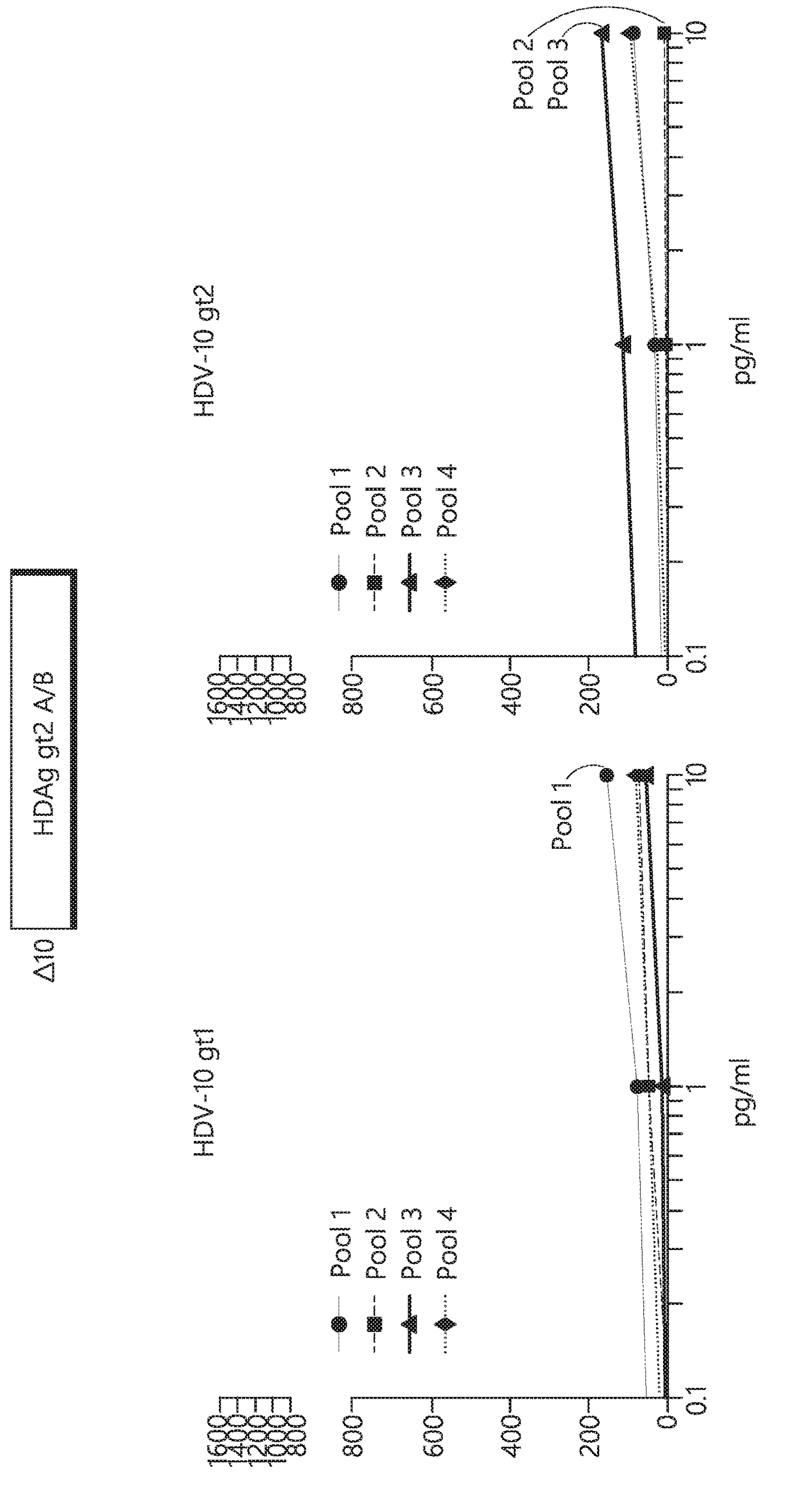

In some alternatives, the compositions can comprise proteins encoded by the chimeric genes. Furthermore compositions comprising chimeric genes and the chimeric proteins are also contemplated. The composition can comprise chimeric genes encoding at least one HDAg and/or chimeric genes encoding hepatitis B core. In some alternatives, the compositions comprise chimeric proteins. The chimeric proteins can comprise the Delta-1, Delta-2, Delta-3, Delta-4, Delta-5, Delta-6, Delta-7, Delta-8, Delta-9, Delta-10 and/or any of the Core constructs as described herein and/or in FIGS. 2 and 3.

In some alternatives, the HDAg sequence comprises a sequence set forth in SEQ ID NO's 3, 4, 8 or 9. In some alternatives, the sequences are codon optimized for expression in humans. In some alternatives, the nucleic acid sequence encodes greater than or equal to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the HDAg polypeptide or an amount that is within a range defined by any two of the aforementioned percentages. Optionally, these sequences can be codon optimized for expression in humans. In some alternatives, the nucleic acid sequence encodes greater than or equal to or any number in between 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, or 195 amino acid residues of the HDAg polypeptide or an amount that is within a range defined by any two of the aforementioned percentages. In some alternatives, the nucleic acid encodes a full length HDAg polypeptide. Optionally, these sequences can be codon optimized for expression in humans. Methods of using the foregoing compositions to generate an immune response (e.g., a T cell and/or antibody specific immune response) or to inhibit, ameliorate, treat, or prevent an HBV and HDV infection in a subject, preferably a human and, optionally a chronically infected human, are contemplated alternatives. Optionally, a subject can be identified as one in need of an immune response to HBV and HDV prior to administration of the composition and/or said subject can be evaluated for the immune response or viral clearance after administration of said compositions and such identification and/or evaluation can be accomplished using readily available diagnostics and/or clinical approaches.

In some alternatives, the self-cleavage polypeptide exists after amino acid residue number 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, or 195 of the HDAg polypeptide. Optionally, these sequences can be codon optimized for expression in humans. In some alternatives, the self-cleavage polypeptide exists before amino acid residue number 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, or 195 of the HDAg polypeptide. Optionally, these sequences can be codon optimized for expression in humans. Methods of using the foregoing compositions to generate an immune response (e.g., a T cell and/or antibody specific immune response) or to inhibit, ameliorate, treat, or prevent HBV and HDV in a subject, preferably a human and, optionally a chronically infected human, are contemplated alternatives. Optionally, a subject can be identified as one in need of an immune response to HBV and HDV prior to administration of the composition and/or said subject can be evaluated for the immune response or viral clearance after administration of said compositions and such identification and/or evaluation can be accomplished using readily available diagnostics and/or clinical approaches.

In some alternatives a composition that comprises anyone or more of the chimeric genes described herein, wherein the chimeric genes encode at least at least-two HDAg protein domains, is provided. In some alternatives, the chimeric gene comprises HDAg sequences, wherein the chimeric gene comprises at least two sequences encoding hepatitis D antigen (HDAg), at least one cleavage sequence and at least one preS1 derived sequence. In some alternatives, the composition comprises a protein encoded by anyone or more of the chimeric genes provided herein.

In some alternatives a composition comprising anyone or more of the chimeric genes encoding HBcAg is provided. In some alternatives, the chimeric gene comprises a sequence encoding an HBV core antigen. In some alternatives, the composition comprises a protein encoded by anyone or more of the chimeric genes provided herein.

In some alternatives a composition comprising a protein encoded by anyone or more of the chimeric genes is provided. In some alternatives, the composition further comprises a chimeric gene of any one or more of the alternatives provided herein.

In some alternatives, the composition further comprises the chimeric protein of anyone of the alternatives described herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, the composition is present or provided in an injection device or an injection device configured to be used in conjunction with an electroporation device.

Methods for Using the Chimeric Gene or Composition

In some alternatives, the chimeric gene or composition of any one of the alternatives is for use in providing an immunogenic composition, generating an immune response in a subject, or for DNA vaccination so as to inhibit, ameliorate, treat, or prevent HBV and HDV infection. In some alternatives, the chimeric gene, chimeric protein or composition is for use in generating an antibody, T-lymphocyte or CTL-specific response in a subject so as to prevent an HBV and HDV infection. In some alternatives, the chimeric gene, chimeric protein or composition of any one of the alternatives described herein is for immunogen delivery so as to inhibit, ameliorate, treat, or prevent HBV and HDV in a subject that has been identified as having and HDV or HBV infection.

In some alternatives, a method of eliciting an immune response is provided wherein the method comprises administering to a subject having HDV infection and/or HBV infection the nucleic acid or composition of any one of the alternatives at a first time. In some alternatives, said administering comprises injecting said nucleic acid into a patient, such as using an IVIN needle with or without electroporation. In some alternatives, the method further comprises administering a second administration of a nucleic acid or composition of any one of the alternatives described herein is provided. In some alternatives, the method further comprises providing an adjuvant. In some alternatives, said adjuvant is a nucleic acid encoding a polypeptide adjuvant, such as IL-12, IL-15, or IL-21. In some alternatives, said adjuvant is IL-12, IL-15, or IL-21. In some alternatives, said second administration is given after said first time. In some alternatives, said adjuvant is given before, during, or after administration of said nucleic acid or composition of any one of the alternatives described herein. In some alternatives, said second administration is given one week, two weeks, three weeks, four weeks, five weeks, or six weeks after the first administration of said nucleic acid or composition of any one of the alternatives described herein.

In some alternatives, a method of inhibiting, ameliorating, treating, or preventing hepatitis D virus in a subject in need is provided, wherein the method comprises administering the composition of anyone or more of the alternatives described herein to the subject in need. In some alternatives, the subject has been identified as a person at risk of contracting HDV or a person having HDV.

In some alternatives, a method of increasing preS1 antibodies in a subject in need is provided, wherein the method comprises administering the compositions of anyone of the alternatives to the subject in need. In some alternatives, the method further comprises administering the composition of anyone of the alternatives described herein to the subject in need.

Various routes of administration may be used for the methods described herein. In some alternatives, the immunogenic composition is administered parenterally (e.g., intramuscularly, intraperitoneally, subcutaneously, or intravenously to a mammal subject). In a preferred alternative, the immunogenic compositions are administered intramuscularly, dermally, or subcutaneously. The methods may also include applying electrical stimulation, which can enhance the administration of the immunogenic compositions. As an example, electroporation may be included in the present methods disclosed herein. Electroporation includes applying electrical stimulation to improve the permeability of cells to the administered composition. Examples of electroporation techniques are disclosed in U.S. Pat. Nos. 6,610,044 and 5,273,525, the disclosures of both of these references are hereby incorporated by reference in their entireties.

The concentration of the nucleic acid or protein in the immunogenic composition to be administered can vary from 0.1 ng/ml to 50 mg/ml. In some aspects, the concentration of the immunogenic composition administered (e.g., a suitable dose of nucleic acid or protein for administration) is between 10 ng/ml to 25 mg/ml. In still other aspects, the concentration is between 100 ng/ml to 10 mg/ml. In some aspects, the suitable dose of nucleic acid or protein for administration is greater than or equal to or less than 100 ng/ml, 150 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml, 850 ng/ml, 900 ng/ml, 950 ng/ml, 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 11 μg/ml, 12 μg/ml, 13 μg/ml, 14 μg/ml, 15 μg/ml, 16 μg/ml, 17 μg/ml, 18 μg/ml, 19 μg/ml, 20 μg/ml, 21 μg/ml, 22 μg/ml, 23 μg/ml, 24 μg/ml, 25 μg/ml, 26 μg/ml, 27 μg/ml, 28 μg/ml, 29 μg/ml, 30 μg/ml, 31 μg/ml, 32 μg/ml, 33 μg/ml, 34 μg/ml, 35 μg/ml, 36 μg/ml, 37 μg/ml, 38 μg/ml, 39 μg/ml, 40 μg/ml, 41 μg/ml, 42 μg/ml, 43 μg/ml, 44 μg/ml, 45 μg/ml, 46 μg/ml, 47 μg/ml, 48 μg/ml, 49 μg/ml, 50 μg/ml, 55 μg/ml, 60 μg/ml, 65 μg/ml, 70 μg/ml, 75 μg/ml, 80 μg/ml, 85 μg/ml, 90 μg/ml, 95 μg/ml, 100 μg/ml, 150 μg/ml, 200 μg/ml, 250 μg/ml, 300 μg/ml, 350 μg/ml, 400 μg/ml, 450 μg/ml, 500 μg/ml, 550 μg/ml, 600 μg/ml, 650 μg/ml, 700 μg/ml, 750 μg/ml, 800 μg/ml, 850 μg/ml, 900 μg/ml, 950 μg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml, 5.1 mg/ml, 5.2 mg/ml, 5.3 mg/ml, 5.4 mg/ml, 5.5 mg/ml, 5.6 mg/ml, 5.7 mg/ml, 5.8 mg/ml, 5.9 mg/ml, 6.0 mg/ml, 6.1 mg/ml, 6.2 mg/ml, 6.3 mg/ml, 6.4 mg/ml, 6.5 mg/ml, 6.6 mg/ml, 6.7 mg/ml, 6.8 mg/ml, 6.9 mg/ml, 7.0 mg/ml, 7.1 mg/ml, 7.2 mg/ml, 7.3 mg/ml, 7.4 mg/ml, 7.5 mg/ml, 7.6 mg/ml, 7.7 mg/ml, 7.8 mg/ml, 7.9 mg/ml, 8.0 mg/ml, 8.1 mg/ml, 8.2 mg/ml, 8.3 mg/ml, 8.4 mg/ml, 8.5 mg/ml, 8.6 mg/ml, 8.7 mg/ml, 8.8 mg/ml, 8.9 mg/ml, 9.0 mg/ml, 9.1 mg/ml, 9.2 mg/ml, 9.3 mg/ml, 9.4 mg/ml, 9.5 mg/ml, 9.6 mg/ml, 9.7 mg/ml, 9.8 mg/ml, 9.9 mg/ml, 10.0 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, or an amount within a range defined by, and including, any two of these values.

The amount of the chimeric gene or protein administered using the methods described herein can vary from 1 ng to 10 g. In some aspects, the amount of nucleic acid or protein contained administered is less than greater than or equal to 1 ng, 5 ng, 10 ng, 20 ng, 30 ng, 40 ng, 50 ng, 60 ng, 70 ng, 80 ng, 90 ng, 100 ng, 150 ng, 200 ng, 250 ng, 300 ng, 350 ng, 400 ng, 500 ng, 600 ng, 700 ng, 800 ng, 900 ng, 1 μg 1 μg, 2 μg, 3 μg, 4 μg, 5 μg, 6 μg, 7 μg, 8 μg, 9 μg, 10 μg, 11 μg, 12 μg, 13 μg, 14 μg, 15 μg, 16 μg, 17 μg, 18 μg, 19 μg, 20 μg, 21 μg, 22 μg, 23 μg, 24 μg, 25 μg, 26 μg, 27 μg, 28 μg, 29 μg, 30 μg, 31 μg, 32 μg, 33 μg, 34 μg, 35 μg, 36 μg, 37 μg, 38 μg, 39 μg, 40 μg, 41 μg, 42 μg, 43 μg, 44 μg, 45 μg, 46 μg, 47 μg, 48 μg, 49 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg 150 μg, 155 μg, 160 μg, 165 μg, 170 μg, 175 μg, 180 μg, 185 μg, 190 μg, 195 μg 200 μg, 205 μg, 210 μg, 215 μg, 220 μg, 225 μg, 230 μg, 235 μg, 240 μg, 245 μg 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg 350 μg, 355 μg, 360 μg, 365 μg, 370 μg, 375 μg, 380 μg, 385 μg, 390 μg, 395 μg 400 μg, 405 μg, 410 μg, 415 μg, 420 μg, 425 μg, 430 μg, 435 μg, 440 μg, 445 μg 450 μg, 455 μg, 460 μg, 465 μg, 470 μg, 475 μg, 480 μg, 485 μg, 490 μg, 495 μg 500 μg, 505 μg, 510 μg, 515 μg, 520 μg, 525 μg, 530 μg, 535 μg, 540 μg, 545 μg 550 μg, 555 μg, 560 μg, 565 μg, 570 μg, 575 μg, 580 μg, 585 μg, 590 μg, 595 μg 600 μg, 605 μg, 610 μg, 615 μg, 620 μg, 625 μg, 630 μg, 635 μg, 640 μg, 645 μg 650 μg, 655 μg, 660 μg, 665 μg, 670 μg, 675 μg, 680 μg, 685 μg, 690 μg, 695 μg, 700 μg, 705 μg, 710 μg, 715 μg, 720 μg, 725 μg, 730 μg, 735 μg, 740 μg, 745 μg 750 μg, 755 μg, 760 μg, 765 μg, 770 μg, 775 μg, 780 μg, 785 μg, 790 μg, 795 μg, 800 μg, 805 μg, 810 μg, 815 μg, 820 μg, 825 μg, 830 μg, 835 μg, 840 μg, 845 μg 850 μg, 855 μg, 860 μg, 865 μg, 870 μg, 875 μg, 880 μg, 885 μg, 890 μg, 895 μg 900 μg, 905 μg, 910 μg, 915 μg, 920 μg, 925 μg, 930 μg, 935 μg, 940 μg, 945 μg 950 μg, 955 μg, 960 μg, 965 μg, 970 μg, 975 μg, 980 μg, 985 μg, 990 μg, 995 μg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 2 g, 3 g, 4 g, 5 g, 6 g, 7 g, 8 g, 9 g, 10 g or within a range defined by, and including, any two of these values.

Materials and Methods.

In some alternatives, compositions are employed and methods performed according to the descriptions below. Other materials and methods are contemplated and consistent with the disclosure herein. Accordingly, the disclosure below should be read as enabling but not limiting to the claimed subject matter.

Materials and methods are drawn from Holmstrom et al., (2013) "A Synthetic Codon-Optimized Hepatitis C Polyfunctional CD8+T Cell Responses in Virus Nonstructural 5A DNA Vaccine Primes Wild-Type and NS5A-Transgenic Mice" J Immunol 190:1113-1124, prepublished online Jan. 2, 2013, which is hereby incorporated by reference in its entirety for all content from pages 1113-1124.

The following sections are provided to illustrate various alternatives of the present invention. It is to be understood that the following discussion is not comprehensive or exhaustive of the many types of alternatives, which can be prepared in accordance with the present invention.

Delivery of the Chimeric Genes, Chimeric Protein or Compositions

In some embodiments the methods described herein comprises delivering to an intracellular space, such as a plurality of muscle cells, of said subject the chimeric gene, chimeric protein or compositions of the alternatives herein. In some embodiments this method comprises delivering to an intracellular space such as a plurality of muscle cells or intradermally of said subject an HBcAg chimeric protein or HDAg chimeric protein or a chimeric gene encoding HDag chimeric protein or HBCAg chimeric proteins as described herein. In some embodiments this method comprises HBcAg chimeric protein encoded by a chimeric gene, and the polynucleotide is delivered to an intracellular space such as a plurality of muscle cells or intradermally of an animal and translated into an HBcAg chimeric protein therein, thereby delivering said HBcAg chimeric protein to said subject. In some alternatives, this method comprises HDAg chimeric protein encoded by a chimeric gene, and the polynucleotide is delivered to an intracellular space such as a plurality of muscle cells or intradermally of an animal and translated into an HDAg chimeric protein therein, thereby delivering said HDAg chimeric protein to said subject. As the HDAg chimeric proteins described herein further comprise a PreS1 A/B domain, this can be used to inhibit, ameliorate, treat, or prevent HBV and/or HDV infections. In some embodiments the components of said immunogenic composition are delivered in a single injection. In some embodiments the components of said immunogenic composition are delivered in two or more injections. In some embodiments this method comprises providing ribavirin to said subject. In some embodiments this method comprises providing pegylated interferon to said subject. In some embodiments the pegylated interferon is pegylated interferon α2a. In some embodiments a boost vaccination is administered within 28 days of the administration of said chimeric gene.

Preferred Constructs and Evaluation for Immunogenicity

Preferred expression constructs comprising one or more of the genes described herein (see e.g., FIG. 2 AND 3, and chimeric genes of or encoding proteins as set forth in SEQ ID NOs: 1-74) are tested in animals to confirm that the introduction of self-cleavage sites into the fusion proteins encoded by the administered nucleic acids improve the immunogenicity (e.g., T cell and/or antibody response of the subject) of the immunogenic compositions. The immunogenicity of several constructs are evaluated after introducing the constructs into animals using the IVIN injector with electroporation (see PCT/IB2012/001321, WO 2012/172424 A1), which was published in English on Dec. 20, 2012 and designated the United States, hereby expressly incorporated by reference in its entirety). In a first set of experiments, the following constructs are evaluated:

(1) expression constructs comprising a chimeric encoding a wild-type HDAg (i.e. HDAg gt 1 A/B, HDag gt 2 A/B, HDAg-L or HDAg-S) sequence or both, and at least one pre-S1 sequence;

(2) expression constructs comprising a nucleic acid encoding a HDAg (i.e. HDAg gt 1 A/B, HDag gt 2 A/B, HDAg-L or HDAg-S) sequence or both, and at least one pre-S1 sequence wherein said nucleic acid is codon optimized for expression in humans;

(3) expression constructs comprising a nucleic acid encoding a HDag (i.e. HDAg gt 1 A/B, HDag gt 2 A/B, HDAg-L or HDAg-S) sequence or both, and at least one pre-S1 sequence wherein said nucleic acid is codon optimized for expression in humans and wherein said nucleic acid additionally encodes a self-cleavage sequence, which may also be codon optimized for expression in humans (e.g., P2A, E2A, F2A, or T2A with or without GSG modification).

(4) expression constructs comprising a nucleic acid encoding a HDAg (i.e. HDAg gt 1 A/B, HDag gt 2 A/B, HDAg-L or HDAg-S) sequence or both, wherein said nucleic acid is codon optimized for expression in humans and wherein said nucleic acid, optionally encodes a self-cleavage sequence, which may also be codon optimized for expression in humans (e.g., P2A, E2A, F2A, or T2A with or without GSG modification) within said i.e. HDAg gt 1 A/B, HDag gt 2 A/B, HDAg-L or HDAg-S sequence or both or at the N or C terminus of said i.e. HDAg gt 1 A/B, HDag gt 2 A/B, HDAg-L or HDAg-S sequence or both. These expression construct can also be administered with an expression construct that comprises a nucleic acid sequence encoding an HBcAg, which may also be codon optimized for expression in humans (e.g., a codon optimized stork or heron HBcAg)

(5) expression constructs comprising a nucleic acid encoding a i.e. HDAg gt 1 A/B, HDag gt 2 A/B, HDAg-L or HDAg-S sequence or both, wherein said nucleic acid is codon optimized for expression in humans and, wherein said nucleic acid, optionally encodes a self-cleavage sequence, which may also be codon optimized for expression in humans (e.g., P2A, E2A, F2A, or T2A with or without GSG modification) within said e.g., HDAg gt 1 A/B, HDag gt 2 A/B, HDAg-L or HDAg-S sequence or both or at the N or C terminus of said HDAg-L or said HDAg-S sequence or both. Additionally the expression construct may be administered with another expression construct which comprises a nucleic acid sequence encoding an HBcAg, which may also be codon optimized for expression in humans (e.g., a codon optimized stork or heron HbcAg).

Assays are then performed to determine the relative impact of having self-cleavage polypeptide sequences in the constructs encoding the HBcAg and/or HDAg polypeptides. Methods are performed largely as described in Antony Chen, Gustaf Ahlen, Erwin D. Brenndörfer, Anette Brass, Fredrik Holmstrom, Margaret Chen, Jonas Söderholm, David R. Milich, Lars Frelin and Matti Sallberg (2011) Heterologous T Cells Can Help Restore Function in Dysfunctional Hepatitis C Virus Nonstructural 3/4A-Specific T Cells during Therapeutic Vaccination. J Immunol 186:5107-5118, the contents of which are hereby incorporated by reference in their entirety as to the entire disclosure of pages 5107 through 5118 inclusive. In sum, the immunogenicity of the constructs tested are evaluated after introducing the constructs into animals using the IVIN injector with electroporation (see PCT/IB2012/001321 (WO 2012/172424 A1, published Dec. 20, 2012), hereby expressly incorporated by reference in its entirety. After administration of the various constructs to the animals, with or without additional boosts, the immunogenicity of the constructs are evaluated (e.g., T helper and CTL-specific immune responses, cytokine responses, and/or antibody responses are evaluated and the efficacy of the various constructs tested are compared). It will be determined that the construct comprising the codon-optimized sequence encoding e.g., HDAg gt 1 A/B, HDag gt 2 A/B, HDAg-L or HDAg-S sequence or both will be more immunogenic (e.g., stronger T helper and CTL-specific immune responses, cytokine responses, and/or antibody responses) than the construct encoding wild-type i.e. HDAg gt 1 A/B, HDag gt 2 A/B, HDAg-L or HDAg-S sequence or both. It will also be determined that the construct encoding a fusion of HBcAg (e.g., a nucleic acid encoding an avian HBcAg that has been codon optimized for expression in humans) when administered with a construct, comprising i.e. HDAg gt 1 A/B, HDag gt 2 A/B, HDAg-L or HDAg-S sequence or both will be more immunogenic (e.g., stronger T helper and CTL-specific immune responses, cytokine responses, and/or antibody responses).

Administration Regimen

Truncated Therapeutic administration of a preventative therapy for HBV and HDV persons of risk is performed in patients with or without an existing HBV infection. Some patients who receive a booster dose start treatment within 1-2 months after the booster dose. Treatment begins after a mean interval of 15 months (range 1-30) from last administration.

Patients are preferably HDV treatment naïve. Patients receive administrations of an HDV-containing immunogenic composition (e.g., one or more of the contracts depicted in FIGS. 2 and/or 3 in the deltoid muscles (e.g., four monthly administrations with 167 μg, 500 μg, or 1,500 μg codon-optimized HDV immunogen formulations delivered by in vivo electroporation (EP) in some approaches). Enrollment may be done with two weeks interval between patients for safety reasons. It is expected that the administration will significantly improve IFNγ producing responses to HDAg during the first six weeks of therapy. Patients are expected to experience 0.6 log 10-2.4 log 10 reduction in serum HDV RNA and some are expected to be effectively treated (e.g., HDV viral titer is reduced) or cured (e.g., HDV viral titer is reduced to undetectable amounts by a clinical assay).

Patients are administered the therapy and in one minute or less electroporation is performed, for example as described in PCT Publication No. WO 2012/172424 A1, published Dec. 20, 2012, which is hereby incorporated by reference in its entirety not only as it relates to electroporation but for all content disclosed therein.

By some approaches, a volume of 0.5 mL 0.9% sodium chloride containing the DNA is injected in the deltoid muscle (alternating left and right) using an IVIN needle at a depth of 1.2 cm. The injection site is marked prior to injection with a surgical pen and then sterilized by swiping with an alcohol pad. Immediately after the injection or along with the injection an IVIN-based electroporator is used at the site of injection and electroporation is administered, as described, for example, in PCT Publication No. WO 2012/172424 A1, published Dec. 20, 2012, incorporated by reference in its entirety here and above. The administration is expected to be safe and well tolerated by recipients.

Patients will demonstrate an increase in relative antibody levels detected by a paired comparison of the samples obtained at week 0 and 2, an effect, which is most pronounced in the two lowest dose groups. Some patients will demonstrate de novo T cell activation. The presence of HBV and/or HDV specific T cell responses before, during and after the therapeutic administration is determined as the number of IFNγ-producing T cells, or spot forming cells (SFCs) by ELISpot, and the level of proliferation as determined by the level of $^3$H-thymidine incorporation. In the ELISpot assay, only the responses to nine peptide pools spanning the whole HDAg region are used for the statistical comparison to avoid repeated use of the same epitope and to overcome HLA-restriction. In some alterantives, the ELISpot assay is performed to assay for the relative antibody levels or the presence of HBV and/or HDV specific T cell responses before, during and after the therapeutic administration. The presence of HDAg-specific T cells can be detected by ELISpot using recombinant HDAG or peptides that can span the complete HDag corresponding to HDV genotypes 1 or 2. In some alternatives, the peptides comprise the amino acid sequences set for in any one of SEQ ID NO's: 75-116.

The number of the IFNγ-producing spots are expected to increase after the two first vaccinations when comparing the number of SFCs at week 0, and the same at weeks 2 and 6. Proliferative T cell responses to HDAg are detected in a substantial number of subjects prior to or after vaccination, de novo ELISpot responses are observed in a fraction of all groups observed. In some patients the activation, or reactivation, of HDV HDAg IFNγ-producing T cells coincides with the suppression of the HDV RNA levels in blood.

A rapid viral response, and complete early viral response and sustained viral response will be seen in a substantial number of patients.

Enzyme-Linked Immunospot (ELISpot) Assay

The Enzyme-linked immunospot (ELISpot) assay is used to determine immune responses. Without being limiting, this can include monitoring cell mediated immunity as this technique is sensitive and can be accurate for the detection of rare antigen specific T cells or B cells. This can be performed after an initial immunization or after a booster after the initial immunization, for example.

In an ELISPOT assay, the surfaces in the wells of microtiter plate are coated with a capture antibody that binds a specific epitope of a protein that is being assayed. During the cell incubation and stimulation step, PBMCs are seeded into the wells of the plate along with the antigen, and form a monolayer on the membrane surface of the well. As the antigen-specific cells are activated, they release the cytokine, which is captured directly on the membrane surface by the immobilized antibody. In the alternatives herein, the ELISpot is used to determine a specific protein using PBMCs that are isolated from the mice. The techniques for the ELISpot are described in Ahlen et al. 2016 (incorporated by reference herein). In some alternatives, Immunization with a Nucleic Acid Immunization can be performed with a nucleic acid, such as RNA or DNA, for example. An approach of reproducibly delivering genetic material in muscle tissue in is by hydrodynamic injection, which is a forced injection of a volume equaling the volume of the tissue to be transfected thereby causing an increased local pressure resulting in an improved uptake of genetic material. In some alternatives, a small injection volume can be delivered to a targeted tissue volume, termed in vivo intracellular injection (IVIN). In some alternatives, a device based on needle(s) with apertures along the needle shafts, where multiple needles can fix the tissue volume to be transfected, is used for immunization with a nucleic acid. In some alternatives, immunization is performed with in vivo electroporation. The technique of using IVIN is described in Ahlen et al. 2016 (incorporated by reference in its entirety). Additional nucleic acid delivery devices with and without electroporation are also contemplated for use in delivering any one or more of the constructs described herein including, without limitation, the Medpulsar®, e.g., as described in U.S. Pat. Nos. 6,748,265, 6,746,441, and 6,763,264; the IGEA device, e.g., as described in U.S. Pat. No. 9,314,621, or the ICHOR device, as described in U.S. Pat. No. 6,278,895, all of which are hereby expressly incorporated by reference in their entireties.

IVIN delivery has been shown to improve the immunogenicity and can be more effective with in vivo electrotransfer.

Experimental Design for Testing the HDV Vaccination

Animals for the Testing of the HDV Vaccination

Groups of 5 mice were immunized with 50 μg of DNA using in vivo electroporation as described (Ahlen et al., 2016; incorporated by reference in its entirety). In brief, mice were immunized with 50 μl of saline containing 50 μg of DNA in the tibialis anterior muscle. Immediately after immunization, the site was treated with in vivo electroperation as described (Ahlen et al., 2016; incorporated by reference in its entirety). Half of the mice were sacrificed after 2 weeks, whereas the other half was boosted exactly the same way at 4 weeks, and then sacrificed two weeks later. Spleens were harvested and the presence of HDAg-specific T cells was detected by ELISpot as described (Ahlen et al., 2016) using recombinant HDAg or peptides spanning the complete HDAg corresponding to HDV genotypes 1 and 2 (see Table 1).

Results. The ELISpot assays showed that 2 weeks after a single immunization HDV specific T cells were primed using the HDV constructs 1-5, and 7-10 towards gt1 peptides (FIGS. 4A-4T) (Table 1; peptides). At two weeks after a booster dose at 4 week the HDV DNA constructs 1-5 and 8-10 primed the HDV specific T cells. Thus, unexpectedly, most constructs were immunogenic in vivo and could therefore potentially be used in humans. As shown below is the sequences that were used that are shown in FIGS. 4A-T and 5A-5T (Table 1).

TABLE 1

Peptide pool design. A total of twenty-one 20-mer peptides (each having 10 amino acid (aa) overlap) covering the full-length HDV large antigen of genotype 1 and 2 were purchased from Sigma Aldrich (St. Louis, MO). The twenty-one peptides were divided into four peptide pools as outlined in the table.

| Peptide Name | Genotype | Sequence | SEQ ID NO: | Peptide pool |
|---|---|---|---|---|
| L-HDAg-gt1-#1 | 1 | MGRSESKRNRDGREGILEQW | 75 | 1 |
| L-HDAg-gt1-#2 | 1 | DGREGILEQWVNGRKKLEDL | 76 | 1 |
| L-HDAg-gt1-#3 | 1 | VNGRKKLEDLEREARKIKKK | 77 | 1 |
| L-HDAg-gt1-#4 | 1 | EREARKIKKKIKKLEDENPW | 78 | 1 |
| L-HDAg-gt1-#5 | 1 | IKKLEDENPWLGNIKGILGK | 79 | 1 |
| L-HDAg-gt1-#6 | 1 | LGNIKGILGKRDKDGEGAPP | 80 | 2 |
| L-HDAg-gt1-#7 | 1 | RDKDGEGAPPAKRARTDQME | 81 | 2 |
| L-HDAg-gt1-#8 | 1 | AKRARTDQMEIDSGPGKRPL | 82 | 2 |
| L-HDAg-gt1-#9 | 1 | IDSGPGKRPLRGGFSDKERQ | 83 | 2 |
| L-HDAg-gt1-#10 | 1 | RGGFSDKERQDHRRRKALEN | 84 | 2 |
| L-HDAg-gt1-#11 | 1 | DHRRRKALENKRKQLAAGGK | 85 | 3 |
| L-HDAg-gt1-#12 | 1 | KRKQLAAGGKHLSKEEEEEL | 86 | 3 |
| L-HDAg-gt1-#13 | 1 | HLSKEEEEELKRLTEEDERR | 87 | 3 |
| L-HDAg-gt1-#14 | 1 | KRLTEEDERRERRTAGPSVG | 88 | 3 |
| L-HDAg-gt1-#15 | 1 | ERRTAGPSVGGVNPLEGGSR | 89 | 3 |
| L-HDAg-gt1-#16 | 1 | GVNPLEGGSRGAPGGGFVPN | 90 | 4 |
| L-HDAg-gt1-#17 | 1 | GAPGGGFVPNMLSVPESPFS | 91 | 4 |
| L-HDAg-gt1-#18 | 1 | MLSVPESPFSRTGEGLDVRG | 92 | 4 |
| L-HDAg-gt1-#19 | 1 | RTGEGLDVRGNQGFPWDILF | 93 | 4 |
| L-HDAg-gt1-#20 | 1 | NQGFPWDILFPADPPFSPQS | 94 | 4 |
| L-HDAg-gt1-#21 | 1 | PADPPFSPQSCRPQ | 95 | 4 |
| L-HDAg-gt2-#1 | 2 | MGQPDSRRPRRGREESLGKW | 96 | 1 |
| L-HDAg-gt2-#2 | 2 | RGREESLGKWIDARRRKEEL | 97 | 1 |
| L-HDAg-gt2-#3 | 2 | IDARRRKEELERDLRKVNKT | 98 | 1 |
| L-HDAg-gt2-#4 | 2 | ERDLRKVNKTIKRLEEDNPW | 99 | 1 |
| L-HDAg-gt2-#5 | 2 | IKRLEEDNPWLGNIRGIIGR | 100 | 1 |
| L-HDAg-gt2-#6 | 2 | LGNIRGIIGRKDKDGEGAPP | 101 | 2 |
| L-HDAg-gt2-#7 | 2 | KDKDGEGAPPAKRARTDQME | 102 | 2 |
| L-HDAg-gt2-#8 | 2 | AKRARTDQMEVDSGPRKRKH | 103 | 2 |
| L-HDAg-gt2-#9 | 2 | VDSGPRKRKHPGGFTEQERR | 104 | 2 |
| L-HDAg-gt2-#10 | 2 | PGGFTEQERRDHRRRKALEN | 105 | 2 |
| L-HDAg-gt2-#11 | 2 | DHRRRKALENKKKQLSSGGK | 106 | 3 |
| L-HDAg-gt2-#12 | 2 | KKKQLSSGGKDLSREEEEEL | 107 | 3 |
| L-HDAg-gt2-#13 | 2 | DLSREEEEELRRLTEEDERR | 108 | 3 |

TABLE 1-continued

Peptide pool design. A total of twenty-one 20-mer peptides (each having 10 amino acid (aa) overlap) covering the full-length HDV large antigen of genotype 1 and 2 were purchased from Sigma Aldrich (St. Louis, MO). The twenty-one peptides were divided into four peptide pools as outlined in the table.

| Peptide Name | Genotype | Sequence | SEQ ID NO: | Peptide pool |
|---|---|---|---|---|
| L-HDAg-gt2-#14 | 2 | RRLTEEDERRERRVAGPRVG | 109 | 3 |
| L-HDAg-gt2-#15 | 2 | ERRVAGPRVGDVNPLDGGPR | 110 | 3 |
| L-HDAg-gt2-#16 | 2 | DVNPLDGGPRGAPGGGFVPS | 111 | 4 |
| L-HDAg-gt2-#17 | 2 | GAPGGGFVPSMQGIPESPFT | 112 | 4 |
| L-HDAg-gt2-#18 | 2 | MQGIPESPFTRRGDGLDTRG | 113 | 4 |
| L-HDAg-gt2-#19 | 2 | RRGDGLDTRGTQEFPWVNPQ | 114 | 4 |
| L-HDAg-gt2-#20 | 2 | TQEFPWVNPQPPPPRLPLLE | 115 | 4 |
| L-HDAg-gt2-#21 | 2 | PPPPRLPLLECTPQ | 116 | 4 |

For FIG. 5, there were ten constructs tested at both two weeks and then 6 weeks.

Expression of the Constructs

Additional Alternatives

Delta 1 wild type constructs can be manufactured with a DNA sequence comprising a sequence set forth in SEQ ID NO: 11, which also comprises restriction sites (HindIII/EcoRI). In some alternatives, the delta 1 construct is optimized for expression in humans and comprises a sequence set forth in SEQ ID NO: 13 (Delta 1 optimized with restriction sites (HindIII and EcoRI).

Delta 2 wild type constructs can be manufactured with a DNA sequence comprising a sequence set forth in SEQ ID NO: 16, which also comprises restriction sites (HindIII/EcoRI). In some alternatives, the Delta 2 construct is optimized for expression in humans and comprises a sequence set forth in SEQ ID NO: 17 or 18 (Delta 2 optimized with restriction sites (HindIII and EcoRI). In some alternatives, the Delta 2 protein comprises a sequence set forth in SEQ ID NO: 19.

Delta 3 wild type constructs can be manufactured with a DNA sequence comprising a sequence set forth in SEQ ID NO: 20 or 21 (with restriction sites HindIII and EcoR1). In some alternatives, the Delta 3 construct is optimized for expression in humans and comprises a sequence set forth in SEQ ID NO: 22 or 23 (Delta 3 codon optimized with restriction sites (HindIII and EcoRI). In some alternatives, the Delta 3 protein comprises a sequence set forth in SEQ ID NO: 24.

Delta 4 wild type constructs can be manufactured with a DNA sequence comprising a sequence set forth in SEQ ID NO: 25 or 26 (with restriction sites HindIII and EcoR1). In some alternatives, the Delta 4 construct is codon optimized for expression in humans and comprises a sequence set forth in SEQ ID NO: 27 or 28 (Delta 4 optimized with restriction sites (HindIII and EcoRI). In some alternatives, the Delta 4 protein comprises a sequence set forth in SEQ ID NO: 29.

Delta 5 wild type constructs can be manufactured with a DNA sequence comprising a sequence set forth in SEQ ID NO: 30 or 31 (with restriction sites HindIII and EcoR1). In some alternatives, the Delta 5 construct is codon optimized for expression in humans and comprises a sequence set forth in SEQ ID NO: 32 or 33 (Delta 5 optimized with restriction sites (HindIII and EcoRI). In some alternatives, the Delta 5 protein comprises a sequence set forth in SEQ ID NO: 34.

Delta 6 wild type constructs can be manufactured with a DNA sequence comprising a sequence set forth in SEQ ID NO: 35 or 36 (with restriction sites HindIII and EcoR1). In some alternatives, the Delta 6 construct is codon optimized for expression in humans and comprises a sequence set forth in SEQ ID NO: 37 or 38 (Delta 6 optimized with restriction sites (HindIII and EcoRI). In some alternatives, the Delta 6 protein comprises a sequence set forth in SEQ ID NO: 39.

Delta 7 wild type constructs can be manufactured with a DNA sequence comprising a sequence set forth in SEQ ID NO: 40 or 41 (with restriction sites HindIII and EcoR1). In some alternatives, the Delta 7 construct is codon optimized for expression in humans and comprises a sequence set forth in SEQ ID NO: 42 or 43 (Delta 7 optimized with restriction sites (HindIII and EcoRI). In some alternatives, the Delta 7 protein comprises a sequence set forth in SEQ ID NO: 44.

Delta 8 wild type constructs can be manufactured with a DNA sequence comprising a sequence set forth in SEQ ID NO: 45 or 46 (with restriction sites HindIII and EcoR1). In some alternatives, the Delta 8 construct is codon optimized for expression in humans and comprises a sequence set forth in SEQ ID NO: 47 or 48 (Delta 8 optimized with restriction sites (HindIII and EcoRI). In some alternatives, the Delta 8 protein comprises a sequence set forth in SEQ ID NO: 49.

Delta 9 wild type constructs can be manufactured with a DNA sequence comprising a sequence set forth in SEQ ID NO: 50 or 51 (with restriction sites HindIII and EcoR1). In some alternatives, the Delta 9 construct is codon optimized for expression in humans and comprises a sequence set forth in SEQ ID NO: 52 or 53 (Delta 9 optimized with restriction sites (HindIII and EcoRI). In some alternatives, the Delta 9 protein comprises a sequence set forth in SEQ ID NO: 54.

Delta 10 wild type constructs can be manufactured with a DNA sequence comprising a sequence set forth in SEQ ID NO: 55 or 56 (with restriction sites HindIII and EcoR1). In some alternatives, the Delta 10 construct is codon optimized for expression in humans and comprises a sequence set forth in SEQ ID NO: 57 or 58 (Delta 10 optimized with restriction sites (HindIII and EcoRI). In some alternatives, the Delta 10 protein comprises a sequence set forth in SEQ ID NO: 59.

Core 1 wild type constructs can be manufactured with a DNA sequence comprising a sequence set forth in SEQ ID NO: 60 or 61 (with restriction sites HindIII and EcoR1). In some alternatives, the Core 1 construct is codon optimized for expression in humans and comprises a sequence set forth in SEQ ID NO: 62 or 63 (Core 1 optimized with restriction sites (HindIII and EcoRI). In some alternatives, the Core 1 protein comprises a sequence set forth in SEQ ID NO: 64.

Pre-C-gt-H wild type constructs can be manufactured with a DNA sequence comprising a sequence set forth in SEQ ID NO: 65 or 66 (with restriction sites HindIII and EcoR1). In some alternatives, the Pre-C-gt-H construct is codon optimized for expression in humans and comprises a sequence set forth in SEQ ID NO: 67 or 68 (Pre-C-gt-H optimized with restriction sites (HindIII and EcoRI) for cloning purposes). In some alternatives, the Pre-C-gt-H protein comprises a sequence set forth in SEQ ID NO: 69.

PreC-C-Mut-gt-H wild type constructs can be manufactured with a DNA sequence comprising a sequence set forth in SEQ ID NO: 70 or 71 (with restriction sites HindIII and EcoR1). In some alternatives, the PreC-C-Mut-gt-H construct is codon optimized for expression in humans and comprises a sequence set forth in SEQ ID NO: 72 or 73 (PreC-C-Mut-gt-H optimized with restriction sites (HindIII and EcoRI) for cloning purposes). In some alternatives, the PreC-C-Mut-gt-H protein comprises a sequence set forth in SEQ ID NO: 74.

In some alternatives, a chimeric gene comprising Core sequences is provided. In some alternatives, the chimeric gene further comprises HDAg sequences. In some alternatives, a protein encoded by the chimeric gene is provided. In some alternatives, a composition is provided, wherein the composition comprises the chimeric gene. In some alternatives, a composition is provided, wherein the composition comprises the protein.

In some alternatives, a chimeric gene comprising HDAg sequences is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ) ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62.

In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In some alternatives, a chimeric protein comprising at least two HDAg protein domains, encoded by the chimeric gene of anyone of the alternatives described herein is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least, one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ) ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59 In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans.

In some alternatives, a composition comprising anyone or more of the chimeric genes of any one of the alternatives is provided. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, the chimeric gene or composition of any one of the alternatives is for use in generating an immune response in a subject or for DNA vaccination so as to inhibit, ameliorate, treat, or prevent HBV and/or HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least, two sequences comprise a full or partial HDAg gene. In some alternatives, the at least, two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, the chimeric gene or composition of any one of the alternatives herein, is for use in generating an antibody, T-lymphocyte or CTL-specific response in a subject so as to inhibit, ameliorate, treat, or prevent an HBV and/or HDV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ED NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ED NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or sub unit of IL-12, IL-15, or IL-21.

In some alternatives, the chimeric gene or composition of any one of the alternatives described herein is for DNA vaccination or to induce an immunogenic response against HBV and/or HDV in a subject that has been identified as having and HDV and/or HBV infection. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21.

In some alternatives, a method of eliciting an immune response is provided, wherein the method comprises administering to a subject having HDV infection and/or HBV infection the nucleic acid or composition of any one of the alternatives herein. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2 A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set, forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprise a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprise a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, said administering comprises injecting said nucleic acid into a patient, such as using an IVIN needle, Medpulsar®, or ICHOR device with or without electroporation. In some alternatives, the method further comprising administering a second administration of a nucleic acid or composition of any one of the alternatives described herein. In some alternatives, the method further comprises providing an adjuvant. In some alternatives, said adjuvant, is a nucleic acid encoding a polypeptide adjuvant, such as IL-12, IL-15, or IL-21. In some alternatives, said adjuvant is IL-12, IL-15, or IL-21. In some alternatives, said second administration is given after said first time. In some alternatives, said adjuvant is given before, during, or after administration of said nucleic acid or composition of any one of claims 1-45. In some alternatives, said second administration is given one week, two weeks, three weeks, four weeks, five weeks, or six weeks after the first administration of said nucleic acid or composition of any one of claims 1-45. In some alternatives, the subject has been identified as a person at risk of contracting HDV or that has HDV. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

In some alternatives, a method of increasing preS1 antibodies in a subject in need, the method comprising administering the compositions of anyone of the alternatives described herein to the subject in need. In some alternatives, the composition comprises anyone or more of the chimeric genes of any one of the alternatives described herein. The chimeric gene can have at least two sequences encoding hepatitis D antigen (HDAg), at least one cleavage sequence and at least one preS1 derived sequence. In some alternatives, the at least two sequences comprise a full or partial HDAg gene. In some alternatives, the at least two sequences encoding HDAg comprises a sequence encoding HDAg genotype 1 A, HDAg genotype 1 B, HDAg genotype 2 A and/or HDAg genotype 2 B. In some alternatives, the at least two sequences encoding hepatitis D antigen (HDAg) are joined by the at least one cleavage sequence. In some alternatives, the at least one cleavage sequence is selected from the group consisting of porcine teschovirus-1 2A (P2A), foot-and-mouth disease virus (FMDV) 2A (F2A), equine rhinitis A virus (ERAV) 2A (E2A) and *Thosea asigna* virus 2A (T2A), wherein each cleavage sequence can be modified to include a GSG (glycine-serine-glycine) motif at an N-terminus. In some alternatives, the at least one preS1 derived sequence is preS1 A and/or preS1 B. In some alternatives, the at least one preS1 derived sequence is preS1 A and comprises an amino acid sequence set forth in SEQ ID NO: 1. In some alternatives, the at least one preS1 derived sequence is preS1 B and comprises an amino acid sequence set forth in SEQ ID NO: 2. In some alternatives, the sequence encoding HDAg genotype 1 A comprises a nucleic acid sequence set forth in SEQ ID NO: 3. In some alternatives, the sequence encoding HDAg genotype 1 B comprises a nucleic acid sequence set forth in SEQ ID NO: 4. In some alternatives, preS1 A is encoded by a nucleic acid sequence set forth in SEQ ID NO: 5. In some alternatives, preS1 B is encoded by a nucleic acid sequence set forth in SEQ ID NO: 6. In some alternatives, the at least one cleavage sequence is a T2A sequence and is encoded by a nucleic acid sequence set forth in SEQ ID NO: 7. In some alternatives, the at least two sequences comprises a sequence encoding HDAg genotype 2A and comprises a sequence set forth in SEQ ID NO: 8. In some alternatives, the at least two sequences comprises a sequence encoding HDAg genotype 2 B and comprises a sequence set forth in SEQ ID NO: 9. In some alternatives, the chimeric gene comprises a nucleic acid sequence set forth in SEQ ID NO's 10 or 12. In some alternatives, the chimeric gene encodes a protein comprises an amino acid sequence set forth in SEQ ID NO: 14. In some alternatives, the chimeric gene comprises a nucleic acid sequence set forth in SEQ ID NO's 15 or 17. In some alternatives, the chimeric gene encodes a protein, wherein the protein comprises an amino acid sequence set forth in SEQ ID NO: 19. In some alternatives, the chimeric gene comprises a nucleic acid sequence set forth in SEQ ID NO's 20 or 22. In some alternatives, the chimeric gene encodes a protein, wherein the protein comprises an amino acid sequence set forth in SEQ ID NO: 24. In some alternatives, the chimeric gene comprises a nucleic acid sequence set forth in SEQ ID NO:'s 25 or 27. In some alternatives, the chimeric gene encodes a protein, wherein the protein comprises an amino acid sequence set forth in SEQ ID NO: 29. In some alternatives, the chimeric gene comprises a nucleic acid sequence set forth in SEQ ID NO's: 30 or 32. In some alternatives, the chimeric gene encodes a protein, wherein the protein comprises an amino acid sequence set forth in SEQ ID NO: 34. In some alternatives, the chimeric gene comprises a nucleic acid sequence set forth in SEQ ID NO:'s 35 or 37. In some alternatives, the chimeric gene encodes a protein, wherein the protein comprises an amino acid sequence set forth in SEQ ID NO: 39. In some alternatives, the chimeric gene comprises a nucleic acid sequence set forth in SEQ ID NO:'s 40 or 42. In some alternatives, the chimeric gene encodes a protein wherein the protein comprises an amino acid sequence set forth in SEQ ID NO: 44. In some alternatives, the chimeric gene comprises a nucleic acid sequence set forth in SEQ ID NO:'s 45 or 47. In some alternatives, the chimeric gene encodes a protein, wherein the protein comprises an amino acid sequence set forth in SEQ ID NO: 49. In some alternatives, the chimeric gene comprises a nucleic acid sequence set forth in SEQ ID NO: 50 or 52. In some alternatives, the chimeric gene encodes a protein, wherein the protein comprises an amino acid sequence set forth in SEQ ID NO: 54. In some alternatives, the chimeric gene comprises a nucleic acid sequence set forth in SEQ ID NO:'s 55 or 57. In some alternatives, the chimeric gene encodes a protein, wherein the protein comprises an amino acid sequence set forth in SEQ ID NO: 59. In some alternatives, the chimeric gene further comprises sequences encoding HBV Core. In some alternatives, the sequences encoding the HBV Core comprises a sequence set forth in SEQ ID NO: 60 or 62. In some alternatives, the HBV Core comprises an amino acid sequence set forth in SEQ ID NO: 64. In some alternatives, the chimeric gene further comprises sequences encoding Pre-C-gt-H. In some alternatives, the sequences encoding the Pre-C-gt-H comprises a sequence set forth in SEQ ID NO: 65 or 67. In some alternatives, the Pre-C-gt-H comprises an amino acid sequence set forth in SEQ ID NO: 69. In some alternatives, the chimeric gene further comprises sequences encoding PreC-C-Mut-gt-H. In some alternatives, the sequences encoding the PreC-C-Mut-gt-H comprises a sequence set forth in SEQ ID NO: 70 or 72. In some alternatives, the PreC-C-Mut-gt-H comprises an amino acid sequence set forth in SEQ ID NO: 74. In some alternatives, the chimeric gene is codon optimized for expression in humans. In some alternatives, the composition further comprises the chimeric protein of anyone of the alternatives herein. In some alternatives, the chimeric protein is encoded by any one of the chimeric genes provided herein. In some alternatives, the composition further comprises an adjuvant. In some alternatives, said adjuvant comprises a nucleic acid encoding a polypeptide adjuvant. In some alternatives, said polypeptide adjuvant, is IL-12, IL-15, or IL-21. In some alternatives, said adjuvant is ribavirin or a CpG-containing nucleic acid. In some alternatives, said adjuvant is a polypeptide. In some alternatives, said adjuvant comprises an adjuvant promoting portion or subunit of IL-12, IL-15, or IL-21. In some alternatives, the method further comprises evaluating the subject for an immunoresponse after administering the compositions of anyone of the alternatives here. In some alternatives, the evaluating is performed by an ELISpot assay. In some alternatives, the ELISpot assay is performed using any one of the peptides comprising a sequence set forth in SEQ ID NO: 75-116.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific alternatives disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Aspects of the invention may also include one or more of the following sequences, alone or in combination or a sequence encoding one or more of the peptide sequences provided:

SEQ ID NO: 1 Pre S1 A

GTNLSTSNPLGFFPDHQLDPAFRANSANPDWDFNPNKDTWPDANKVG

SEQ ID NO: 2 PreS1 B

GQNLSTSNPLGFFPDHQLDPAFRANTANPDWDFNPNKDTWPDANKVG

-continued

SEQ ID NO: 3 HDAg genotype 1 A
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAG

SEQ ID NO: 4 HDAg genotype 1 B nucleic acid
AGCCGCAGCGAAAGCAAAAAAAACCGCGGCGGCCGCGAAGAAGTGCTGGAA

CAGTGGGTGAACGGCCGCAAAAAACTGGAAGAACTGGAACGCGAACTGCGC

CGCGCGCGCAAAAAAATTAAAAAACTGGAAGATGATAACCCGTGGCTGGGC

AACGTGAAAGGCATTCTGGGCAAAAAAGATAAAGATGGCGAAGGCGCGCCG

CCGGCGAAACGCGCGCGCACCGATCAGATGGAAATTGATAGCGGCCCGCGCA

AACGCCCGCTGCGCGGCGGCTTTACCGATCGCGAACGCCAGGATCATCGCCG

CCGCAAAGCGCTGAAAAACAAAAAAAAACAGCTGAGCGCGGGCGGCAAAAG

CCTGAGCAAAGAAGAAGAAGAAGAACTGAAACGCCTGACCCGCGAAGATGA

AGAACGCAAAAAAGAAGAACATGGCCCGAGCCGCCTGGGCGTGAACCCGAG

CGAAGGCGGCCCGCGCGGCGCGCCGGGCGGCGGCTTTGTGCCGAGCATGCAG

GGCATTCCGGAAAGCCGCTTTACCCGCACCGGCGAAGGCCTGGATGTGCGCG

GCAGCCGCGGCTTTCCGCAGGATATTCTGTTTCCGAGCGATCCGCCGTTTAGC

CCGCAGAGCTGCCGCCCGCAG

SEQ ID NO: 5 preS1 derived sequence is preS1
GGCACCAACCTGAGCACCAGCAACCCGCTGGGCTTTTTTCCGGATCATCAGCT

GGATCCGGCGTTTCGCGCGAACAGCGCGAACCCGGATTGGGATTTTAACCCG

AACAAAGATACCTGGCCGGATGCGAACAAAGTGGGC

SEQ ID NO: 6 preS1 B
GGCCAGAACCTGAGCACCAGCAACCCGCTGGGCTTTTTTCCGGATCATCAGCT

GGATCCGGCGTTTCGCGCGAACACCGCGAACCCGGATTGGGATTTTAACCCG

AACAAAGATACCTGGCCGGATGCGAACAAAGTGGGC

SEQ ID NO: T2A nucleic acid
GGAAGCGGAGCTACTAACTTCAGCCTGCTGAAGCAGGCTGGAGACGTGGAGG

AGAACCCTGGACCT

SEQ ID NO: 8 HDAg gentotype 2 A (wt)
ATGAGCCAGAGCGAAACCCGCCGCGGCCGCCGCGGCACCCGCGAAGAAACC

CTGGAAAAATGGATTACCGCGCGCAAAAAAGCGGAAGAACTGGAAAAAGAT

CTGCGCAAAACCCGCAAAACCATTAAAAAACTGGAAGAAGAAAACCCGTGG

-continued

CTGGGCAACATTGTGGGCATTATTCGCAAAGGCAAAGATGGCGAAGGCGCGC

CGCCGGCGAAACGCCCGCGCACCGATCAGATGGAAGTGGATAGCGGCCCGG

GCAAACGCCCGCATAAAAGCGGCTTTACCGATAAAGAACGCGAAGATCATCG

CCGCCGCAAAGCGCTGGAAAACAAAAAAAAACAGCTGAGCGCGGGCGGCAA

AATTCTGAGCAAAGAAGAAGAAGAAGAACTGCGCCGCCTGACCGATGAAGA

TGAAGAACGCAAACGCCGCGTGGCGGGCCCGCGCGTGGGCGATGTGAACCCG

AGCCGCGGCGGCCCGCGCGGCGCGCCGGGCGGCGGCTTTGTGCCGCAGATGG

CGGGCGTGCCGGAAAGCCCGTTTAGCCGCACCGGCGAAGGCCTGGATATTCG

CGGCACCCAGGGCTTTCCGTGGGTGAGCCCGAGCCCGCCGCAGCAGCGCCTG

CCGCTGCTGGAATGCACCCCGCAG

SEQ ID NO: 9 HDAg gentotype 2 B (wt)
AGCCAGAGCGAAAGCAAAAAAAACCGCCGCGGCGGCCGCGAAGATATTCTG

GAAAAATGGATTACCACCCGCCGCAAAGCGGAAGAACTGGAAAAAGATCTG

CGCAAAGCGCGCAAAACCATTAAAAAACTGGAAGATGAAAACCCGTGGCTG

GGCAACATTATTGGCATTATTCGCAAAGGCAAAGATGGCGAAGGCGCGCCGC

CGGCGAAACGCCCGCGCACCGATCAGATGGAAATTGATAGCGGCACCGGCAA

ACGCCCGCATAAAAGCGGCTTTACCGATAAAGAACGCGAAGATCATCGCCGC

CGCAAAGCGCTGGAAAACAAAAAAAAACAGCTGAGCAGCGGCGGCAAAAAC

CTGAGCCGCGAAGAAGAAGAAGAACTGGGCCGCCTGACCGTGGAAGATGAA

GAACGCCGCCGCCGCGTGGCGGGCCCGCGCACCGGCGATGTGAACCTGAGCG

GCGGCGGCCCGCGCGGCGCGCCGGGCGGCGGCTTTGTGCCGCGCATGGAAGG

CGTGCCGGAAAGCCCGTTTACCCGCACCGGCGAAGGCCTGGATATTCGCGGC

AACCAGGGCTTTCCGTGGGTGCGCCCGAGCCCGCCGCAGCAGCGCCTGCCGC

TGCTGGAATGCACCCCGCAG

SEQ ID NO: 10 delta 1 wt
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGAGCCGCAGCGAAAGCAAAAAAAACCGCGGC

GGCCGCGAAGAAGTGCTGGAACAGTGGGTGAACGGCCGCAAAAAACTGGAA

GAACTGGAACGCGAACTGCGCCGCGCGCGCAAAAAAATTAAAAAACTGGAA

GATGATAACCCGTGGCTGGGCAACGTGAAAGGCATTCTGGGCAAAAAAGATA

AAGATGGCGAAGGCGCGCCGCCGGCGAAACGCGCGCGCACCGATCAGATGG

-continued

AAATTGATAGCGGCCCGCGCAAACGCCCGCTGCGCGGCGGCTTTACCGATCG

CGAACGCCAGGATCATCGCCGCCGCAAAGCGCTGAAAAACAAAAAAAAACA

GCTGAGCGCGGGCGGCAAAAGCCTGAGCAAAGAAGAAGAAGAAGAACTGAA

ACGCCTGACCCGCGAAGATGAAGAACGCAAAAAAGAAGAACATGGCCCGAG

CCGCCTGGGCGTGAACCCGAGCGAAGGCGGCCCGCGCGGCGCGCCGGGCGG

CGGCTTTGTGCCGAGCATGCAGGGCATTCCGGAAAGCCGGTTTACCCGCACC

GGCGAAGGCCTGGATGTGCGCGGCAGCCGCGGCTTTCCGCAGGATATTCTGT

TTCCGAGCGATCCGCCGTTTAGCCCGCAGAGCTGCCGCCCGCAGGGCACCAA

CCTGAGCACCAGCAACCCGCTGGGCTTTTTTCCGGATCATCAGCTGGATCCGG

CGTTTCGCGCGAACAGCGCGAACCCGGATTGGGATTTTAACCCGAACAAAGA

TACCTGGCCGGATGCGAACAAAGTGGGCGGCCAGAACCTGAGCACCAGCAAC

CCGCTGGGCTTTTTTCCGGATCATCAGCTGGATCCGGCGTTTCGCGCGAACAC

CGCGAACCCGGATTGGGATTTTAACCCGAACAAAGATACCTGGCCGGATGCG

AACAAAGTGGGCGGAAGCGGAGCTACTAACTTCAGCCTGCTGAAGCAGGCTG

GAGACGTGGAGGAGAACCCTGGACCTATGAGCCAGAGCGAAACCCGCCGCG

GCCGCCGCGGCACCCGCGAAGAAACCCTGGAAAAATGGATTACCGCGCGCAA

AAAAGCGGAAGAACTGGAAAAAGATCTGCGCAAAACCCGCAAAACCATTAA

AAAACTGGAAGAAGAAAACCCGTGGCTGGGCAACATTTGTGGGCATTATTCGC

AAAGGCAAAGATGGCGAAGGCGCGCCGCCGGCGAAACGCCCGCGCACCGAT

CAGATGGAAGTGGATAGCGGCCCGGGCAAACGCCCGCATAAAAGCGGCTTTA

CCGATAAAGAACGCGAAGATCATCGCCGCCGCAAAGCGCTGGAAAACAAAA

AAAAACAGCTGAGCGCGGGCGGCAAAATTCTGAGCAAAGAAGAAGAAGAAG

AACTGCGCCGCCTGACCGATGAAGATGAAGAACGCAAACGCCGCGTGGCGG

GCCCGCGCGTGGGCGATGTGAACCCGAGCCGCGGCGGCCCGCGCGGCGCGCC

GGGCGGCGGCTTTGTGCCGCAGATGGCGGGCGTGCCGGAAAGCCCGTTTAGC

CGCACCGGCGAAGGCCTGGATATTCGCGGCACCCAGGGCTTTCCGTGGGTGA

GCCCGAGCCCGCCGCAGCAGCGCCTGCCGCTGCTGGAATGCACCCCGCAGAG

CCAGAGCGAAAGCAAAAAAAACCGCCGCGGCGGCCGCGAAGATATTCTGGA

AAAATGGATTACCACCCGCCGCAAAGCGGAAGAACTGGAAAAAGATCTGCG

CAAAGCGCGCAAAACCATTAAAAAACTGGAAGATGAAAACCCGTGGCTGGG

CAACATTATTGGCATTATTCGCAAAGGCAAAGATGGCGAAGGCGCGCCGCCG

GCGAAACGCCCGCGCACCGATCAGATGGAAATTGATAGCGGCACCGGCAAAC

GCCCGCATAAAAGCGGCTTTACCGATAAAGAACGCGAAGATCATCGCCGCCG

CAAAGCGCTGGAAAACAAAAAAAAACAGCTGAGCAGCGGCGGCAAAAACCT

GAGCCGCGAAGAAGAAGAAGAACTGGGCCGCCTGACCGTGGAAGATGAAGA

ACGCCGCCGCCGCGTGGCGGGCCCGCGCACCGGCGATGTGAACCTGAGCGGC

GGCGGCCCGCGCGGCGCGCCGGGCGGCGGCTTTGTGCCGCGCATGGAAGGCG

TGCCGGAAAGCCCGTTTACCCGCACCGGCGAAGGCCTGGATATTCGCGGCAA

CCAGGGCTTTCCGTGGGTGCGCCCGAGCCCGCCGCAGCAGCGCCTGCCGCTG

CTGGAATGCACCCCGCAGGGCACCAACCTGAGCACCAGCAACCCGCTGGGCT

-continued

TTTTTCCGGATCATCAGCTGGATCCGGCGTTTCGCGCGAACAGCGCGAACCCG

GATTGGGATTTTAACCCGAACAAAGATACCTGGCCGGATGCGAACAAAGTGG

GCGGCCAGAACCTGAGCACCAGCAACCCGCTGGGCTTTTTTCCGGATCATCA

GCTGGATCCGGCGTTTCGCGCGAACACCGCGAACCCGGATTGGGATTTTAAC

CCGAACAAAGATACCTGGCCGGATGCGAACAAAGTGGGC

SEQ ID NO: 11 delta1 wt with restriction sites
(HindIII/EcoRI)
A↓AGCTT*GCACC*ATGGCCAGCCGCAGCGAAAGCAAAAAAAACCGCGGCGGC

CGCGAAGAAATTCTGGAACAGTGGGTGGGCGCGCGCAAAAAACTGGAAGAA

CTGGAACGCGATCTGCGCAAAATTAAAAAAAAAATTAAAAAACTGGAAGAA

GAAAACCCGTGGCTGGGCAACATTAAAGGCATTCTGGGCAAAAAAGATCGCG

AAGGCGAAGGCGCGCCGCCGGCGAAACGCGCGCGCGCGGATCAGATGGAAG

TGGATAGCGGCCCGCGCAAACGCCCGTTTCGCGGCGAATTTACCGATAAAGA

ACGCCGCGATCATCGCCGCCGCAAAGCGCTGGAAAACAAACGCAAACAGCTG

AGCAGCGGCGGCAAAAGCCTGAGCAAAGAAGAAGAAGAAGAACTGCGCAAA

CTGACCGAAGAAGATGAACGCCGCGAACGCCGCGTGGCGGGCCCGCGCGTG

GGCGGCGTGAACCCGCTGGAAGGCGGCACCCGCGGCGCGCCGGGCGGCGGC

TTTGTGCCGAGCATGCAGGGCGTGCCGGAAAGCCCGTTTGCGCGCACCGGCG

AAGGCCTGGATGTGCGCGGCAACCAGGGCTTTCCGTGGGATATTCTGTTTCCG

GCGGATCCGCCGTTTAGCCCGCAGAGCTGCCGCCCGCAGAGCCGCAGCGAAA

GCAAAAAAAACCGCGGCGGCCGCGAAGAAGTGCTGGAACAGTGGGTGAACG

GCCGCAAAAAACTGGAAGAACTGGAACGCGAACTGCGCCGCGCGCGCAAAA

AAATTAAAAAACTGGAAGATGATAACCCGTGGCTGGGCAACGTGAAAGGCAT

TCTGGGCAAAAAAGATAAAGATGGCGAAGGCGCGCCGCCGGCGAAACGCGC

GCGCACCGATCAGATGGAAATTGATAGCGGCCCGCGCAAACGCCCGCTGCGC

GGCGGCTTTACCGATCGCGAACGCCAGGATCATCGCCGCCGCAAAGCGCTGA

AAAACAAAAAAAAACAGCTGAGCGCGGGCGGCAAAAGCCTGAGCAAAGAAG

AAGAAGAAGAACTGAAACGCCTGACCCGCGAAGATGAAGAACGCAAAAAAG

AAGAACATGGCCCGAGCCGCCTGGGCGTGAACCCGAGCGAAGGCGGCCCGC

GCGGCGCGCCGGGCGGCGGCTTTGTGCCGAGCATGCAGGGCATTCCGGAAAG

CCGCTTTACCCGCACCGGCGAAGGCCTGGATGTGCGCGGCAGCCGCGGGTTT

CCGCAGGATATTCTGTTTCCGAGCGATCCGCCGTTTAGCCCGCAGAGCTGCCG

CCCGCAGGGCACCAACCTGAGCACCAGCAACCCGCTGGGCTTTTTTCCGGAT

CATCAGCTGGATCCGGCGTTTCGCGCGAACAGCGCGAACCCGGATTGGGATT

TTAACCCGAACAAAGATACCTGGCCGGATGCGAACAAAGTGGGCGGCCAGA

ACCTGAGCACCAGCAACCCGCTGGGCTTTTTTCCGGATCATCAGCTGGATCCG

GCGTTTCGCGCGAACACCGCGAACCCGGATTGGGATTTTAACCCGAACAAAG

ATACCTGGCCGGATGCGAACAAAGTGGGCGGAAGCGGAGCTACTAACTTCAG

CCTGCTGAAGCAGGCTGGAGACGTGGAGGAGAACCCTGGACCTATGAGCCA

GAGCGAAACCCGCCGCGGCCGCCGCGGCACCCGCGAAGAAACCCTGGAAAA

ATGGATTACCGCGCGCAAAAAAGCGGAAGAACTGGAAAAAGATCTGCGCAA

AACCCGCAAAACCATTAAAAAACTGGAAGAAGAAAACCCGTGGCTGGGCAA

-continued

CATTGTGGGCATTATTCGCAAAGGCAAAGATGGCGAAGGCGCGCCGCCGGCG

AAACGCCCGCGCACCGATCAGATGGAAGTGGATAGCGGCCCGGGCAAACGC

CCGCATAAAAGCGGCTTTACCGATAAAGAACGCGAAGATCATCGCCGCCGCA

AAGCGCTGGAAAACAAAAAAAAACAGCTGAGCGCGGGCGGCAAAATTCTGA

GCAAAGAAGAAGAAGAAGAACTGCGCCGCCTGACCGATGAAGATGAAGAAC

GCAAACGCCGCGTGGCGGGCCCGCGCGTGGGCGATGTGAACCCGAGCCGCGG

CGGCCCGCGCGGCGCGCCGGGCGGCGGCTTTGTGCCGCAGATGGCGGGCGTG

CCGGAAAGCCCGTTTAGCCGCACCGGCGAAGGCCTGGATATTCGCGGCACCC

AGGGCTTTCCGTGGGTGAGCCCGAGCCCGCCGCAGCAGCGCCTGCCGCTGCT

GGAATGCACCCCGCAGAGCCAGAGCGAAAGCAAAAAAAACCGCCGCGGCGG

CCGCGAAGATATTCTGGAAAAATGGATTACCACCCGCCGCAAAGCGGAAGAA

CTGGAAAAAGATCTGCGCAAAGCGCGCAAAACCATTAAAAAACTGGAAGAT

GAAAACCCGTGGCTGGGCAACATTATTGGCATTATTCGCAAAGGCAAAGATG

GCGAAGGCGCGCCGCCGGCGAAACGCCCGCGCACCGATCAGATGGAAATTG

ATAGCGGCACCGGCAAACGCCCGCATAAAAGCGGCTTTACCGATAAAGAACG

CGAAGATCATCGCCGCCGCAAAGCGCTGGAAAACAAAAAAAAACAGCTGAG

CAGCGGCGGCAAAAACCTGAGCCGCGAAGAAGAAGAAGAACTGGGCCGCCT

GACCGTGGAAGATGAAGAACGCCGCCGCCGCGTGGCGGGCCCGCGCACCGG

CGATGTGAACCTGAGCGGCGGCGGCCCGCGCGGCGCGCCGGGCGGCGGCTTT

GTGCCGCGCATGGAAGGCGTGCCGGAAAGCCCGTTTACCCGCACCGGCGAAG

GCCTGGATATTCGCGGCAACCAGGGCTTTCCGTGGGTGCGCCCGAGCCCGCC

GCAGCAGCGCCTGCCGCTGCTGGAATGCACCCCGCAGGGCACCAACCTGAGC

ACCAGCAACCCGCTGGGCTTTTTTCCGGATCATCAGCTGGATCCGGCGTTTCG

CGCGAACAGCGCGAACCCGGATTGGGATTTTAACCCGAACAAAGATACCTGG

CCGGATGCGAACAAAGTGGGCGGCCAGAACCTGAGCACCAGCAACCCGCTG

GGCTTTTTTCCGGATCATCAGCTGGATCCGGCGTTTCGCGCGAACACCGCGAA

CCCGGATTGGGATTTTAACCCGAACAAAGATACCTGGCCGGATGCGAACAAA

GTGGGCTGATGAG↓AATTCCGT

SEQ ID NO: 12 codon optimized delta 1
GCCAGCAGAAGTGAATCAAAAAAGAATCGGGGAGGGCGGGAAGAAATCCTGGAACAGTGG

GTCGGAGCACGGAAGAAACTGGAAGAACTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATCGGGAGGGAGAGGGAGGACCACCTGCAAAGAGGGCCAGAGCCGACCAGATGGAG

GTGGATAGCGGACCAAGGAAGCGCCCTTTCAGAGGAGAGTTTACCGACAAGGAGCGGAGA

GATCACAGGCGCCGGAAGGCCCTGGAGAACAAGAGGAAGCAGCTGAGCTCCGGCGGCAAG

TCCCTGTCTAAGGAGGAGGAGGAGGAGCTGCGCAAGCTGACAGAGGAGGACGAGAGAAGG

GAGAGGAGGGTGGCAGGACCTAGGGTGGGAGCGTGGAACCCACTGGAGGGAGGAACCAGA

GGAGCACCTGGAGGAGGATTCGTGCCATCCATGCAGGGAGTGCCCGAGTCTCCTTTTGCC

CGGACAGGCGAGGGCCTGGATGTGAGAGGCAATCAGGGCTTCCCCTGGGACATCCTGTTT

CCTGCCGATCCACCCTTCTCTCCTCAGAGCTGCCGGCCACAGAGCAGATCCGAGTCTAAG

AAGAACAGGGGAGGAAGAGAGGAGGTGCTGGAGCAGTGGGTGAATGGCCGGAAGAAGCTG

-continued

GAGGAGCTGGAGCGGGAGCTGAGAAGGGCCAGAAAGAAGATCAAGAAGCTGGAAGACGAT

AATCCTTGGCTGGGCAATGTGAAAGGCATCCTGGGCAAGAAGGACAAGGATGGAGAGGGA

GCACCTCCAGCAAAGAGGGCAAGAACCGACCAGATGGAGATCGATTCTGGACCAAGGAAG

CGCCCCCTGAGAGGAGGCTTCACAGACCGGGAGAGACAGGATCACCGCCGGAGAAAGGCC

CTGATGAACAAGAAGAAGCAGCTGTCCGCCGGAGGCAAGAGCCTGTCCAAAGAAGAGGAA

GAGGAGCTGAAGAGGCTGACCCGCGAGGACGAGGAGAGGAAGAAGGAGGAGCACGGACCA

AGCAGGCTGGGAGTGAATCCTTCCGAGGGAGGACCTAGGGGAGCACCAGGAGGAGGCTTC

GTGCCATCTATGCAGGGCATCCCCGAGAGCCGGTTTACCAGAACAGGAGAGGGCCTGGAC

GTGAGGGGCTCCCGCGGCTTTCCTCAGGACATCCTGTTCCCATCTGATCCCCCTTTTTCC

CCCCAGTCTTGTAGGCCTCAGGGCACCAACCTGTCTACAAGCAATCCACTGGGCTTCTTT

CCCGACCACCAGCTGGATCCTGCCTTCCGCGCCAACAGCGCCAATCCCGACTGGGACTTC

AACCCAAATAAGGACACCTGGCCAGATGCCAACAAGGTCGGCGGCCAGAACCTGTCCACA

TCTAATCCTCTGGGCTTCTTTCCAGACCACCAGCTGGATCCAGCCTTCCGGGCCAACACA

GCTAACCCTGACTGGGACTTCAACCCCAATAAGGATACTTGGCCCGACGCCAACAAGGTC

GGCGGAAGCGGAGCTACTAACTTCAGCCTGCTGAAGCAGGCTGGAGACGTGGAGGAGAAC

CCTGGACCTATGAGCCAGTCCGAGACAAGGAGGGGCCGGAGAGGAACCAGGGAGGAGACA

CTGGAGAAGTGGATCACAGCCCGCAAGAAGGCCGAGGAGCTGGAGAAGGACCTGCGGAAG

ACCAGAAAGACAATCAAGAAGCTGGAAGAAGAGAACCCATGGCTGGGCAATATCGTGGGC

ATCATCAGAAAGGGCAAGGACGGCGAGGGAGCACCACCAGCAAAGAGGCCCAGGACTGAT

CAGATGGAAGTCGATAGCGGACCAGGCAAGCGGCCTCACAAGTCCGGCTTCACAGACAAG

GAGAGAGAGGACCATAGGCGCCGGAAGGCCCTGGAAAACAAGAAGAAGCAATTATCCGCC

GGCGGCAAGATCCTGTCCAAAGAGGAAGAAGAGGAGCTGAGAAGGCTGACCGACGAGGAT

GAGGAGAGGAAAAGAAGGGTGGCAGGACCAAGGGTGGGCGACGTGAATCCCAGCAGGGGA

GGACCAAGAGGCGCCCCTGGCGGCGGCTTCGTGCCACAGATGGCAGGAGTGCCAGAGAGC

CCCTTTTCCAGGACAGGAGAGGGCCTGGATATCAGAGGCACCCAGGGCTTTCCTTGGGTG

TCTCCAAGCCCTCCACAGCAGCGGCTGCCACTGCTGGAGTGCACCCCTCAGTCCCAGTCT

GAGAGCAAGAAGAACAGAAGGGGCGGCAGAGAGGACATCCTGGAGAAGTGGATCACCACA

CGCAGAAAAGCTGAAGAACTGGAAAAGGACCTGAGGAAGGCCCGCAAAACAATCAAGAAG

CTGGAGGATGAAAATCCATGGCTGGGAAACATCATCGGCATCATGAGGAAGGGCAAGGAC

GGGGAAGGCGCACCACCTGCAAAGCGGCCTAGAACAGATCAGATGGAAATCGATTCTGGC

ACCGGCAAGAGGCCACACAAGAGCGGCTTCACCGACAAGGAGCGCGAGGATCACAGAAGG

C

GCAAGGCCCTGGAGAACAAGAAGAACCAATTAACCAGCGGCCGCAAGAATCTGTCCACAG

AAGAAGAGGAGGAGCTGGGCCGCCTGACCGTGGAGGACGAGGAGCGGAGAAGGCGCGTGG

CAGGACCACGCACAGGCGATGTGAACGTGTCCGGAGGAGGACCAAGGGGAGCACCTGGAG

GCGGCTTCGTGCCTAGAATGGAGGGAGTGCCTGAGTCCCCCTTCACCCGCACCGGAGAGG

GCCTCGACATCAGAGGGAATGAGGGATTGCCATGGGTGAGGCCCAGCCGACCACAGGAGC

GCCTGCCACTGCTGGAGTGTACCCCCCAGGGCACAAACCTGTCCACCTCTAATCCCCTGG

GCTTCTTTCCTGATCATCAGCTGGACCCAGCCTTCAGGGCCAACTCCGCCAATCCAGATT

GGGACTTCAACCCGAATAAGGATACTTGGCCAGATGCAAACAAGGTCGGAGGACAGAACC

-continued

TGAGCACATCCAACCCTCTGGGCTTCTTTCCTGACCATCAGCTGGATCCCGCCTTTCGCG

CCAATACCGCCAACCCTGATTGGGACTTCAACCCTAATAAGGATACTTGGCCTGATGCTA

ATAAGGTCGGG

SEQ ID NO: 13: Delta 1 optimized with restriction
sites (HindIII and EcoRI)
A↓AGCTT*GCACC*ATGGCCAGCAGAAGTGAATCAAAAAAGAATCGGGGAGGG

CGGGAAGAAATCCTGGAACAGTGGGTCGGAGCACGGAAGAAACTGGAAGAA

CTGGAGAGGGACCTGCGCAAGATCAAGAAGAAGATCAAGAAGCTGGAGGAG

GAGAACCCCTGGCTGGGCAATATCAAGGGCATCCTGGGCAAGAAGGATCGGG

AGGGAGAGGGAGCACCACCTGCAAAGAGGGCCAGAGCCGACCAGATGGAGG

TGGATAGCGGACCAAGGAAGCGCCCTTTCAGAGGAGAGTTTACCGACAAGGA

GCGGAGAGATCACAGGCGCCGGAAGGCCCTGGAGAACAAGAGGAAGCAGCT

GAGCTCCGGCGGCAAGTCCCTGTCTAAGGAGGAGGAGGAGGAGCTGCGCAA

GCTGACAGAGGAGGACGAGAGAAGGGAGAGGAGGGTGGCAGGACCTAGGGT

GGGAGGCGTGAACCCACTGGAGGGAGGAACCAGAGGAGCACGTGGAGGAGG

ATTCGTGCCATCCATGCAGGGAGTGCCCGAGTCTCCTTTTGCCCGGACAGGCG

AGGGCCTGGATGTGAGAGGCAATCAGGGCTTCCCCTGGGACATCCTGTTTCCT

GCCGATCCACCCTTCTCTCCTCAGAGCTTGCCGGCCACAGAGCAGATCCGAGTC

TAAGAAGAACAGGGGAGGAAGAGAGGAGGTGCTGGAGCAGTGGGTGAATGG

CCGGAAGAAGCTGGAGGAGCTGGAGCGGGAGCTGAGAAGGGCCAGAAAGAA

GATCAAGAAGCTGGAAGACGATAATCCTTGGCTGGGCAATGTGAAAGGCATC

CTGGGCAAGAAGGACAAGGATGGAGAGGGAGCACCTCCAGCAAAGAGGGCA

AGAACCGACCAGATGGAGATCGATTCTGGACCAAGGAAGCGCCCCCTGAGAG

GAGGCTTCACAGACCGGGAGAGACAGGATCACCGCCGGAGAAAGGCCCTGA

AGAACAAGAAGAAGGAGCTGTCCGCCGGAGGCAAGAGCCTGTCCAAAGAAG

AGGAAGAGGAGCTGAAGAGGCTGACCCGCGAGGACGAGGAGAGGAAGAAG

GAGGAGCACGGACCAAGCAGGCTGGGAGTGAATCCTTCCGAGGGAGGACCT

AGGGGAGCACCAGGAGGAGGCTTCGTGCCATCTATGCAGGGCATCCCCGAGA

GCCGGTTTACCAGAACAGGAGAGGGCCTGGACGTGAGGGGCTCCCGCGGCTT

TCCTCAGGACATCCTGTTCCCATCTGATCCCCCTTTTTCCCCCCAGTCTTGTAG

GCCTCAGGGCACCAACCTGTCTACAAGCAATCCACTGGGCTTCTTTCCCGACC

ACCAGCTGGATCCTGCCTTCCGCGCCAACAGCGCCAATCCCGACTGGGACTTC

AACCCAAATAAGGACACCTGGCCAGATGCCAACAAGGTCGGCGGCCAGAAC

CTGTCCACATCTAATCCTCTGGGCTTCTTTCCAGACCACCAGCTGGATCCAGC

CTTCCGGGCCAACACAGCTAACCCTGACTGGGACTTCAACCCCAATAAGGAT

ACTTGGCCCGACGCCAACAAGGTCGGCGGAAGCGGAGCTACTAACTTCAGCC

TGCTGAAGCAGGCTGGAGACGTGGAGGAGAACCCTGGACCTATGAGCCAGTC

CGAGACAAGGAGGGGCCGGAGAGGAACCAGGGAGGAGACACTGGAGAAGTG

GATCACAGCCCGCAAGAAGGCCGAGGAGCTGGAGAAGGACCTGCGGAAGAC

CAGAAAGACAATCAAGAAGCTGGAAGAAGAGAACCCATGGCTGGGCAATAT

CGTGGGCATCATCAGAAAGGGCAAGGACGGCGAGGGAGCACCACCAGCAAA

GAGGCCCAGGACTGATCAGATGGAAGTCGATAGCGGACCAGGCAAGCGGCC

-continued

TCACAAGTCCGGCTTCACAGACAAGGAGAGAGAGGACCATAGGCGCCGGAA

GGCCCTGGAAAACAAGAAGAAGCAATTATCCGCCGGCGGCAAGATCCTGTCC

AAAGAGGAAGAAGAGGAGCTGAGAAGGCTGACCGACGAGGATGAGGAGAG

GAAAAGAAGGGTGGCAGGACCAAGGGTGGGCGACGTGAATCCCAGCAGGGG

AGGACCAAGAGGCGCCCCTGGCGGCGGCTTCGTGCCACAGATGGCAGGAGTG

CCAGAGAGCCCCTTTTCCAGGACAGGAGAGGGCCTGGATATCAGAGGCACCC

AGGGCTTTCCTTGGGTGTCTCCAAGCCCTCCACAGCAGCGGCTGCCACTGCTG

GAGTGCACCCCTCAGTCCCAGTCTGAGAGCAAGAAGAACAGAAGGGGCGGC

AGAGAGGACATCCTGGAGAAGTGGATCACCACACGCAGAAAAGCTGAAGAA

CTGGAAAAGGACCTGAGGAAGGCCCGCAAAACAATCAAGAAGCTGGAGGAT

GAAAATCCATGGCTGGGAAACATCATCGGCATCATCAGGAAGGGCAAGGAC

GGGGAAGGCGCACCACCTGCAAAGCGGCCTAGAACAGATCAGATGGAAATC

GATTCTGGCACCGGCAAGAGGCCACACAAGAGCGGCTTCACCGACAAGGAGC

GCGAGGATCACAGAAGGC

GCAAGGCCCTGGAGAACAAGAAGAAGCAATTAAGCAGCGGCGGCAAGAATC

TGTCCAGAGAAGAAGAGGAGGAGCTGGGCCGCCTGACCGTGGAGGACGAGG

AGCGGAGAAGGCGCGTGGCAGGACCACGCACAGGCGATGTGAACCTGTCCG

GAGGAGGACCAAGGGGAGCACCTGGAGGCGGCTTCGTGCCTAGAATGGAGG

GAGTGCCTGAGTCCCCCTTCACCCGCACCGGAGAGGGCCTGGACATCAGAGG

CAATCAGGGATTCCCATGGGTGAGGCCCAGCCCACCACAGCAGCGCCTGCCA

CTGCTGGAGTGTACCCCCCAGGGCACAAACCTGTCCACCTCTAATCCCCTGGG

CTTCTTTCCTGATCATCAGCTGGACCCAGCCTTCAGGGCCAACTCCGCCAATC

CAGATTGGGACTTCAACCCGAATAAGGATACTTGGCCAGATGCAAACAAGGT

CGGAGGACAGAACCTGAGCACATCCAACCCTCTGGGCTTCTTTCCTGACCATC

AGCTGGATCCCGCCTTTCGCGCCAATACCGCCAACCCTGATTGGGACTTCAAC

CCTAATAAGGATACTTGGCCTGATGCTAATAAGGTCGGGTGATGAG↓AATTC

CGT

SEQ ID NO: 14 DELTA 1 protein
MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKAL

ENKRKQLSSGGKSLSKEEEEELRKLTEEDERRERRVAGPRVGGVNPLEGGTRGAP

GGGFVPSMQGVPESPFARTGEGLDVRGNQGFPWDILFPADPPFSPQSCRPQSRSES

KKNRGGREEVLEQWVNGRKKLEELERELRRARKKIKKLEDDNPWLGNVKGILG

KKDKDGEGAPPAKRARTDQMEIDSGPRKRPLRGGFTDRERQDHRRRKALKNKK

KQLSAGGKSLSKEEEEELKRLTREDEERKKEEHGPSRLGVNPSEGGPRGAPGGGF

VPSMQGIPESRFTRTGEGLDVRGSRGFPQDILFPSDPPFSPQSCRPQGTNLSTSNPL

GFFPDHQLDPAFRANSANPDWDFNPNKDTWPDANKVGGQNLSTSNPLGFFPDHQ

LDPAFRANTANPDWDFNPNKDTWPDANKVGGSGATNFSLLKQAGDVEENPGPM

SQSETRRGRRGTREETLEKWITARKKAEELEKDLRKTRKTIKKLEEENPWLGNIV

GIIRKGKDGEGAPPAKPPRTDQMEVDSGPGKRPHKSGFTDKEREDHRRRKALEN

KKKQLSAGGKILSKEEEEELRRLTDEDEERKRRVAGPRVGDVNPSRGGPRGAPG

-continued

GGFVPQMAGVPESPFSRTGEGLDIRGTQGFPWVSPSPPQQRLPLLECTPQSQSESK

KNRRGGREDILEKWITTRRKAEELEKDLRKARKTIKKLEDENPWLGNIIGIIRKGK

DGEGAPPAKRPRTDQMEIDSGTGKRPHKSGFTDKEREDHRRRKALENKKKQLSS

GGKNLSREEEEELGRLTVEDEERRRRVAGPRTGDVNLSGGGPRGAPGGGFVPRM

EGVPESPFTRTGEGLDIRGNQGFPWVRPSPPQQRLPLLECTPQGTNLSTSNPLGFFP

DHQLDPAFRANSANPDWDFNPNKDTWPDANKVGGQNLSTSNPLGFFPDHQLDP

AFRANTANPDWDFNPNKDTWPDANKVG Delta 1 protein

SEQ ID NO: 15 Delta 2 sequence wt
GGCACCAACCTGAGCACCAGCAACCCGCTGGGCTTTTTTCCGGATCATCAGCT

GGATCCGGCGTTTCGCGCGAACAGCGCGAACCCGGATTGGGATTTTAACCCG

AACAAAGATACCTGGCCGGATGCGAACAAAGTGGGCGGCCAGAACCTGAGC

ACCAGCAACCCGCTGGGCTTTTTTCCGGATCATCAGCTGGATCCGGCGTTTCG

CGCGAACACCGCGAACCCGGATTGGGATTTTAACCCGAACAAAGATACCTGG

CCGGATGCGAACAAAGTGGGCAGCCGCAGCGAAAGCAAAAAAAACCGCGGC

GGCCGCGAAGAAATTCTGGAACAGTGGGTGGGCGCGCGCAAAAAACTGGAA

GAACTGGAACGCGATCTGCGCAAAATTAAAAAAAAAATTAAAAAACTGGAA

GAAGAAAACCCGTGGCTGGGCAACATTAAAGGCATTCTGGGCAAAAAAGATC

GCGAAGGCGAAGGCGCGCCGCCGGCGAAACGCGCGCGCGGATCAGATGG

AAGTGGATAGCGGCCCGCGCAAACGCCCGTTTCGCGGCGAATTTACCGATAA

AGAACGCCGCGATCATCGCCGCCGCAAAGCGCTGGAAAACAAACGCAAACA

GCTGAGCAGCGGCGGCAAAAGCCTGAGCAAAGAAGAAGAAGAAGAACTGCG

CAAACTGACCGAAGAAGATGAACGCCGCGAACGCCGCGTGGCGGGCCCGCG

CGTGGGCGGCGTGAACCCGCTGGAAGGCGGCACCCGCGGCGCGCCGGGCGG

CGGCTTTGTGCCGAGCATGCAGGGCGTGCCGGAAAGCCCGTTTGCGCGCACC

GGCGAAGGCCTGGATGTGCGCGGCAACCAGGGCTTTCCGTGGGATATTCTGT

TTCCGGCGGATCCGCCGTTTAGCCCGCAGAGCTGCCGCCCGCAGAGCCGCAG

CGAAAGCAAAAAAAACCGCGGCGGCCGCGAAGAAGTGCTGGAACAGTGGGT

GAACGGCCGCAAAAAACTGGAAGAACTGGAACGCGAACTGCGCCGCGCGCG

CAAAAAAATTAAAAAACTGGAAGATGATAACCCGTGGCTGGGCAACGTGAA

AGGCATTCTGGGCAAAAAAGATAAAGATGGCGAAGGCGCGCCGCCGGCGAA

ACGCGCGCACCGATCAGATGGAAATTGATAGCGGCCCGCGCAAACGCCCG

CTGCGCGGCGGCTTTACCGATCGCGAACGCCAGGATCATCGCCGCCGCAAAG

CGCTGAAAAACAAAAAAAAACAGCTGAGCGCGGGCGGCAAAAGCCTGAGCA

AAGAAGAAGAAGAAGAACTGAAACGCCTGACCCGCGAAGATGAAGAACGCA

AAAAAGAAGAACATGGCCCGAGCCGCCTGGGCGTGAACCCGAGCGAAGGCG

GCCCGCGCGGCGCGCCGGGCGGCGGCTTTGTGCCGAGCATGCAGGGCATTCC

GGAAAGCCGCTTTACCCGCACCGGCGAAGGCCTGGATGTGCGCGGCAGCCGC

GGCTTTCCGCAGGATATTCTGTTTCCGAGCGATCCGCCGTTTAGCCCGCAGAG

CTGCCGCCCGCAGGGAAGCGGAGCTACTAACTTCAGCCTGCTGAAGCAGGCT

GGAGACGTGGAGGAGAACCCTGGACCTATGGGCACCAACCTGAGCACCAGC

AACCCGCTGGGCTTTTTTCCGGATCATCAGCTGGATCCGGCGTTTCGCGCGAA

-continued

CAGCGCGAACCCGGATTGGGATTTTAACCCGAACAAAGATACCTGGCCGGAT

GCGAACAAAGTGGGCGGCCAGAACCTGAGCACCAGCAACCCGCTGGGCTTTT

TTCCGGATCATCAGCTGGATCCGGCGTTTCGCGCGAACACCGCGAACCCGGA

TTGGGATTTTAACCCGAACAAAGATACCTGGCCGGATGCGAACAAAGTGGGC

AGCCAGAGCGAAACCCGCCGCGGCCGCCGCGGCACCCGCGAAGAAACCCTG

GAAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

GGCAACATTGTGGGCATTATTCGCAAAGGCAAAGATGGCGAAGGCGCGCCGC

CGGCGAAACGCCCGCGCACCGATCAGATGGAAGTGGATAGCGGCCCGGGCA

AACGCCCGCATAAAAGCGGCTTTACCGATAAAGAACGCGAAGATCATCGCCG

CCGCAAAGCGCTGGAAAACAAAAAAAAACAGCTGAGCGCGGGCGGCAAAAT

TCTGAGCAAAGAAGAAGAAGAAGAACTGCGCCGCCTGACCGATGAAGATGA

AGAACGCAAACGCCGCGTGGCGGGCCCGCGCGTGGGCGATGTGAACCCGAG

CCGCGGCGGCCCGCGCGGCGCGCCGGGCGGCGGCTTTGTGCCGCAGATGGCG

GGCGTGCCGGAAAGCCCGTTTAGCCGCACCGGCGAAGGCCTGGATATTCGCG

GCACCCAGGGCTTTCCGTGGGTGAGCCCGAGCCCGCCGCAGCAGCGCCTGCC

GCTGCTGGAATGCACCCCGCAGAGCCAGAGCGAAAGCAAAAAAAACCGCCG

CGGCGGCCGCGAAGATATTCTGGAAAAATGGATTACCACCCGCCGCAAAGCG

GAAGAACTGGAAAAAGATCTGCGCAAAGCGCGCAAAACCATTAAAAAACTG

GAAGATGAAAACCCGTGGCTGGGCAACATTATTGGCATTATTCGCAAAGGCA

AAGATGGCGAAGGCGCGCCGCCGGCGAAACGCCCGCGCACCGATCAGATGG

AAATTGATAGCGGCACCGGCAAACGCCCGCATAAAAGCGGCTTTACCGATAA

AGAACGCGAAGATCATCGCCGCCGCAAAGCGCTGGAAAACAAAAAAAAACA

GCTGAGCAGCGGCGGCAAAAACCTGAGCCGCGAAGAAGAAGAAGAACTGGG

CCGCCTGACCGTGGAAGATGAAGAACGCCGCCGCCGCGTGGCGGGCCCGCGC

ACCGGCGATGTGAACCTGAGCGGCGGCGGCCCGCGCGGCGCGCCGGGCGGC

GGCTTTGTGCCGCGCATGGAAGGCGTGCCGGAAAGCCCGTTTACCCGCACCG

GCGAAGGCCTGGATATTCGCGGCAACCAGGGCTTTCCGTGGGTGCGCCCGAG

CCCGCCGCAGCAGCGCCTGCCGCTGCTGGAATGCACCCCGCAG

SEQ ID NO: 16 Delta 2 wt with restriction sites
(HindIII/EcoRI)
A↓AGCTT*GCACC*ATG*G*CCGGCACCAACCTGAGCACCAGCAACCCGCTGGGCT

TTTTTCCGGATCATCAGCTGGATCCGGCGTTTCGCGCGAACAGCGCGAACCCG

GATTGGGATTTTAACCCGAACAAAGATACCTGGCCGGATGCGAACAAAGTGG

GCGGCCAGAACCTGAGCACCAGCAACCCGCTGGGCTTTTTTCCGGATCATCA

GCTGGATCCGGCGTTTCGCGCGAACACCGCGAACCCGGATTGGGATTTTAAC

CCGAACAAAGATACCTGGCCGGATGCGAACAAAGTGGGCAGCCGCAGCCAA

AGCAAAAAAAACCGCGGCGGCCGCGAAGAAATTCTGGAACAGTGGGTGGGC

GCGCGCAAAAAACTGGAAGAACTGGAACGCGATCTGCGCAAAATTAAAAAA

AAAATTAAAAAACTGGAAGAAGAAAACCCGTGGCTGGGCAACATTAAAGGC

ATTCTGGGCAAAAAAGATCGCGAAGGCGAAGGCGCGCCGCCGGCGAAACGC

-continued

GCGCGCGCGGATCAGATGGAAGTGGATAGCGGCCCGCGCAAACGCCCGTTTC

GCGGCGAATTTACCGATAAAGAACGCCGCGATCATCGCCGCCGCAAAGCGCT

GGAAAACAAACGCAAACAGCTGAGCAGCGGCGGCAAAAGCCTGAGCAAAGA

AGAAGAAGAAGAACTGCGCAAACTGACCGAAGAAGATGAACGCCGCGAACG

CCGCGTGGCGGGCCCGCGCGTGGGCGGCGTGAACCCGCTGGAAGGCGGCACC

CGCGGCGCGCCGGGCGGCGGCTTTGTGCCGAGCATGCAGGGCGTGCCGGAAA

GCCCGTTTGCGCGCACCGGCGAAGGCCTGGATGTGCGCGGCAACCAGGGCTT

TCCGTGGGATATTCTGTTTCCGGCGGATCCGCCGTTTAGCCCGCAGAGCTGCC

GCCCGCAGAGCCGCAGCGAAAGCAAAAAAAACCGCGGCGGCCGCGAAGAAG

TGCTGGAACAGTGGGTGAACGGCCGCAAAAAACTGGAAGAACTGGAACGCG

AACTGCGCCGCGCGCGCAAAAAAATTAAAAAACTGGAAGATGATAACCCGTG

GCTGGGCAACGTGAAAGGCATTCTGGGCAAAAAAGATAAAGATGGCGAAGG

CGCGCCGCCGGCGAAACGCGCGCGCACCGATCAGATGGAAATTGATAGCGGC

CCGCGCAAACGCCCGCTGCGCGGCGGCTTTACCGATCGCGAACGCCAGGATC

ATCGCCGCCGCAAAGCGCTGAAAAACAAAAAAAAACAGCTGAGCGCGGGCG

GCAAAAGCCTGAGCAAAGAAGAAGAAGAAGAACTGAAACGCCTGACCCGCG

AAGATGAAGAACGCAAAAAAGAAGAACATGGCCCGAGCCGCCTGGGCGTGA

ACCCGAGCGAAGGCGGCCCGCGCGGCGCGCCGGGCGGCGGCTTTGTGCCGAG

CATGCAGGGCATTCCGGAAAGCCGCTTTACCCGCACCGGCGAAGGCCTGGAT

GTGCGCGGCAGCCGCGGCTTTCCGCAGGATATTCTGTTTCCGAGCGATCCGCC

GTTTAGCCCGCAGAGCTGCCGCCCGCAGGGAAGCGGAGCTACTAACTTCAGC

CTGCTGAAGCAGGCTGGAGACGTGGAGGAGAACCCTGGACCTATGGGCACC

AACCTGAGCACCAGCAACCCGCTGGGCTTTTTTCCGGATCATCAGCTGGATCC

GGCGTTTCGCGCGAACAGCGCGAACCCGGATTGGGATTTTAACCCGAACAAA

GATACCTGGCCGGATGCGAACAAAGTGGGCGGCCAGAACCTGAGCACCAGC

AACCCGCTGGGCTTTTTTCCGGATCATCAGCTGGATCCGGCGTTTCGCGCGAA

CACCGCGAACCCGGATTGGGATTTTAACCCGAACAAAGATACCTGGCCGGAT

GCGAACAAAGTGGGCAGCCAGAGCGAAACCCGCCGCGGCCGCCGCGGCACC

CGCGAAGAAACCCTGGAAAAATGGATTACCGCGCGCAAAAAAGCGGAAGAA

CTGGAAAAAGATCTGCGCAAAACCCGCAAAACCATTAAAAAACTGGAAGAA

GAAAACCCGTGGCTGGGCAACATTGTGGGCATTATTCGCAAAGGCAAAGATG

GCGAAGGCGCGCCGCCGGCGAAACGCCCGCGCACCGATCAGATGGAAGTGG

ATAGCGGCCCGGGCAAACGCCCGCATAAAAGCGGCTTTACCGATAAAGAACG

CGAAGATCATCGCCGCCGCAAAGCGCTGGAAAACAAAAAAAAACAGCTGAG

CGCCAGGCGGCAAAATTCTGAGCAAAGAAGAAGAAGAAGAACTGCGCCGCCT

GACCGATGAAGATGAAGAACGCAAACGCCGCGTGGCGGGCCCGCGCGTGGG

CGATGTGAACCCGAGCCGCGGCGGCCCGCGCGGCGCGCCGGGCGGCGGCTTT

GTGCCGCAGATGGCGGGCGTGCCGGAAAGCCCGTTTAGCCGCACCGGCGAAG

GCCTGGATATTCGCGGCACCCAGGGCTTTTCCGTGGGTGAGCCCGAGCCCGCC

GCAGCAGCGCCTGCCGCTGCTGGAATGCACCCCGCAGAGCCAGAGCGAAAGC

AAAAAAAACCGCCGCGGCGGCCGCGAAGATATTCTGGAAAAATGGATTACCA

-continued

CCCGCCGCAAAGCGGAAGAACTGGAAAAAGATCTGCGCAAAGCGCGCAAAA

CCATTAAAAAACTGGAAGATGAAAACCCGTGGCTGGGCAACATTATTTGGCAT

TATTCGCAAAGGCAAAGATGGCGAAGGCGCGCCGCCGGCGAAACGCCCGCG

CACCGATCAGATGGAAATTGATAGCGGCACCGGCAAACGCCCGCATAAAAGC

GGCTTTACCGATAAAGAACGCGAAGATCATCGCCGCCGCAAAGCGCTGGAAA

ACAAAAAAAAACAGCTGAGGAGCGGCGGCAAAAACCTGAGCCGCGAAGAAG

AAGAAGAACTGGGCCGCCTGACCGTGGAAGATGAAGAACGCCGCCGCCGCG

TGGCGGGCCCGCGCACCGGCGATGTGAACCTGAGCGGCGGCGGCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGTGATGAG↓AATTCCGT

SEQ ID NO: 17 delta 2 optimized
GCCGGCACTAACCTGTCTACATCAAACCCTCTGGGATTTTTCCCCGATCATCAGCTGGAC

CCCGCATTTCGCGCTAACTCTGCTAACCCTGACTGGGATTTCAACCCTAATAAGGACACA

TGGCCAGATGCCAACAAGGTCGGCGGCCAGAACCTGTCCACCTCTAATCCCCTGGGCTTC

TTTCCTGACCACCAGCTGGATCCTGCCTTCAGGGCCAACACCGCCAATCCCGACTGGGAC

TTCAACCCAAATAAGGATACCTGGCCTGACGCTAACAAGGTCGGCAGCCGGTCCGAGTCT

AAGAAGAATAGGGGAGGAAGGGAGGAGATCCTGGAGCAGTGGGTGGGCGCCAGAAAGAAG

CTGGAGGAGCTGGAGCGGGACCTGAGAAAGATCAAGAAGAAGATCAAGAAGCTGGAGGAG

GAGAACCCCTGGCTGGGCAATATCAAGGGCATCCTGGGCAAGAAGGATCGGGAGGGAGAG

GGAGCACCACCTGCAAAGAGGGCCAGAGCCGACCAGATGGAGGTGGATTCCGGCCCTAGG

AAGCGCCCATTCAGAGGCGAGTTTACAGACAAGGAGCGGAGAGATCACAGGCGCCGSAAG

GCCCTGGAGAACAAGAGGAAGCAGCTGAGCTCCGGCGGCAAGAGCCTGTCCAAGGAGGAG

GAGGAGGAGCTGCGCAAGCTGACCGAGGAGGACGAGAGAAGGGAGAGGAGGGTGGCAGGA

CCTAGGGTGGGAGGCGTGAACCCACTGGAGGGAGGAACAAGAGGAGCACCCGGAGGAGGC

TTCGTGCCTTCTATGCAGGGCGTGCCTGAGAGCCCATTTGCCAGGACCGGAGAGGGCCTG

GACGTGAGAGGCAATCAGGGCTTCCCATGGGACATCCTGTTTCCCGCCGATCCACCCTTC

AGCCCACAGTCCTGCAGGCCCCAGTCTCGCAGCGAGTCCAAGAAGAACAGAGGCGGAAGG

GAGGAGGTGCTGGAGCAGTGGGTGAATGGCAGGAAGAAGCTGGAAGAACTGGAGAGGGAG

CTGAGAAGGGCCCGCAAGAAGATCAAGAAGCTGGAAGACGATAATCCTTGGCTGGGCAAT

GTGAAAGGCATCCTGGGCAAGAAGGACAAGGATGGAGAGGGAGCACCTCCAGCAAAGAGG

GCAAGAACAGACCAGATGGAGATCGATTCCGGACCAAGGAAGCGCCCTCTGAGGGGAGGC

TTCACCGACCGGGAGAGACAGGATCACCGCCGGAGAAAGGCCCTGAAGAACAAGAAGAAG

CAGCTGAGCGCCGGCGGCAAGTCTCTGAGTAAAGAAGAAGAGGAGGAGCTGAAGCGGCTG

ACAAGAGAGGACGAGGAGAGGAAGAAGGAGGAGCACGGACCATCCAGGCTGGGAGTGAAT

CCTTCTGAGGGAGGACCAAGGGGCGCCCCTGGCGGAGGCTTCGTGCCTAGCATGCAGGGC

ATCCCAGAGTCCAGGTTTACCAGGACAGGCGAAGGCCTGGACGTGCGGGGCTCTAGAGGC

TTTCCCCAGGACATCCTGTTCCCTAGCGATCCCCCTTTTTCTCCTCAGAGCTGTAGACCA

CAGGGAAGCGGAGCTACTAACTTCAGCCTGCTGAAGCAGGCTGGAGACGTGGAGGAGAAC

CCTGGACCTATGGGCACCAACCTGTCCACATCTAACCCTCTGGGCTTCTTTCCAGATCAT

-continued

CAGCTGGACCCAGCCTTCAGGGCCAACAGCGCCAATCCAGACTGGGACTTCAACCCCAAT

AAGGACACATGGCCTGACGCAAACAAGGTCGGAGGACAGAACCTGAGCACCTCCAATCCA

CTGGGCTTCTTTCCCGACCACCAGCTGGATCCAGCCTTCCGCGCCAACACTGCTAACCCT

GATTGGGACTTCAACCCTAATAAGGATACATGGCCTGATGCCAATAAGGTCGGCTCTCAG

AGCGAGACAAGGAGGGGCCGGAGAGGAACCAGGGAGGAGACACTGGAGAAGTGGATCACC

GCCCGCAAGAAGGCCGAGGAGCTGGAGAAGGACCTGAGGAAGACCCGCAAGACAATCAAG

AAGCTGGAAGAAGAGAACCCATGGCTGGGCAATATCGTGGGCATCATCAGAAAGGGCAAG

GACGGCGAGGGAGCACCACCAGCAAAGAGGCCCCGCACAGATCAGATGGAAGTGGATTCC

GGACCTGGCAAGCGGCCACACAAGTCTGGCTTCACCGACAAGGAGAGAGAGGACCATAGG

CGCCGGAAGGCCCTGGAAAACAAGAAGAAGCAATTATCTGCCGGCGGCAAGATCCTGAGT

AAAGAAGAGGAAGAGGAGCTGAGAAGGCTGACCGACGAGGATGAGGAGAGGAAGCGCCGG

GTGGCCGGCCCACGCGTGGGCGACGTGAATCCCTCCAGGGGAGGACCAAGAGGAGCACCT

GGAGGCGGCTTCGTGCCCCAGATGGCCGGCGTGCCCGAGTCCCCTTTTTCTCGGACCGGC

GAGGGCCTGGATATCAGAGGCACACAGGGCTTTCCATGGGTGTCCCCCTCTCCTCCACAG

CAGAGGCTGCCACTGCTGGAGTGCACACCCCAGAGCCAGAGCGAATCTAAGAAGAACAGA

A

GGGGAGGCCGCGAGGACATCCTGGAAAAATGGATCACCACACGCAGAAAAGCTGAAGAAC

TGGAAAAGGACCTGCGGAAGGCCAGAAAGACCATCAAGAAGCTGGAGGATGAAAATCCAT

GGCTGGGAAACATCATCGGCATCATCCGGAAGGGCAAGGACGGGGAAGGCGCACCACCTG

CAAAGCGGCCTAGAACCGATCAGATGGAAATCGATAGCGGCACAGGCAAGAGGCCACACA

AGTCCGGCTTCACCGATAAAGAGCGCGAGGATCACAGAAGGCGCAAGGCCCTGGAGAACA

AGAAGAAGCAATTAAGCAGCGGCGGCAAGAATCTGTCCAGAGAAGAGGAGGAAGAGCTGG

GCCGCCTGACAGTGGAGGACGAGGAGCGGAGAAGGCGCGTGGCAGGACCCAGAACCGGCG

ATGTGAACCTGTCCGGAGGAGGACCTAGGGGAGCACCAGGAGGCGGCTTCGTGCCTAGAA

TGGAGGGCGTGCCAGAGTCTCCCTTTACCCGGACAGGCGAGGGCCTGGACATCAGAGGCA

ATCAGGGCTTTCCCTGGGTCCGCCCCTCCCCCCCTCAGCAGAGACTGCCACTGCTGGAAT

GCACACCACAG

SEQ ID NO: 18 delta 2 codon optimized + Restriction sites
A↓AGCTT*GCACC*ATG*G*CCGGCACTAACCTGTCTACATCAAACCCTCTGGGATTTTTCCCC

GATCATCAGCTGGACCCCGCATTTCGCGCTAACTCTGCTAACCCTGACTGGGATTTCAAC

CCTAATAAGGACACATGGCCAGATGCCAACAAGGTCGGCGGCCAGAACCTGTCCACCTCT

AATCCCCTGGGCTTCTTTCCTGACCACCAGCTGGATCCTGCCTTCAGGGCCAACACCGCC

AATCCCGACTGGGACTTCAACCCAAATAAGGATACCTGGCCTGACGCTAACAAGGTCGGC

AGCCGGTCCGAGTCTAAGAAGAATAGGGGAGGAAGGGAGGAGATCCTGGAGCAGTGGGTG

GGCGCCAGAAAGAAGCTGGAGGAGCTGGAGCGGGACCTGAGAAAGATCAAGAAGAAGATC

AAGAAGCTGGAGGAGGAGAACCCCTGGCTGGGCAATATCAAGGGCATCCTGGGCAAGAAG

GATCGGGAGGGAGAGGGAGCACCACCTGCAAAGAGGGCCAGAGCCGACCAGATGGAGGTG

GATTCCGGCCCTAGGAAGCGCCCATTCAGAGGCGAGTTTACAGACAAGGAGCGGAGAGAT

CACAGGCGCCGGAAGGCCCTGGAGAACAAGAGGAAGCAGCTGAGCTCCGGCGGCAAGAGC

CTGTCCAAGGAGGAGGAGGAGGAGCTGCGCAAGCTGACCGAGGAGGACGAGAGATGGGAG

AGGAGGGTGGCAGGACCTAGGGTGGGAGGCGTGAACCCACTGGAGGGAGGAACAAGAGGA

-continued

GCACCCGGAGGAGGCTTCGTGCCTTCTATGCAGGGCGTGCCTGAGAGCCCATTTGCCAGG

ACCGGAGAGGGCCTGGACGTGAGAGGCAATCAGGGCTTCCCATGGGACATCCTGTTTCCC

GCCGATCCACCCTTCAGCCCACAGTCCTGCAGGCCCCAGTCTCGCAGCGAGTCCAAGAAG

AACAGAGGCGGAAGGGAGGAGGTGCTGGAGCAGTGGGTGAATGGCAGGAAGAAGCTGGAA

GAACTGGAGAGGGAGCTGAGAAGGGCCCGCAAGAAGATCAAGAAGCTGGAAGACGATAAT

CCTTGGCTGGGCAATGTGAAAGGCATCCTGGGCAAGAAGGACAAGGATGGAGAGGGAGCA

CCTCCAGCAAAGAGGGCAAGAACAGACCAGATGGAGATCGATTCCGGACCAAGGAAGCGC

CCTCTGAGGGGAGGCTTCACCGACCGGGAGAGACAGGATCACCGCCGGAGAAAGGCCCTG

AAGAACAAGAAGAAGCAGCTGAGCGCCGGCGGCAAGTCTCTGAGTAAAGAAGAAGAGGAG

GAGCTGAAGCGGCTGACAAGAGAGGACGAGGAGAGGAAGAAGGAGGAGCACGGACCATCC

AGGCTGGGAGTGAATCCTTCTGAGGGAGGACCAAGGGGCGCCCCTGGCGGAGGCTTCGTG

CCTAGCATGCAGGGCATCCCAGAGTCCAGGTTTACCAGGACAGGCGAAGGCCTGGACGTG

CGGGGCTCTAGAGGCTTTCCCCAGGACATCCTGTTCCCTAGCGATCCCCCTTTTTCTCCT

CAGAGCTGTAGACCACAGGGAAGCCGAGCTACTAACTTCAGCCTGCTGAAGCAGGCTGGA

GACGTGGAGGAGAACCCTGGACCTATGGGCACCAACCTGTCCACATCTAACCCTCTGGGC

TTCTTTCCAGATCATCAGCTGGACCCAGCCTTCAGGGCCAACAGCGCCAATCCAGACTCC

GACTTCAACCCCAATAAGGACACATGGCCTGACGCAAACAAGGTCGGAGGACAGAACCTG

AGCACCTCCAATCCACTGGGCTTCTTTCCCGACCACCAGCTGGATCCAGCCTTCCGCGCC

AACACTGCTAACCCTGATTGGGACTTCAACCCTAATAAGGATACATGGCCTGATGCCAAT

AAGGTCGGCTCTCAGAGCGAGACAAGGAGGGGCCGGAGAGGAACCAGGGAGGAGACACTG

GAGAAGTGGATCACCGCCCGCAAGAAGGCCGAGGAGCTGGAGAAGGACCTGAGGAAGACC

CGCAAGACAATCAAGAAGCTGGAAGAAGAGAACCCATGGCTGGGCAATATCGTGGGCATC

ATCAGAAAGGGCAAGGACGGCGAGGGAGCACCACCAGCAAAGAGGCCCCGCACAGATCAG

ATGGAAGTGGATTCCGGACCTGGCAAGCGGCCACACAAGTCTGGCTTCACCGACAAGGAG

AGAGAGGACCATAGGCGCCGGAAGGCCCTGGAAAACAAGAAGAAGCAATTATCTGCCGGC

GGCAAGATCCTGAGTAAAGAAGAGGAAGAGGAGCTGAGAAGGCTGACCGACGAGGATGAG

GAGAGGAAGCGCCGGGTGGCCGGCCCACGCGTGGGCGACGTGAATCCCTCCAGGGGAGGA

CCAAGAGGAGCACCTGGAGGCGGCTTCGTGCCCCAGATGGCCGGCGTGCCCGAGTCCCCT

TTTTCTCGGACCGGCGAGGGCCTGGATATCAGAGGCACACAGGGCTTTCCATGGGTGTCC

CCCTCTCCTCCACAGCAGAGGCTGCCACTCCTCGACTGCACACCCCAGAGCCAGAGCGAA

TCTAAGAAGAACAGAA

GGGGAGGCCGCGAGGACATCCTGGAAAAATGGATCACCACACGCAGAAAAGCTGAAGAAC

TGGAAAAGGACCTGCGGAAGGCCAGAAAGACCATCAAGAAGCTGGAGGATGAAAATCCAT

GGCTGGGAAACATCATCGGCATCATCCGGAAGGGCAAGGACGGGGAAGGCGCACCACCTG

CAAAGCGGCCTAGAACCGATCAGATGGAAATCGATAGCGGCACAGGCAAGAGGCCACACA

AGTCCGGCTTCACCGATAAAGAGCGCGAGGATCACAGAAGGCGCAAGGCCCTGGAGAACA

AGAAGAAGCAATTAAGCAGCGGCGGCAAGAATCTGTCCAGAGAAGAGGAGGAAGAGCTCC

GCCCCCTGACAGTGGAGGACGAGGAGCGGAGAAGGCGCCTGGCAGGACCCAGAACCGGCG

ATGTGAACCTGTCCGGAGGAGGACCTAGGGGAGCACCAGGAGGCGGCTTCGTGCCTAGAA

TGGAGGGCGTGCCAGAGTCTCCCTTTACCCGGACAGGCGAGGGCCTGGACATCAGAGGCA

-continued

ATCAGGGCTTTCCCTGGGTCCGCCCCTCCCCCCCTCAGCAGAGACTGCCACTGCTGGAAT

GCACACCACAGTGATGAG↓AATTCCGT

SEQ ID NO: 19 delta 2 protein
MAGTNLSTSNPLGFFPDHQLDPAFRANSANPDWDFNPNKDTWPDANKVGGQNL

STSNPLGFFPDHQLDPAFRANTANPDWDFNPNKDTWPDANKVGSRSESKKNRGG

REEILEQWVGARKKLEELERDLRKIKKKIKKLEEENPWLGNIKGILGKKDREGEG

APPAKRARADQMEVDSGPRKRPFRGEFTDKERRDHRRRKALENKRKQLSSGGKS

LSKEEEEELRKLTEEDERRERRVAGPRVGGVNPLEGGTRGAPGGGFVPSMQGVP

ESPFARTGEGLDVRGNQGFPWDILFPADPPFSPQSCRPQSRSESKKNRGGREEVLE

QWVNGRKKLEELERELRRARKKIKKLEDDNPWLGNVKGILGKKDKDGEGAPPA

KRARTDQMEIDSGPRKRPLRGGFTDRERQDHRRRKALKNKKKQLSAGGKSLSKE

EEEELKRLTREDEERKKEEHGPSRLGVNPSEGGPRGAPGGGFVPSMQGIPESRFTR

TGEGLDVRGSRGFPQDILFPSDPPFSPQSCRPQGSGATNFSLLKQAGDVEENPGPM

GTNLSTSNPLGFFPDHQLDPAFRANSANPDWDFNPNKDTWPDANKVGGQNLSTS

NPLGFFPDHQLDPAFRANTANPDWDFNPNKDTWPDANKVGSQSETRRGRRGTR

EETLEKWITARKKAEELEKDLRKTRKTIKKLEENPWLGNIVGIIRKGKDGEGAPP

AKRPRTDQMEVDSGPGKRPHKSGFTDKEREDHRRRKALENKKKQLSAGGKILSK

EEEEELRRLTDEDEERKRRVAGPRVGDVNPSRGGPRGAPGGGFVPQMAGVPESP

FSRTGEGLDIRGTQGFPWVSPSPPQQRLPLLECTPQSQSESKKNRRGGREDILEKW

ITTRRKAEELEKDLRKARKTIKKLEDENPWLGNIIGIIRKGKDGEGAPPAKRPRTD

QMEIDSGTGKRPHKSGFTDKEREDHRRRKALENKKKQLSSGGKNLSREEEEELG

RLTVEDEERRRRVAGPRTGDVNLSGGGPRGAPGGGFVPRMEGVPESPFTRTGEG

LDIRGNQGFPWVRPSPPQQRLPLLECTPQ

SEQ ID NO: 20: delta 3 wt
GGCACCAACCTGAGCACCAGCAACCCGCTGGGCTTTTTCCGGATCATCAGCT

GGATCCGGCGTTTCGCGCGAACAGCGCGAACCCGGATTGGGATTTTAACCCG

AACAAAGATACCTTGGCCGGATGCGAACAAAGTGGGCGGCCAGAACCTGAGC

ACCAGCAACCCGCTGGGCTTTTTCCGGATCATCAGCTGGATCCGGCGTTTCG

CGCGAACACCGCGAACCCGGATTGGGATTTTAACCCGAACAAAGATACCTGG

CCGGATGCGAACAAAGTGGGCAGCCGCAGCGAAAGGAAAAAAACCGCGGC

GGCCGCGAAGAAATTCTGGAACAGTGGGTGGGCGCGCGCAAAAAACTGGAA

GAACTGGAACGCGATCTGCGCAAAATTAAAAAAAAAATTAAAAAACTGGAA

GAAGAAAACCCGTGGCTGGGCAACATTAAAGGCATTCTGGGCAAAAAAGATC

GCGAAGGCGAAGGCGCGCCGCCGGCGAAACGCGCGCGCGCGGATCAGATGG

AAGTGGATAGCGGCCCGCGCAAACGCCCGTTTCGCGGCGAATTTACCGATAA

AGAACGCCGCGATCATCGCCGCCGCAAAGCGCTGGAAAACAAACGCAAACA

GCTGAGCAGCGGCGGCAAAAGCCTGAGCAAAGAAGAAGAAGAAGAACTGCG

CAAACTGACCGAAGAAGATGAACGCCGCGAACGCCGCGTGGCGGGCCCGCG

CGTGGGCGGCGTGAACCCGCTGGAAGGCGGCACCCGCGGCGCGCCGGGCGG

CGGCTTTGTGCCGAGCATGCAGGGCGTGCCGGAAAGCCCGTTTGCGCGCACC

GGCGAAGGCCTGGATGTGCGCGGCAACCAGGGCTTTCCGTGGGATATTCTGT

TTCCGGCGGATCCGCCGTTTAGCCCGCAGAGCTGCCGCCCGCAGAGCCGCAG

-continued

CGAAAGCAAAAAAAACCGCGGCGGCCGCGAAGAAGTGCTGGAACAGTGGGT

GAACGGCCGCAAAAAACTGGAAGAACTGGAACGCGAACTGCGCCGCGCGCG

CAAAAAAATTAAAAAACTGGAAGATGATAACCCGTGGCTGGGCAACGTGAA

AGGCATTCTGGGCAAAAAAGATAAAGATGGCGAAGGCGCGCCGCCGGCGAA

ACGCGCGCGCACCGATCAGATGGAAATTGATAGCGGCCCGCGCAAACGCCCG

CTGCGCGGCGGCTTTACCGATCGCGAACGCCAGGATCATCGCCGCCGCAAAG

CGCTGAAAAACAAAAAAAAACAGCTGAGCGCGGGCGGCAAAAGCCTGAGCA

AAGAAGAAGAAGAAGAACTGAAACGCCTGACCCGCGAAGATGAAGAACGCA

AAAAAGAAGAACATGGCCCGAGCCGCCTGGGCGTGAACCCGAGCGAAGGCG

GCCCGCGCGGCGCGCCGGGCGGCGGCTTTGTGCCGAGCATGCAGGGCATTCC

GGAAAGCCGCTTTACCCGCACCGGCGAAGGCCTGGATGTGCGCGGCAGCCGC

GGCTTTCCGCAGGATATTCTGTTTCCGAGCGATCCGCCGTTTAGCCCGCAGAG

CTGCCGCCCGCAGGGCACCAACCTGAGCACCAGCAACCCGCTGGGCTTTTTTC

CGGATCATCAGCTGGATCCGGCGTTTCGCGCGAACAGCGCGAACCCGGATTCG

GGATTTTAACCCGAACAAAGATACCTGGCCGGATGCGAACAAAGTGGGCGGC

CAGAACCTGAGCACCAGCAACCCGCTGGGCTTTTTTCCGGATCATCAGCTGGA

TCCGGCGTTTCGCGCGAACACCGCGAACCCGGATTGGGATTTTAACCCGAAC

AAAGATACCTGGCCGGATGCGAACAAAGTGGGCGGAAGCGGAGCTACTAACTTC

AGCCTGCTGAAGCAGGCTGGAGACGTGGAGGAGAACCCTGGACCTATGGGCACCAACC

TGAGCACCAGCAACCCGCTGGGCTTTTTTCCGGATCATCAGCTGGATCCGGCG

TTTCGCGCGAACAGCGCGAACCCGGATTGGGATTTTAACCCGAACAAAGATA

CCTGGCCGGATGCGAACAAAGTGGGCGGCCAGAACCTGAGCACCAGCAACCC

GCTGGGCTTTTTTCCGGATCATCAGCTGGATCCGGCGTTTCGCGCGAACACCG

CGAACCCGGATTGGGATTTTAACCCGAACAAAGATACCTGGCCGGATGCGAA

CAAAGTGGGCAGCCAGAGCGAAACCCGCCGCGGCCGCCGCGGCACCCGCGA

AGAAACCCTGGAAAAATGGATTACCGCGCGCAAAAAAGCGGAAGAACTGGA

AAAAGATCTGCGCAAAACCCGCAAAACCATTAAAAAACTGGAAGAAGAAAA

CCCGTGGCTGGGCAACATTGTGGGCATTATTCGCAAAGGCAAAGATGGCGAA

GGCGCGCCGCCGGCGAAACGCCCGCGCACCGATCAGATGGAAGTGGATAGC

GGCCCGGGCAAACGCCCGCATAAAAGCGGCTTTACCGATAAAGAACGCGAA

GATCATCGCCGCCGCAAAGCGCTGGAAAACAAAAAAAAACAGCTGAGCGCG

GGCGGCAAAATTCTGAGCAAAGAAGAAGAAGAAGAACTGCGCCGCCTGACC

GATGAAGATGAAGAACGCAAACGCCGCGTGGCGGGCCCGCGCGTGGGCGAT

GTGAACCCGAGCCGCGGCGGCCCGCGCGGCGCGCCGGGCGGCGGCTTTGTGC

CGCAGATGGCGGGCGTGCCGGAAAGCCCGTTTAGCCGCACCGGCGAAGGCCT

GGATATTCGCGGCACCCAGGGCTTTCCGTGGGTGAGCCCGAGCCCGCCGCAG

CAGCGCCTGCCGCTGCTGGAATGCACCCCGCAGAGCCAGAGCGAAAGCAAAA

AAAACCGCCGCGGCGGCCGCGAAGATATTCTGGAAAAATGGKTTACCACCCG

CCGCAAAGCGGAAGAACTGGAAAAAGATCTGCGCAAAGCGCGCAAAACCAT

TAAAAAACTGGAAGATGAAAACCCGTGGCTGGGCAACATTATTGGCATTATT

-continued
CGCAAAGGCAAAGATGGCGAAGGCGCGCCGCCGGCGAAACGCCCGCGCACC

GATCAGATGGAAATTGATAGCGGCACCGGCAAACGCCCGCATAAAAGCGGCT

TTACCGATAAAGAACGCGAAGATCATCGCCGCCGCAAAGCGCTGGAAAACAA

AAAAAAACAGCTGAGCAGCGGCGGCAAAAACCTGAGCCGCGAAGAAGAAGA

AGAACTGGGCCGCCTGACCGTGGAAGATGAAGAACGCCGCCGCCGCGTGGCG

GGCCCGCGCACCGGCGATGTGAACCTGAGCGGCGGCGGCCCGCGCGGCGCGC

CGGGCGGCGGCTTTGTGCCGCGCATGGAAGGCGTGCCGGAAAGCCCGTTTAC

CCGCACCGGCGAAGGCCTGGATATTCGCGGCAACCAGGGCTTTCCGTGGGTG

CGCCCGAGCCCGCCGCAGCAGCGCCTGCCGCTGCTGGAATGCACCCCGCAGG

GCACCAACCTGAGCACCAGCAACCCGCTGGGCTTTTTTCCGGATCATCAGCTG

GATCCGGCGTTTCGCGCGAACAGCGCGAACCCGGATTGGGATTTTAACCCGA

ACAAAGATACCTGGCCGGATGCGAACAAAGTGGGCGGCCAGAACCTGAGCA

CCAGCAACCCGCTGGGCTTTTTTCCGGATCATCAGCTGGATCCGGCGTTTCGC

GCGAACACCGCGAACCCGGATTGGGATTCTTAACCCGAACAAAGATACCTGGC

CGGATGCGAACAAAGTGGGC

SEQ ID NO: 21 delta 3 wt + with restriction sites
(HindIII/EcoRI)
A1AGCTTGCACCATGGCCGGCACCAACCTGAGCACCAGCAACCCGCTGGGCTTTT

TTCCGGATCATCAGCTGGATCCGGCGTTTCGCGCGAACAGCGCGAACCCGGA

TTGGGATTTTAACCCGAACAAAGATACCTGGCCGGATGCGAACAAAGTGGGC

GGCCAGAACCTGAGCACCAGCAACCCGCTGGGCTTTTTTCCGGATCATCAGCT

GGATCCGGCGTTTCGCGCGAACACCGCGAACCCGGATTGGGATTTTAACCCG

AACAAAGATACCTGGCCGGATGCGAACAAAGTGGGCAGCCGCAGCGAAAGC

AAAAAAAACCGCGGCGGCCGCGAAGAAATTCTGGAACAGTGGGTGGGCGCG

CGCAAAAAACTGGAAGAACTGGAACGCGATCTGCGCAAAATTAAAAAAAAA

ATTAAAAAACTGGAAGAAGAAAACCCGTGGCTGGGCAACATTAAAGGCATTC

TGGGCAAAAAAGATCGCGAAGGCGAAGGCGCGCCGCCGGCGAAACGCGCGC

GCGCGGATCAGATGGAAGTGGATAGCGGCCCGCGCAAACGCCCGTTTCGCGG

CGAATTTACCGATAAAGAACGCCGCGATCATCGCCGCCGCAAAGCGCTGGAA

AACAAACGCAAACAGCTGAGCAGCGGCGGCAAAAGCCTGAGCAAAGAAGAA

GAAGAAGAACTGCGCAAACTGACCGAAGAAGATGAACGCCGCGAACGCCGC

GTGGCGGGCCCGCGCGTGGGCGGCGTGAACCCGCTGGAAGGCGGCACCCGCG

GCGCGCCGGGCGGCGGCTTTGTGCCGAGCATGCAGGGCGTGCCGGAAAGCCC

GTTTGCGCGCACCGGCGAAGGCCTGGATGTGCGCGGCAACCAGGGCTTTCCG

TGGGATATTCTGTTTCCGGCGGATCCGCCGTTTAGCCCGCAGAGCTGCCGCCC

GCAGAGCCGCAGCGAAAGCAAAAAAAACCGCGGCGGCCGCGAAGAAGTGCT

GGAACAGTGGGTGAACGGCCGCAAAAAACTGGAAGAACTGGAACGCGAACT

GCGCCGCGCGCGCAAAAAAATTAAAAAACTGGAAGATGATAACCCGTGGCTG

GGCAACGTGAAAGGCATTCTGGGCAAAAAAGATAAAGATGGCGAAGGCGCG

CCGCCGGCGAAACGCGCGCGCACCGATCAGATGGAAATTGATAGCGGCCCGC

GCAAACGCCCGCTGCGCGGCGGCTTTACCGATCGCGAACGCCAGGATCATCG

CCGCCGCAAAGCGCTGAAAAACAAAAAAAAACAGCTGAGCGCGGGCGGCAA

-continued

AAGCCTGAGCAAAGAAGAAGAAGAAGAACTGAAACGCCTGACCCGCGAAGA

TGAAGAACGCAAAAAAGAAGAACATGGCCCGAGCCGCCTGGGCGTGAACCC

GAGCGAAGGCGGCCCGCGCGGCGCGCCGGGCGGCGGCTTTGTGCCGAGCATG

CAGGGCATTCCGGAAAGCCGCTTTACCCGCACCGGCGAAGGCCTGGATGTGC

GCGGCAGCCGCGGCTTTCCGCAGGATATTCTGTTTCCGAGCGATCCGCCGTTT

AGCCCGCAGAGCTGCCGCCCGCAGGGCACCAACCTGAGCACCAGCAACCCGC

TGGGCTTTTTTCCGGATCATCAGCTGGATCCGGCGTTTCGCGCGAACAGCGCG

AACCCGGATTGGGATTTTAACCCGAACAAAGATACCTGGCCGGATGCGAACA

AAGTGGGCGGCCAGAACCTGAGCACCAGCAACCCGCTGGGCTTTTTTCCGGA

TCATCAGCTGGATCCGGCGTTTCGCGCGAACACCGCGAACCCGGATTGGGAT

TTTAACCCGAACAAAGATACCTGGCCGGATGCGAACAAAGTGGGCGGAAGCGG

AGCTACTAACTTCAGCCTGCTGAAGCAGGCTGGAGACGTGGAGGAGAACCCTGGACCTA

TGGGGCACCAACCTGAGCACCAGCAACCCGCTGGGCTTTTTTCCGGATCATCA

GCTGGATCCGGCGTTTCGCGCGAACAGCGCGAACCCGGATTGGGATTTTAAC

CCGAACAAAGATACCTGGCCGGATGCGAACAAAGTGGGCGGCCAGAACCTG

AGCACCAGCAACCCGCTGGGCTTTTTTCCGGATCATCAGCTGGATCCGGCGTT

TCGCGCGAACACCGCGAACCCGGATTGGGATTTTAACCCGAACAAAGATACC

TGGCCGGATGCGAACAAAGTGGGCAGCCAGAGCGAAACCCGCCGCGGCCGC

CGCGGCACCCGCGAAGAAACCCTGGAAAAATGGATTACCGCGCGCAAAAAA

GCGGAAGAACTGGAAAAAGATCTGCGCAAAACCCGCAAAACCATTAAAAAA

CTGGAAGAAGAAAACCCGTGGCTGGGCAACATTGTGGGCATTATTCGCAAAG

GCAAAGATGGCGAAGGCGCGCCGCCGGCGAAACGCCCGCGCACCGATCAGA

TGGAAGTGGATAGCGGCCCGGGCAAACGCCCGCATAAAAGCGGCTTTACCGA

TAAAGAACGCGAAGATCATCGCCGCCGCAAAGCGCTGGAAAACAAAAAAAA

ACAGCTGAGCGCGGGCGGCAAAATTCTGAGCAAAGAAGAAGAAGAAGAACT

GCGCCGCCTGACCGATGAAGATGAAGAACGCAAACGCCGCGTGGCGGGCCC

GCGCGTGGGCGATGTGAACCCGAGCCGCGGCGGCCCGCGCGGCGCGCCGGGC

GGCGGCTTTGTGCCGCAGATGGCGGGCGTGCCGGAAAGCCCGTTTAGCCGCA

CCGGCGAAGGCCTGGATATTCGCGGCACCCAGGGCTTTCCGTGGGTGAGCCC

GAGCCCGCCGCAGCAGCGCCTGCCGCTGCTGGAATGCACCCCGCAGAGCCAG

AGCGAAAGCAAAAAAAACCGCCGCGGCGGCCGCGAAGATATTCTGGAAAAA

TGGATTACCACCCGCCGCAAAGCGGAAGAACTGGAAAAAGATCTGCGCAAA

GCGCGCAAAACCATTAAAAAACTGGAAGATGAAAACCCGTGGCTGGGCAAC

ATTATTGGCATTATTCGCAAAGGCAAAGATGGCGAAGGCGCGCCGCCGGCGA

AACGCCCGCGCACCGATCAGATGGAAATTGATAGCGGCACCGGCAAACGCCC

GCATAAAAGCGGCTTTACCGATAAAGAACGCGAAGATCATCGCCGCCGCAAA

GCGCTGGAAAACAAAAAAAAACAGCTGAGCAGCGGCGGCAAAAACCTGAGC

CGCGAAGAAGAAGAAGAACTGGGCCGCCTGACCGTGGAAGATGAAGAACGC

CGCCGCCGCGTGGCGGGCCCGCGCACCGGCGATGTGAACCTGAGCGGCGGCG

GCCCGCGCGGCGCGCCGGGCGGCGGCTTTGTGCCGCGCATGGAAGGCGTGCC

-continued

GGAAAGCCCGTTTACCCGCACCGGCGAAGGCCTGGATATTCGCGGCAACCAG

GGCTTTCCGTGGGTGCGCCCGAGCCCGCCGCAGCAGCGCCTGCCGCTGCTGG

AATGCACCCCGCAGGGCACCAACCTGAGCACCAGCAACCCGCTGGGCTTTTT

TCCGGATCATCAGCTGGATCCGGCGTTTCGCGCGAACAGCGCGAACCCGGAT

TGGGATTTTAACCCGAACAAAGATACCTGGCCGGATGCGAACAAAGTGGGCG

GCCAGAACCTGAGCACCAGCAACCCGCRTGGCTTTTTTCCGGATCATCAGCTG

GATCCGGCGTTTCGCGCGAACACCGCGAACCCGGATTGGGATTTTAACCCGA

ACAAAGATACCTGGCCGGATGCGAACAAAGTGGGCTGATGAG↓AATTCCGT

SEQ ID NO: 22: delta 3 optimized

GCCGGCACCAATCTGTCTACCTCAAATCCCCTGGGCTTCTTCCCCGATCATCA

GCTGGACCCTGCCTTCCGAGCAAATTCCGCTAATCCTGATTGGGATTTCAACC

CAAATAAGGACACATGGCCAGATGCCAACAAGGTCGGCGGCCAGAACCTGTC

CACCTCTAATCCTCTGGGCTTCTTTCCAGACCACCAGCTGGATCCCGCCTTCA

GGGCCAACACAGCCAATCCCGACTGGGACTTCAACCCTAATAAGGACACCTG

GCCTGACGCCAACAAGGTCGGCAGCAGGTCCGAGTCTAAGAAGAATAGGGG

AGGAAGGGAGGAGATCCTGGAGCAGTGGGTGGGAGCACGCAAGAAGCTGGA

GGAGCTGGAGCGGGACCTGAGAAAGATCAAGAAGAAGATCAAGAAGCTGGA

GGAGGAGAACCCCTGGCTGGGCAATATCAAGGGCATCCTGGGCAAGAAGGA

TCGGGAGGGAGAGGGAGCACCACCTGCAAAGAGGGCCAGAGCCGACCAGAT

GGAGGTGGATTCCGGACCAAGGAAGCGCCCTTTCAGAGGAGAGTTTACAGAC

AAGGAGCGGAGAGATCACAGGCGCCGGAAGGCCCTGGAGAACAAGCGGAAG

CAGCTGAGCTCCGGCGGCAAGAGCCTGTCCAAGGAGGAGGAGGAGGAGCTG

AGAAAGCTGACCGAGGAGGACCTAGAGAAGGGAGAGGAGGGTGGCCGGCCCC

AGGGTGGGCGGCGTGAACCCTCTGGAGGGAGGAACAAGGGGAGCACCAGGA

GGAGGCTTCGTGCCTTCCATGCAGGGCGTGCCCGAGTCTCCTTTTGCCAGGAC

CGGAGAGGGCCTGGACGTGCGCGGCAATCAGGGCTTCCCATGGGACATCCTG

TTTCCCGCCGATCCACCCTTCTCTCCCCAGAGCTGCAGGCCTCAGTCTCGCAG

CGAGTCCAAGAAGAACAGAGGCGGAAGGGAGGAGGTGCTGGAGCAGTGGGT

GAATGGCAGGAAGAAGCTGGAAGAACTGGAGAGGGAGCTGAGAAGGGCCCG

CAAGAAGATCAAGAAGCTGGAAGACGATAATCCTTGGCTGGGCAATGTGAAA

GGCATCCTGGGCAAGAAGGACAAGGATGGAGAGGGAGCACCTCCAGCAAAG

AGGGCAAGAACAGACCAGATGGAGATCGATTCTGGACCAAGGAAGCGCCCC

CTGAGGGGAGGCTTCACCGACCGGGAGAGACAGGATCACCGCCGGAGAAAG

GCCCTGAAGAACAAGAAGAAGCAGCTGAGCGCCGGCGGCAAGTCTCTGAGT

AAAGAAGAAGAGGAGGAGCTGAAGCGGCTGACCAGAGAGGACGAGGAGCG

GAAGAAGGAGGAGCACGGCCCAAGCAGACTGGGAGTGAATCCATCCGAGGG

AGGACCTAGAGGCGCCCCTGGCGGCGGCTTCGTGCCTTCTATGCAGGGCATC

CCAGAGAGCAGGTTTACCAGGACAGGCGAAGGCCTGGACGTGCGGGGCTCCA

GAGGCTTTCCCCAGGACATCCTGTTCCCTTCTGATCCCCCTTTTTCCCCACAGT

CTTGTAGGCCCCAGGGCACCAACCTGTCCACATCTAACCCACTGGGCTTCTTT

CCTGATCACCAGCTGGATCCAGCCTTCCGCGCCAACTCCGCCAATCCAGACTG

-continued

GGACTTCAACCCCAATAAGGACACATGGCCTGATGCTAACAAGGTCGGAGGC

CAGAACCTGAGCACCTCCAATCCCTGGGCTTCTTTCCTGACCACCAGCTGGA

TCCTGCCTTCCGCGCCAACACAGCTAACCCTGATTGGGACTTCAACCCAAATA

AGGATACCTGGCCTGATGCAAACAAGGTCGGAGGAAGCGGAGCTACTAACTT

CAGCCTGCTGAAGCAGGCTGGAGACGTGGAGGAGAACCCTGGACCTATGGGC

ACCAACCTGTCTACAAGCAATCCACTGGGCTTCTTTCCCGACCATCAGCTGGA

CCCAGCCTTCAGGGCCAACAGCGCCAACCCTGACTGGGACTTCAACCCAAAT

AAGGACACGTGGCCTGATGCCAACAAGGTCGGAGGACAAAACCTGTCCACCT

CTAACCCCCTGGGCTTCTTTCCCGATCATCAATTAGACCCAGCCTTCCGCGCT

AACACTGCTAACCCTGACTGGGACTTCAACCCGAATAAGGATACTTGGCCTG

ATGCCAATAAGGTCGGCAGCCAGTCCGAGACAAGGAGGGGCCGGAGAGGAA

CGAGGGAGGAGAGACTGGAGAAGTGGATCACCGCCAGAAAGAAGGCCGAGG

AGCTGGAGAAGGACCTGAGGAAGACCCGCAAGACAATCAAGAAGCTGGAAG

AAGAGAACCCTTGGCTGGGCAATATCGTGGGCATCATCAGAAAGGGCAAGGA

CGGCGAGGGAGCACCACCAGCCAAGAGGCCACGCACAGATCAGATGGAAGT

GGATAGCGGACCAGGCAAGAGGCCTCACAAGTCCGGCTTCACCGACAAGGA

GAGGGAGGACCATAGGCGCCGGAAGGCCCTGGAAAACAAGAAGAAGCAATT

ATCCGCCGGCGGCAAGATCCTGTCTAAAGAAGAGGAAGAAGAGC

TGAGAAGGCTGACCGACGAGGATGAGGAGAGGAAGAGGAGGGTGGCAGGAC

CTAGAGTGGGCGACGTGAATCCATCCAGGGGAGGACCAAGAGGAGCACCAG

GAGGCGGCTTCGTGCCACAGATGGCAGGAGTGCCAGAGAGCCCCTTTTCCAG

GACAGGAGAGGGCCTGGATATCAGGGGAACCCAGGGCTTTCCTTGGGTGTCT

CCAAGCCCTCCACAGCAGCGGCTGCCACTGCTGGAGTGCACACCCCAGTCCC

AGTCTGAGAGCAAGAAGAACAGAAGGGGCGGCAGAGAGGACATCCTGGAAA

AATGGATCACCACACGCAGAAAAGCTGAAGAACTGGAAAAGGACCTGCGGA

AGGCCAGAAAGACCATCAAGAAGCTGGAGGATGAAAATCCATGGCTGGGAA

ATATCATCGGCATCATCCGGAAGGGCAAGGACGGGGAAGGCGCACCACCTGC

AAAGCGGCCCAGGACCGATCAGATGGAAATCGATTCTGGAACCGGCAAGCG

GCCTCACAAGAGTGGCTTCACCGATAAGGAGAGAGAGGATCACAGAAGGCG

CAAGGCCCTGGAGAACAAGAAGAAGCAATTAAGCAGCGGCGGCAAGAATCT

GTCCAGAGAAGAGGAAGAGGAGCTGGGCAGACTGACAGTGGAGGACGAGGA

GCGGAGAAGGCGCGTGGCAGGACCAAGAACCGGCGATGTGAACCTGTCCGG

AGGAGGACCAAGGGGAGCACCTGGGGGAGGCTTCGTGCCAAGGATGGAGGG

AGTGCCTGAGTCCCCCTTCACCAGAACCGGCGAAGGCCTGGACATCAGGGGC

AATCAGGGATTCCCATGGGTGCGGCCCTCCCCACCCCAGCAGAGACTGCCTC

TGCTGGAGTGTACCCCAGAGGGCACTAACCTGTCCACCTCTAACCCGTTAGGC

TTCTTTCCTGACCATCAATTAGATCCCGCCTTCCGGGCCAACAGCGCCAATCC

TGATTGGGACTTCAACCCGAATAAGGACACCTGGCCCGACGCAAACAAGGTC

GGAGGGCAAAACCTGAGCACCTCCAACCCTTTAGGCTTCTTTCCAGATCATCA

GCTGGATCCAGCCTTTAGAGCCAATACCGCGAACCCTGACTGGGATTTCAACC

CTAACAAAGATACCTGGCCCGACGCTAACAAAGTGGGA

-continued

SEQ ID NO: 23 delta 3 codon optimized with
restriction sites (HindIII/EcoRI)

A↓AGCTT*GCACC*ATG*G*CCGGCACCAATCTGTCTACCTCAAATCCCCTGGGCTT

CTTCCCCGATCATCAGCTGGACCCTGCCTTCCGAGCAAATTCCGCTAATCCTG

ATTGGGATTTCAACCCAAATAAGGACACATGGCCAGATGCCAACAAGGTCGG

CGGCCAGAACCTGTCCACCTCTAATCCTCTGGGCTTCTTTCCAGACCACCAGC

TGGATCCCGCCTTCAGGGCCAACACAGCCAATCCCGACTGGGACTTCAACCC

TAATAAGGACACCTGGCCTGACGCCAACAAGGTCGGCAGCAGGTCCGAGTCT

AAGAAGAATAGGGGAGGAAGGGAGGAGATCCTGGAGCAGTGGGTGGGAGCA

CGCAAGAAGCTGGAGGAGCTGGAGCGGGACCTGAGAAAGATCAAGAAGAAG

ATCAAGAAGCTGGAGGAGGAGAACCCCTGGCTGGGCAATATCAAGGGCATCC

TGGGCAAGAAGGATCGGGAGGGAGAGGGAGCACCACCTGCAAAGAGGGCCA

GAGCCGACCAGATGGAGGTGGATTCCGGACCAAGGAAGCGCCCTTTCAGAGG

AGAGTTTACAGACAAGGAGCGGAGAGATCACAGGCGCCGGAAGGCCCTGGA

GAACAAGCGGAAGCAGCTGAGCTCCGGCGGCAAGAGCCTGTCCAAGGAGGA

GGAGGAGGAGCTGAGAAAGCTGACCGAGGAGGACGAGAGAAGGGAGAGGA

GGGTGGCCGGCCCCAGGGTGGGCGGCGTGAACCCTCTGGAGGGAGGAACAA

GGGGAGCACCAGGAGGAGGCTTCGTGCCTTCCATGCAGGGCGTGCCCGAGTC

TCCTTTTGCCAGGACCGGAGAGGGCCTGGACGTGCGCGGCAATCAGGGCTTC

CCATGGGACATCCTGTTTCCCGCCGATCCACCCTTCTCTCCCCAGAGCTGCAG

GCCTCAGTCTCGCAGCGAGTCCAAGAAGAACAGAGGCGGAAGGGAGGAGGT

GCTGGAGCAGTGGGTGAATGGCAGGAAGAAGCTGGAAGAACTGGAGAGGGA

GCTGAGAAGGGCCCGCAAGAAGATCAAGAAGCTGGAAGACGATAATCCTTG

GCTGGGCAATGTGAAAGGCATCCTGGGCAAGAAGGACAAGGATGGAGAGGG

AGCACCTCCAGCAAAGAGGGCAAGAACAGACCAGATGGAGATCGATTCTGG

ACCAAGGAAGCGCCCCCTGAGGGGAGGCTTCACCGACCGGGAGAGACAGGA

TCACCGCCGGAGAAAGGCCCTGAAGAACAAGAAGAAGCAGCTGAGCGCCGG

CGGCAAGTCTCTGAGTAAAGAAGAAGAGGAGGAGCTGAAGCGGCTGACCAG

AGAGGACGAGGAGCGGAAGAAGGAGGAGCACGGCCCAAGCAGACTGGGAGT

GAATCCATCCGAGGGAGGACCTAGAGGCGCCCCTGGCGGCGGCTTCGTGCCT

TCTATGCAGGGCATCCCAGAGAGCAGGTTTACCAGGACAGGCGAAGGCCTGG

ACGTGCGGGGCTCCAGAGGCTTTCCCCAGGACATCCTGTTCCCTTCTGATCCC

CCTTTTTCCCCACAGTCTTGTAGGCCCCAGGGCACCAACCTGTCCACATCTAA

CCCACTGGGCTTCTTTCCTGATCACCAGCTGGATCCAGCCTTCCGCGCCAACT

CCGCCAATCCAGACTGGGACTTCAACCCCAATAAGGACACATGGCCTGATGC

TAACAAGGTCGGAGGCCAGAACCTGAGCACCTCCAATCCCCTGGGCTTCTTTC

CTGACCACCAGCTGGATCCTGCCTTCCGCGCCAACACAGCTAACCCTGATTGG

GACTTCAACCCAAATAAGGATACCTGGCCTGATGCAAACAAGGTCGGAGGAA

GCGGAGCTACTAACTTCAGCCTGCTGAAGCAGGCTGGAGACGTGGAGGAGAA

CCCTGGACCTATGGGCACCAACCTGTCTACAAGCAATCCACTGGGCTTCTTTC

CCGACCATCAGCTGGACCCAGCCTTCAGGGCCAACAGCGCCAACCCTGACTG

-continued

GGACTTCAACCCAAATAAGGACACGTGGCCTGATGCCAACAAGGTCGGAGGA

CAAAACCTGTCCACCTCTAACCCCCTGGGCTTCTTTCCCGATCATCAATTAGA

CCCAGCCTTCCGCGCTAACACTGCTAACCCTGACTGGGACTTCAACCCGAATA

AGGATACTTGGCCTGATGCCAATAAGGTCGGCAGCCAGTCCGAGACAAGGAG

GGGCCGGAGAGGAACCAGGGAGGAGACACTGGAGAAGTGGATCACCGCCAG

AAAGAAGGCCGAGGAGCTGGAGAAGGACCTGAGGAAGACCCGCAAGACAAT

CAAGAAGCTGGAAGAAGAGAACCCTTGGCTGGGCAATATCGTGGGCATCATC

AGAAAGGGCAAGGACGGCGAGGGAGCACCACCAGCCAAGAGGCCACGCACA

GATCAGATGGAAGTGGATAGCGGACCAGGCAAGAGGCCTCACAAGTCCGGCT

TCACCGACAAGGAGAGGGAGGACCATAGGCGCCGGAAGGCCCTGGAAAACA

AGAAGAAGCAATTATCCGCCGGCGGCAAGATCCTGTCTAAAGAAGAGGAAG

AAGAGC

TGAGAAGGCTGACCGACGAGGATGAGGAGAGGAAGAGGAGGGTGGCAGGAC

CTAGAGTGGGCGACGTGAATCCATCCAGGGGAGGACCAAGAGGAGCACCAG

GAGGCGGCTTCGTGCCACAGATGGCAGGAGTGCCAGAGAGCCCCTTTTCCAG

GACAGGAGAGGGCCTGGATATCAGGGGAACCCAGGGCTTTCCTTGGGTGTCT

CCAAGCCCTCCACAGCAGCGGCTGCCACTGCTGGAGTGCACACCCCAGTCCC

AGTCTGAGAGCAAGAAGAACAGAAGGGGCGGCAGAGAGGACATCCTGGAAA

AATGGATCACCACACGCAGAAAAGCTGAAGAACTGGAAAAGGACCTGCGGA

AGGCCAGAAAGACCATCAAGAAGCTGGAGGATGAAAATCCATGGCTGGGAA

ATATCATCGGCATCATCCGGAAGGGCAAGGACGGGGAAGGCGCACCACCTGC

AAAGCGGCCCAGGACCGATCAGATGGAAATCGATTCTGGAACCGGCAAGCG

GCCTCACAAGAGTGGCTTCACCGATAAGGAGAGAGAGGATCACAGAAGGCG

CAAGGCCCTGGAGAACAAGAAGAAGCAATTAAGCAGCGGCGGCAAGAATCT

GTCCAGAGAAGAGGAAGAGGAGCTGGGCAGACTGACAGTGGAGGACGAGGA

GCGGAGAAGGCGCGTGGCAGGACCAAGAACCGGCGATGTGAACCTGTCCGG

AGGAGGACCAAGGGGAGCACCTGGGGGAGGCTTCGTGCCAAGGATGGAGGG

AGTGCCTGAGTCCCCCTTCACCAGAACCGGCGAAGGCCTGGACATCAGGGGC

AATCAGGGATTCCCATGGGTGCGGCCCTCCCCACCCCAGCAGAGACTGCCTTC

TGCTGGAGTGTACCCCACAGGGCACTAACCTGTCCACCTCTAACCCGTTAGGC

TTCTTTCCTGACCATCAATTAGATCCCGCCTTCCGGGCCAACAGCGCCAATCC

TGATTGGGACTTCAACCCGAATAAGGACACCTGGCCCGACGCAAACAAGGTC

GGAGGGCAAAACCTGAGCACCTCCAACCCTTTAGGCTTCTTTCCAGATCATCA

GCTGGATCCAGCCTTTAGAGCCAATACCGCCAACCCTGACTGGGATTTCAACC

CTAACAAAGATACCTGGCCCGACGCTAACAAAGTGGGATGATGAG↓AATTCC

GT

SEQ ID NO: 24 Delta 3 protein
MAGTNLSTSNPLGFFPDHQLDPAFRANSANPDWDFNPNKDTWPDANKVGGQNL

STSNPLGFFPDHQLDPAFRANTANPDWDFNPNKDTWPDANKVGSRSESKKNRGG

REEILEQWVGARKKLEELERDLRKIKKKIKKLEEENPWLGNIKGILGKKDREGEG

APPAKRARADQMEVDSGPRKRPFRGEFTDKERRDHRRRKALENKRKQLSSGGKS

-continued

LSKEEEEELRKLTEEDERRERRVAGPRVGGVNPLEGGTRGAPGGGFVPSMQGVP

ESPFARTGEGLDVRGNQGFPWDILFPADPPFSPQSCRPQSRSESKKNRGGREEVLE

QWVNGRKKLEELERELRRARKKIKKLEDDNPWLGNVKGILGKKDKDGEGAPPA

KRARTDQMEIDSGPRKRPLRGGFTDRERQDHRRRKALKNKKKQLSAGGKSLSKE

EEEELKRLTREDEERKKEEHGPSRLGVNPSEGGPRGAPGGGFVPSMQGIPESRFTR

TGEGLDVRGSRGFPQDILFPSDPPFSPQSCRPQGTNLSTSNPLGFFPDHQLDPAFRA

NSANPDWDFNPNKDTWPDANKVGGQNLSTSNPLGFFPDHQLDPAFRANTANPD

WDFNPNKDTWPDANKVGGSGATNFSLLKQAGDVEENPGPMGTNLSTSNPLGFFP

DHQLDPAFRANSANPDWDFNPNKDTWPDANKVGGQNLSTSNPLGFFPDHQLDP

AFRANTANPDWDFNPNKDTWPDANKVGSQSETRRGRRGTREETTEKWITARKK

AEELEKDLRKTRKTIKKLEEENPWLGNIVGIIRKGKDGEGAPPAKRPRTDQMEVD

SGPGKRPHKSGFTDKEREDHRRRKALENKKKQLSAGGKILSKEEEEELRRLTDED

EERKRRVAGPRVGDVNPSRGGPRGAPGGGFVPQMAGVPESPFSRTGEGLDIRGT

QGFPWVSPSPPQQRLPLLECTPQSQSESKKNRRGGREDILEKWITTRRKAEELEKD

LRKARKTIKKLEDENPWLGNIIGIIRKGKDGEGAPPAKRPRTDQMEIDSGTGKRPH

KSGFTDKEREDHRRRKALENKKKQLSSGGKNLSREEEEELGRLTVEDEERRRRV

AGPRTGDVNLSGGGPRGAPGGGFVPRMEGNTESPFTRTGEGLDIRGNQGFPWVR

PSPPQQRLPLLECTPQGTNLSTSNPLCFFPDHQLDPAFRANSANPDWDFNPNKDT

WPDANKVGGQNLSTSNPLGFFPDHQLDPAFRANTANPDWDFNPNKDTWPDANK

VG

SEQ ID NO: 25 delta 4 wt
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGGGCACCAACCTGAGCACCAGCAACCCGCTGG

GCTTTTTTCCGGATCATCAGCTGGATCCGGCGTTTCGCGCGAACAGCGCGAAC

CCGGATTGGGATTTTAACCCGAACAAAGATACCTGGCCGGATGCGAACAAAG

TGGGCGGCCAGAACCTGAGCACCAGCAACCCGCTGGGCTTTTTTCCGGATCAT

CAGCTGGATCCGGCGTTTCGCGCGAACACCGCGAACCCGGATTGGGATTTTA

ACCCGAACAAAGATACCTGGCCGGATGCGAACAAAGTGGGCGGAAGCGGAGCT

ACTAACTTCAGCCTGCTGAAGCAGGCTGGAGACGTGGAGGAGAACCCTGGACCTATGAG

CCGCAGCGAAAGCAAAAAAAACCGCGGCGGCCGCGAAGAAGTGCTGGAACA

-continued

GTGGGTGAACGGCCGCAAAAAACTGGAAGAACTGGAACGCGAACTGCGCCG

CGCGCGCAAAAAAATTAAAAAACTGGAAGATGATAACCCGTGGCTGGGCAA

CGTGAAAGGCATTCTGGGCAAAAAAGATAAAGATGGCGAAGGCGCGCCGCC

GGCGAAACGCGCGCGCACCGATCAGATGGAAATTGATAGCGGCCCGCGCAA

ACGCCCGCTGCGCGGCGGCTTTACCGATCGCGAACGCCAGGATCATCGCCGC

CGCAAAGCGCTGAAAAACAAAAAAAAACAGCTGAGCGCGGGCGGCAAAAGC

CTGAGCAAAGAAGAAGAAGAAGAACTGAAACGCCTGACCCGCGAAGATGAA

GAACGCAAAAAAGAAGAACATGGCCCGAGCCGCCTGGGCGTGAACCCGAGC

GAAGGCGGCCCGCGCGGCGCGCCGGGCGGCGGCTTTGTGCCGAGCATGCAGG

GCATTCCGGAAAGCCGCTTTACCCGCACCGGCGAAGGCCTGGATGTGCGCGG

CAGCCGCGGCTTTCCGCAGGATATTCTGTTTCCGAGCGATCCGCCGTTTAGCC

CGCAGAGCTGCCGCCCGCAGGGCACCAACCTGAGCACCAGCAACCCGCTGGG

CTTTTTTCCGGATCATCAGCTGGATCCGGCGTTTCGCGCGAACAGCGCGAACC

CGGATTGGGATTTTAACCCGAACAAAGATACCTGGCCGGATGCGAACAAAGT

GGGCGGCCAGAACCTGAGCACCAGCAACCCGCTGGGCTTTTTTCCGGATCAT

CAGCTGGATCCGGCGTTTCGCGCGAACACCGCGAACCCGGATTGGGATTTTA

ACCCGAACAAAGATACCTGGCCGGATGCGAACAAAGTGGGCGGAAGCGGAGGCT

ACTAACTTCAGCCTGCTGAAGCAGGCTGGAGACGTGGAGGAGAACCCTGGACCTATGAG

CCAGAGCGAAACCCGCCGCGGCCGCCGCGGCACCCGCGAAGAAACCCTGGA

AAAATGGATTACCGCGCGCAAAAAAGCGGAAGAACTGGAAAAAGATCTGCG

CAAAACCCGCAAAACCATTAAAAAACTGGAAGAAGAAAACCCGTGGCTGGG

CAACATTGTGGGCATTATTCGCAAAGGCAAAGATGGCGAAGGCGCGCCGCCG

GCGAAACGCCCGCGCACCGATCAGATGGAAGTGGATAGCGGCCCGGGCAAA

CGCCCGCATAAAAGCGGCTTTACCGATAAAGAACGCGAAGATCATCGCCGCC

GCAAAGCGCTGGAAAACAAAAAAAAACAGCTGAGCGCGGGCGGCAAAATTC

TGAGCAAAGAAGAAGAAGAAGAACTGCGCCGCCTGACCGATGAAGATGAAG

AACGCAAACGCCGCGTGGCGGGCCCGCGCGTGGGCGATGTGAACCCGAGCCG

CGGCGGCCCGCGCGGCGCGCCGGGCGGCGGCTTTGTGCCGCAGATGGCGGGC

GTGCCGGAAAGCCCGTTTAGCCGCACCGGCGAAGGCCTGGATATTCGCGGCA

CCCAGGGCTTTCCGTGGGTGAGCCCGAGCCCGCCGCAGCAGCGCCTGCCGCT

GCTGGAATGCACCCCGCAGGGCACCAACCTGAGCACCAGCAACCCGCTGGGC

TTTTTTCCGGATCATCAGCTGGATCCGGCGTTTCGCGCGAACAGCGCGAACCC

GGATTGGGATTTTAACCCGAACAAAGATACCTGGCCGGATGCGAACAAAGTG

GGCGGCCAGAACCTGAGCACCAGCAACCCGCTGGGCTTTTTTCCGGATCATC

AGCTGGATCCGGCGTTTCGCGCGAACACCGCGAACCCGGATTGGGATTTTAA

CCCGAACAAAGATACCTGGCCGGATGCGAACAAAGTGGGCGGAAGCGGAGCTA

CTAACTTCAGCCTGCTGAAGCAGGCTGGAGACGTGGAGGAGAACCCTGGACCTATGAGC

CAGAGCGAAAGCAAAAAAAACCGCCGCGGCGGCCGCGAAGATATTCTGGAA

AAATGGATTACCACCCGCCGCAAAGCGGAAGAACTGGAAAAAGATCTGCGC

AAAGCGCGCAAAACCATTAAAAAACTGGAAGATGAAAACCCGTGGCTGGGC

AACATTATTGGCATTATTCGCAAAGGCAAAGATGGCGAAGGCGCGCCGCCGG

-continued

CGAAACGCCCGCGCACCGATCAGATGGAAATTGATAGCGGCACCGGCAAACG

CCCGCATAAAAGCGGCTTTACCGATAAAGAACGCGAAGATCATCGCCGCCGC

AAAGCGCTGGAAAACAAAAAAAAACAGCTGAGCAGCGGCGGCAAAAACCTG

AGCCGCGAAGAAGAAGAAGAACTGGGCCGCCTGACCGTGGAAGATGAAGAA

CGCCGCCGCCGCGTGGCGGGCCCGCGCACCGGCGATGTGAACCTGAGCGGCG

GCGGCCCGCGCGGCGCGCCGGGCGGCGGCTTTGTGCCGCGCATGGAAGGCGT

GCCGGAAAGCCCGTTTACCCGCACCGGCGAAGGCCTGGATATTCGCGGCAAC

CAGGGCTTTCCGTGGGTGCGCCCGAGCCCGCCGCAGCAGCGCCTGCCGCTGC

TGGAATGCACCCCGCAGGGCACCAACCTGAGCACCAGCAACCCGCTGGGCTT

TTTTCCGGATCATCAGCTGGATCCGGCGTTTCGCGCGAACAGCGCGAACCCGG

ATTGGGATTTTAACCCGAACAAAGATACCTGGCCGGATGCGAACAAAGTGGG

CGGCCAGAACCTGAGCACCAGCAACCCGCTGGGCTTTTTTCCGGATCATCAGC

TGGATCCGGCGTTTCGCGCGAACACCGCGAACCCGGATTGGGATTTTAACCC

GAACAAAGATACCTGGCCGGATGCGAACAAAGTGGGC

SEQ ID NO: 26 delta 4 wt with restriction sites
(HindIII/EcoRI)
A↓AGCTT*GCACC*ATGGCCAGCCGCAGCGAAAGCAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAAATTAAAAAACTGGAAGAAGA

AAACCCGTGGCTGGGCAACATTAAAGGCATTCTGGGCAAAAAAGATCGCGAA

GGCGAAGGCGCGCCGCCGGCGAAACGCGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGTAAGAAGAACTGCGCAAAC

TGACCGAAGAAGATGAACGCCGCGAACGCCGCGTGGCGGGCCCGCGCGTGG

GCGGCGTGAACCCGCTGGAAGGCGGCACCCGCGGCGCGCCGGGCGGCGGCTT

TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

GGATCCGCCGTTTAGCCCGCAGAGCTGCCGCCCGCAGGGCACCAACCTGAGC

ACCAGGAACCCGCTGGGCTTTTTTCCGGATCATCAGCTGGATCCGGCGTTTCG

CGCGAACAGCGCGAACCCGGATTGGGATTTTAACCCGAACAAAGATACCTGG

CCGGATGCGAACAAAGTGGGCGGCCAGAACCTGAGCACCAGCAACCCGCTG

GGCTTTTTTCCGGATCATCAGCTGGATCCGGCGTTTCGCGCGAACACCGCGAA

CCCGGATTGGGATTTTAACCCGAACAAAGATACCTGGCCGGATGCGAACAAA

GTGGGCGGAAGCGGAGCTACTAACTTCAGCCTGCTGAAGCAGGCTGGAGACGTGGAGGA

GAACCCTGGACCTATGAGCCGCAGCGAAAGCAAAAAAAACCGCGGCGGCCGCG

AAGAAGTGCTGGAACAGTGGGTGAACGGCCGCAAAAAACTGGAAGAACTGG

AACGCGAACTGCGCCGCGCGCGCAAAAAAATTAAAAAACTGGAAGATGATA

ACCCGTGGCTGGGCAACGTGAAAGGCATTCTGGGCAAAAAAGATAAAGATGG

CGAAGGCGCGCCGCCGGCGAAACGCGCGCGCACCGATCAGATGGAAATTGAT

AGCGGCCCGCGCAAACGCCCGCTGCGCGGCGGCTTTACCGATCGCGAACGCC

-continued

AGGATCATCGCCGCCGCAAAGCGCTGAAAAACAAAAAAAAACAGCTGAGCG

CGGGCGGCAAAAGCCTGAGCAAAGAAGAAGAAGAAGAACTGAAACGCCTGA

CCCGCGAAGATGAAGAACGCAAAAAAGAAGAACATGGCCCGAGCCGCCTGG

GCGTGAACCCGAGCGAAGGCGGCCCGCGCGGCGCGCCGGGCGGCGGCTTTGT

GCCGAGCATGCAGGGCATTCCGGAAAGCCGCTTTACCCGCACCGGCGAAGGC

CTGGATGTGCGCGGCAGCCGCGGCTTTCCGCAGGATATTCTGTTTCCGAGCGA

TCCGCCGTTTAGCCCGCAGAGCTGCCGCCCGCAGGGCACCAACCTGAGCACC

AGCAACCCGCTGGGCTTTTTTCCGGATCATCAGCTGGATCCGGCGTTTCGCGC

GAACAGCGCGAACCCGGATTGGGATTTTAACCCGAACAAAGATACCTGGCCG

GATGCGAACAAAGTGGGCGGCCAGAACCTGAGCACCAGCAACCCGCTGGGCT

TTTTTCCGGATCATCAGCTGGATCCGGCGTTTCGCGCGAACACCGCGAACCCG

GATTGGGATTTTAACCCGAACAAAGATACCTGGCCGGATGCGAACAAAGTGG

GCGGAAGCGGAGCTACTAACTTCAGCCTGCTGAAGCAGGCTGGAGACGTGGAGGAGAAC

CCTGGACCTATGAGCCAGAGCGAAACCCGCCGCGGCCGCCGCGGCACCCGCG

AAGAAACCCTGGAAAAATGGATTACCGCGCGCAAAAAAGCGGAAGAACTGG

AAAAAGATCTGCGCAAAACCCGCAAAACCATTAAAAAACTGGAAGAAGAAA

ACCCGTGGCTGGGCAACATTGTTGGGCATTATTCGCAAAGGCAAAGATGGCGA

AGGCGCGCCGCCGGCGAAACGCCCGCGCACCGATCAGATGGAAGTGGATAG

CGGCCCGGGCAAACGCCCGCATAAAAGCGGCTTTACCGATAAAGAACGCGAA

GATCATCGCCGCCGCAAAGCGCTGGAAAACAAAAAAAAACAGCTGAGCGCG

GGCGGCAAAATTCTGAGCAAAGAAGAAGAAGAAGAACTGCGCCGCCTGACC

GATGAAGATGAAGAACGCAAACGCCGCGTGGCGGGCCCGCGCGTGGGCGAT

GTGAACCCGAGCCGCGGCGGCCCGCGCGGCGCGCCGGGCGGCGGCTTTGTGC

CGCAGATGGCGGGCGTGCCGGAAAGCCCGTTTAGCCGCACCGGCGAAGGCCT

GGATATTCGCGGCACCCAGGGCTTTCCGTGGGTGAGCCCGAGCCCGCCGCAG

CAGCGCCTGCCGCTGCTGGAATGCACCCCGCAGGGCACCAACCTGAGCACCA

GCAACCCGCTGGGCTTTTTTCCGGATCATCAGCTGGATCCGGCGTTTCGCGCG

AACAGCGCGAACCCGGATTGGGATTTTAACCCGAACAAAGATACCTGGCCGG

ATGCGAACAAAGTGGGCGGCCAGAACCTGAGCACCAGCAACCCGCTGGGCTT

TTTTCCGGATCATCAGCTGGATCCGGCGTTTCGCGCGAACACCGCGAACCCGG

ATTGGGATTTTAACCCGAACAAAGATACCTGGCCGGATGCGAACAAAGTGGG

CGGAAGCGGAGCTACTAACTTCAGCCTGCTGAAGCAGGCTGGAGACGTGGAGGAGAACCC

TGGACCTATGAGCCAGAGCGAAAGCAAAAAAAAACCGCCGCGGCGGCCGCGAA

GATATTCTGGAAAAATGGATTACCACCCGCCGCAAAGCGGAAGAACTGGAAA

AAGATCTGCGCAAAGCGCGCAAAACCATTAAAAAACTGGAAGATGAAAACC

CGTGGCTGGGCAACATTATTGGCATTATTCGCAAAGGCAAAGATGGCGAAGG

CGCGCCGCCGGCGAAACGCCCGCGCACCGATCAGATGGAAATTGATAGCGGC

ACCGGCAAACGCCCGCATAAAAGCGGCTTTACCGATAAAGAACGCGAAGATC

ATCGCCGCCGCAAAGCGCTGGAAAACAAAAAAAAACAGCTGAGCAGCGGCG

GCAAAAACCTGAGCCGCGAAGAAGAAGAAGAACTGGGCCGCCTGACCGTGG

AAGATGAAGAACGCCGCCGCCGCGTGGCGGGCCCGCGCACCGGCGATGTGA

-continued

ACCTGAGCGGCGGCGGCCCGCGCGGCGCGCCGGGCGGCGGCTTTGTGCCGCG

CATGGAAGGCGTGCCGGAAAGCCCGTTTACCCGCACCGGCGAAGGCCTGGAT

ATTCGCGGCAACCAGGGCTTTCCGTGGGTGCGCCCGAGCCCGCCGCAGCAGC

GCCTGCCGCTGCTGGAATGCACCCCGCAGGGCACCAACCTGAGCACCAGCAA

CCCGCTGGGCTTTTTTCCGGATCATCAGCTGGATCCGGCGTTTCGCGCGAACA

GCGCGAACCCGGATTGGGATTTTAACCCGAACAAAGATACCTGGCCGGATGC

GAACAAAGTGGGCGGCCAGAACCTGAGCACCAGCAACCCGCTGGGCTTTTTT

CCGGATCATCAGCTGGATCCGGCGTTTCGCGCGAACACCGCGAACCCGGATT

GGGATTTTAACCCGAACAAAGATACCTGGCCGGATGCGAACAAAGTGGGCTG

ATGAG↓AATTCCGT

SEQ ID NO: 27 delta 4 codon optimized
GCCAGTCGGAGCGAATCAAAGAAAAATAGGGGAGGGCGGGAAGAAATCCTGGAGCAGTGG

GTCGGAGCACGAAAGAAACTGGAAGAACTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATCGGGAGGGAGAGGGAGCACCACCTGCAAAGAGGGCCAGAGCCGACCAGATGGAG

GTGGATAGCGGCCCTAGGAAGCGCCCATTCAGAGGCGAGTTTACAGACAAGGAGCGGAGA

GATCACAGGCGCCGGAAGGCCCTGGAGAACAAGCGGAAGCAGCTGAGCTCCGGCGGCAAG

TCCCTGTCTAAGGAGGAGGAGGAGGAGCTGAGAAAGCTGACCGAGGAGGACGAGAGAAGG

GAGAGGAGGGTGGCAGGACCTAGGGTGGGAGGCGTGAACCCACTGGAGGGAGGAACAAGG

GGAGCACCTGGAGGAGGATTCGTGCCATCCATGCAGGGAGTGCCTGAGTCTCCATTTGCC

AGGACCGGAGAGGGCCTGGATGTGCGCGGAAATCAGGGCTTCCCCTGGGACATCCTGTTT

CCTGCCGATCCACCCTTCTCCCCACAGTCTTGCAGGCCACAGGGAACCAACCTGAGCACA

TCCAATCCTCTGGGCTTCTTTCCAGACCACCAGCTGGATCCTGCCTTCAGAGCCAACTCC

GCCAATCCAGACTGGGACTTCAACCCCAATAAGGACACATGGCCTGATGCCAACAAGGTC

GGCGGCCAGAACCTGTCTACCAGCAATCCCCTGGGCTTCTTTCCTGACCACCAGCTGGAT

CCAGCCTTCCGGGCCAACACTGCTAACCCTGATTGGGACTTCAACCCTAATAAGGATACC

TGGCCAGACGCCAACAAGGTCGGCGGAAGCGGAGCTACTAACTTCAGCCTGCTGAAGCAG

GCTGGAGACGTGGAGGAGAACCCTGGACCTATGTCCAGGTCTGAGAGCAAGAAGAATAGG

GGAGGAAGAGAGGAGGTGCTGGAGCAGTGGGTGAACGGCCGCAAGAAGCTGGAGGAGCTG

GAGAGGGAGCTGAGAAGGGCCCGCAAGAAGATCAAGAAGCTGGAAGACGATAATCCTTGG

CTGGGCAATGTGAAAGGCATCCTGGGCAAGAAGGACAAGGATGGAGAGGGAGCACCTCCA

GCAAAGAGGGCAAGAACAGACCAGATGGAGATCGATTCTGGACCAAGGAAGCGCCCTCTG

AGGGGAGGCTTCACCGACCGGGAGAGACAGGATCACCGCCGGAGAAAGGCCCTGAAGAAC

AAGAAGAAGCAGCTGTCCGCCGGCGGCAAGTCCCTGAGCAAAGAAGAGGAAGAGGAGCTG

AAGAGGCTGACCCGCGAGGACGAGGAGCGGAAGAAGGAGGAGCACGGACCAAGCAGACTG

GGAGTGAATCCTTCCGAGGGAGGACCAAGAGGAGCACCCGGAGGAGGCTTCGTGCCATCT

ATGCAGGGCATCCCCGAGAGCCGGTTTACCAGAACAGGAGAGGGCCTGGACGTGAGGGGC

TCCCGCGGCTTTCCTCAGGACATCCTGTTCCCATCTGATCCCCCTTTTAGCCCACAGTCC

TGTAGGCCCCAGGGCACTAACCTGAGCACATCCAACCCACTGGGCTTCTTTCCTGATCAT

CAGCTGGACCCAGCCTTCCGCGCCAACAGCGCCAACCCTGACTGGGACTTCAACCCAAAT

AAGGACACATGGCCAGATGCTAACAAGGTCGGAGGACAAAACCTGTCTACCAGCAACCCT

-continued

CTGGGCTTCTTTCCCGATCATCAGCTGGACCCCGCCTTCAGGGCCAACACAGCCAATCCC

GACTGGGACTTCAACCCGAATAAGGACACCTGGCCAGATGCAAACAAGGTCGGAGGAAGC

GGAGCTACTAACTTCAGCCTGCTGAAGCAGGCTGGAGACGTGGAGGAGAACCCTGGACCT

ATGAGCCAGTCTGAGACAAGGAGGGGCCGGAGAGGAACCAGGGAGGAGACACTGGAGAAG

TGGATCACCGCCAGAAAGAAGGCCGAGGAGCTGGAGAAGGACCTGCGGAAGACCAGAAAG

ACAATCAAGAAGCTGGAAGAAGAGAACCCATGGCTGGGCAATATCGTGGGCATCATCCGC

AAGGGCAAGGACGGCGAGGGAGCACCACCAGCAAAGAGGCCCCGCACAGATCAGATGGAA

GTGGATAGCGGCCCTGGCAAGAGGCCACACAAGTCCGGCTTCACCGACAAGGAGAGGGAG

GACCATAGGCGCCGGAAGGCCCTGGAAAACAAGAAGAAGCAATTATCCGCCGGCGGCAAG

ATCCTGTCCAAAGAGGAAGAAGAGGAGCTGAGAAGGCTGACCGACGAGGATGAGGAGAGG

AAAAGAAGGGTGGCACGACCAAGAGTGGGCGACGTGAATCCCACCAGAGGCGGACCAAGA

GGAGCACCTGGAGGCGGCTTCGTGCCCCAGATGGCCGGCGTGCCCGAGTCTCCTTTTAGC

AGAACTGGAGAGGGCCTGGATATCAGGGGAACACAGGGCTTTCCATGGGTGAGCCCATCC

C

CTCCACAGCAGAGGCTGCCACTCCTGGAGTGCACCCCTCAGGGAACCAACCTGTCTACCA

GCAACCCGCTGGGCTTCTTTCCCGACCATCAGCTGGACCCTGCCTTCCGCGCCAACTCCG

CCAACCCTGATTGGGACTTCAACCCGAATAAGGATACCTGGCCCGACGCTAACAAGGTCG

GAGGCCAGAACCTGTCCACCTCTAACCCCTTAGGCTTCTTTCCCGATCACCAGCTGGATC

CCGCCTTCAGAGCCAACACTGCTAACCCCGATTGGGACTTCAACCCGAATAAGGACACGT

GGCCAGACGCTAACAAGGTCGGGGGAAGCGGAGCTACTAACTTCAGCCTGCTGAAGCAGG

CTGGCCACGTGGAGGAGAACCCTGGACCTATGTCGCAGTCCGAGTCTAAGAAGAATAGAA

GGGGCGGCCGGGAGGATATCCTGGAAAAATGGATCACCACACGCAGAAAAGCTGAAGAAC

TGGAAAAGGACCTGAGGAAGGCCCGCAAGACCATCAAGAAGCTGGAGGATGAAAATCCAT

GGCTGGGAAACATCATCGGCATCATCAGAAAGGGCAAGGACGGGGAAGGCGCCCCACCTG

CAAAGCGGCCTAGAACCGATCAGATGGAAATCGATTCTGGCACAGGCAAGCGGCCACACA

AGAGTGGCTTCACCGATAAGGAGAGAGAGGATCACAGAAGGCGCAAGGCCCTGGAGAACA

AGAAGAAGCAATTAAGGAGCGGCGGCAAGAATCTGTCCAGAGAAGAAGAGGAGGAGCTGG

GCAGACTGACAGTGGAGGACGAGGAGCGGAGAAGGCGCGTGGCAGGACCAAGGACCGGCG

ATGTGAACCTGAGCGGAGGAGGACCTAGGGGAGCACCAGGAGGCGGCATCGTGCCTAGGA

TGGAGGGAGTGCCAGAGTCCCCCTTTACCAGGACTCGCGAGGGCCTGGACATCAGGGGAA

ATCAGGGATTCCCATGGGTGCGGCCTAGCCCACCACAGCAGAGACTGCCACTGCTGGAGT

GTACACCCCAGGGCACAAACCTGAGCACATCCAATCCGCTGGGCTTCTTTCCAGATCATC

AATTAGATCCAGCCTTCAGGGCCAACTCCGCCAATCCGGATTGGGACTTCAACCCGAATA

AGGACACTTGGCCCGACGCAAACAAGGTCGGAGGGCAAAACCTGTCTACCAGCAATCCAC

TTGGCTTCTTTCCTGACCATCAGCTGGATCCCGCCTTTCGCGCCAATACCGCCAATCCTG

ACTGGGACTTCAATCCTAACAAAGACACCTGGCCCGACGCAAACAAAGTGGGA

SEQ ID NO: 28 delta 4 optimized with restriction sites
(HindIII/EcoRI)
A↓AGCTT*GCACC*ATGGCCAGTCGGAGCGAATCAAAGAAAAATAGGGGAGGGCGGGAAGAA

ATCCTGGAGCAGTGGGTCGGAGCACGAAAGAAACTGGAAGAACTGGAGAGGGACCTGCGC

AAGATCAAGAAGAAGATCAAGAAGCTGGAGGAGGAGAACCCCTGGCTGGGCAATATCAAG

-continued

GGCATCCTGGGCAAGAAGGATCGGGAGGGAGAGGGAGCACCACCTGCAAAGAGGGCCAGA

GCCGACCAGATGGAGGTGGATAGCGGCCCTAGGAAGCGCCCATTCAGAGGCGAGTTTACA

GACAAGGAGCGGAGAGATCACAGGCGCCGGAAGGCCCTGGAGAACAAGCGGAAGGAGCTG

AGCTCCGGCGGCAAGTCCCTGTCTAAGGAGGAGGAGGAGGAGCTGAGAAAGCTGACCGAG

GAGGACGAGAGAAGGGAGAGGAGGGTGGCAGGACCTAGGGTGGGAGGCGTGAACCCACTG

GAGGGAGGAACAAGGGGAGCACCTGGAGGAGGATTCGTGCCATCCATGCAGGGAGTGCCT

GAGTCTCCATTTGCCAGGACCGGAGAGGGCCTGGATGTGCGCGGAAATCAGGGCTTCCCC

TGGGACATCCTGTTTCCTGCCGATCCACCCTTCTCCCCACAGTCTTGCAGGCCACAGGGA

ACCAACCTGAGCACATCCAATCCTCTGGGCTTCTTTCCAGACCACCAGCTGGATCCTGCC

TTCAGAGCCAACTCCGCCAATCCAGACTGGGACTTCAACCCCAATAAGGACACATGGCCT

GATGCCAACAAGGTCGGCGGCCAGAACCTGTCTACCAGCAATCCCCTGGGCTTCTTTCCT

GACCACCAGCTGGATCCAGCCTTCCGGGCCAACACTGCTAACCCTGATTGGGACTTCAAC

CCTAATAAGGATACCTGGCCAGACGCCAACAAGGTCGGCGGAAGCGGAGCTACTAACTTC

AGCCTGCTGAAGGAGGCTGGAGACGTGGAGGAGAACCCTGGACCTATGTCCAGGTCTGAG

AGCAAGAAGAATAGGGGAGGAAGAGAGGAGGTGCTGGAGCAGTGGGTGAACGGCCGCAAG

AAGCTGGAGGAGCTGGAGAGGGAGCTGAGAAGGGCCCGCAAGAAGATCAAGAAGCTGGAA

GACGATAATCCTTGGCTGGGCAATGTGAAAGGCATCCTGGGCAAGAAGGACAAGGATGGA

GAGGGAGCACCTCCAGCAAAGAGGGCAAGAACAGACCAGATGGAGATCGATTCTGGACCA

AGGAAGCGCCCTCTGAGGGGAGGCTTCACCGACCGGGAGAGACAGGATCACCGCCGGAGA

AAGGCCCTGAAGAACAAGAAGAAGCAGCTGTCCGCCGGCGGCAAGTCCCTGAGCAAAGAA

GAGGAAGAGGAGCTGAAGAGGCTGACCCGCGAGGACGAGGAGCGGAAGAAGGAGGAGCAC

GGACCAAGCAGACTGGGAGTGAATCCTTCCGAGGGAGGACCAAGAGGAGCACCCGGAGGA

GGCTTCGTGCCATCTATGCAGGGCATCCCCGAGAGCCGGTTTACCAGAACAGGAGAGGGC

CTGGACGTGAGGGGCTCCCGCGGCTTTCCTCAGGACATCCTGTTCCCATCTCATCCCCCT

TTTAGCCCACAGTCCTGTAGGCCCCAGGGCACTAACCTGAGCACATCCAACCCACTGGGC

TTCTTTCCTGATCATCAGCTGGACCCAGCCTTCCGCGCCAACAGCGCCAACCCTGACTGG

GACTTCAACCCAAATAAGGACACATGGCCAGATGCTAACAAGGTCGGAGGACAAAACCTG

TCTACCAGCAACCCTCTGGGCTTCTTTCCCGATCATCAGCTGGACCCCGCCTTCAGGGCC

AACACAGCCAATCCCGACTGGGACTTCAACCCGAATAAGGACACCTGGCCAGATGCAAAC

AAGGTCGGAGGAAGCGGAGCTACTAACTTCAGCCTGCTGAAGCAGGCTGGAGACGTGGAG

GAGAACCCTGGACCTATGAGCCAGTCTGAGACAAGGAGGGGCCGGAGAGGAACCAGGGAG

GAGACACTGGAGAAGTGGATCACCGCCAGAAAGAAGGCCGAGGAGCTGGAGAAGGACCTG

CGGAAGACCAGAAAGACAATCAAGAAGCTGGAAGAAGAGAACCCATGGCTGGGCAATATC

GTGGGCATCATCCGCAAGGGCAAGGACGGCGAGGGAGCACCACCAGCAAAGAGGCCCCGC

ACAGATCAGATGGAAGTGGATAGCGGCCCTGGCAAGAGGCCACACAAGTCCGGCTTCACC

GACAAGGAGAGGGAGGACCATAGGCGCCGGAAGGCCCTGGAAAACAAGAAGAAGCAATTA

TCCGCCGGCGGCAAGATCCTGTCCAAAGAGGAAGAAGAGGAGCTGAGAAGGCTGACCGAC

GAGGATGAGGAGAGGAAAAGAAGGGTGGCAGGACCAAGAGTGGGCGACGTGAATCCCAGC

AGAGGCGGACCAAGAGGAGCACCTGGAGGCGGCTTCGTGCCCCAGATGGCCGGCGTGCCC

GAGTCTCCTTTTAGCAGAACTGGAGAGGGCCTGGATATCAGGGGAACACAGGGCTTTCCA

TGGGTGAGCCCATCCC

-continued

CTCCACAGCAGAGGCTGCCACTGCTGGAGTGCACCCCTCAGGGAACCAACCTGTCTACCA

GCAACCCGCTGGGCTTCTTTCCCGACCATCAGCTGGACCCTGCCTTCCGCGCCAACTCCG

CCAACCCTGATTGGGACTTCAACCCGAATAAGGATACCTGGCCCGACGCTAACAAGGTCG

GAGGCCAGAACCTGTCCACCTCTAACCCCTTAGGCTTCTTTCCCGATCACCAGCTGGATC

CCGCCTTCAGAGCCAACACTGCTAACCCCGATTGGGACTTCAACCCGAATAAGGACACGT

GGCCAGACGCTATCAAGGTCGGGGGAAGCGGAGCTACTAACTTCAGCCTGCTGAAGCAGG

CTGGAGACGTGGAGGAGAACCCTGGACCTATGTCGCAGTCCGAGTCTAAGAAGAATAGAA

GGGGCGGCCGGGAGGATATCCTGGAAAAATGGATCACCACACGCAGAAAAGCTGAAGAAC

TGGAAAAGGACCTGAGGAAGGCCCGCAAGACCATCAAGAAGCTGGAGGATGAAAATCCAT

GGCTGGGAAACATCATCGGCATCATCAGAAAGGGCAAGGACGGGGAAGGCGCCCCACCTG

CAAAGCGGCCTAGAACCGATCAGATGGAAATCGATTCTGGCACAGGCAAGCGGCCACACA

AGAGTGGCTTCACCGATAAGGAGAGAGAGGATCACAGAAGGCGCAAGGCCCTGGAGAACA

AGAAGAAGCAATTAAGCAGCGGCGGCAAGAATCTGTCCAGAGAAGAAGAGGAGGAGCTGG

GCAGACTGACAGTGGAGGACGAGGAGCGGAGAAGGCGCGTGGCAGGACCAAGGACCGGCG

ATGTGAACCTGAGCGGAGGAGGACCTAGGGGAGCACCAGGAGGCGGCTTCGTGCCTAGGA

TGGAGGGAGTGCCAGAGTCCCCCTTTACCAGGACTGGCGAGGGCCTGGACATCAGGGGAA

ATCAGGGATTCCCATGGGTGCGGCCTAGCCCACCACAGCAGAGACTGCCACTGCTGGAGT

GTACACCCCAGGGCACAAACCTGAGCACATCCAATCCGCTGGGCTTCTTTCCAGATCATC

AATTAGATCCAGCCTTCAGGGCCAACTCCGCCAATCCGGATTGGCACTTCAACCCGAATA

AGGACACTTGGCCCGACGCAAACAAGGTCGGAGGGCAAAACCTGTCTACCAGCAATCCAC

TTGGCTTCTTTCCTGACCATCAGCTGGATCCCGCCTTTCGCGCCAATACCGCCAATCCTG

ACTGGGACTTCAATCCTAACAAAGACACCTGGCCCGACGCAAACAAAGTGGGATGATGA<u>G</u>

<u>↓AATTC</u>CGT

SEQ ID NO: 29 delta 4 protein
MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKAL

ENKRKQLSSGGKSLSKEEEEELRKLTEEDERRERRVGPRVGGVNPLEGGTRGAP

GGGFVPSMQGVPESPFARTGEGLDVRGNQGFPWDILFPADPPFSPQSCRPQGTNL

STSNPLGFFPDHQLDPAFRANSANPDWDFNPNKDTWPDANKVGGQNLSTSNPLG

FFPDHQLDPAFRANTANPDWDFNPNKDTWPDANKVGGSGATNFSLLKQAGDVE

ENPGPMSRSESKKNRGGREEVLEQWVNGRKKLEELERELRRARKKIKKLEDDNP

WLGNVKGILGKKDKDGEGAPPAKRARTDQMEIDSGPRKRPLRGGFTDRERQDH

RRRKALKNKKKQLSAGGKSLSKEEEEELKRLTREDEERKKEEHGPSRLGVNPSEG

GPRGAPGGGFVPSMQGIPESRFTRTGEGLDVRGSRGFPQDILFPSDPPFSPQSCRPQ

GTNLSTSNPLGFFPDHQLDPAFRANSANPDWDFNPNKDTWPDANKVGGQNLSTS

NPLGFFPDHQLDPAFRANTANPDWDFNPNKDTWPDANKVGGSGATNFSLLKQA

GDVEENPGPMSQSETRRGRRGTREETLEKWITARKKAEELEKDLRKTRKTIKKLE

EENPWLGNIVGIIRKGKDGEGAPPAKRPRTDQMEVDSGPGKRPHKSGFTDKERED

HRRRKALENKKKQLSAGGKILSKEEEEELRRLTDEDEERKRRVAGPRVGDVNPS

RGGPRGAPGGGFVPQMAGVPESPFSRTGEGLDIRGTQGFPWVSPSPPQQRLPLLE

CTPQGTNLSTSNPLGFFPDHQLDPAFRANSANPDWDFNPNKDTWPDANKVGGQ

-continued

NLSTSNPLGFFPDHQLDPAFRANTANPDWDFNPNKDTWPDANKVGGSGATNFSL

LKQAGDVEENPGPMSQSESKKNRRGGREDILEKWITTRRKAEELEKDLRKARKTI

KKLEDENPWLGNIIGIIRKGKDGEGAPPAKRPRTDQMEIDSGTGKRPHKSGFTDKE

REDHRRRKALENKKKQLSSGGKNLSREEEEELGRLTVEDEERRRRVAGPRTGDV

NLSGGGPRGAPGGGFVPRMEGVPESPFTRTGEGLDIRGNQGFPWVRPSPPQQRLP

LLECTPQGTNLSTSNPLGFFPDHQLDPAFRANSANPDWDFNPNKDTWPDANKVG

GQNLSTSNPLGFFPDHQLDPAFRANTANPDWDFNPNKDTWPDANKVG

SEQ ID NO: 30 delta 5 wt
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGAGCCGCAGCGAAAGCAAAAAAAACCGCGGC

GGCCGCGAAGAAGTGCTGGAACAGTGGGTGAACGGCCGCAAAAAACTGGAA

GAACTGGAACGCGAACTGCGCCGCGCGCGCAAAAAAATTAAAAAACTGGAA

GATGATAACCCGTGGCTGGGCAACGTGAAAGGCATTCTGGGCAAAAAAGATA

AAGATGGCGAAGGCGCGCCGCCGGCGAAACGCGCGCGCACCGATCAGATGG

AAATTGATAGCGGCCCGCGCAAACGCCCGCTGCGCGGCGGCTTTACCGATCG

CGAACGCCAGGATCATCGCCGCCGCAAAGCGCTGAAAAACAAAAAAAAACA

GCTGAGCGCGGGCGGCAAAAGCCTGAGCAAAGAAGAAGAAGAAGAACTGAA

ACGCCTGACCCGCGAAGATGAAGAACGCAAAAAAGAAGAACATGGCCCGAG

CCGCCTGGGCGTGAACCCGAGCGAAGGCGGCCCGCGCGGCGCGCCGGGCGG

CGGCTTTGTGCCGAGCATGCAGGGCATTCCGGAAAGCCGCTTTACCCGCACC

GGCGAAGGCCTGGATGTGCGCGGCAGCCGCGGCTTTCCGCAGGATATTCTGT

TTCCGAGCGATCCGCCGTTTAGCCCGCAGAGCTGCCGCCCGCAGGGAAGCGGAG

CTACTAACTTCAGCCTGCTGAAGCAGGCTGGAGACGTGGAGGAGAACCCTGGACCTATG

AGCCAGAGCGAAACCCGCCGCGGCCGCCGCGGCACCCGCGAAGAAACCCTG

GAAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

GGCAACATTGTGGGCATTATTCGCAAAGGCAAAGATGGCGAAGGCGCGCCGC

CGGCGAAACGCCCGCGCACCGATCAGATGGAAGTGGATAGCGGCCCGGGCA

AACGCCCGCATAAAAGCGGCTTTACCGATAAAGAACGCGAAGATCATCGCCG

CCGCAAAGCGCTGGAAAACAAAAAAAAACAGCTGAGCGCGGGCGGCAAAAT

-continued

TCTGAGCAAAGAAGAAGAAGAAGAACTGCGCCGCCTGACCGATGAAGATGA

AGAACGCAAACGCCGCGTGGCGGGCCCGCGCGTGGGCGATGTGAACCCGAG

CCGCGGCGGCCCGCGCGGCGCGCCGGGCGGCGGCTTTGTGCCGCAGATGGCG

GGCGTGCCGGAAAGCCCGTTTAGCCGCACCGGCGAAGGCCTGGATATTCGCG

GCACCCAGGGCTTTCCGTGGGTGAGCCCGAGCCCGCCGCAGCAGCGCCTGCC

GCTGCTGGAATGCACCCCGCAGAGCCAGAGCGAAAGCAAAAAAAACCGCCG

CGGCGGCCGCGAAGATTATTCTGGAAAAATGGATTACCACCCGCCGCAAAGCG

GAAGAACTGGAAAAAGATCTGCGCAAAGCGCGCAAAACCATTAAAAAACTG

GAAGATGAAAACCCGTGGCTGGGCAACATTATTGGCATTATTCGCAAAGGCA

AAGATGGCGAAGGCGCGCCGCCGGCGAAACGCCCGCGCACCGATCAGATGG

AAATTGATAGCGGCACCGGCAAACGCCCGCATAAAAGCGGCTTTACCGATAA

AGAACGCGAAGATCATCGCCGCCGCAAAGCGCTGGAAAACAAAAAAAAACA

GCTGAGCAGCGGCGGCAAAAACCTGAGCCGCGAAGAAGAAGAAGAACTGGG

CCGCCTGACCGTGGAAGATGAAGAACGCCGCCGCCGCGTGGCGGGCCCGCGC

ACCGGCGATGTGAACCTGAGCGGCGGCGGCCCGCGCGGCGCGCCGGGCGGC

GGCTTTGTGCCGCGCATGGAAGGCGTGCCGGAAAGCCCGTTTACCCGCACCG

GCGAAGGCCTGGATATTCGCGGCAACCAGGGCTTTCCGTGGGTGCGCCCGAG

CCCGCCGCAGCAGCGCCTGCCGCTGCTGGAATGCACCCCGCAG

SEQ ID NO: 31 delta 5 wt with restriction sites
(HindIII/EcoRI)
A↓AGCTT*GCACC*ATGGCCAGCCGCAGCGAAAGGAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAAATTAAAAAACTGGAAGAAGA

AAACCCGTGGCTGGGCAACATTAAAGGCATTCTGGGCAAAAAAGATCGCGAA

GGCGAAGGCGCCTCCGCCGGCGAAACGCGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGAAGAAGAACTGCGCAAAC

TGACCGAAGAAGATGAACGCCGCGAACGCCGCGTGGCGGGCCCGCGCGTGG

GCGGCGTGAACCCGCTGGAAGGCGGCACCCGCGGCGCGCCGGGCGGCGGCTT

TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

GGATCCGCCGTTTAGCCCGCAGAGCTGCCGCCCGCAGAGCCGCAGCGAAACTC

AAAAAAAACCGCGGCGGCCGCGAAGAAGTGCTGGAACAGTGGGTGAACGGC

CGCAAAAAACTGGAAGAACTGGAACGCGAACTGCGCCCGCGCGCGCAAAAAA

ATTAAAAAACTGGAAGATGATAACCCGTGGCTGGGCAACGTGAAAGGCATTC

TGGGCAAAAAAGATAAAGATGGCGAAGGCGCGCCGCCGGCGAAACGCGCGC

GCACCGATCAGATGGAAATTGATAGCGGCCCGCGCAAACGCCCGCTGCGCGG

CGGCTTTACCGATCGCGAACGCCAGGATCATCGCCGCCGCAAAGCGCTGAAA

AACAAAAAAAAACAGCTGAGCGCGGGCGGCAAAAGCCTGAGCAAAGAAGAA

GAAGAAGAACTGAAACGCCTGACCCGCGAAGATGAAGAACGCAAAAAAGAA

-continued

GAACATGGCCCGAGCCGCCTGGGCGTGAACCCGAGCGAAGGCGGCCCGCGC

GGCGCGCCGGGCGGCGGCTTTGTGCCGAGCATGCAGGGCATTCCGGAAAGCC

GCTTTACCCGCACCGGCGAAGGCCTGGATGTGCGCGGCAGCCGCGGCTTTCC

GCAGGATATTCTGTTTCCGAGCGATCCGCCGTTTAGCCCGCAGAGCTGCCGCC

CGCAGGGAAGCGGAGCTACTAACTTCAGCCTCCTGAAGCAGCCTGGAGACGTGGAGGAG

AACCCTGGACCTATGAGCCAGAGCGAAACCCGCCGCGGCCGCCGCGGCACCCG

CGAAGAAACCCTGGAAAAATGGATTACCGCGCGCAAAAAAGCGGAAGAACT

GGAAAAAGATCTGCGCAAAACCCGCAAAACCATTAAAAAACTGGAAGAAGA

AAACCCGTGGCTGGGCAACATTGTGGGCATTATTCGCAAAGGCAAAGATGGC

GAAGGCGCGCCGCCGGCGAAACGCCCGCGCACCGATCAGATGGAAGTGGAT

AGCGGCCCGGGCAAACGCCCGCATAAAAGCGGCTTTACCGATAAAGAACGCG

AAGATCATCGCCGCCGCAAAGCGCTGGAAAACAAAAAAAAACAGCTGAGCG

CGGGCGGCAAAATTCTGAGCAAAGAAGAAGAAGAACTGCGCCGCCTGA

CCGATGAAGATGAAGAACGCAAACGCCGCGTGGCGGGCCCGCGCGTGGGCG

ATGTGAACCCGAGCCGCGGCGGCCCGCGCGGCGCGCCGGGCGGCGGCTTTGT

GCCGCAGATGGCGGGCGTGCCGGAAAGCCCGTTTAGCCGCACCGGCGAAGGC

CTGGATATTCGCGGCACCCAGGGCTTTCCGTGGGTGAGCCCGAGCCCGCCGC

AGCAGCGCCTGCCGCTGCTGGAATGCACCCCGCAGAGCCAGAGCGAAAGCAA

AAAAAACCGCCGCGGCGGCCGCGAAGATATTCTGGAAAAATGGATTACCACC

CGCCGCAAAGCGGAAGAACTGGAAAAAGATCTGCGCAAAGCGCGCAAAACC

ATTAAAAAACTGGAAGATGAAAACCCGTGGCTGGGCAACATTATTGGCATTA

TTCGCAAAGGCAAAGATGGCGAAGGCGCGCCGCCGGCGAAACGCCCGCGCA

CCGATCAGATGGAAATTGATAGCGGCACCGGCAAACGCCCGCATAAAAGCGG

CTTTACCGATAAAGAACGCGAAGATCATCGCCGCCGCAAAGCGCTGGAAAAC

AAAAAAAAACAGCTGAGCAGCGGCGGCAAAAACCTGAGCCGCGAAGAAGAA

GAAGAACTGGGCCGCCTGACCGTGGAAGATGAAGAACGCCGCCGCCGCGTG

GCGGGCCCGCGCACCGGCGATGTGAACCTGAGCGGCGGCGGCCCGCGCGGCG

CGCCGGGCGGCGGCTTTGTGCCGCGCATGGAAGGCGTGCCGGAAAGCCCGTT

TACCCGCACCGGCGAAGGCCTGGATATTCGCGGCAACCAGGGCTTTCCGTGG

GTGCGCCCGAGCCCGCCGCAGCAGCGCCTGCCGCTGCTGGAATGCACCCCGC

AGTGATGAG↓AATTCCGT

SEQ ID NO: 32 delta 5 codon optimized
GCCTCACGGTCAGAGTCAAAGAAAAATAGGGGGGGCGGGAAGAAATCCTGGAACAGTGG

GTCGGAGCACGGAAAAAACTGGAAGAGCTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATCGGGAGGGAGAGGGAGCACCACCTGCAAAGAGGGCCAGAGCCGACCAGATGGAG

GTGGATAGCGGCCCTAGGAAGCGCCCATTCAGAGGCGAGTTTACCGACAAGGAGCGGAGA

GATCACAGGCGCCGGAAGGCCCTGGAGTCCAAGCGGAAGCAGCTGAGCTCCGGCGGCAAG

TCCCTGTCTAAGGAGGAGGAGGAGGAGCTGAGAAAGCTGACAGAGGAGGACGAGAGAAGG

GAGCGCCGGGTGGCCGGCCCAAGGGTGGGCGGCGTGAACCCCCTGGAGGGAGGAACCAGG

GGAGCACCTGGAGGAGGCTTCGTGCCATCTATGCAGGGCGTGCCTGAGAGCCCATTTGCC

-continued

AGGACAGGAGAGGGCCTGGATGTGCGCGGCAATCAGGGCTTCCCCTGGGACATCCTGTTT

CCTGCCGATCCACCCTTCAGCCCACAGTCCTGCAGGCCTCAGAGCAGATCCGAGTCTAAG

AAGAACAGGGGAGGAAGAGAGGAGGTGCTGGAGCAGTGGGTGAATGGCCGGAAGAAGCTG

GAGGAGCTGGAGCGGGAGCTGAGAAGGGCCAGAAAGAAGATCAAGAAGCTGGAAGACGAT

AATCCTTGGCTGGGCAATGTGAAAGGCATCCTGGGCAAGAAGGACAAGGATGGAGAGGGA

GCACCTCCAGCAAAGAGGGCAAGAACCGACCAGATGGAGATCGATAGCGGACCAAGGAAG

CGCCCTCTGAGAGGAGGCTTCACAGACCGGGAGAGACAGGATCACCGCCGGAGAAAGGCC

CTAAGAACAAGAAGTAAGCAGCTGTCCGCCGGAGGCAAGAGCCTGTCCAAAGAAGAGGAA

GAGGAGCTGAAGAGGCTGACCCGCGAGGACGAGGAGCGGAAGAAGGAGGAGCACGGCCCT

TCCAGACTGGGCGTGAATCCATCTGAGGGAGGACCAAGGGGAGCACCAGGCGGCGGCTTC

GTGCCAAGCATGCAGGGCATCCCCGAGTCCCGGTTTACCAGAACAGGAGAGGGCCTGGAC

GTGAGGGGCTCTCGCGGCTTTCCTCAGGACATCCTGTTCCCAAGCGATCCCCCTTTTTCT

CCACAGAGCTGTCGCCCCCAGGGAAGCGGAGCTACTAACTTCAGCCTGCTGAAGCAGGCT

GGAGACGTGGAGGAGAACCCTGGACCTATGTCTCAGAGCGAGACAAGGAGGGGCCGGAGA

GGAACCAGGGAGGAGACACTGGAGAAGTGGATCACAGCCAGAAAGAAGGCCGAGGAGCTG

GAGAAGGACCTGCGGAAGACCAGAAAGACAATCAAGAAGCTGGAAGAAGAAAATCCATGG

CTGGGAAATATCGTGGGCATCATCAGGAAGGGCAAGGACGGCGAGGGAGCACCACCAGCC

AAGAGGCCTCGCACTGATCAGATGGAGGTGGATTCCGGCCCTGGCAAGAGGCCACACAAG

TCTGGCTTCACAGACAAGGAGAGGGAGGACCATAGGCGCCGGAAGGCCCTGGAAAACAAG

AAGAAGCAATTATCTGCCGGCGGCAAGATCCTGAGCAAAGAGGAAGAGGAGGAGCTGAGA

AGGCTGACCGACGAGGATGAGGAGAGGAAGAGGAGGGTGGCAGGACCAAGAGTGGGCGAC

GTGAATCCTAGCAGAGGCGGACCAAGAGGCGCCCCAGGCGGGGGCTTCGTGCCACAGATG

GCAGGAGTGCCAGAGTCCCCTTTTTCTAGGACCGGAGAGGGCCTGGATATCAGGGGAACA

CAGGGCTTTCCATGGGTGTCCCCATCTCCTCCACAGCAGAGGCTGCCACTGCTGGAGTGC

ACCCCTCAGAGCCAGTCCGAGTCTAAGAAGAATAGAAGGGGCGGCCGCGAGGACATCCTG

GAGAAGTGGATCACCACACGCAGAAAAGCTGAAGAACTGGAAAAGGACCTGAGGAAGGCC

CGCAAAACAATCAAGAAGCTGGAGGATGAGAACCCTTGGCTGGGCAATATCATCGGAATT

ATCAGGAAGGGCAAGGATGGCGAAGGCGCCCCACCTGCAAAGCGGCCAAGGACTGATCAG

ATGGAAATCGATAGCGGAACAGGCAAGCGGCCCCACAAGTCCGGCTTCACCGACAAGGAG

AGAGAGGATCACAGAAGGCGCAAGGCCCTGGAGAACAAGAAGAAGCAATTAAGCAGCGGC

GGCAAGAATCTGTCCAGAGAAGAAGAGGAGGAGCTGGGCAGACTGACCGTGGAGGACGAG

GAGCGGAGAAGGCGCGTGGCAGGACCTCGCACAGGCGATGTGAACCTGTCCGGAGGAGGA

CCTAGGGGAGCACCAGGAGGCGGCTTCGTGCCACGCATGGAGGGCGTGCCAGAGTCTCCC

TTTACCCGCACCGGAGAGGGCCTGGACATCAGGGGCAATCAGGGCTTTCCCTGGGTCCGC

CCCTCCCCCCCTCAGCAGAGACTGCCCCTGCTGGAATGCACACCACAG

SEQ ID NO: 33 delta 5 codon optimized with restriction sites (HindIII/EcoRI)

A↓AGCTT*GCACC*ATGGCCTCACGGTCAGAGTCAAAGAAAAATAGGGGGGGGCGGGAAGAA

ATCCTGGAACAGTGGGTCGGAGCACGGAAAAAACTGGAAGAGCTGGAGAGGGACCTGCGC

AAGATCAAGAAGAAGATCAAGAAGCTGGAGGAGGAGAACCCCTGGCTGGGCAATATCAAG

GGCATCCTGGGCAAGAAGGATCGGGAGGGAGAGGGAGCACCACCTGCAAAGAGGGCCAGA

GCCGACCAGATGGAGGTGGATAGCGGCCCTAGGAAGCGCCCATTCAGAGGCGAGTTTACC

-continued

GACAAGGAGCGGAGAGATCACAGGCGCCGGAAGGCCCTGGAGAACAAGCCGAAGCAGCTG

AGCTCCGGCGGCAAGTCCCTGTCTAAGGAGGAGGAGGAGGAGCTGAGAAAGCTGACAGAG

GAGGACGAGAGAAGGGAGCGCCGGGTGGCCGGCCCAAGGGTGGGCGGCGTGAACCCCCTG

GAGGACGAGAGAAGGGAGCGCCGGGTGGCCGGCCCAAGGGTGGGCGGCGTGAACCCCCTG

GAGAGCCCATTTGCCAGGACAGGAGAGGGCCTGGATGTGCGCGGCAATCAGGGCTTCCCC

TGGGACATCCTGTTTCCTGCCGATCCACCCTTCAGCCCACAGTCCTGCAGGCCTCAGAGC

AGATCCGAGTCTAAGAAGAACAGGGGAGGAAGAGAGGAGGTGCTGGAGCAGTGGGTGAAT

GGCCGGAAGAAGCTGGAGGAGCTGGAGCGGGAGCTGAGAAGGGCCAGAAAGAAGATCAAG

AAGCTGGAAGACGATAATCCTTGGCTGGGCAATGTGAAAGGCATCCTGGGCAAGAAGGAC

AAGGATGGAGAGGGAGCACCTCCAGCAAAGAGGGCAAGAACCGACCAGATGGAGATCGAT

AGCGGACCAAGGAAGCGCCCTCTGAGAGGAGGCTTCACAGACCGGGAGAGACAGGATCAC

CGCCGGAGAAAGGCCCTGAAGAACAAGAAGAAGCAGCTGTCCGCCGGAGGCAAGAGCCTG

TCCAAAGAAGAGGAAGAGGAGCTGAAGAGGCTGACCCGCGAGGACGAGGAGCGGAAGAAG

GAGGAGCACGGCCCTTCCAGACTGGGCGTGAATCCATCTGAGGGAGGACCAAGGGGAGCA

CCAGGCGGCGGCTTCGTGCCAAGCATGCAGGGCATCCCCGAGTCCCGGTTTACCAGAACA

GGAGAGGGCCTGGACGTGAGGGGCTCTCGCGGCTTTCCTCAGGACATCCTGTTCCCAAGC

GATCCCCCTTTTTCTCCACAGAGCTGTCGCCCCCAGGGAAGCGGAGCTACTAACTTCAGC

CTGCTGAAGCAGGCTGGAGACGTGGAGGAGAACCCTGGACCTATGTCTCAGAGCGAGACA

AGGAGGGGCCGGAGAGGAACCAGGGAGGAGACACTGGAGAAGTGGATCACAGCCAGAAAG

AAGGCCGAGGAGCTGGAGAAGGACCTCCGGAAGACCAGAAAGACAATCAAGAAGCTGGAA

GAAGAAAATCCATGGCTGGGAAATATCGTGGGCATCATCAGGAAGGGCAAGGACGGCGAG

GGAGCACCACCAGCCAAGAGGCCTCGCACTGATCAGATGGAGGTGGATTCCGGCCCTCCC

AAGAGGCCACACAAGTCTGGCTTCACAGACAAGGAGAGGGAGGACCATAGGCGCCGGAAG

GCCCTGGAAAACAAGAAGAAGCAATTATCTGCCGGCGGCAAGATCCTGAGCAAAGAGGAA

GAGGAGGAGCTGAGAAGGCTGACCGACGAGGATGAGGAGAGGAAGAGGAGGGTGGCAGGA

CCAAGAGTGGGCGACGTGAATCCTAGCAGAGGCGGACCAAGAGGCGCCCCAGGCGGGGGC

TTCGTGCCACAGATGGCAGGAGTGCCAGAGTCCCCTTTTTCTAGGACCGGAGAGGGCCTG

GATATCAGGGGAACACAGGGCTTTCCATGGGTGTCCCCATCTCCTCCACAGCAGAGGCTG

CCACTCCTGGAGTGCACCCCTCAGAGCCAGTCCGAGTCTAAGAAGAATAGAAGGGGCCGC

CGCGAGGACATCCTGGAGAAGTGGATCACCACACGCAGAAAAGCTGAAGAACTGGAAAAG

GACCTGAGGAAGGCCCGCAAAACAATCAAGAAGCTGGAGGATGAGAACCCTTGGCTGGGC

AATATCATCGGAATTATCAGGAAGGGCAAGGATGGCGAAGGCGCCCCACCTGCAAAGCGG

CCAAGGACTGATCAGATGGAAATCGATAGCGGAACAGGCAAGCGGCCCCACAAGTCCGGC

TTCACCGACAAGGAGAGAGAGGATCACAGAAGGCGCAAGGCCCTGGAGAACAAGAAGAAG

CAATTAAGCAGCGGCGGCAAGAATCTGTCCAGAGAAGAAGAGGAGGAGCTGGGCAGACTG

ACCGTGGAGGACGAGGAGCGGAGAAGGCGCGTGGCAGGACCTCGCACAGGCGATGTGAAC

CTGTCCGGAGGAGGACCTAGGGGAGCACCAGGAGGCGGCTTCGTGCCACGCATGGAGGGC

GTGCCAGAGTCTCCCTTTACCCGCACCGGAGAGGGCCTGGACATCAGGGGCAATCAGGGC

TTTCCCTGGGTCCGCCCCTCCCCCCCTCAGCAGAGACTGCCCCTGCTGGAATGCACACCA

CAGTGATGAGIAATTCCGT

-continued

SEQ ID NO: 34 delta 5 protein
MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKAL

ENKRKQLSSGGKSLSKEEEEELRKLTEEDERRERRVAGPRVGGVNPLEGGTRGAP

GGGFVPSMQGVPESPFARTGEGLDVRGNQGFPWDILFPADPPFSPQSCRPQSRSES

KKNRGGREEVLEQWVNGRKKLEELERELRRARKKIKKLEDDNPWLGNVKGILG

KKDKDGEGAPPAKRARTDQMEIDSGPRKRPLRGGFTDRERQDHRRRKALKNKK

KQLSAGGKSLSKEEEEELKRLTREDEERKKEEHGPSRLGVNPSEGGPRGAPGGGF

VPSMQGIPESRFTRTGEGLDVRGSRGFPQDILFPSDPPFSPQSCRPQGSGATNFSLL

KQAGDVEENPGPMSQSETRRGRRGTREETLEKWITARKKAEELEKDLRKTRKTIK

KLEEENPWLGNIVGIIRKGKDGEGAPPAKRPRTDQMEVDSGPGKRPHKSGFTDKE

REDHRRRKALENKKKQLSAGGKILSKEEEEELRRLTDEDEERKRRVAGPRVGDV

NPSRGGPRGAPGGGFVPQMAGVPESPFSRTGEGLDIRGTQGFPWVSPSPPQQRLP

LLECTPQSQSESKKNRRGGREDILEKWITTRRKAEELEKDLRKARKTIKKLEDENP

WLGNIIGIIRKGKDGEGAPPAKRPRTDQMEIDSGTGKRPHKSGFTDKEREDHRRR

KALENKKKQLSSGGKNLSREEEEELGRLTVEDEERRRRVAGPRTGDVNLSGGGP

RGAPGGGFVPRMEGVPESPFTRTGEGLDIRGNQGFPWVRPSPPQQRLPLLECTPQ

SEQ ID NO: 35 delta 6 wt
AGCCGCAGCGAAAGCAAAAAAAACCGCGGCGGCCGCGAAGAAATTCTGGAA

CAGTGGGTTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGGGAAGCGGAGCTACTAACTTCAGCCTGCTGAAGCAG

GCTGGAGACGTGGAGGAGAACCCTGGACCTATGAGCCGCAGCGAAAGCAAAAAAA

ACCGCGGCGGCCGCGAAGAAGTGCTGGAACAGTGGGTGAACGGCCGCAAAA

AACTGGAAGAACTGGAACGCGAACTGCGCCGCGCGCGCAAAAAAATTAAAA

AACTGGAAGATGATAACCCGTGGCTGGGCAACGTGAAAGGCATTCTGGGCAA

AAAAGATAAAGATGGCGAAGGCGCGCCGCCGGCGAAACGCGCGCGCACCGA

TCAGATGGAAATTGATAGCGGCCCGCGCAAACGCCCGCTGCGCGGCGGCTTT

ACCGATCGCGAACGCCAGGATCATCGCCGCCGCAAAGCGCTGAAAAACAAA

AAAAAACAGCTGAGCGCGGGCGGCAAAAGCCTGAGCAAAGAAGAAGAAGAA

GAACTGAAACGCCTGACCCGCGAAGATGAAGAACGCAAAAAAGAAGAACAT

GGCCCGAGCCGCCTGGGCGTGAACCCGAGCGAAGGCGGCCCGCGCGGCGCG

CCGGGCGGCGGCTTTGTGCCGAGCATGCAGGGCATTCCGGAAAGCCGCTTTA

-continued

CCCGCACCGGCGAAGGCCTGGATGTGCGCGGCAGCCGCGGCTTTCCGCAGGA

TATTCTGTTTCCGAGCGATCCGCCGTTTAGCCCGCAGAGCTGCCGCCCGCAGG

GAAGCGGAGCTACTAACTTCAGCCTGCTGAAGCAGGCTGGAGACGTGGAGGAGAACCCTG

GACCTATGAGCCAGAGCGAAACCCGCCGCGGCCGCCGCGGCACCCGCGAAGA

AACCCTGGAAAAATGGATTACCGCGCGCAAAAAAGCGGAAGAACTGGAAAA

AGATCTGCGCAAAACCCGCAAAACCATTAAAAAACTGGAAGAAGAAAACCC

GTGGCTGGGCAACATTGTGGGCATTATTCGCAAAGGCAAAGATGGCGAAGGC

GCGCCGCCGGCGAAACGCCCGCGCACCGATCAGATGGAAGTGGATAGCGGCC

CGGGCAAACGCCCGCATAAAAGCGGCTTTACCGATAAAGAACGCGAAGATCA

TCGCCGCCGCAAAGCGCTGGAAAACAAAAAAAAACAGCTGAGCGCGGGCGG

CAAAATTCTGAGCAAAGAAGAAGAAGAAGAACTGCGCCGCCTGACCGATGA

AGATGAAGAACGCAAACGCCGCGTGGCGGGCCCGCGCGTGGGCGATGTGAA

CCCGAGCCGCGGCGGCCCGCGCGGCGCGCCGGGCGGCGGCTTTGTGCCGCAG

ATGGCGGGCGTGCCGGAAAGCCCGTTTAGCCGCACCGGCGAAGGCCTGGATA

TTCGCGGCACCCAGGGCTTTCCGTGGGTGAGCCCGAGCCCGCCGCAGCAGCG

CCTGCCGCTGCTGGAATGCACCCCGCAGGGAAGCGGAGCTACTAACTTCAGCCTGC

TGAAGCAGGCTGGAGACGTGGAGGAGAACCCTGGACCTATGAGCCAGAGCGAAAGC

AAAAAAAACCGCCGCGGCGGCCGCGAAGATATTCTGGAAAAATGGATTACCA

CCCGCCGCAAAGCGGAAGAACTGGAAAAAGATCTGCGCAAAGCGCGCAAAA

CCATTAAAAAACTGGAAGATGAAAACCCGTGGCTGGGCAACATTATTGGCAT

TATTCGCAAAGGCAAAGATGGCGAAGGCGCGCCGCCGGCGAAACGCCCGCG

CACCGATCAGATGGAAATTGATAGCGGCACCGGCAAACGCCCGCATAAAAGC

GGCTTTACCGATAAAGAACGCGAAGATCATCGCCGCCGCAAAGCGCTGGAAA

ACAAAAAAAAACAGCTGAGCAGCGGCGGCAAAAACCTGAGCCGCGAAGAAG

AAGAAGAACTGGGCCGCCTGACCGTGGAAGATGAAGAACGCCGCCGCCGCG

TGGCGGGCCCGCGCACCGGCGATGTGAACCTGAGCGGCGGCGGCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAG

SEQ ID NO: 36 delta 6 wt with restriction sites
(HindIII/EcoRI)
A↓AGCTT*GCACC*ATGGCCAGCCGCAGCGAAAGCAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAAATTAAAAAACTGGAAGAAGA

AAACCCGTGGCTGGGCAACATTAAAGGCATTCTGGGCAAAAAAGATCGCGAA

GGCGAAGGCGCGCCGCCGGCGAAACGCGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGAAGAAGAACTGCGCAAAC

TGACCGAAGAAGATGAACGCCGCGAACGCCGCGTGGCGGGCCCGCGCGTGG

-continued

GCGGCGTGAACCCGCTGGAAGGCGGCACCCGCGGCGCGCCGGGCGGCGGCTT

TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

GGATCCGCCGTTTAGCCCGCAGAGCTGCCGCCCGCAGGGAAGCGGAGCTACTAA

CTTCAGCCTGCTGAAGCAGGCTGGAGACGTGGAGGAGAACCCTGGACCTATGAGCCGC

AGCGAAAGCAAAAAAAACCGCGGCGGCCGCGAAGAAGTGCTGGAACAGTGG

GTGAACGGCCGCAAAAAACTGGAAGAACTGGAACGCGAACTGCGCCGCGCG

CGCAAAAAAATTAAAAAACTGGAAGATGATAACCCGTGGCTGGGCAACGTGA

AAGGCATTCTGGGCAAAAAAGATAAAGATGGCGAAGGCGCGCCGCCGGCGA

AACGCGCGCGCACCGATCAGATGGAAATTGATAGCGGCCCGCGCAAACGCCC

GCTGCGCGGCGGCTTTACCGATCGCGAACGCCAGGATCATCGCCGCCGCAAA

GCGCTGAAAAACAAAAAAAAACAGCTGAGCGCGGGCGGCAAAAGCCTGAGC

AAAGAAGAAGAAGAAGAACTGAAACGCCTGACCCGCGAAGATGAAGAACGC

AAAAAAGAAGAACATGGCCCGAGCCGCCTGGGCGTGAACCCGAGCGAAGGC

GGCCCGCGCGGCGCGCCGGGCGGCGGCTTTGTGCCGAGCATGCAGGGCATTC

CGGAAAGCCGCTTTACCCGCACCGGCGAAGGCCTGGATGTGCGCGGCAGCCG

CGGCTTTCCGCAGGATATTCTGTTTCCGAGCGATCCGCCGTTTAGCCCGCAGA

GCTGCCGCCCGCAGGGAAGCGGAGCTACTAACTTCAGCCTGCTGAAGCAGGCTGGAGA

CGTGGAGGAGAACCCTGGACCTATGAGCCAGAGCGAAACCCGCCGCCTGCCGCCG

CGGCACCCGCGAAGAAACCCTGGAAAAATGGATTACCGCGCGCAAAAAAGC

GGAAGAACTGGAAAAAGATCTGCGCAAAACCCGCAAAACCATTAAAAAACT

GGAAGAAGAAAACCCGTGGCTGGGCAACATTGTGGGCATTATTCGCAAAGGC

AAAGATGGCGAAGGCGCGCCGCCGGCGAAACGCCCGCGCACCGATCAGATG

GAAGTGGATAGCGGCCCGGGCAAACGCCCGCATAAAAGCGGCTTTACCGATA

AAGAACGCGAAGATCATCGCCGCCGCAAAGCGCTGGAAAACAAAAAAAAAC

AGCTGAGCGCGGGCGGCAAAATTCTGAGCAAAGAAGAAGAAGAAGAACTGC

GCCGCCTGACCGATGAAGATGAAGAACGCAAACGCCGCGTGGCGGGCCCGC

GCGTGGGCGATGTGAACCCGAGCCGCGGCGGCCCGCGCGGCGCGCCGGGCG

GCGGCTTTGTGCCGCAGATGGCGGGCGTGCCGGAAAGCCCGTTTAGCCGCAC

CGGCGAAGGCCTGGATATTCGCGGCACCCAGGGCTTTCCGTGGGTGAGCCCG

AGCCCGCCGCAGCAGCGCCTGCCGCTGCTGGAATGCACCCCGCAGGGAAGCGG

AGCTACTAACTTCAGCCTGCTGAAGCAGGCTGGAGACGTGGAGGAGAACCCTGGACCTA

TGAGCCAGAGCGAAAGCAAAAAAAACCGCCGCGGCGGCCGCGAAGATATTC

TGGAAAAATGGATTACCACCCGCCGCAAAGCGGAAGAACTGGAAAAAGATC

TGCGCAAAGCGCGCAAAACCATTAAAAAACTGGAAGATGAAAACCCGTGGCT

GGGCAACATTATTGGCATTATTCGCAAAGGCAAAGATGGCGAAGGCGCGCCG

CCGGCGAAACGCCCGCGCACCGATCAGATGGAAATTGATAGCGGCACCGGCA

AACGCCCGCATAAAAGCGGCTTTACCGATAAAGAACGCGAAGATCATCGCCG

CCGCAAAGCGCTGGAAAACAAAAAAAAACAGCTGAGCAGCCTGCGGCAAAAA

CCTGAGCCGCGAAGAAGAAGAAGAACTGGGCCGCCTGACCGTGGAAGATGA

AGAACGCCGCCGCCGCGTGGCGGGCCCGCGCACCGGCGATGTGAACCTGAGC

-continued

GGCGGCGGCCCGCGCGGCGCGCCGGGCGGCGGCTTTGTGCCGCGCATGGAAG

GCGTGCCGGAAAGCCCGTTTACCCGCACCGGCGAAGGCCTGGATATTCGCGG

CAACCAGGGCTTTCCGTGGGTGCGCCCGAGCCCGCCGCAGCAGCGCCTGCCG

CTGCTGGAATGCACCCCGCAGTGATGAG↓AATTCCGT

SEQ ID NO: 37 delta 6 codon optimized
GCCTCACGGTCAGAGTCAAAGAAGAACAGAGGCGGAAGAGAAGAAATCCTGGAGCAGTGG

GTCGGAGCACGGAAAAAGCTGGAAGAACTGGAGAGGGACCTGCGCAAGATCAAGAAGAAG

ATCAAGAAGCTGGAGGAGGAGAACCCCTGGCTGGGCAATATCAAGGGCATCCTGGGCAAG

AAGGATAGGGAGGGAGAGGGAGCACCACCTGCAAAGAGGGCCAGAGCCGACCAGATGGAG

GTGGATAGCGGACCAAGGAAGCGCCCCTTCCGCGGAGAGTTTACCGACAAGGAGCGGAGA

GATCACAGGCGCCGGAAGGCCCTGGAGAACAAGAGGAAGCAGCTGAGCTCCGGCGGCAAG

TCCCTGTCTAAGGAGGAGGAGGAGGAGCTGCGCAAGCTGAGAGAGGAGGACGAGAGAAGG

GAGAGGAGGGTGGCAGCACCAAGGGTGGGAGGAGTGAATCCTCTGGAGGGAGGAACCAGA

GGAGCACCAGGAGGAGGCTTCGTGCCAAGCATGCAGGGAGTGCCAGAGTCCCCCTTTGCC

AGGACAGGAGAGGGCCTGGACGTGAGAGGCAACCAGGGCTTCCCTTGGGACATCCTGTTT

CCAGCCGATCCACCCTTCAGCCCTCACTCCTGCAGGCCACAGGGAAGCGGAGCTACTAAC

TTCAGCCTGCTGAAGCAGGCTGGAGACGTGGAGGAGAACCCTGGACCTATGAGCCGGTCC

GAGTCTAAGAAGAATAGGGGAGGAAGAGAGGAGGTGCTGGAGCAGTGGGTGAACGGCAGA

AAGAAGCTGGAGGAGCTGGAGAGGGAGCTGAGAAGGGCCCGCAAGAAGATCAAGAAGCTG

GAAGACGATAATCCTTGGCTGGGCAATGTGAAAGGCATCCTGGGCAAGAAGGACAAGGAT

GGAGAGGGAGCACCTCCAGCAAAGAGGGCAAGAACCGACCAGATGGAGATCGATAGCGGA

CCTAGGAAGCGCCCACTGAGGGGAGGCTTTACAGACCGGGAGAGACAGGATCACCGCCGG

AGAAAGGCCCTGAAGAACAAGAAGAAGCAGCTGTCCGCCGGAGGCAAGAGCCTGTCCAAA

GAAGAGGAAGAGGAGCTGAAGAGGCTGACCCGCGAGGACGAGGAGAGGAAGAAGGAGGAG

CACGGACCATCTAGGCTGGGAGTGAATCCCAGCGAGGGAGGACCAAGGGGAGCACCTGGA

GGAGGCTTCGTGCCCTCCATGCAGGGCATCCCTGAGTCTCGGTTTACCAGAACCGGCGAG

GGCCTGGACGTGAGGGGCAGTTTCCGCGGCCCACAGGACATCCTCTTCCCCTCCGATCCC

CCTTTTTCTCCCCAGAGCTGTCGCCCTCAAGGAAGCGGAGCTACTAACTTCAGCCTGCTG

AAGCAGGCTCGAGACGTGGAGGAGAACCCTGGACCTATGTCTCAGAGCGAGACAAGGAGG

GGCCGGAGAGGAACCAGGGAGGAGACACTGGAGAAGTGGATCACAGCCCGCAAGAAGGCC

GAGGAGCTGGAGAAGGACCTGCGGAAGACCAGAAAGACAATCAAGAAGCTGGAAGAAGAG

AACCCTTGGCTGGGCAATATCGTGGGCATCATCAGGAAGGGCAAGGACGGCGAGGGAGCA

CCACCAGCCAAGAGGCCACGCACTGATCAGATGGAGGTGGATTCTGGACCAGGCAAGCGG

CCCCACAAGAGCGGCTTCACAGACAAGGAGAGAGAGGACCATAGGCGCCGGAAGGCCCTG

GAAAACAAGAAGAAGCAATTAAGCGCCGGCGGCAAGATCCTGTCCAAAGAGGAAGAGGAG

GAGCTGAGAAGGCTGACCGACGAGGATGAGGAGAGGAAAAGAAGGGTGGCAGGACCTAGG

GTGGGCGACGTGAATCCAAGCAGGGGAGGACCTAGAGGAGCACCAGGAGGCGGCTTCGTG

CCACAGATGGCAGGAGTGCCTGAGTCCCCATTTTCTCGGACCGGCGAGGGCCTGGATATC

AGAGGCACACAGGGCTTCCCCTGGGTGTCCCCTTCTCCTCCACAGCAGCGGCTGCCTCTG

CTGGAGTGCACCCCTCAGGGAAGCGGAGCTACTAACTTCAGCCTGCTGAAGCAGGCTGGA

GACGTGGAGGAGAACCCTGGACCTATGTCGCAGAGCGAATCTAAGAAGAATAGAAGGGGC

-continued

GGCAGAGAGGATATCCTGGAGAAGTGGATCACCACACGCAGAAAAGCTGAAGAACTGGAA

AAGGACCTGAGGAAGGCCCGCAAGACCATCAAGAAGCTGGAGGATGAAAATCCATGGCTG

GGAAATATCATCGGCATCATCCGGAAGGGCAAGGACGGGGAAGGCGCCCCACCTGCAAAG

CGGCCCAGGACTGATCAGATGGAAATCGATTCCGGCACAGGCAAGAGGCCTCACAAGTCT

GGCTTCACAGATAAAGAGCGCGAGGATCACAGAAGGCGCAAGGCCCTGGAGAACAAGAAG

AAGCAATTATCTAGCGGCGGCAAGAATCTGTCCAGAGAAGAAGAGGAGGAGCTGGGCCGC

CTGACCGTGGAGGACGAGGAGCGGAGAAGGCGCGTGGCAGGACCAAGAACAGGCGATGTG

AACCTGTCTGGAGGCGGCCCAAGGGGCGCCCCCGGCGGAGGCTTCGTGCCAAGAATGGAA

GGCGTGCCAGAGTCCCCTTTTACCCGGACAGGGGAAGGCCTGGACATTAGAGGCAATCAG

GGCTTTCCCTGGGTGCGACCAAGCCCCCCTCAGCAGCGACTGCCTCTGCTGGAGTGTACC

CCTCAG

SEQ ID NO: 38 delta 6 codon optimized with restriction
sites (HindIII/EcoRI)
A↓AGCTT*GCACC*ATGGCCTCACGGTCAGAGTCAAAGAAGAACAGAGGCGGAAGAGAAGAA

ATCCTGGAGCAGTGGGTCGGAGCACGGAAAAAGCTGGAAGAACTGGAGAGGGACCTGCGC

AAGATCAAGAAGAAGATCAAGAAGCTGGAGGAGGAGAACCCCTGGCTGGGCAATATCAAG

GGCATCCTGGGCAAGAAGGATAGGGAGGGAGAGGGAGCACCACCTGCAAAGAGGGCCAGA

GCCGACCAGATGGAGGTGGATAGCGGACCAAGGAAGCGCCCCTTCCGCGGAGAGTTTACC

GACAAGGAGCGGAGAGATCACAGGCGCCGGAAGGCCCTGGAGAACAAGAGGAAGCAGCTG

AGCTCCGGCGGCAAGTCCCTGTCTAAGGAGGAGGAGGAGGAGCTGCGCAAGCTGACAGAG

GAGGACGAGAGAAGGGAGAGGAGGGTGGCAGGACCAAGGGTGGGAGGAGTGAATCCTCTG

GAGGGAGGAACCAGAGGAGCACCAGGAGGAGGCTTCGTGCCAAGCATGCAGGGAGTGCCA

GAGTCCCCCTTTGCCAGGACAGGAGAGGGCCTGGACGTGAGAGGCAACCAGGGCTTCCCT

TGGGACATCCTGTTTCCAGCCGATCCACCCTTCAGCCCTCAGTCCTGCAGGCCACAGGGA

AGCGGAGCTACTAACTTCAGCCTGCTGAAGCAGGCTGGAGACGTGGAGGAGAACCCTGGA

CCTATGAGCCGGTCCGAGTCTAAGAAGAATAGGGGAGGAAGAGAGGAGGTGCTGGAGCAG

TGGGTGAACGGCAGAAAGAAGCTGGAGGAGCTGGAGAGGGAGCTGAGAAGGGCCCGCAAG

AAGATCAAGAAGCTGGAAGACGATAATCCTTGGCTGGGCAATGTGAAAGGCATCCTGGGC

AAGAAGGACAAGGATGGAGAGGGAGCACCTCCAGCAAAGAGGGCAAGAACCGACCAGATG

GAGATCGATAGCGGACCTAGGAAGCGCCCACTGAGGGGAGGCTTTACAGACCGGGAGAGA

CAGGATCACCGCCGGAGAAAGGCCCTGAAGAACAAGAA6AAGCAGCTGTCCGCCGGAGGC

AAGAGCCTGTCCAAAGAAGAGGAAGAGGAGCTGAAGAGGCTGACCCGCGAGGACGAGGAG

AGGAAGAAGGAGGAGCACGGACCATCTAGGCTGGGAGTGAATCCCAGCGAGGGAGGACCA

AGGGGAGCACCTGGAGGAGGCTTCGTGCCCTCCATGCAGGGCATCCCTGAGTCTCGGTTT

ACCAGAACCGGCGAGGGCCTGGACGTGAGGGGCAGCCGCGGCTTTCCACAGGACATCCTG

TTCCCCTCCGATCCCCCTTTTTCTCCCCAGAGCTGTCGCCCTCAAGGAAGCGGAGCTACT

AACTTCAGCCTGCTGAAGCAGGCTGGAGACGTGGAGGAGAACCCTGGACCTATGTCTCAG

AGCGAGACAAGGAGGGGCCGGAGAGGAACCAGGGAGGAGACACTGGAGAAGTGGATCACA

GCCCGCAAGAAGGCCGAGGAGCTGGAGAAGGACCTGCGGAAGACCAGAAAGACAATCAAG

AAGCTGGAAGAAGAGAACCCTTGGCTGGGCAATATCGTGGGCATCATCAGGAAGGGCAAG

GACGGCGAGGGAGCACCACCAGCCAAGAGGCCACGCACTGATCAGATGGAGGTGGATTCT

-continued

GGACCAGGCAAGCGGCCCCACAAGAGCGGCTTCACAGACAAGGAGAGAGAGGACCATAGG

CGCCGGAAGGCCCTGGAAAACAAGAAGAAGCAATTAAGCGCCGGCGGCAAGATCCTGTCC

AAAGAGGAAGAGGAGGAGCTGAGAAGGCTGACCGACGAGGATGAGGAGAGGAAAAGAAGG

GTGGCAGGACCTAGGGTGGGCGACGTGAATCCAAGCAGGGGAGGACCTAGAGGAGCACCA

GGAGGCGGCTTCGTGCCACAGATGGCAGGAGTGCCTGAGTCCCCATTTTCTCGGACCGGC

GAGGGCCTGGATATCAGAGGCACACAGGGCTTCCCCTGGGTGTCCCCTTCTCCTCCACAG

CAGCGGCTGCCTCTGCTGGAGTGCACCCCTCAGGGAAGCGGAGCTACTAACTTCAGCCTG

CTGAAGCAGGCTGGAGACGTGGAGGAGAACCCTGGACCTATGTCGCAGAGCGAATCTAAG

AAGAATAGAAGGGGCGGCAGAGAGGATATCCTGGAGAAGTGGATCACCACACGCAGAAAA

GCTGAAGAACTGGAAAAGGACCTGAGGAAGGCCCGCAAGACCATCAAGAAGCTGGAGGAT

GAAAATCCATGGCTGGGAAATATCATCGGCATCATCCGGAAGGGCAAGGACGGGGAAGGC

GCCCCACCTGCAAAGCGGCCCAGGACTGATCAGATGGAAATCGATTCCGGCACAGGCAAG

AGGCCTCACAAGTCTGGCTTCACAGATAAAGAGCGCGAGGATCACAGAAGGCGCAAGGCC

CTGGAGAACAAGAAGAAGCAATTATCTAGCGGCGGCAAGAATCTGTCCAGAGAAGAAGAG

GAGGAGCTGGGCCGCCTGACCGTGGAGGACGAGGAGCGGAGAAGGCGCGTGGCAGGACCA

AGAACAGGCGATGTGAACCTGTCTGGAGGCGGCCCAAGGGGCGCCCCCGGCGGAGGCTTC

GTGCCAAGAATGGAAGGCGTGCCAGAGTCCCCTTTTACCCGGACAGGGGAAGGCCTGGAC

ATTAGAGGCAATCAGGGCTTTCCCTGGGTGCGACCAAGCCCCCCTCAGCAGCGACTGCCT

CTGCTGGAGTGTACCCCTCAGTGATGAG↓AATTCCGT

SEQ ID NO: 39 delta 6 protein
MASRSESKKNRGGREEILEQWVGARKKLEELERDLRKFKKKIKKLEEENPWLGNI

KGILGKKDREGEGAPPAKRARADQMEVDSGPRKRPFRGEFTDKERRDHRRRKAL

ENKRKQLSSGGKSLSKEEEEELRKLTEEDERRERRVAGPRVGGVNPLEGGTRGAP

GGGFVPSMQGVPESPFFARTGEGLDVRGNQGFPWDILFPADPPFSPQSCRPQGSGA

TNFSLLKQAGDVEENPGPMSRSESKKNRGGREEVLEQWVNGRKKLEELERELRR

ARKKIKKLEDDNPWLGNVKGILGKKDKDGEGAPPAKRARTDQMEIDSGPRKRPL

RGGFTDRERQDHRRRKALKNKKKQLSAGGKSLSKEEEEELKRLTREDEERKKEE

HGPSRLGVNPSEGGPRGAPGGGFVPSMQGIPESRFTRTGEGLDVRGSRGFPQDILF

PSDPPFSPQSCRPQGSGATNFSLLKQAGDVEENPGPMSQSETRRGRRGTREETLEK

WITARKKAEELEKDLRKTRKTIKKLEEENPWLGNIVGIIRKGKDGEGAPPAKRPRT

DQMEVDSGPGKRPHKSGFTDKEREDHRRRKALENKKKQLSAGGKILSKEEEEEL

RRLTDEDEERKRRVAGPRVGDVNPSRGGPRGAPGGGFVPQMAGVPESPFSRTGE

GLDIRGTQGFPVVVSPSPPOQRLPLLECTPQGSGATNFSLLKOAGDVEENPGPMSQ

SESKKNRRGGREDILEKWITTRRKAEELEKDLRKARKTIKKLEDENPWLGNIIGIIR

KGKDGEGAPPAKRPRTDQMEIDSGTGKRPHKSGFTDKEREDHRRRKALENKKK

QLSSGGKNLSREEEEELGRLTVEDEERRRRVAGPRTGDVNLSGGGPRGAPGGGF

VPRMEGVPESPFTRTGEGLDIRGNQGFPWVRPSPPQQRLPLLECTPQ

SEQ ID NO: 40 delta 7 wt
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

-continued

CCGGCGAAACGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGAGCCGCAGCGAAAGCAAAAAAAACCGCGGC

GGCCGCGAAGAAGTGCTGGAACAGTGGGTGAACGGCCGCAAAAAACTGGAA

GAACTGGAACGCGAACTGCGCCGCGCGCGCAAAAAAATTAAAAAACTGGAA

GATGATAACCCGTGGCTGGGCAACGTGAAAGGCATTCTGGGCAAAAAAGATA

AAGATGGCGAAGGCGCGCCGCCGGCGAAACGCGCGCGCACCGATCAGATGG

AAATTGATAGCGGCCCGCGCAAACGCCCGCTGCGCGGCGGCTTTACCGATCG

CGAACGCCAGGATCATCGCCGCCGCAAAGCGCTGAAAAACAAAAAAAAACA

GCTGAGCGCGGGCGGCAAAAGCCTGAGCAAAGAAGAAGAAGAAGAACTGAA

ACGCCTGACCCGCGAAGATGAAGAACCiCAAAAAAGAAGAACATGGCCCGAG

CCGCCTGGGCGTGAACCCGAGCGAAGGCGGCCCGCGCGGCGCGCCGGGCGG

CGGCTTTGTGCCGAGCATGCAGGGCATTCCGGAAAGCCGCTTTACCCGCACC

GGCGAAGGCCTGGATGTGCGCGGCAGCCGCGGCTTTCCGCAGGATATTCTGT

TTCCGAGCGATCCGCCGTTTAGCCCGCAGAGCTGCCGCCCGCAGGGCACCAA

CCTGAGCACCAGCAACCCGCTGGGCTTTTTTCCGGATCATCAGCTGGATCCGG

CGTTTCGCGCGAACAGCGCGAACCCGGATTGGGATTTTAACCCGAACAAAGA

TACCTGGCCGGATGCGAACAAAGTGGGCGGCCAGAACCTGAGCACCAGCAAC

CCGCTGGGCTTTTTTCCGGATCATCAGCTGGATCCGGCGTTTCGCGCGAACAC

CGCGAACCCGGATTGGGATTTTAACCCGAACAAAGATACCTGGCCGGATGCG

AACAAAGTGGGC

SEQ ID NO: 41 delta 7 wt with restriction sites
(HindIII/EcoRI)
A↓AGCTT*GCACC*ATGGCCAGCCGCAGCGAAAGCAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAAATTAAAAAACTGGAAGAAGA

AAACCCGTGGCTGGGCAACATTAAAGGCATTCTGGGCAAAAAAGATCGCGAA

GGCGAAGGCGCGCCGCCGGCGAAACGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGAAGAAGAACTGCGCAAAC

TGACCGAAGAAGATGAACGCCGCGAACGCCGCGTGGCGGGCCCGCGCGTGG

GCGGCGTGAACCCGCTGGAAGGCGGCACCCGCGGCGCGCCGGGCGGCGGCTT

TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

-continued

GGATCCGCCGTTTAGCCCGCAGAGCTGCCGCCCGCAGAGCCGCAGCGAAAGC

AAAAAAAACCGCGGCGGCCGCGAAGAAGTGCTGGAACAGTGGGTGAACGGC

CGCAAAAAACTGGAAGAACTGGAACGCGAACTGCGCCGCGCGCGCAAAAAA

ATTAAAAAACTGGAAGATGATAACCCGTGGCTGGGCAACGTGAAAGGCATTC

TGGGCAAAAAAGATAAAGATGGCGAAGGCGCGCCGCCGGCGAAACGCGCGC

GCACCGATCAGATGGAAATTGATAGCGGCCCGCGCAAACGCCCGCTGCGCGG

CGGCTTTACCGATCGCGAACGCCAGGATCATCGCCGCCGCAAAGCGCTGAAA

AACAAAAAAAAACAGCTGAGCGCGGGCGGCAAAAGCCTGAGCAAAGAAGAA

GAAGAAGAACTGAAACGCCTGACCCGCGAAGATGAAGAACGCAAAAAAGAA

GAACATGGCCCGAGCCGCCTGGGCGTGAACCCGAGCGAAGGCGGCCCGCGC

GGCGCGCCGGGCGGCGGCTTTGTGCCGAGCATGCAGGGCATTCCGGAAAGCC

GCTTTACCCGCACCGGCGAAGGCCTGGATGTGCGCGGCAGCCGCGGCTTTCC

GCAGGATATTCTGTTTCCGAGCGATCCGCCGTTTAGCCCGCAGAGCTGCCGCC

CGCAGGGCACCAACCTGAGCACCAGCAACCCGCTGGGCTTTTTTCCGGATCAT

CAGCTGGATCCGGCGTTTCGCGCGAACAGCGCGAACCCGGATTGGGATTTTA

ACCCGAACAAAGATACCTGGCCGGATGCGAACAAAGTGGGCGGCCAGAACC

TGAGCACCAGCAACCCGCTGGGCTTTTTTCCGGATCATCAGCTGGATCCGGCG

TTTCGCGCGAACACCGCGAACCCGGATTGGGATTTTAACCCGAACAAAGATA

CCTGGCCGGATGCGAACAAAGTGGGCTGATGAG↓AATTCCGT

SEQ ID NO: 42 delta 7 codon optimized

GCCTCACGGTCTGAGTCAAAGAAGAATCGGGGGGGAAGAGAAGAAATCCTGGAACAGTGG

GTCGGCGCACGGAAAAAACTGGAAGAACTGGAGCGGGACCTGAGAAAGATCAAGAAGAAG

ATCAAGAAGCTGGAGGAAGAGAACCCCTGGCTGGGCAATATCAAGGGCATCCTGGGCAAG

AAGGATCGGGAGGGCGAGGGAGCACCACCTGCAAAGAGGGCAAGGGCAGACCAGATGGAG

GTGGATTCCGGACCTAGGAAGCGGCCCTTCCGGGGAGAGTTTACCGACAAGGAGCGGAGA

GATCACAGGCGCCGGAAGGCCCTGGAGAACAAGCGGAAGCAGCTGAGCTCCGGCGGCAAG

TCTCTGACCAAGGAGGAGGAGGAGGAGCTGAGAAAGCTGACAGAGGAGGACGAGAGAAGG

GAGCGCCGGGTGGCCGGCCCAAGGGTGGGCGGCGTGAACCCCCTGGAGGGAGGAACCAGG

GGAGCACCAGGAGGAGGCTTCGTGCCTTCTATGCAGGGCGTGCCAGAGAGCCCCTTTGCC

AGGACAGGAGAGGGCCTGGATGTGCGCGGCAATCAGGGCTTCCCATGGGACATCCTGTTT

CCCGCCGATCCACCCTTCTCCCCTCAGTCTTGCAGGCCACAGTCCCGCTCTGAGAGCAAG

AAGAACAGGGGAGGAAGGGAGGAGGTGCTGGAGCAGTGGGTGAATGGCAGGAAGAAGCTG

GAGGAGCTGGAGCGGGAGCTGAGAAGGGCCAGAAAGAAGATCAAGAAGCTGGAAGACGAT

AATCCTTGGCTGGGCAATGTGAAAGGCATCCTGGGCAAGAAGGACAAGGATGGAGAGGGA

GCACCTCCAGCAAAGAGGGCACGCACCGACCAGATGGAGATCGATTCCGGACCAAGGAAG

CGGCCCCTGAGGGGAGGCTTCACAGACAGGGAGCGCCAGGATCACCGCCGGAGAAAGGCC

CTGAAGAACAAGAAGAAGCAGCTGTCTGCCGGCGGCAAGTCCCTGTCTAAAGAAGAGGAG

GAGGAGCTGAAGCGGCTGACCAGAGAGGACGAGGAGCGGAAGAAGGAGGAGCACGGCCCT

TCCAGACTGGGCGTGAATCCATCTGAGGGAGGACCAAGAGGCGCCCCTGGCGGAGGCTTC

GTGCCTAGCATGCAGGGCATCCCAGAGTCCAGGTTTACCAGAACCGGAGAGGGCCTGGAC

GTGCGGGGCTCTAGAGGCTTTCCCCAGGACATCCTGTTCCCTAGCGATCCCCCTTTTAGC

-continued

CCCCAGTCCTGTAGGCCTCAGGGCACCAACCTGAGCACATCCAATCCACTGGGCTTCTTT

CCAGACCACCAGCTGGATCCAGCCTTCCGCGCCAACAGCGCCAATCCAGACTGGGACTTC

AACCCCAATAAGGACACCTGGCCTGATGCCAACAAGGTCGGCGGCCAGAACCTGTCTACA

AGCAATCCTCTGGGCTTCTTTCCTGATCACCAGCTGGATCCTGCCTTTCGGGCCAATACA

GCCAACCCTGACTGGGACTTCAATCCTAACAAAGACACTTGGCCCGATGCTAATAAGGTC

GGC

SEQ ID NO: 43 delta 7 codon optimized with restriction sites (HindIII/EcoRI)

A↓AGCTT*GCACC*ATGGCCTCACGGTCTGAGTCAAAGAAGAATCGGGGGGGAAGAGAAGAA

ATCCTGGAACAGTGGGTCGGCGCACGGAAAAAACTGGAAGAACTGGAGCGGGACCTGAGA

AAGATCAAGAAGAAGATCAAGAAGCTGGAGGAAGAGAACCCCTGGCTGGGCAATATCAAG

GGCATCCTGGGCAAGAAGGATCGGGAGGGCGAGGGAGCACCACCTGCAAAGAGGGCAAGG

GCAGACCAGATGGAGGTGGATTCCGGACCTAGGAAGCGGCCCTTCCGGGGAGAGTTTACC

GACAAGGAGCGGAGAGATCACAGGCGCCGGAAGGCCCTGGAGAACAAGCGGAAGCAGCTG

AGCTCCGGCGGCAAGTCTCTGAGCAAGGAGGAGGAGGAGGAGCTGAGAAAGCTGACAGAG

GAGGACGAGAGAAGGGAGCGCCGGGTGGCCGGCCCAAGGGTGGGCGGCGTGAACCCCCTG

GAGGGAGGAACCAGGGGAGCACCAGGAGGAGGCTTCGTGCCTTCTATGCAGGGCGTGCCA

GAGAGCCCCTTTGCCAGGACAGGAGAGGGCCTGGATGTGCGCGGCAATCAGGGCTTCCCA

TGGGACATCCTGTTTCCCGCCGATCCACCCTTCTCCCCTCAGTCTTGCAGGCCACAGTCC

CGCTCTGAGAGCAAGAAGAACAGGGGAGGAAGGGAGGAGGTGCTGGAGCAGTGGGTGAAT

GGCAGGAAGAAGCTGGAGGAGCTGGAGCGGGAGCTGAGAAGGGCCAGAAAGAAGATCAAG

AAGCTGGAAGACGATAATCCTTGGCTGGGCAATGTGAAAGGCATCCTGGGCAAGAAGGAC

AAGGATGGAGAGGGAGCACCTCCAGCAAAGAGGGCACGCACCGACCAGATGGAGATCGAT

TCCGGACCAAGGAAGCGGCCCCTGAGGGGAGGCTTCACAGACAGGGAGCGCCAGGATCAC

CGCCGGAGAAAGGCCCTGAAGAACAAGAAGAAGCAGCTGTCTGCCGGCGGCAAGTCCCTG

TCTAAAGAAGAGGAGGAGGAGCTGAAGCGGCTGACCAGAGAGGACGAGGAGCGGAAGAAG

GAGGAGCACGGCCCTTCCAGACTGGGCGTGAATCCATCTGAGGGAGGACCAAGAGGCGCC

CCTGGCGGAGGCTTCGTGCCTAGCATGCAGGGCATCCCAGAGTCCAGGTTTACCAGAACC

GGAGAGGGCCTGGACGTGCGGGGCTCTAGAGGCTTTCCCCAGGACATCCTGTTCCCTAGC

GATCCCCCTTTTAGCCCCCAGTCCTGTAGGCCTCAGGGCACCAACCTGAGCACATCCAAT

CCACTGGGCTTCTTTCCAGACCACCAGCTGGATCCAGCCTTCCGCGCCAACAGCGCCAAT

CCAGACTGGGACTTCAACCCCAATAAGGACACCTGGCCTGATGCCAACAAGGTCGGCGGC

CAGAACCTGTCTACAAGCAATCCTCTGGGCTTCTTTCCTGATCACCAGCTGGATCCTGCC

TTTCGGGCCAATACAGCCAACCCTGACTGGGACTTCAATCCTAACAAAGACACTTGGCCC

GATGCTAATAAGGTCGGCTGATGAG↓AATTCCGT

SEQ ID NO: 44 delta 7 protein

MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKAL

ENKRKQLSSGGKSLSKEEEEELRKLTEEDERRERRVAGPRVGGVNPLEGGTRGAP

GGGFVPSMQGVPESPFARTGEGLDVRGNQGFPWDILFPADPPFSPQSCRPQSRSES

KKNRGGREEVLEQWVNGRKKLEELERELRRARKKIKKLEDDNPWLGNVKGILG

KKDKDGEGAPPAKRARTDQMEIDSGPRKRPLRGGFTDRERQDHRRRKALKNKK

-continued

KQLSAGGKSLSKEEEEELKRLTREDEERKKEEHGPSRLGVNPSEGGPRGAPGGGF

VPSMQGIPESRFTRTGEGLDVRGSRGFPQDILFPSDPPFSPQSCRPQGTNLSTSNPL

GFFPDHQLDPAFRANSANPDWDFNPNKDTWPDANKVGGQNLSTSNPLGFFPDHQ

LDPAFRANTANPDWDFNPNKDTWPDANKVG

SEQ ID NO: 45 delta 8 wt
AGCCAGAGCGAAACCCGCCGCGGCCGCCGCGGCACCCGCGAAGAAACCCTG

GAAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

GGCAACATTGTGGGCATTATTCGCAAAGGCAAAGATGGCGAAGGCGCGCCGC

CGGCGAAACGCCCGCGCACCGATCAGATGGAAGTGGATAGCGGCCCGGGCA

AACGCCCGCATAAAAGCGGCTTTACCGATAAAGAACGCGAAGATCATCGCCG

CCGCAAAGCGCTGGAAAACAAAAAAAAACAGCTGAGCGCGGGCGGCAAAAT

TCTGAGCAAAGAAGAAGAAGAAGAACTGCGCCGCCTGACCGATGAAGATGA

AGAACGCAAACGCCGCGTGGCGGGCCCGCGCGTGGGCGATGTGAACCCGAG

CCGCGGCGGCCCGCGCGGCGCGCCGGGCGGCGGCTTTGTGCCGCAGATGGCG

GGCGTGCCGGAAAGCCCGTTTAGCCGCACCGGCGAAGGCCTGGATATTCGCG

GCACCCAGGGCTTTCCGTGGGTGAGCCCGAGCCCGCCGCAGCAGCGCCTGCC

GCTGCTGGAATGCACCCCGCAGAGCCAGAGCGAAAGCAAAAAAAACCGCCG

CGGCGGCCGCGAAGATATTCTGGAAAAATGGATTACCACCCGCCGCAAAGCG

GAAGAACTGGAAAAAGATCTGCGCAAAGCGCGCAAAACCATTAAAAAACTG

GAAGATGAAAACCCGTGGCTGGGCAACATTATTGGCATTATTCGCAAAGGCA

AAGATGGCGAAGGCGCGCCGCCGGCGAAACGCCCGCGCACCGATCAGATGG

AAATTGATAGCGGCACCGGCAAACGCCCGCATAAAAGCGGCTTTACCGATAA

AGAACGCGAAGATCATCGCCGCCGCAAAGCGCTGGAAAACAAAAAAAAACA

GCTGAGCAGCGGCGGCAAAAACCTGAGCCGCGAAGAAGAAGAAGAACTGGG

CCGCCTGACCGTGGAAGATGAAGAACGCCGCCGCCGCGTGGCGGGCCCGCGC

ACCGGCGATGTGAACCTGAGCGGCGGCGGCCCGCGCGGCGCGCCGGGCGGC

GGCTTTGTGCCGCGCATGGAAGGCGTGCCGGAAAGCCCGTTTACCCGCACCG

GCGAAGGCCTGGATATTCGCGGCAACCAGGGCTTTCCGTGGGTGCGCCCGAG

CCCGCCGCAGCAGCGCCTGCCGCTGCTGGAATGCACCCCGCAGGGCACCAAC

CTGAGCACCAGCAACCCGCTGGGCTTTTTTCCGGATCATCAGCTGGATCCGGC

GTTTCGCGCGAACAGCGCGAACCCGGATTGGGATTTTAACCCGAACAAAGAT

ACCTGGCCGGATGCGAACAAAGTGGGCGGCCAGAACCTGAGCACCAGCAAC

CCGCTGGGCTTTTTTCCGGATCATCAGCTGGATCCGGCGTTTCGCGCGAACAC

CGCGAACCCGGATTGGGATTTTAACCCGAACAAAGATACCTGGCCGGATGCG

AACAAAGTGGGC

SEQ ID NO: 46 delta 8 wt with restriction sites
(HindIII/EcoRI)
A↓AGCTT*GCACC*ATGGCCAGCCAGAGCGAAACCCGCCGCGGCCGCCGCGGCACC

CGCGAAGAAACCCTGGAAAAATGGATTACCGCGCGCAAAAAAGCGGAAGAA

CTGGAAAAAGATCTGCGCAAAACCCGCAAAACCATTAAAAAACTGGAAGAA

GAAAACCCGTGGCTGGGCAACATTGTGGGCATTATTCGCAAAGGCAAAGATG

-continued

GCGAAGGCGCGCCGCCGGCGAAACGCCCGCGCACGATCAGATGGAAGTGG

ATAGCGGCCCGGGCAAACGCCCGCATAAAAGCGGCTTTACCGATAAAGAACG

CGAAGATCATCGCCGCCGCAAAGCGCTGGAAAACAAAAAAAAACAGCTGAG

CGCGGGCGGCAAAATTCTGAGCAAAGAAGAAGAAGAAGAACTGCGCCGCCT

GACCGATGAAGATGAAGAACGCAAACGCCGCGTGGCGGGCCCGCGCGTGGG

CGATGTGAACCCGAGCCGCGGCGGCCCGCGCGGCGCGCCGGGCGGCGGCTTT

GTGCCGCAGATGGCGGGCGTGCCGGAAAGCCCGTTTAGCCGCACCGGCGAAG

GCCTGGATATTCGCGGCACCCAGGGCTTTCCGTGGGTGAGCCCGAGCCCGCC

GCAGCAGCGCCTGCCGCTGCTGGAATGCACCCCGCAGAGCCAGAGCGAAAGC

AAAAAAAACCGCCGCGGCGGCCGCGAAGATATTCTGGAAAAATGGATTACCA

CCCGCCGCAAAGCGGAAGAACTGGAAAAAGATCTGCGCAAAGCGCGCAAAA

CCATTAAAAAACTGGAAGATGAAAACCCGTGGCTGGGCAACATTATTGGCAT

TATTCGCAAAGGCAAAGATGGCGAAGGCGCGCCGCCGGCGAAACGCCCGCG

CACCGATCAGATGGAAATTGATAGCGGCACCGGCAAACGCCCGCATAAAAGC

GGCTTTACCGATAAAGAACGCGAAGATCATCGCCGCCGCAAAGCGCTGGAAA

ACAAAAAAAAACAGCTGAGCAGCGGCGGCAAAAACCTGAGCCGCGAAGAAG

AAGAAGAACTGGGCCGCCTGACCGTGGAAGATGAAGAACGCCGCCGCCGCG

TGGCGGGCCCGCGCACCGGCGATGTGAACCTGAGCGGCGGCGGCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGGGCACCAACCTGAGCACCAGCAACCCGCTGGGCTTTTTTCCGGATCATCA

GCTGGATCCGGCGTTTCGCGCGAACAGCGCGAACCCGGATTGGGATTTTAAC

CCGAACAAAGATACCTGGCCGGATGCGAACAAAGTGGGCGGCCAGAACCTG

AGCACCAGCAACCCGCTGGGCTTTTTTCCGGATCATCAGCTGGATCCGGCGTT

TCGCGCGAACACCGCGAACCCGGATTGGGATTTTAACCCGAACAAAGATACC

TGGCCGGATGCGAACAAAGTGGGCTGATGAG↓AATTCCGT

SEQ ID NO: 47 delta 8 optimized
GCCAGTCAGAGCGAGACCCGCAGAGGACGGAGAGGAACACGAGAAGAGACACTGGAGAAA

TGGATTACAGCACGGAAGAAGGCAGAAGAGCTGGAGAAGGACCTGAGGAAGACCCGCAAG

ACAATCAAGAAGCTGGAGGAGGAGAACCCCTGGCTGGGCAATATCGTGGGCATCATCAGG

AAGGGCAAGGATGGAGAGGGAGCACCACCTGCCAAGAGGCCTCGCACAGACCAGATGGAG

GTGGATAGCGGACCAGGCAAGCGGCCTCACAAGTCCGGCTTCACCGACAAGGAGAGAGAG

GATCACCGGAGAAGGAAGGCCCTGGAGAACAAGAAGAAGCAGCTGTCCGCCGGCGGCAAG

ATCCTGTCTAAGGAGGAGGAGGAGGAGCTGCGCCGGCTGACAGACGAGGATGAGGAGAGG

AAGAGAAGGGTGGCAGGACCAAGGGTGGGCGACGTGAATCCTTCTAGGGGAGGACCAAGG

GGAGCACCAGGAGGAGGCTTCGTGCCTCAGATGGCCGGCGTGCCAGAGTCTCCCTTTAGC

CGGACAGGCGAGGGCCTGGATATCAGAGGCACCCAGGGCTTTCCTTGGGTGTCTCCAAGC

CCACCACAGCAGCGGCTGCCACTGCTGGAGTGCACACCCCAGTCCCAGTCTGAGAGCAAG

AAGAACAGGAGGGGAGGAAGAGAGGACATCCTGGAGAAGTGGATCACCACAAGAAGGAAG

GCCGAGGAGCTGGAGAAGGACCTGCGGAAGGCCAGAAAGACCATCAAGAAGCTGGAGGAT

-continued

GAAAATCCTTGGCTGGGAAATATCATCGGAATTATTAGAAAAGGCAAGGACGGAGAGGGA

GCACCTCCAGCAAAGCGGCCAAGAACAGACCAGATGGAGATCGATTCTGGAACCGGCAAG

AGGCCCCACAAGAGTGGCTTCACCGATAAGGAGCGCGAGGATCACCGCCGGAGAAAGGCC

CTGGAAAACAAGAAGAAGCAATTAAGCTCCGGCGGCAAGAATCTGAGCAGAGAAGAAGAG

GAGGAGCTGGGCCGCCTGACAGTGGAGGACGAGGAGAGGCGCCGGAGAGTGGCAGGACCT

AGAACCGGCGATGTGAACCTGTCCGGAGGCGGCCCAAGGGGAGCACCTGGAGGCGGCTTC

GTGCCACGCATGGAGGGCGTGCCTGAGTCTCCCTTCACCAGGACAGGAGAGGGCCTGGAC

ATCAGAGGCAATCAGGGATTCCCATGGGTGCGGCCCAGCCCACCTCAGCAGAGACTGCCT

CTGCTGGAGTGTACCCCACAGGGCACAAACCTGTCCACCTCTAATCCTCTGGGCTTCTTT

CCAGACCACCAGCTGGATCCAGCCTTCAGGGCCAACTCCGCCAACCCTGACTGGGACTTC

AACCCTAATAAGGACACATGGCCAGATGCCAACAAGGTCGGCGGCCAGAACCTGAGCACC

TCCAATCCCCTGGGCTTCTTTCCTGACCACCAGCTGGATCCCGCCTTTCGCGCCAATACC

GCCAATCCCGACTGGGACTTCAATCCAAATAAGGACACCTGGCCCGATGCTAACAAAGTG

GGA

SEQ ID NO: 48 delta 8 codon optimized with restriction
sites (HindIII/EcoRI)
A!AGCTT*GCACC*ATGGCCAGTCAGAGCGAGACCCGCAGAGGACGGAGAGGAACACGAGAA

GAGACACTGGAGAAATGGATTACAGCACGGAAGAAGGCAGAAGAGCTGGAGAAGGACCTG

AGGAAGACCCGCAAGACAATCAAGAAGCTGGAGGAGGAGAACCCCTGGCTGGGCAATATC

GTGGGCATCATCAGGAAGGGCAAGGATGGAGAGGGAGCACCACCTGCCAAGAGGCCTCGC

ACAGACCAGATGGAGGTGGATAGCGGACCAGGCAAGCGGCCTCACAAGTCCGGCTTCACC

GACAAGGAGAGAGAGGATCACCGGAGAAGGAAGGCCCTGGAGAACAAGAAGAAGCAGCTG

TCCGCCGGCGGCAAGATCCTGTCTAAGGAGGAGGAGGAGGAGCTGCGCCGGCTGACAGAC

GAGGATGAGGAGAGGAAGAGAAGGGTGGCAGGACCAAGGGTGGGCGACGTGAATCCTTCT

AGGGGAGGACCAAGGGGAGCACCAGGAGGAGGCTTCGTGCCTCAGATGGCCGGCGTGCCA

GAGTCTCCCTTTAGCCGGACAGGCGAGGGCCTGGATATCAGAGGCACCCAGGGCTTTCCT

TGGGTGTCTCCAAGCCCACCACAGCAGCGGCTGCCACTGCTGGAGTGCACACCCCAGTCC

CAGTCTGAGAGCAAGAAGAACAGGAGGGGAGGAAGAGAGGACATCCTGGAGAAGTGGATC

ACCACAAGAAGGAAGGCCGAGGAGCTGGAGAAGGACCTGCGGAAGGCCAGAAAGACCATC

AAGAAGCTGGAGGATGAAAATCCTTGGCTGGGAAATATCATCGGAATTATTAGAAAAGGC

AAGGACGGAGAGGGAGCACCTCCAGCAAAGCGGCCAAGAACAGACCAGATGGAGATCGAT

TCTGGAACCGGCAAGAGGCCCCACAAGAGTGGCTTCACCGATAAGGAGCGCGAGGATCAC

CGCCGGAGAAAGGCCCTGGAAAACAAGAAGAAGCAATTAAGCTCCGGCGGCAAGAATCTG

AGCAGAGAAGAAGAGGAGGAGCTGGGCCGCCTGACAGTGGAGGACGAGGAGAGGCGCCGG

AGAGTGGCAGGACCTAGAACCGGCGATGTGAACCTGTCCGGAGGCGGCCCAAGGGGAGCA

CCTGGAGGCGGCTTCGTGCCACGCATGGAGGGCGTGCCTGAGTCTCCCTTCACCAGGACA

GGAGAGGGCCTGGACATCAGAGGCAATCAGGGATTCCCATGGGTGCGGCCCAGCCCACCT

CAGCAGAGACTGCCTCTGCTGGAGTGTACCCCACAGGGCACAAACCTGTCCACCTCTAAT

CCTCTGGGCTTCTTTCCAGACCACCAGCTGGATCCAGCCTTCAGGGCCAACTCCGCCAAC

CCTGACTGGGACTTCAACCCTAATAAGGACACATGGCCAGATGCCAACAAGGTCGGCGGC

CAGAACCTGAGCACCTCCAATCCCCTGGGCTTCTTTCCTGACCACCAGCTGGATCCCGCC

-continued

TTTCGCGCCAATACCGCCAATCCCGACTGGGACTTCAATCCAAATAAGGACACCTGGCCC

GATGCTAACAAAGTGGGTGATGAG↓AATTCCGT

SEQ ID NO: 49 delta 8 protein
MASQSETRRGRRGTREETLEKWITARKKAEELEKDLRKTRKTIKKLEEENPWLG

NIVGIIRKGKDGEGAPPAKRPRTDQMEVDSGPGKRPHKSGFTDKEREDIIRRRKAL

ENKKKQLSAGGKILSKEEEEELRRLTDEDEERKRRVAGPRVGDVNPSRGGPRGAP

GGGFVPQMAGYTESPFSRTGEGLDIRGTQGFPWVSPSPPQQRLPLLECTPQSQSES

KKNRRGGREDILEKWITTRRKAEELEKDLRKARKTIKKLEDENPWLGNIIGIIRKG

KDGEGAPPAKRPRTDQMEIDSGTGKRPHKSGFTDKEREDHRRRKALENKKKQLS

SGGKNLSREEEEELGRLTVEDEERRRRVAGPRTGDVNLSGGGPRGAPGGGFVPR

MEGVPESPFTRTGEGLDIRGNQGFPWVRPSPPQRLPLLECTPQGTNLSTSNPLGF

FPDHQLDPAFRANSANPDWDFNTNTCDTVVPDANKVGGQNLSTSNPLGFFPDHQLD

PAFRANTANPDWDFNPNKDTWPDANKVG

SEQ ID NO: 50 delta 9 wt
AGCCGCAGCGAAAGCAAAAAAAACCGCGGCGGCCGCGAAGAAATTCTGGAA

CAGTGGGTGGGCGCGCGCAAAAAACTGGAAGAACTGGAACGCGATCTGCGC

AAAATTAAAAAAAAAATTAAAAAACTGGAAGAAGAAAACCCGTGGCTGGGC

AACATTAAAGGCATTCTGGGCAAAAAAGATCGCGAAGGCGAAGGCGCGCCG

CCGGCGAAACGCGCGCGCGCGGATCAGATGGAAGTGGATAGCGGCCCGCGC

AAACGCCCGTTTCGCGGCGAATTTACCGATAAAGAACGCCGCGATCATCGCC

GCCGCAAAGCGCTGGAAAACAAACGCAAACAGCTGAGCAGCGGCGGCAAAA

GCCTGAGCAAAGAAGAAGAAGAAGAACTGCGCAAACTGACCGAAGAAGATG

AACGCCGCGAACGCCGCGTGGCGGGCCCGCGCGTGGGCGGCGTGAACCCGCT

GGAAGGCGGCACCCGCGGCGCGCCGGGCGGCGGCTTTGTGCCGAGCATGCAG

GGCGTGCCGGAAAGCCCGTTTGCGCGCACCGGCGAAGGCCTGGATGTGCGCG

GCAACCAGGGCTTTCCGTGGGATATTCTGTTTCCGGCGGATCCGCCGTTTAGC

CCGCAGAGCTGCCGCCCGCAGAGCCGCAGCGAAAGCAAAAAAAACCGCGGC

GGCCGCGAAGAAGTGCTGGAACAGTGGGTGAACGGCCGCAAAAAACTGGAA

GAACTGGAACGCGAACTGCGCCGCGCGCGCAAAAAAATTAAAAAACTGGAA

GATGATAACCCGTGGCTGGGCAACGTGAAAGGCATTCTGGGCAAAAAAGATA

AAGATGGCGAAGGCGCGCCGCCGGCGAAACGCGCGCGCACCGATCAGATGG

AAATTGATAGCGGCCCGCGCAAACGCCCGCTGCGCGGCGGCTTTACCGATCG

CGAACGCCAGGATCATCGCCGCCGCAAAGCGCTGAAAAACAAAAAAAAACA

GCTGAGCGCGGGCGGCAAAAGCCTGAGCAAAGAAGAAGAAGAAGAACTGAA

ACGCCTGACCCGCGAAGATGAAGAACGCAAAAAAGAAGAACATGGCCCGAG

CCGCCTGGGCGTGAACCCGAGCGAAGGCGGCCCGCGCGGCGCGCCGGGCGG

CGGCTTTGTGCCGAGCATGCAGGGCATTCCGGAAAGCCGCTTTACCCGCACC

GGCGAAGGCCTGGATGTGCGCGGCAGCCGCGGCTTTCCGCAGGATATTCTGT

TTCCGAGCGATCCGCCGTTTAGCCCGCAGAGCTGCCGCCCGCAG

-continued

SEQ ID NO: 51 delta 9 wt with restriction sites
(HindIII/EcoRI)
A↓AGCTT*GCACC*ATGGCCAGCCGCAGCGAAAGCAAAAAAAACCGCGGCGGCCG

CGAAGAAATTCTGGAACAGTGGGTGGGCGCGCGCAAAAAACTGGAAGAACT

GGAACGCGATCTGCGCAAAATTAAAAAAAAAATTAAAAAACTGGAAGAAGA

AAACCCGTGGCTGGGCAACATTAAAGGCATTCTGGGCAAAAAAGATCGCGAA

GGCGAAGGCGCGCCGCCGGCGAAACGCGCGCGCGGATCAGATGGAAGTG

GATAGCGGCCCGCGCAAACGCCCGTTTCGCGGCGAATTTACCGATAAAGAAC

GCCGCGATCATCGCCGCCGCAAAGCGCTGGAAAACAAACGCAAACAGCTGA

GCAGCGGCGGCAAAAGCCTGAGCAAAGAAGAAGAAGAAGAACTGCGCAAAC

TGACCGAAGAAGATGAACGCCGCGAACGCCGCGTGGCGGGCCCGCGCGTGG

GCGGCGTGAACCCGCTGGAAGGCGGCACCCGCGGCGCGCCGGGCGGCGGCTT

TGTGCCGAGCATGCAGGGCGTGCCGGAAAGCCCGTTTGCGCGCACCGGCGAA

GGCCTGGATGTGCGCGGCAACCAGGGCTTTCCGTGGGATATTCTGTTTCCGGC

GGATCCGCCGTTTAGCCCGCAGAGCTGCCGCCCGCAGAGCCGCAGCGAAAGC

AAAAAAAACCGCGGCGGCCGCGAAGAAGTGCTGGAACAGTGGGTGAACGGC

CGCAAAAAACTGGAAGAACTGGAACGCGAACTGCGCCGCGCGCGCAAAAAA

ATTAAAAAACTGGAAGATGATAACCCGTGGCTGGGCAACGTGAAAGGCATTC

TGGGCAAAAAAGATAAAGATGGCGAAGGCGCGCCGCCGGCGAAACGCGCGC

GCACCGATCAGATGGAAATTGATAGCGGCCCGCGCAAACGCCCGCTGCGCGG

CGGCTTTACCGATCGCGAACGCCAGGATCATCGCCGCCGCAAAGCGCTGAAA

AACAAAAAAAAACAGCTGAGCGCGGGCGGCAAAAGCCTGAGCAAAGAAGAA

GAAGAAGAACTGAAACGCCTGACCCGCGAAGATGAAGAACGCAAAAAAGAA

GAACATGGCCCGAGCCGCCTGGGCGTGAACCCGAGCGAAGGCGGCCCGCGC

GGCGCGCCGGGCGGCGGCTTTGTGCCGAGCATGCAGGGCATTCCGGAAAGCC

GCTTTACCCGCACCGGCGAAGGCCTGGATGTGCGCGGCAGCCGCGGCTTTCC

GCAGGATATTCTGTTTCCGAGCGATCCGCCGTTTAGCCCGCAGAGCTGCCGCC

CGCAGTGATGAG↓AATTCCGT

SEQ ID NO: 52 delta 9 codon optimized
GCCAGTCGGAGCGAATCAAAGAAAAATAGAGGGGGAAGAGAAGAAATCCTGGAGCAGTGG

GTCGGGGCACGGAAAAAACTGGAAGAACTGGAGCGGGACCTGAGAAAGATCAAGAAGAAG

ATCAAGAAGCTGGAGGAAGAGAACCCCTGGCTGGGCAATATCAAGGGCATCCTGGGCAAG

AAGGATAGGGAGGGCGAGGGAGCACCACCTGCAAAGAGGGCAAGGGCAGACCAGATGGAG

GTGGATTCCGGACCAAGGAAGCGGCCCTTCCGGGGAGAGTTTACCGACAAGGAGCGGAGA

GATCACAGGCGCCGGAAGGCCCTGGAGAACAAGCGGAAGCAGCTGAGCTCCGGCGGCAAG

TCTCTGAGCAAGGAGGAGGAGGAGGAGCTGAGAAAGCTGACAGAGGAGGACGAGAGAAGG

GAGAGGAGGGTGGCAGGACCTAGGGTGGGAGGCGTGAACCCACTGGAGGGAGGAACCAGG

GGAGCACCTGGAGGAGGCTTTGTGCCATCTATGCAGGGAGTGCCAGAGAGCCCTTTCGCC

AGGACAGGAGAGGGCCTGGATGTGCGCGGCAATCAGGGCTTCCCCTGGGACATCCTGTTT

CCTGCCGATCCACCCTTCAGCCCACAGTCCTGCAGGCCACAGTCCCGCTCTGAGAGCAAG

AAGAACAGGGGAGGAAGGGAGGAGGTGCTGGAGCAGTGGGTGAATGGCCGGAAGAAGCTG

GAGGAGCTGGAGCGGGAGCTGAGAAGGGCCAGAAAGAAGATCAAGAAGCTGGAAGACGAT

-continued

AATCCTTGGCTGGGCAATGTGAAAGGCATCCTGGGCAAGAAGGACAAGGATGGAGAGGGA

GCACCTCCAGCAAAGAGGGCACGCACCGACCAGATGGAGATCGATTCTGGACCTAGGAAG

CGGCCCCTGAGAGGAGGCTTTACAGACAGGGAGCGCCAGGATCACCGCCGGAGAAAGGCC

CTGAAGAACAAGAAGAAGCAGCTGAGCGCCGGCGGCAAGTCCCTGTCTAAAGAAGAGGAG

GAGGAGCTGAAGCGGCTGACCAGAGAGGACGAGGAGCGGAAGAAGGAGGAGCACGGACCA

TCCAGACTGGGAGTGAATCCTTCTGAGGGAGGACCAAGAGGCGCCCCAGGCGGCGGCTTT

GTGCCAAGCATGCAGGGCATCCCCGAGTCCAGGTTCACCAGAACCGGCGAAGGCCTGGAT

GTGCGGGGCAGCAGAGGCTTCCCCCAGGATATTCTGTTTCCCTCCGACCCCCCCTTCAGT

CCCCAGTCTTGCCGACCTCAG

SEQ ID NO: 53 delta 9 codon optimized with restriction sites (HindIII/EcoRI)

A↓AGCTT*GCACC*ATGGCCAGTCGGAGCGAATCAAAGAAAAATAGAGGGGGAAGAGAAGAA

ATCCTGGAGCAGTGGGTCGGGGCACGGAAAAAACTGGAAGAACTGGAGCGGGACCTGAGA

AAGATCAAGAAGAAGATCAAGAAGCTGGAGGAAGAGAACCCCTGGCTGGGCAATATCAAG

GGCATCCTGGGCAAGAAGGATAGGGAGGGCGAGGGAGCACCACCTGCAAAGAGGGCAAGG

GCAGACCAGATGGAGGTGGATTCCGGACCAAGGAAGCGGCCCTTCCGGGGAGAGTTTACC

GACAAGGAGCGGAGAGATCACAGGCGCCGGAAGGCCCTGGAGAACAAGCGGAAGCAGCTG

AGCTCCGGCGGCAAGTCTCTGAGCAAGGAGGAGGAGGAGGAGCTGAGAAAGCTGACAGAG

GAGGACGAGAGAAGGGAGAGGAGGGTGGCAGGACCTAGGGTGGGAGGCGTGAACCCACTG

GAGGGAGGAACCAGGGGAGCACCTGGAGGAGGCTTTGTGCCATCTATGCAGGGAGTGCCA

GAGAGCCCTTTCGCCAGGACAGGAGAGGGCCTGGATGTGCGCGGCAATCAGGGCTTCCCC

TGGGACATCCTGTTTCCTGCCGATCCACCCTTCAGCCCACAGTCCTGCAGGCCACAGTCC

CGCTCTGAGAGCAAGAAGAACAGGGGAGGAAGGGAGGAGGTGCTGGAGCAGTGGGTGAAT

GGCCGGAAGAAGCTGGAGGAGCTGGAGCGGGAGCTGAGAAGGGCCAGAAAGAAGATCAAG

AAGCTGGAAGACGATAATCCTTGGCTGGGCAATGTGAAAGGCATCCTGGGCAAGAAGGAC

AAGGATGGAGAGGGAGCACCTCCAGCAAAGAGGGCACGCACCGACCAGATGGAGATCGAT

TCTGGACCTAGGAAGCGGCCCCTGAGAGGAGGCTTTACAGACAGGGAGCGCCAGGATCAC

CGCCGGAGAAAGGCCCTGAAGAACAAGAAGAAGCAGCTGAGCGCCGGCGGCAAGTCCCTG

TCTAAAGAAGAGGAGGAGGAGCTGAAGCGGCTGACCAGAGAGGACGAGGAGCGGAAGAAG

GAGGAGCACGGACCATCCAGACTGGGAGTGAATCCTTCTGAGGGAGGACCAAGAGGCGCC

CCAGGCGGCGGCTTTGTGCCAAGCATGCAGGGCATCCCCGAGTCCAGGTTCACCAGAACC

GGCGAAGGCCTGGATGTGCGGGGCAGCAGAGGCTTCCCCCAGGATATTCTGTTTCCCTCC

GACCCCCCCTTCAGTCCCCAGTCTTGCCGACCTCAGTGATGAG↓AATTCCGT

SEQ ID NO: 54 delta 9 protein

MASRSESKKNRGGREEILEQWVGARKKLEELERDLRKIKKKIKKLEEENPWLGNI

KGILGKKDREGEGAPPAKRARADQMEVDSGPRKRPFRGEFTDKERRDHRRRKAL

ENKRKQLSSGGKSLSKEEEEELRKLTEEDERRERRVAGPRVGGVNPLEGGTRGAP

GGGFVPSMQGVPESPFARTGEGLDVRGNQGFPWDIEFPADPPFSPQSCRPQSRSES

KKNRGGREEVLEQWVNGRKKLEELERELRRARKKIKKLEDDNPWLGNVKGILG

KKDKDGEGAPPAKRARTDQMEIDSGPRKRPLRGGFTDRERQDHRRRKALKNKK

KQLSAGGKSLSKEEEEELKRLTREDEERKKEEHGPSRLGWPSEGGPRGAPGGGF

VPSMQGIPESRFTRTGEGLDVRGSRGFPQDILFPSDPPFSPQSCRPQ

-continued

SEQ ID NO: 55 delta 10 wt
AGCCAGAGCGAAACCCGCCGCGGCCGCCGCGGCACCCGCGAAGAAACCCTG

GAAAAATGGATTACCGCGCGCAAAAAAGCGGAAGAACTGGAAAAAGATCTG

CGCAAAACCCGCAAAACCATTAAAAAACTGGAAGAAGAAAACCCGTGGCTG

GGCAACATTGTGGGCATTATTCGCAAAGGCAAAGATGGCGAAGGCGCGCCGC

CGGCGAAACGCCCGCGCACCGATCAGATGGAAGTGGATAGCGGCCCGGGCA

AACGCCCGCATAAAAGCGGCTTTACCGATAAAGAACGCGAAGATCATCGCCG

CCGCAAAGCGCTGGAAAACAAAAAAAAACAGCTGAGCGCGGGCGGCAAAAT

TCTGAGCAAAGAAGAAGAAGAAGAACTGCGCCGCCTGACCGATGAAGATGA

AGAACGCAAACGCCGCGTGGCGGGCCCGCGCGTGGGCGATGTGAACCCGAG

CCGCGGCGGCCCGCGCGGCGCGCCGGGCGGCGGCTTTGTGCCGCAGATGGCG

GGCGTGCCGGAAAGCCCGTTTAGCCGCACCGGCGAAGGCCTGGATATTCGCG

GCACCCAGGGCTTTCCGTGGGTGAGCCCGAGCCCGCCGCAGCAGCGCCTGCC

GCTGCTGGAATGCACCCCGCAGAGCCAGAGCGAAAGCAAAAAAAACCGCCG

CGGCGGCCGCGAAGATATTCTGGAAAAATGGATTACCACCCGCCGCAAAGCG

GAAGAACTGGAAAAAGATCTGCGCAAAGCGCGCAAAACCATTAAAAAACTG

GAAGATGAAAACCCGTGGCTGGGCAACATTATTGGCATTATTCGCAAAGGCA

AAGATGGCGAAGGCGCGCCGCCGGCGAAACGCCCGCGCACCGATCAGATGG

AAATTGATAGCGGCACCGGCAAACGCCCGCATAAAAGCGGCTTTACCGATAA

AGAACGCGAAGATCATCGCCGCCGCAAAGCGCTGGAAAACAAAAAAAAACA

GCTGAGCAGCGGCGGCAAAAACCTGAGCCGCGAAGAAGAAGAAGAACTGGG

CCGCCTGACCGTGGAAGATGAAGAACGCCGCCGCCGCGTGGCGGGCCCGCGC

ACCGGCGATGTGAACCTGAGCGGCGGCGGCCCGCGCGGCGCGCCGGGCGGC

GGCTTTGTGCCGCGCATGGAAGGCGTGCCGGAAAGCCCGTTTACCCGCACCG

GCGAAGGCCTGGATATTCGCGGCAACCAGGGCTTTCCGTGGGTGCGCCCGAG

CCCGCCGCAGCAGCGCCTGCCGCTGCTGGAATGCACCCCGCAG

SEQ ID NO: 56 delta 10 wt with restriction sites
(HindIII/EcoRI)
A↓AGCTT*GCACC*ATGGCCAGCCAGAGCGAAACCCGCCGCGGCCGCCGCGGCACC

CGCGAAGAAACCCTGGAAAAATGGATTACCGCGCGCAAAAAAGCGGAAGAA

CTGGAAAAAGATCTGCGCAAAACCCGCAAAACCATTAAAAAACTGGAAGAA

GAAAACCCGTGGCTGGGCAACATTGTGGGCATTATTCGCAAAGGCAAAGATG

GCGAAGGCGCGCCGCCGGCGAAACGCCCGCGCACCGATCAGATGGAAGTGG

ATAGCGGCCCGGGCAAACGCCCGCATAAAAGCGGCTTTACCGATAAAGAACG

CGAAGATCATCGCCGCCGCAAAGCGCTGGAAAACAAAAAAAAACAGCTGAG

CGCGGGCGGCAAAATTCTGAGCAAAGAAGAAGAAGAAGAACTGCGCCGCCT

GACCGATGAAGATGAAGAACGCAAACGCCGCGTGGCGGGCCCGCGCGTGGG

CGATGTGAACCCGAGCCGCGGCGGCCCGCGCGGCGCGCCGGGCGGCGGCTTT

GTGCCGCAGATGGCGGGCGTGCCGGAAAGCCCGTTTAGCCGCACCGGCGAAG

GCCTGGATATTCGCGGCACCCAGGGCTTTCCGTGGGTGAGCCCGAGCCCGCC

GCAGCAGCGCCTGCCGCTGCTGGAATGCACCCCGCAGAGCCAGAGCGAAAGC

AAAAAAAACCGCCGCGGCGGCCGCGAAGATATTCTGGAAAAATGGATTACCA

-continued

CCCGCCGCAAAGCGGAAGAACTGGAAAAAGATCTGCGCAAAGCGCGCAAAA

CCATTAAAAAACTGGAAGATGAAAACCCGTGGCTGGGCAACATTATTGGCAT

TATTCGCAAAGGCAAAGATGGCGAAGGCGCGCCGCCGGCGAAACGCCCGCG

CACCGATCAGATGGAAATTGATAGCGGCACCGGCAAACGCCCGCATAAAAGC

GGCTTTACCGATAAAGAACGCGAAGATCATCGCCGCCGCAAAGCGCTGGAAA

ACAAAAAAAAACAGCTGAGCAGCGGCGGCAAAAACCTGAGCCGCGAAGAAG

AAGAAGAACTGGGCCGCCTGACCGTGGAAGATGAAGAACGCCGCCGCCGCG

TGGCGGGCCCGCGCACCGGCGATGTGAACCTGAGCGGCGGCGGCCCGCGCGG

CGCGCCGGGCGGCGGCTTTGTGCCGCGCATGGAAGGCGTGCCGGAAAGCCCG

TTTACCCGCACCGGCGAAGGCCTGGATATTCGCGGCAACCAGGGCTTTCCGTG

GGTGCGCCCGAGCCCGCCGCAGCAGCGCCTGCCGCTGCTGGAATGCACCCCG

CAGTGATGA<u>G↓AATTC</u>CGT

SEQ ID NO: 57 delta 10 codon optimized
GCCTCACAGAGCGAAACACGGCGGGGGCGGAGGGGAACTAGAGAGGAAACACTGGAAAAA

TGGATTACAGCACGGAAAAAGGCAGAGGAACTGGAGAAGGACCTGAGGAAGACCCGCAAG

ACAATCAAGAAGCTGGAGGAGGAGAACCCATGGCTGGGCAATATCGTGGGCATCATCCGG

AAGGGCAAGGATGGAGAGGGAGCACCACCTGCAAAGAGGCCCCGCACCGACCAGATGGAG

GTGGATTCTGGCCCTGGCAAGAGGCCACACAAGAGCGGCTTCACAGACAAGGAGCGCGAG

GATCACCGGAGAAGGAAGGCCCTGGAGAACAAGAAGAAGCAGCTGAGCGCCGGCGGCAAG

ATCCTGTCCAAGGAGGAGGAGGAGGAGCTGCGCCGGCTGACCGACGAGGATGAGGAGCGG

AAGAGAAGGGTGGCAGGACCAAGAGTGGGCGACGTGAATCCCTCTAGGGGAGGACCAAGG

GGAGCACCTGGAGGAGGCTTCGTGCCTCAGATGGCAGGAGTGCCAGAGTCCCCTTTTTCT

AGGACCGGAGAGGGCCTGGATATCAGGGGAACACAGGGCTTTCCATGGGTGTCTCCAAGC

CCACCACAGCAGAGGCTGCCACTGCTGGAGTGCACCCCTCAGTCCCAGTCTGAGAGCAAG

AAGAACAGGAGGGGAGGAAGGGAGGACATCCTGGAGAAGTGGATCACCACAAGAAGGAAG

GCCGAGGAGCTGGAGAAGGACCTGCGGAAGGCCAGAAAAACAATCAAGAAGCTGGAAGAT

GAGAACCCCTGGCTGGGCAATATCATCGGCATCATCAGAAAAGGCAAGGACGGCGAGGGA

GCACCTCCAGCAAAGCGGCCTAGAACCGACCAGATGGAGATCGATTCCGGCACAGGCAAG

CGGCCACACAAGTCTGGCTTCACCGACAAGGAGAGAGAGGATCACCGCCGGAGAAAGGCC

CTGGAAAACAAGAAGAAGCAATTAAGCTCCGGCGGCAAGAATCTGAGCAGAGAAGAAGAG

GAGGAGCTGGGCAGACTGACCGTGGAGGACGAGGAGAGGCGCCGGAGAGTGGCAGGACCC

AGAACAGGCGATGTGAACCTGAGCGGAGGAGGACCTAGGGGAGCACCAGGAGGCGGCTTC

GTGCCTAGAATGGAGGGCGTGCCAGAGTCCCCCTTTACCAGGACAGGAGAGGGCCTGGAC

ATCAGGGGCAATCAGGGCTTTCCCTGGGTCCGCCCTTCACCACCACAGCAGAGACTGCCC

CTGCTGGAATGCACACCACAG

SEQ ID NO: 58 delta 10 codon optimized with restriction sites (HindIII/EcoRI)
<u>A↓AGCTT</u>*GCACC*ATGGCCTCACAGAGCGAAACACGGCGGGGGCGGAGGGGAACTAGAGAG

GAAACACTGGAAAAATGGATTACAGCACGGAAAAAGGCAGAGGAACTGGAGAAGGACCTG

AGGAAGACCCGCAAGACAATCAAGAAGCTGGAGGAGGAGAACCCATGGCTGGGCAATATC

GTGGGCATCATCCGGAAGGGCAAGGATGGAGAGGGAGCACCACCTGCAAAGAGGCCCCGC

ACCGACCAGATGGAGGTGGATTCTGGCCCTGGCAAGAGGCCACACAAGAGCGGCTTCACA

-continued

GACAAGGAGCGCGAGGATCACCGGAGAAGGAAGGCCCTGGAGAACAAGAAGAAGCAGCTG

AGCGCCGGCGGCAAGATCCTGTCCAAGGAGGAGGAGGAGGAGCTGCGCCGGCTGACCGAC

GAGGATGAGGAGCGGAAGAGAAGGGTGGCAGGACCAAGAGTGGGCGACGTGAATCCCTCT

AGGGGAGGACCAAGGGGAGCACCTGGAGGAGGCTTCGTGCCTCAGATGGCAGGAGTGCCA

GAGTCCCCTTTTTCTAGGACCGGAGAGGGCCTGGATATCAGGGGAACACAGGGCTTTCCA

TGGGTGTCTCCAAGCCCACCACAGCAGAGGCTGCCACTGCTGGAGTGCACCCCTCAGTCC

CAGTCTGAGAGCAAGAAGAACAGGAGGGGAGGAAGGGAGGACATCCTGGAGAAGTGGATC

ACCACAAGAAGGAAGGCCGAGGAGCTGGAGAAGGACCTGCGGAAGGCCAGAAAAACAATC

AAGAAGCTGGAAGATGAGAACCCCTGGCTGGGCAATATCATCGGCATCATCAGAAAAGGC

AAGGACGGCGAGGGAGCACCTCCAGCAAAGCGGCCTAGAACCGACCAGATGGAGATCGAT

TCCGGCACAGGCAAGCGGCCACACAAGTCTGGCTTCACCGACAAGGAGAGAGAGGATCAC

CGCCGGAGAAAGGCCCTGGAAAACAAGAAGAAGCAATTAAGCTCCGGCGGCAAGAATCTG

AGCAGAGAAGAAGAGGAGGAGCTGGGCAGACTGACCGTGGAGGACGAGGAGAGGCGCCGG

AGAGTGGCAGGACCCAGAACAGGCGATGTGAACCTGAGCGGAGGAGGACCTAGGGGAGCA

CCAGGAGGCGGCTTCGTGCCTAGAATGGAGGGCGTGCCAGAGTCCCCCTTTACCAGGACA

GGAGAGGGCCTGGACATCAGGGGCAATCAGGGCTTTCCCTGGGTCCGCCCTTCACCACCA

CAGCAGAGACTGCCCCTGCTGGAATGCACACCACAGTGATGAG↓AATTCCGT

SEQ ID NO: 59 delta 10 protein
MASQSETRRGRRGTREETLEKWITARKKAEELEKDLRKTRKTIKKLEEENPWLG

NIVGIIRKGKDGEGAPPAKRPRTDQMEVDSGPGKRPHKSGFTDKEREDHRRRKAL

ENKKKQLSAGGKILSKEEEEELRRLTDEDEERKRRVAGPRVGDVNPSRGGPRGAP

GGGFYPQMAGVPESPFSRTGEGLDIRGTQGFPWVSPSPPQQRLPLLECTPQSQSES

KKNRRGGREDILEKWITTRRKAEELEKDLRKARKTIKKLEDENPWLGNIIGIIRKG

KDGEGAPPAKRPRTDQMEIDSGTGKRPHKSGFTDKEREDHRRRKALENKKKQLS

SGGKNLSREEEEELGRLTVEDEERRRRVAGPRTGDVNLSGGGPRGAPGGGFVPR

MEGVPESPFTRTGEGLDIRGNQGFPWVRPSPPQQRLPLLECTPQ

SEQ ID NO: 60 Core 1 wt (C-gt-H)
GATATTGATCCGTATAAAGAATTTGGCGCGAGCGTGGAACTGCTGAGCTTTCTGCCGAGC

GATTTTTTTCCGAGCGTGCGCGATCTGCTGGATACCGCGAGCGCGCTGTATCGCGATGCG

CTGGAAAGCCCGGAACATTGCACCCCGAACCATACCGCGCTGCGCCAGGCGATTCTGTGC

TGGGGCGAACTGATGACCCTGGCGAGCTGGGTGGGCAACAACCTGGAAGATCCGGCGGCG

CGCGATCTGGTGGTGAACTATGTGAACACCAACATGGGCCTGAAAATTCGCCAGCTGCTG

TGGTTTCATATTAGCTGCCTGACCTTTGGCCGCGAAACCGTGCTGGAATATCTGGTGAGC

TTTGGCGTGTGGATTCGCACCCCGCCGGCGTATCGCCCGCCGAACGCGCCGATTCTGAGC

ACCCTGCCGGAAACCACCGTGGTGCGCCAGCGCGGCCGCGCGCCGCGCCGCCGCACCCCG

AGCCCGCGCCGCCGCCGCAGCCAGAGCCCGCGCCGCCGCCGCAGCCAGAGCCCGGCGAGC

CAGTGC

SEQ ID NO: 61 core 1 wt with restriction sites
(HindIII/EcoRI)
A↓AGCTT*GCACC*ATGGATATTGATCCGTATAAAGAATTTGGCGCGAGCGTGGAACTGCTG

AGCTTTCTGCCGAGCGATTTTTTTCCGAGCGTGCGCGATCTGCTGGATACCGCGAGCGCG

CTGTATCGCGATGCGCTGGAAAGCCCGGAACATTGCACCCCGAACCATACCGCGCTGCGC

-continued

CAGGCGATTCTGTGCTGGGGCGAACTGATGACCCTGGCGAGCTGGGTGGGCAACAACCTG

GAAGATCCGGCGGCGCGCGATCTGGTGGTGAACTATGTGAACACCAACATGGGCCTGAAA

ATTCGCCAGCTGCTGTGGTTTCATATTAGCTGCCTGACCTTTGGCCGCGAAACCGTGCTG

GAATATCTGGTGAGCTTTGGCGTGTGGATTCGCACCCCGCCGGCGTATCGCCCGCCGAAC

GCGCCGATTCTGAGCACCCTGCCGGAAACCACCGTGGTGCGCCAGCGCGGCCGCGCGCCG

CGCCGCCGCACCCCGAGCCCGCGCCGCCGCCGCAGCCAGAGCCCGCGCCGCCGCCGCAGC

CAGAGCCCGGCGAGCCAGTGCTGATGAG↓AATTCCGT

SEQ ID NO: 62 core 1 codon optimized
GATATTGATCCCTATAAGGAGTTTGGAGCCTCTGTGGAGCTGCTGAGT7TTCTGCCATCC

GATTTCTTTCCCAGTGTCCGAGACCTGCTGGACACCGCAAGCGCCCTG7ACAGGGATGCA

CTGGAGTCCCCAGAGCACTGCACCCCTAACCACACAGCCCTGAGGCAGGCAATCCTGTGC

TGGGGAGAGCTGATGACCCTGGCAAGCTGGGTGGGCAACAATCTGGAGGACCCTGCAGCA

CGGGATCTGGTGGTGAATTATGTGAACACAAATATGGGCCTGAAGATCCGGCAGCTGCTG

TGGTTCCACATCTCTTGCCTGACCTTTGGCAGAGAGACAGTGCTGGAGTACCTGGTGAGC

TTCGGCGTGTGGATCAGGACCCCACCTGCATATAGGCCACCAAACGCACCAATCCTGTCC

ACACTGCCAGAGACAACAGTGGTGCGCCAGAGGGGAAGAGCACCACGGAGAAGGACACCT

TCTCCAAGACGAAGGCGAAGCCAGAGCCCCAGGCGAAGACGAAGCCAGTCCCCAGCAAGC

CAGTGC

SEQ ID NO: 63 core 1 codon optimized with restriction
sites (HindIII/EcoRI)
A↓AGCTT*GCACC*ATGGATATTGATCCCTATAAGGAGTTTGGAGCCTCTGTGGAGCTGCTG

AGTTTTCTGCCATCCGATTTCTTTCCCAGTGTCCGAGACCTGCTGGACACCGCAAGCGCC

CTGTACAGGGATGCACTGGAGTCCCCAGAGCACTGCACCCCTAACCACACAGCCCTGAGG

CAGGCAATCCTGTGCTGGGGAGAGCTGATGACCCTGGCAAGCTGGGTGGGCAACAATCTG

GAGGACCCTGCAGCACGGGATCTGGTGGTGAATTATGTGAACACAAATATGGGCCTGAAG

ATCCGGCAGCTGCTGTGGTTCCACATCTCTTGCCTGACCTTTGGCAGAGAGACAGTGCTG

GAGTACCTGGTGAGCTTCGGCGTGTGGATCAGGACCCCACCTGCATATAGGCCACCAAAC

GCACCAATCCTGTCCACACTGCCAGAGACAACAGTGGTGCGCCAGAGGGGAAGAGCACCA

CGGAGAAGGACACCTTCTCCAAGACGAAGGCGAAGCCAGAGCCCCAGGCGAAGACGAAGC

CAGTCCCCAGCAAGCCAGTGCTGATGAG↓AATTCCGT

SEQ ID NO: 64 core 1 protein
MDIDPYKEFGASVELLSFLPSDFFPSVRDLLDTASALYRDALESPEHCTPNHTALR

QAILCWGELMTLASWVGNNLEDPAARDLVVNYVNTNMGLKIRQLLWFHISCLTF

GRETVLEYLVSFGVWIRTPPAYRPPNAPILSTLPETTVVRQRGRAPRRRTPSPRRR

RSQSPRRRRSQSPASQC

SEQ ID NO: 65 Pre-C-gt-H wt
CAGCTGTTTCATCTGTGCCTGATTATTTTTTGCAGCTGCCCGACCGTGCAGGCGAGCAAA

CTGTGCCTGGGCTGGCTGTGGGGCATGGATATTGATCCGTATAAAGAATTTGGCGCGAGC

GTGGAACTGCTGAGCTTTCTGCCGAGCGATTTTTTTCCGAGCGTGCGCGATCTGCTGGAT

ACCGCGAGCGCGCTGTATCGCGATGCGCTGGAAAGCCCGGAACATTGCACCCCGAACCAT

ACCGCGCTGCGCCAGGCGATTCTGTGCTGGGGCGAACTGATGACCCTGGCGAGCTGGGTG

GGCAACAACCTGGAAGATCCGGCGGCGCGCGATCTGGTGGTGAACTATGTGAACACCAAC

ATGGGCCTGAAAATTCGCCAGCTGCTGTGGTTTCATATTAGCTGCCTGACCTTTGGCCGC

-continued

GAAACCGTGCTGGAATATCTGGTGAGCTTTGGCGTGTGGATTCGCACCCCGCCGGCGTAT

CGCCCGCCGAACGCGCCGATTCTGAGCACCCTGCCGGAAACCACCGTGGTGCGCCAGCGC

GGCCGCGCGCCGCGCCGCCGCACCCCGAGCCCGCGCCGCCGCCGCAGCCAGAGCCCGCGC

CGCCGCCGCAGCCAGAGCCCGGCGAGCCAGTGC

SEQ ID NO: 66 Pre-C-gt-H wt with restriction sites (HindIII/EcoRI)

A↓AGCTT*GCACC*ATGGCCCAGCTGTTTCATCTGTGCCTGATTATTTTTTGCAGCTGCCCG

ACCGTGCAGGCGAGCAAACTGTGCCTGGGCTGGCTGTGGGGCATGGATATTGATCCGTAT

AAAGAATTTGGCGCGAGCGTGGAACTGCTGAGCTTTCTGCCGAGCGATTTTTTTCCGAGC

GTGCGCGATCTGCTGGATACCGCGAGCGCGCTGTATCGCGATGCGCTGGAAAGCCCGGAA

CATTGCACCCCGAACCATACCGCGCTGCGCCAGGCGATTCTGTGCTGGGGCGAACTGATG

ACCCTGGCGAGCTGGGTGGGCAACAACCTGGAAGATCCGGCGGCGCGCGATCTGGTGGTG

AACTATGTGAACACCAACATGGGCCTGAAAATTCGCCAGCTGCTGTGGTTTCATATTAGC

TGCCTGACCTTTGGCCGCGAAACCGTGCTGGAATATCTGGTGAGCTTTGGCGTGTGGATT

CGCACCCCGCCGGCGTATCGCCCGCCGAACGCGCCGATTCTGAGCACCCTGCCGGAAACC

ACCGTGGTGCGCCAGCGCGGCCGCGCGCCGCGCCGCCGCACCCCGAGCCCGCGCCGCCGC

CGCAGCCAGAGCCCGCGCCGCCGCCGCAGCCAGAGCCCGGCGAGCCAGTGCTGATGAG↓A

ATTCCGT

SEQ ID NO: 67 Pre-C-gt-H codon optimized

GCCCAGCTGTTTCATCTGTGCCTGATTATTTTCTGTTCATGCCCTACCGTCCAGGCTTCT

AAACTGTGCCTGGGGTGGCTGTGGGGAATGGACATCGATCCCTACAAGGAGTTCGGCGCC

AGCGTGGAGCTGCTGAGCTTTCTGCCCTCCGACTTCTTTCCTTCTGTGCGGGACCTGCTG

GATACCGCAAGCGCCCTGTATAGAGATGCACTGGAGTCCCCAGAGCACTGCACCCCAAAC

CACACAGCCCTGAGGCAGGCAATCCTGTGCTGGGGAGAGCTGATGACCCTGGCATCCTGG

GTGGGCAACAATCTGGAGGACCCTGCCGCCAGAGATCTGGTGGTGAATTACGTGAACACA

AATATGGGCCTGAAGATCAGGCAGCTGCTGTGGTTCCACATCTCTTGCCTGACCTTTGGC

CGCGAGACAGTGCTGGAGTACCTGGTGAGCTTCGGCGTGTGGATCAGGACCCCCACCTGCA

TATAGGCCACCAAACGCACCTATCCTGTCCACACTGCCAGAGACAACAGTGGTGCGCCAG

AGGGGAAGAGCACCACGGAGAAGGACACCTTCTCCAAGGAGGAGAAGAAGCCAGTCCCCA

CGAAGAAGACGAAGCCAGAGCCCAGCCAGCCAGTGT

SEQ ID NO: 68 Pre-C-gt-H codon optimized with restriction sites (HindIII/EcoRI)

A↓AGCTT*GCACC*ATGGCCCAGCTGTTTCATCTGTGCCTGATTATTTTCTGTTCATGCCCT

ACCGTCCAGGCTTCTAAACTGTGCCTGGGGTGGCTGTGGGGAATGGACATCGATCCCTAC

AAGGAGTTCGGCGCCAGCGTGGAGCTGCTGAGCTTTCTGCCCTCCGACTTCTTTCCTTCT

GTGCGGGACCTGCTGGATACCGCAAGCGCCCTGTATAGAGATGCACTGGAGTCCCCAGAG

CACTGCACCCCAAACCACACAGCCCTGAGGCAGGCAATCCTGTGCTGGGGAGAGCTGATG

ACCCTGGCATCCTGGGTGGGCAACAATCTGGAGGACCCTGCCGCCAGAGATCTGGTGGTG

AATTACGTGAACACAAATATGGGCCTGAAGATCAGGCAGCTGCTGTGGTTCCACATCTCT

TGCCTGACCTTTGGCCGCGAGACAGTGCTGGAGTACCTGGTGAGCTTCGGCGTGTGGATC

AGGACCCCCACCTGCATATAGGCCACCAAACGCACCTATCCTGTCCACACTGCCAGAGACA

-continued

ACAGTGGTGCGCCAGAGGGGAAGAGCACCACGGAGAAGGACACCTTCTCCAAGGAGGAGA

AGAAGCCAGTCCCCACGAAGAAGACGAAGCCAGAGCCCAGCCAGCCAGTGTTGATGAG↓A

ATTCCGT

SEQ ID NO: 69 Pre-C-gt-H protein
MAQLFHLCLHFCSCPTVQASKLCLGWLVVGMDIDPYKEFGASVELLSFLPSDFFPS

VRDLLDTASALYRDALESPEHCTPNHTALRQAILCWGELMTLASWVGNNLEDPA

ARDLVVNYVNTNMGLKIRQLLWFHISCLTFGRETVLEYLVSFGWIRTPPAYRPP

NAPILSTLPETTVVRQRGRAPRRRTPSPRRRRSQSPRRRRSQSPASQC

SEQ ID NO: 70 PreC-C-Mut-gt-H wt
CAGCTGTTTCATCTGTGCCTGATTATTTTTGCAGCTGCCCGACCTTTCAGTTTCCGAAA

CTGTGCCTGGGCTGGCTGTGGGGCATGGATATTGATCCGTATAAAGAATTTGGCGCGAGC

GTGGAACTGCTGAGCTTTCTGCCGAGCGATTTTTTTCCGAGCGTGCGCGATCTGCTGGAT

ACCGCGAGCGCGCTGTATCGCGATGCGCTGGAAAGCCCGGAACATTGCACCCCGAACCAT

ACCGCGCTGCGCCAGGCGATTCTGTGCTGGGGCGAACTGATGACCCTGGCGAGCTGGGTG

GGCAACAACCTGGAAGATCCGGCGGCGCGCGATCTGGTGGTGAACTATGTGAACACCAAC

ATGGGCCTGAAAATTCGCCAGCTGCTGTGGTTTCATATTAGCTGCCTGACCTTTGGCCGC

GAAACCGTGCTGGAATATCTGGTGAGCTTTGGCGTGTGGATTCGCACCCCGCCGGCGTAT

CGCCCGCCGAACGCGCCGATTCTGAGCACCCTGCCGGAAACCACCGTGGTGCGCCAGCGC

GGCCGCGCGCCGCGCCGCCGCACCCCGAGCCCGCGCCGCCGCCGCAGCCAGAGCCCGCGC

CGCCGCCGCAGCCAGAGCCCGGCGAGCCAGTGC

SEQ ID NO: 71 PreC-C-Mut-gt-H wt with restriction sites
(HindIII/EcoRI)
A↓AGCTT*GCACC*ATGGCCCAGCTGTTTCATCTGTGCCTGATTATTTTTGCAGCTGCCCG

ACCTTTCAGTTTCCGAAACTGTGCCTGGGCTGGCTGTGGGGCATGGATATTGATCCGTAT

AAAGAATTTGGCGCGAGCGTGGAACTGCTGAGCTTTCTGCCGAGCGATTTTTTTCCGAGC

GTGCGCGATCTGCTGGATACCGCGAGCGCGCTGTATCGCGATGCGCTGGAAAGCCCGGAA

CATTGCACCCCGAACCATACCGCGCTGCGCCAGGCGATTCTGTGCTGGGGCGAACTGATG

ACCCTGGCGAGCTGGGTGGGCAACAACCTGGAAGATCCGGCGGCGCGCGATCTGGTGGTG

AACTATGTGAACACCAACATGGGCCTGAAAATTCGCCAGCTGCTGTGGTTTCATATTAGC

TGCCTGACCTTTGGCCGCGAAACCGTGCTGGAATATCTGGTGAGCTTTGGCGTGTGGATT

CGCACCCCGCCGGCGTATCGCCCGCCGAACGCGCCGATTCTGAGCACCCTGCCGGAAACC

ACCGTGGTGCGCCAGCGCGGCCGCGCGCCGCGCCGCCGCACCCCGAGCCCGCGCCGCCGC

CGCAGCCAGAGCCCGCGCCGCCGCCGCAGCCAGAGCCCGGCGAGCCAGTGCTGATGAG↓A

ATTCCGT

SEQ ID NO: 72 PreC-C-Mut-gt-H codon optimized
GCCCAGCTGTTTCATCTGTGCCTGATTATTTTCTGTTCATGCCCTACCTTCCAGTTCCCC

AAACTGTGCCTGGGGTGGCTGTGGGGAATGGACATCGATCCCTACAAGGAGTTCGGCGCC

AGCGTGGAGCTGCTGAGCTTTCTGCCCTCCGACTTCTTTCCTTCTGTGCGGGACCTGCTG

GATACCGCAAGCGCCCTGTATAGAGATGCACTGGAGTCCCCAGAGCACTGCACCCCAAAC

CACACAGCCCTGAGGCAGGCAATCCTGTGCTGGGGAGAGCTGATGACCCTGGCATCCTGG

GTGGGCAACAATCTGGAGGACCCTGCCGCCAGAGATCTGGTGGTGAATTACGTGAACACA

AATATGGGCCTGAAGATCAGGCAGCTGCTGTGGTTCCACATCTCTTGCCTGACCTTTGGC

CGCGAGACAGTGCTGGAGTACCTGGTGAGCTTCGGCGTGTGGATCAGGACCCCACCTGCA

-continued

TATAGGCCACCAAACGCACCTATCCTGTCCACACTGCCAGAGACAACAGTGGTGCGCCAG

AGGGGAAGAGCACCACGGAGAAGGACACCTTCTCCAAGGAGGAGAAGAAGCCAGTCCCCA

CGAAGAAGACGAAGCCAGAGCCCAGCCAGCCAGTGT

SEQ ID NO: 73 PreC-C-Mut-gt-H codon optimized with restriction sites (HindIII/EcoRI)
A↓AGCTT*GCACC*ATGGCCCAGCTGTTTCATCTGTGCCTGATTATTTTCTGTTCATGCCCT

ACCTTCCAGTTCCCCAAACTGTGCCTGGGGTGGCTGTGGGGAATGGACATCGATCCCTAC

AAGGAGTTCGGCGCCAGCGTGGAGCTGCTGAGCTTTCTGCCCTCCGACTTCTTTCCTTCT

GTGCGGGACCTGCTGGATACCGCAAGCGCCCTGTATAGAGATGCACTGGAGTCCCCAGAG

CACTGCACCCCAAACCACACAGCCCTGAGGCAGGCAATCCTGTGCTGGGGAGAGCTGATG

ACCCTGGCATCCTGGGTGGGCAACAATCTGGAGGACCCTGCCGCCAGAGATCTGGTGGTG

AATTACGTGAACACAAATATGGGCCTGAAGATCAGGCAGCTGCTGTGGTTCCACATCTCT

TGCCTGACCTTTGGCCGCGAGACAGTGCTGGAGTACCTGGTGAGCTTCGGCGTGTGGATC

AGGACCCCACCTGCATATAGGCCACCAAACGCACCTATCCTGTCCACACTGCCAGAGACA

ACAGTGGTGCGCCAGAGGGGAAGAGCACCACGGAGAAGGACACCTTCTCCAAGGAGGAGA

AGAAGCCAGTCCCCACGAAGAAGACGAAGCCAGAGCCCAGCCAGCCAGTGTTGATGAG↓A

ATTCCGT

SEQ ID NO: 74 PreC-C-Mut-gt-H protein
MAQLFHLCLIIFCSCPTFQFPKLCLGWLWGMDIDPYKEFGASVELLSFLPSDFFPSV

RDLLDTASALYRDALESPEHCTPNHTALRQAILCWGELMTLASWVGNNLEDPAA

RDLVVNYVNTNMGLKIRQLLWFHISCLTFGRETVLEYLVSFGVWIRTPPAYRPPN

APILSTLPETTVVRQRGRAPRRRTPSPRRRRSQSPRRRRSQSPASQC

---

What is claimed is:

1. A chimeric gene comprising in sequential order:

a nucleic acid construct encoding a hepatitis D antigen genotype 1 A (HDAg gt1 A) domain, a hepatitis B virus PreS1 A (PreS1 A) or a hepatitis B virus PreS1 B (PreS1 B) domain or both, a porcine teschovirus-1 2A (P2A) domain, a hepatitis D antigen genotype 1 B (HDAg gt1 B) domain, a second PreS1 A or PreS1 B domain or both, and a second P2A domain.

2. The chimeric gene of claim 1, further comprising in sequential order:

a second nucleic acid construct encoding a hepatitis D antigen genotype 2 A (HDAg gt2 A) domain, a PreS1 A or a PreS1 B domain or both, a P2A domain, a hepatitis D antigen genotype 2 B (HDAg gt1 B) domain, and a second PreS1 A domain or PreS1 B domain or both, wherein said second nucleic acid construct is joined to said nucleic acid construct encoding a HDAg gt1 A domain, a PreS1 A or a PreS1 B domain or both, a P2A domain, a HDAg gt1 B domain, a second PreS1 A or PreS1 B domain or both, and a second P2A domain.

3. The chimeric gene of claim 1, wherein at least one P2A domain modified to include a GSG (glycine-serine-glycine) motif at an N-terminus.

4. The chimeric gene of claim 2, wherein at least one P2A domain is modified to include a GSG (glycine-serine-glycine) motif at an N-terminus.

5. The chimeric gene of claim 1, wherein at least one preS1 sequence is preS1 A and comprises an amino acid sequence set forth in SEQ ID NO: 1 or wherein the at least one preS1 derived sequence is preS1 B and comprises an amino acid sequence set forth in SEQ ID NO: 2.

6. The chimeric gene of claim 1, wherein the sequence encoding HDAg gt1 A comprises a nucleic acid sequence set forth in SEQ ID NO: 3 and wherein the sequence encoding HDAg gt1 B comprises a nucleic acid sequence set forth in SEQ ID NO: 4.

7. The chimeric gene of claim 1, wherein at least one preS1 A is encoded by a nucleic acid sequence set forth in SEQ ID NO: 5.

8. The chimeric gene of claim 1, wherein at least one preS1 B is encoded by a nucleic acid sequence set forth in SEQ ID NO: 6.

9. A composition comprising the chimeric gene of claim 1.

10. The composition chimeric gene of claim 2, wherein the sequence encoding HDAg gt2 A is set forth in SEQ ID NO: 8.

11. The chimeric gene of claim 2, wherein the sequence encoding HDAg gt2 B is set forth in SEQ ID NO: 9.

12. The chimeric gene of claim 1, wherein the chimeric gene comprises a nucleic acid sequence set forth in SEQ ID NO's 25, 26, 27, or 28 or a nucleic acid encoding the amino acid sequence set forth in SEQ ID NO 29.

13. The chimeric gene of claim 1, wherein the chimeric gene further comprises a sequence encoding an human HBV Core antigen or an immunogenic portion thereof, a rodent HBV Core antigen or an immunogenic portion thereof, or an avian HBV Core antigen or immunogenic portion thereof.

14. A chimeric protein encoded by the chimeric gene of claim 1.

15. A composition comprising the chimeric gene of claim 2.

16. The chimeric gene of claim 2, wherein the at least one preS1 sequence is preS1 A and comprises an amino acid sequence set forth in SEQ ID NO: 1 or wherein the at least one preS1 sequence is preS1 B and comprises an amino acid sequence set forth in SEQ ID NO: 2.

17. The composition chimeric gene of claim 2, wherein at least one preS1 A is encoded by a nucleic acid sequence set forth in SEQ ID NO: 5.

18. The composition chimeric gene of claim 2, wherein at least one preS1 B is encoded by a nucleic acid sequence set forth in SEQ ID NO: 6.

19. The chimeric gene of claim 2, wherein the chimeric gene further comprises a sequence encoding an human HBV Core antigen or an immunogenic portion thereof, a rodent HBV Core antigen or an immunogenic portion thereof, or an avian HBV Core antigen or an immunogenic portion thereof.

20. A chimeric protein encoded by the chimeric gene of claim 2.

21. A method of eliciting an immune response comprising administering to a subject having HDV infection or HBV infection a composition comprising the chimeric claim 1.

22. The method of claim 21, further comprising providing an adjuvant, wherein said adjuvant is a nucleic acid encoding IL-12, IL-15, or IL-21.

23. The method of claim 21, wherein the subject has been identified as a person at risk of contracting HDV or that has HDV.

24. A method of eliciting an immune response comprising administering to a subject having HDV infection or HBV infection a composition comprising the chimeric gene of claim 2.

* * * * *

SEQUENCE LISTING

<160> NUMBER OF SEQ ID NOS: 116

<210> SEQ ID NO 1
<211> LENGTH: 47
<212> TYPE: PRT
<213> ORGANISM: Artificial Sequence
<220> FEATURE:
<223> OTHER INFORMATION: Pre S1 A

<400> SEQUENCE: 1

```
Gly Thr Asn Leu Ser Thr Ser Asn Pro Leu Gly Phe Phe Pro Asp His
1               5                   10                  15

Gln Leu Asp Pro Ala Phe Arg Ala Asn Ser Ala Asn Pro Asp Trp Asp
            20                  25                  30

Phe Asn Pro Asn Lys Asp Thr Trp Pro Asp Ala Asn Lys Val Gly
        35                  40                  45
```

<210> SEQ ID NO 2
<211> LENGTH: 47
<212> TYPE: PRT
<213> ORGANISM: Artificial Sequence
<220> FEATURE:
<223> OTHER INFORMATION: PreS1 B

<400> SEQUENCE: 2

```
Gly Gln Asn Leu Ser Thr Ser Asn Pro Leu Gly Phe Phe Pro Asp His
1               5                   10                  15
```

-continued

```
Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45


<210> SEQ ID NO 3
<211> LENGTH: 639
<212> TYPE: PRT
<213> ORGANISM: Artificial Sequence
<220> FEATURE:
<223> OTHER INFORMATION: HDAg genotype 1 A

<400> SEQUENCE: 3

Ala Gly Cys Cys Gly Cys Ala Gly Cys Gly Ala Ala Ala Gly Cys Ala
1               5                   10                  15

Ala Ala Ala Ala Ala Ala Ala Cys Cys Gly Cys Gly Gly Cys Gly Gly
            20                  25                  30

Cys Cys Gly Cys Gly Ala Ala Gly Ala Ala Ala Thr Thr Cys Thr Gly
        35                  40                  45

Gly Ala Ala Cys Ala Gly Thr Gly Gly Gly Thr Gly Gly Gly Cys Gly
    50                  55                  60

Cys Gly Cys Gly Cys Ala Ala Ala Ala Ala Ala Cys Thr Gly Gly Ala
65                  70                  75                  80

Ala Gly Ala Ala Cys Thr Gly Gly Ala Ala Cys Gly Cys Gly Ala Thr
                85                  90                  95

Cys Thr Gly Cys Gly Cys Ala Ala Ala Ala Thr Thr Ala Ala Ala Ala
            100                 105                 110

Ala Ala Ala Ala Ala Ala Thr Thr Ala Ala Ala Ala Ala Ala Cys Thr
        115                 120                 125

Gly Gly Ala Ala Gly Ala Ala Gly Ala Ala Ala Ala Cys Cys Cys Gly
    130                 135                 140

Thr Gly Gly Cys Thr Gly Gly Gly Cys Ala Ala Cys Ala Thr Thr Ala
145                 150                 155                 160

Ala Ala Gly Gly Cys Ala Thr Thr Cys Thr Gly Gly Gly Cys Ala Ala
                165                 170                 175

Ala Ala Ala Ala Gly Ala Thr Cys Gly Cys Gly Ala Ala Gly Gly Cys
            180                 185                 190

Gly Ala Ala Gly Gly Cys Gly Cys Gly Cys Cys Gly Cys Cys Gly Gly
        195                 200                 205

Cys Gly Ala Ala Ala Cys Gly Cys Gly Cys Gly Cys Gly Cys Gly Cys
    210                 215                 220

Gly Gly Ala Thr Cys Ala Gly Ala Thr Gly Gly Ala Ala Gly Thr Gly
225                 230                 235                 240

Gly Ala Thr Ala Gly Cys Gly Gly Cys Cys Cys Gly Cys Gly Cys Ala
                245                 250                 255

Ala Ala Cys Gly Cys Cys Cys Gly Thr Thr Thr Cys Gly Cys Gly Gly
            260                 265                 270

Cys Gly Ala Ala Thr Thr Thr Ala Cys Cys Gly Ala Thr Ala Ala Ala
        275                 280                 285

Gly Ala Ala Cys Gly Cys Cys Gly Cys Gly Ala Thr Cys Ala Thr Cys
    290                 295                 300

Gly Cys Cys Gly Cys Cys Gly Cys Ala Ala Ala Gly Cys Gly Cys Thr
305                 310                 315                 320

Gly Gly Ala Ala Ala Ala Cys Ala Ala Ala Cys Gly Cys Ala Ala Ala
                325                 330                 335
```

-continued

```
Cys Ala Gly Cys Thr Gly Ala Gly Cys Ala Gly Cys Gly Gly Cys Gly
            340                 345                 350

Gly Cys Ala Ala Ala Ala Gly Cys Cys Thr Gly Ala Gly Cys Ala Ala
        355                 360                 365

Ala Gly Ala Ala Gly Ala Ala Gly Ala Ala Gly Ala Ala Gly Ala Ala
    370                 375                 380

Cys Thr Gly Cys Gly Cys Ala Ala Ala Cys Thr Gly Ala Cys Cys Gly
385                 390                 395                 400

Ala Ala Gly Ala Ala Gly Ala Thr Gly Ala Ala Cys Gly Cys Cys Gly
                405                 410                 415

Cys Gly Ala Ala Cys Gly Cys Cys Gly Cys Gly Thr Gly Gly Cys Gly
            420                 425                 430

Gly Gly Cys Cys Cys Gly Cys Gly Cys Gly Thr Gly Gly Gly Cys Gly
        435                 440                 445

Gly Cys Gly Thr Gly Ala Ala Cys Cys Cys Gly Cys Thr Gly Gly Ala
    450                 455                 460

Ala Gly Gly Cys Gly Gly Cys Ala Cys Cys Cys Gly Cys Gly Gly Cys
465                 470                 475                 480

Gly Cys Gly Cys Cys Gly Gly Gly Cys Gly Gly Cys Gly Gly Cys Thr
                485                 490                 495

Thr Thr Gly Thr Gly Cys Cys Gly Ala Gly Cys Ala Thr Gly Cys Ala
            500                 505                 510

Gly Gly Gly Cys Gly Thr Gly Cys Cys Gly Gly Ala Ala Ala Gly Cys
        515                 520                 525

Cys Cys Gly Thr Thr Thr Gly Cys Gly Cys Gly Cys Ala Cys Cys Gly
    530                 535                 540

Gly Cys Gly Ala Ala Gly Gly Cys Cys Thr Gly Gly Ala Thr Gly Thr
545                 550                 555                 560

Gly Cys Gly Cys Gly Gly Cys Ala Ala Cys Cys Ala Gly Gly Gly Cys
                565                 570                 575

Thr Thr Thr Cys Cys Gly Thr Gly Gly Gly Ala Thr Ala Thr Thr Cys
            580                 585                 590

Thr Gly Thr Thr Thr Cys Cys Gly Gly Cys Gly Gly Ala Thr Cys Cys
        595                 600                 605

Gly Cys Cys Gly Thr Thr Thr Ala Gly Cys Cys Cys Gly Cys Ala Gly
    610                 615                 620

Ala Gly Cys Thr Gly Cys Cys Gly Cys Cys Cys Gly Cys Ala Gly
625                 630                 635


<210> SEQ ID NO 4
<211> LENGTH: 639
<212> TYPE: DNA
<213> ORGANISM: Artificial Sequence
<220> FEATURE:
<223> OTHER INFORMATION: HDAg genotype 1 B nucleic acid

<400> SEQUENCE: 4

agccgcagcg aaagcaaaaa aaaccgcggc ggccgcgaag aagtgctgga acagtgggtg      60

aacggccgca aaaaactgga agaactggaa cgcgaactgc gccgcgcgcg caaaaaaatt     120

aaaaaactgg aagatgataa cccgtggctg ggcaacgtga aaggcattct gggcaaaaaa     180

gataaagatg gcgaaggcgc gccgccggcg aaacgcgcgc gcaccgatca gatggaaatt     240

gatagcggcc cgcgcaaacg cccgctgcgc ggcggcttta ccgatcgcga acgccaggat     300

catcgccgcc gcaaagcgct gaaaaacaaa aaaaaacagc tgagcgcggg cggcaaaagc     360
```

ctgagcaaag aagaagaaga agaactgaaa cgcctgaccc gcgaagatga agaacgcaaa 420
aaagaagaac atggcccgag ccgcctgggc gtgaacccga gcgaaggcgg cccgcgcggc 480
gcgccgggcg gcggctttgt gccgagcatg cagggcattc cggaaagccg ctttacccgc 540
accggcgaag gcctggatgt gcgcggcagc cgcggctttc cgcaggatat tctgtttccg 600
agcgatccgc cgtttagccc gcagagctgc cgcccgcag 639

<210> SEQ ID NO 5
<211> LENGTH: 141
<212> TYPE: DNA
<213> ORGANISM: Artificial Sequence
<220> FEATURE:
<223> OTHER INFORMATION: PreS1 derived sequence is preS1

<400> SEQUENCE: 5
ggcaccaacc tgagcaccag caacccgctg ggctttttc cggatcatca gctggatccg 60
gcgtttcgcg cgaacagcgc gaacccggat tgggatttta acccgaacaa agatacctgg 120
ccggatgcga acaaagtggg c 141

<210> SEQ ID NO 6
<211> LENGTH: 141
<212> TYPE: DNA
<213> ORGANISM: Artificial Sequence
<220> FEATURE:
<223> OTHER INFORMATION: PreS1 B

<400> SEQUENCE: 6
ggccagaacc tgagcaccag caacccgctg ggctttttc cggatcatca gctggatccg 60
gcgtttcgcg cgaacaccgc gaacccggat tgggatttta acccgaacaa agatacctgg 120
ccggatgcga acaaagtggg c 141

<210> SEQ ID NO 7
<211> LENGTH: 66
<212> TYPE: DNA
<213> ORGANISM: Artificial Sequence
<220> FEATURE:
<223> OTHER INFORMATION: T2A nucleic acid

<400> SEQUENCE: 7
ggaagcggag ctactaactt cagcctgctg aagcaggctg gagacgtgga ggagaaccct 60
ggacct 66

<210> SEQ ID NO 8
<211> LENGTH: 642
<212> TYPE: DNA
<213> ORGANISM: Artificial Sequence
<220> FEATURE:
<223> OTHER INFORMATION: HDAg gentotype 2 A (wt)

<400> SEQUENCE: 8
atgagccaga gcgaaacccg ccgcggccgc cgcggcaccc gcgaagaaac cctggaaaaa 60
tggattaccg cgcgcaaaaa agcggaagaa ctggaaaaag atctgcgcaa aacccgcaaa 120
accattaaaa aactggaaga agaaaacccg tggctgggca acattgtggg cattattcgc 180
aaaggcaaag atggcgaagg cgcgccgccg gcgaaacgcc cgcgcaccga tcagatggaa 240
gtggatagcg gcccgggcaa acgcccgcat aaaagcggct ttaccgataa agaacgcgaa 300
gatcatcgcc gccgcaaagc gctggaaaac aaaaaaaaac agctgagcgc gggcggcaaa 360
attctgagca aagaagaaga agaagaactg cgccgcctga ccgatgaaga tgaagaacgc 420
aaacgccgcg tggcgggccc gcgcgtgggc gatgtgaacc cgagccgcgg cggcccgcgc 480
ggcgcgccgg gcggcggctt tgtgccgcag atggcgggcg tgccggaaag cccgtttagc 540
cgcaccggcg aaggcctgga tattcgcggc acccagggct ttccgtgggt gagcccgagc 600
ccgccgcagc agcgcctgcc gctgctggaa tgcaccccgc ag 642

<210> SEQ ID NO 9
<211> LENGTH: 639
<212> TYPE: DNA
<213> ORGANISM: Artificial Sequence
<220> FEATURE:
<223> OTHER INFORMATION: HDAg gentotype 2 B (wt)

<400> SEQUENCE: 9
agccagagcg aaagcaaaaa aaaccgccgc ggcggccgcg aagatattct ggaaaaatgg 60
attaccaccc gccgcaaagc ggaagaactg gaaaaagatc tgcgcaaagc gcgcaaaacc 120
attaaaaaac tggaagatga aaacccgtgg ctgggcaaca ttattggcat tattcgcaaa 180
ggcaaagatg gcgaaggcgc gccgccggcg aaacgcccgc gcaccgatca gatggaaatt 240
gatagcggca ccggcaaacg cccgcataaa agcggcttta ccgataaaga acgcgaagat 300
catcgccgcc gcaaagcgct ggaaaacaaa aaaaaacagc tgagcagcgg cggcaaaaac 360
ctgagccgcg aagaagaaga agaactgggc cgcctgaccg tggaagatga agaacgccgc 420
cgccgcgtgg cgggcccgcg caccggcgat gtgaacctga gcggcggcgg cccgcgcggc 480
gcgccgggcg gcggctttgt gccgcgcatg gaaggcgtgc cggaaagccc gtttacccgc 540
accggcgaag gcctggatat tcgcggcaac cagggctttc cgtgggtgcg cccgagcccg 600
ccgcagcagc gcctgccgct gctggaatgc accccgcag 639

<210> SEQ ID NO 10
<211> LENGTH: 3189
<212> TYPE: DNA
<213> ORGANISM: Artificial Sequence
<220> FEATURE:
<223> OTHER INFORMATION: Delta 1 wt

<400> SEQUENCE: 10
agccgcagcg aaagcaaaaa aaaccgcggc ggccgcgaag aaattctgga acagtgggtg 60
ggcgcgcgca aaaaactgga agaactggaa cgcgatctgc gcaaaattaa aaaaaaaatt 120
aaaaaactgg aagaagaaaa cccgtggctg ggcaacatta aaggcattct gggcaaaaaa 180
gatcgcgaag gcgaaggcgc gccgccggcg aaacgcgcgc gcgcggatca gatggaagtg 240
gatagcggcc cgcgcaaacg cccgtttcgc ggcgaattta ccgataaaga acgccgcgat 300
catcgccgcc gcaaagcgct ggaaaacaaa cgcaaacagc tgagcagcgg cggcaaaagc 360
ctgagcaaag aagaagaaga agaactgcgc aaactgaccg aagaagatga acgccgcgaa 420
cgccgcgtgg cgggcccgcg cgtgggcggc gtgaacccgc tggaaggcgg cacccgcggc 480
gcgccgggcg gcggctttgt gccgagcatg cagggcgtgc cggaaagccc gtttgcgcgc 540
accggcgaag gcctggatgt gcgcggcaac cagggctttc cgtgggatat tctgtttccg 600
gcggatccgc cgtttagccc gcagagctgc cgcccgcaga gccgcagcga aagcaaaaaa 660
aaccgcggcg gccgcgaaga agtgctggaa cagtgggtga acggccgcaa aaaactggaa 720
gaactggaac gcgaactgcg ccgcgcgcgc aaaaaaatta aaaaactgga agatgataac 780
ccgtggctgg gcaacgtgaa aggcattctg ggcaaaaaag ataaagatgg cgaaggcgcg 840

-continued

```
ccgccggcga aacgcgcgcg caccgatcag atggaaattg atagcggccc gcgcaaacgc    900
ccgctgcgcg gcggctttac cgatcgcgaa cgccaggatc atcgccgccg caaagcgctg    960
aaaaacaaaa aaaaacagct gagcgcgggc ggcaaaagcc tgagcaaaga agaagaagaa   1020
gaactgaaac gcctgacccg cgaagatgaa gaacgcaaaa aagaagaaca tggcccgagc   1080
cgcctgggcg tgaacccgag cgaaggcggc ccgcgcggcg cgccgggcgg cggctttgtg   1140
ccgagcatgc agggcattcc ggaaagccgc tttacccgca ccggcgaagg cctggatgtg   1200
cgcggcagcc gcggctttcc gcaggatatt ctgtttccga gcgatccgcc gtttagcccg   1260
cagagctgcc gcccgcaggg caccaacctg agcaccagca acccgctggg ctttttttccg   1320
gatcatcagc tggatccggc gtttcgcgcg aacagcgcga acccggattg ggattttaac   1380
ccgaacaaag atacctggcc ggatgcgaac aaagtgggcg gccagaacct gagcaccagc   1440
aacccgctgg gctttttttcc ggatcatcag ctggatccgg cgtttcgcgc gaacaccgcg   1500
aacccggatt gggattttaa cccgaacaaa gatacctggc cggatgcgaa caaagtgggc   1560
ggaagcggag ctactaactt cagcctgctg aagcaggctg gagacgtgga ggagaaccct   1620
ggacctatga gccagagcga aacccgccgc ggccgccgcg gcacccgcga agaaaccctg   1680
gaaaaatgga ttaccgcgcg caaaaaagcg gaagaactgg aaaaagatct gcgcaaaacc   1740
cgcaaaacca ttaaaaaact ggaagaagaa aacccgtggc tgggcaacat tgtgggcatt   1800
attcgcaaag gcaaagatgg cgaaggcgcg ccgccggcga aacgcccgcg caccgatcag   1860
atggaagtgg atagcggccc gggcaaacgc ccgcataaaa gcggctttac cgataaagaa   1920
cgcgaagatc atcgccgccg caaagcgctg gaaaacaaaa aaaaacagct gagcgcgggc   1980
ggcaaaattc tgagcaaaga agaagaagaa gaactgcgcc gcctgaccga tgaagatgaa   2040
gaacgcaaac gccgcgtggc gggcccgcgc gtgggcgatg tgaacccgag ccgcggcggc   2100
ccgcgcggcg cgccgggcgg cggctttgtg ccgcagatgg cgggcgtgcc ggaaagcccg   2160
tttagccgca ccggcgaagg cctggatatt cgcggcaccc agggctttcc gtgggtgagc   2220
ccgagcccgc cgcagcagcg cctgccgctg ctggaatgca ccccgcagag ccagagcgaa   2280
agcaaaaaaa accgccgcgg cggccgcgaa gatattctgg aaaaatggat taccacccgc   2340
cgcaaagcgg aagaactgga aaaagatctg cgcaaagcgc gcaaaaccat taaaaaactg   2400
gaagatgaaa acccgtggct gggcaacatt attggcatta ttcgcaaagg caaagatggc   2460
gaaggcgcgc cgccggcgaa acgcccgcgc accgatcaga tggaaattga tagcggcacc   2520
ggcaaacgcc cgcataaaag cggctttacc gataaagaac gcgaagatca tcgccgccgc   2580
aaagcgctgg aaaacaaaaa aaaacagctg agcagcggcg gcaaaaacct gagccgcgaa   2640
gaagaagaag aactgggccg cctgaccgtg gaagatgaag aacgccgccg ccgcgtggcg   2700
ggcccgcgca ccggcgatgt gaacctgagc ggcggcggcc cgcgcggcgc gccgggcggc   2760
ggctttgtgc cgcgcatgga aggcgtgccg gaaagcccgt ttacccgcac cggcgaaggc   2820
ctggatattc gcggcaacca gggctttccg tgggtgcgcc cgagcccgcc gcagcagcgc   2880
ctgccgctgc tggaatgcac cccgcagggc accaacctga gcaccagcaa cccgctgggc   2940
tttttttccgg atcatcagct ggatccggcg tttcgcgcga acagcgcgaa cccggattgg   3000
gattttaacc cgaacaaaga tacctggccg gatgcgaaca aagtgggcgg ccagaacctg   3060
agcaccagca acccgctggg ctttttttccg gatcatcagc tggatccggc gtttcgcgcg   3120
aacaccgcga acccggattg ggattttaac ccgaacaaag atacctggcc ggatgcgaac   3180
aaagtgggc                                                           3189
```

<210> SEQ ID NO 11
<211> LENGTH: 3221
<212> TYPE: DNA
<213> ORGANISM: Artificial Sequence
<220> FEATURE:
<223> OTHER INFORMATION: Delta1 wt with restriction sites (HindIII/
EcoRI)

<400> SEQUENCE: 11
aagcttgcac catggccagc cgcagcgaaa gcaaaaaaaa ccgcggcggc cgcgaagaaa 60
ttctggaaca gtgggtgggc gcgcgcaaaa aactggaaga actggaacgc gatctgcgca 120
aaattaaaaa aaaaattaaa aaactggaag aagaaaaccc gtggctgggc aacattaaag 180
gcattctggg caaaaaagat cgcgaaggcg aaggcgcgcc gccggcgaaa cgcgcgcgcg 240
cggatcagat ggaagtggat agcggcccgc gcaaacgccc gtttcgcggc gaatttaccg 300
ataaagaacg ccgcgatcat cgccgccgca aagcgctgga aaacaaacgc aaacagctga 360
gcagcggcgg caaaagcctg agcaaagaag aagaagaaga actgcgcaaa ctgaccgaag 420
aagatgaacg ccgcgaacgc cgcgtggcgg gcccgcgcgt gggcggcgtg aacccgctgg 480
aaggcggcac ccgcggcgcg ccgggcggcg gctttgtgcc gagcatgcag ggcgtgccgg 540
aaagcccgtt tgcgcgcacc ggcgaaggcc tggatgtgcg cggcaaccag ggctttccgt 600
gggatattct gtttccggcg gatccgccgt ttagcccgca gagctgccgc ccgcagagcc 660
gcagcgaaag caaaaaaaac cgcggcggcc gcgaagaagt gctggaacag tgggtgaacg 720
gccgcaaaaa actggaagaa ctggaacgcg aactgcgccg cgcgcgcaaa aaaattaaaa 780
aactggaaga tgataacccg tggctgggca acgtgaaagg cattctgggc aaaaaagata 840
aagatggcga aggcgcgccg ccggcgaaac gcgcgcgcac cgatcagatg gaaattgata 900
gcggcccgcg caaacgcccg ctgcgcggcg gctttaccga tcgcgaacgc caggatcatc 960
gccgccgcaa agcgctgaaa aacaaaaaaa aacagctgag cgcgggcggc aaaagcctga 1020
gcaaagaaga agaagaagaa ctgaaacgcc tgacccgcga agatgaagaa cgcaaaaaag 1080
aagaacatgg cccgagccgc ctgggcgtga acccgagcga aggcggcccg cgcggcgcgc 1140
cgggcggcgg ctttgtgccg agcatgcagg gcattccgga aagccgcttt acccgcaccg 1200
gcgaaggcct ggatgtgcgc ggcagccgcg gctttccgca ggatattctg tttccgagcg 1260
atccgccgtt tagcccgcag agctgccgcc cgcagggcac caacctgagc accagcaacc 1320
cgctgggctt ttttccggat catcagctgg atccggcgtt tcgcgcgaac agcgcgaacc 1380
cggattggga ttttaacccg aacaaagata cctggccgga tgcgaacaaa gtgggcggcc 1440
agaacctgag caccagcaac ccgctgggct tttttccgga tcatcagctg gatccggcgt 1500
ttcgcgcgaa caccgcgaac ccggattggg attttaaccc gaacaaagat acctggccgg 1560
atgcgaacaa agtgggcgga agcggagcta ctaacttcag cctgctgaag caggctggag 1620
acgtggagga gaaccctgga cctatgagcc agagcgaaac ccgccgcggc cgccgcggca 1680
cccgcgaaga aaccctggaa aaatggatta ccgcgcgcaa aaaagcggaa gaactggaaa 1740
aagatctgcg caaaacccgc aaaaccatta aaaaactgga agaagaaaac ccgtggctgg 1800
gcaacattgt gggcattatt cgcaaaggca aagatggcga aggcgcgccg ccggcgaaac 1860
gcccgcgcac cgatcagatg gaagtggata gcggcccggg caaacgcccg cataaaagcg 1920
gctttaccga taaagaacgc gaagatcatc gccgccgcaa agcgctggaa aacaaaaaaa 1980
aacagctgag cgcgggcggc aaaattctga gcaaagaaga agaagaagaa ctgcgccgcc 2040
tgaccgatga agatgaagaa cgcaaacgcc gcgtggcggg cccgcgcgtg ggcgatgtga 2100
acccgagccg cggcggcccg cgcggcgcgc cgggcggcgg ctttgtgccg cagatggcgg 2160
gcgtgccgga aagcccgttt agccgcaccg gcgaaggcct ggatattcgc ggcacccagg 2220
gctttccgtg ggtgagcccg agcccgccgc agcagcgcct gccgctgctg gaatgcaccc 2280
cgcagagcca gagcgaaagc aaaaaaaacc gccgcggcgg ccgcgaagat attctggaaa 2340
aatggattac cacccgccgc aaagcggaag aactggaaaa agatctgcgc aaagcgcgca 2400
aaaccattaa aaaactggaa gatgaaaacc cgtggctggg caacattatt ggcattattc 2460
gcaaaggcaa agatggcgaa ggcgcgccgc cggcgaaacg cccgcgcacc gatcagatgg 2520
aaattgatag cggcaccggc aaacgcccgc ataaaagcgg ctttaccgat aaagaacgcg 2580
aagatcatcg ccgccgcaaa gcgctggaaa acaaaaaaaa acagctgagc agcggcggca 2640
aaaacctgag ccgcgaagaa gaagaagaac tgggccgcct gaccgtggaa gatgaagaac 2700
gccgccgccg cgtggcgggc ccgcgcaccg gcgatgtgaa cctgagcggc ggcggcccgc 2760
gcggcgcgcc gggcggcggc tttgtgccgc gcatggaagg cgtgccggaa agcccgttta 2820
cccgcaccgg cgaaggcctg gatattcgcg gcaaccaggg ctttccgtgg gtgcgcccga 2880
gcccgccgca gcagcgcctg ccgctgctgg aatgcacccc gcagggcacc aacctgagca 2940
ccagcaaccc gctgggcttt tttccggatc atcagctgga tccggcgttt cgcgcgaaca 3000
gcgcgaaccc ggattgggat tttaacccga acaaagatac ctggccggat gcgaacaaag 3060
tgggcggcca gaacctgagc accagcaacc cgctgggctt ttttccggat catcagctgg 3120
atccggcgtt tcgcgcgaac accgcgaacc cggattggga ttttaacccg aacaaagata 3180
cctggccgga tgcgaacaaa gtgggctgat gagaattccg t 3221

<210> SEQ ID NO 12
<211> LENGTH: 3192
<212> TYPE: DNA
<213> ORGANISM: Artificial Sequence
<220> FEATURE:
<223> OTHER INFORMATION: Codon optimized delta 1

<400> SEQUENCE: 12
gccagcagaa gtgaatcaaa aaagaatcgg ggagggcggg aagaaatcct ggaacagtgg 60
gtcggagcac ggaagaaact ggaagaactg gagagggacc tgcgcaagat caagaagaag 120
atcaagaagc tggaggagga gaacccctgg ctgggcaata tcaagggcat cctgggcaag 180
aaggatcggg agggagaggg agcaccacct gcaaagaggg ccagagccga ccagatggag 240
gtggatagcg gaccaaggaa gcgccctttc agaggagagt ttaccgacaa ggagcggaga 300
gatcacaggc gccggaaggc cctggagaac aagaggaagc agctgagctc cggcggcaag 360
tccctgtcta aggaggagga ggaggagctg cgcaagctga cagaggagga cgagagaagg 420
gagaggaggg tggcaggacc tagggtggga ggcgtgaacc cactggaggg aggaaccaga 480
ggagcacctg gaggaggatt cgtgccatcc atgcagggag tgcccgagtc tcctttttgcc 540 cggacaggcg agggcctgga tgtgagaggc aatcagggct tcccctggga catcctgttt 600
cctgccgatc cacccttctc tcctcagagc tgccggccac agagcagatc cgagtctaag 660
aagaacaggg gaggaagaga ggaggtgctg gagcagtggg tgaatggccg gaagaagctg 720
gaggagctgg agcgggagct gagaagggcc agaaagaaga tcaagaagct ggaagacgat 780
aatccttggc tgggcaatgt gaaaggcatc ctgggcaaga aggacaagga tggagaggga 840

-continued

```
gcacctccag caaagagggc aagaaccgac cagatggaga tcgattctgg accaaggaag    900
cgccccctga gaggaggctt cacagaccgg gagagacagg atcaccgccg gagaaaggcc    960
ctgaagaaca agaagaagca gctgtccgcc ggaggcaaga gcctgtccaa agaagaggaa   1020
gaggagctga agaggctgac ccgcgaggac gaggagagga agaaggagga gcacggacca   1080
agcaggctgg gagtgaatcc ttccgaggga ggacctaggg gagcaccagg aggaggcttc   1140
gtgccatcta tgcagggcat ccccgagagc cggtttacca gaacaggaga gggcctggac   1200
gtgaggggct cccgcggctt tcctcaggac atcctgttcc catctgatcc cccttttttcc  1260
ccccagtctt gtaggcctca gggcaccaac ctgtctacaa gcaatccact gggcttcttt   1320
cccgaccacc agctggatcc tgccttccgc gccaacagcg ccaatcccga ctgggacttc   1380
aacccaaata aggacacctg gccagatgcc aacaaggtcg gcggccagaa cctgtccaca   1440
tctaatcctc tgggcttctt tccagaccac cagctggatc cagccttccg ggccaacaca   1500
gctaaccctg actgggactt caaccccaat aaggatactt ggcccgacgc caacaaggtc   1560
ggcggaagcg gagctactaa cttcagcctg ctgaagcagg ctggagacgt ggaggagaac   1620
cctggaccta tgagccagtc cgagacaagg aggggccgga gaggaaccag ggaggagaca   1680
ctggagaagt ggatcacagc ccgcaagaag gccgaggagc tggagaagga cctgcggaag   1740
accagaaaga caatcaagaa gctggaagaa gagaacccat ggctgggcaa tatcgtgggc   1800
atcatcagaa agggcaagga cggcgaggga gcaccaccag caaagaggcc caggactgat   1860
cagatggaag tcgatagcgg accaggcaag cggcctcaca agtccggctt cacagacaag   1920
gagagagagg accataggcg ccggaaggcc ctggaaaaca agaagaagca attatccgcc   1980
ggcggcaaga tcctgtccaa agaggaagaa gaggagctga gaaggctgac cgacgaggat   2040
gaggagagga aaagaagggt ggcaggacca agggtgggcg acgtgaatcc cagcagggga   2100
ggaccaagag gcgcccctgg cggcggcttc gtgccacaga tggcaggagt gccagagagc   2160
cccttttcca ggacaggaga gggcctggat atcagaggca cccagggctt tccttgggtg   2220
tctccaagcc ctccacagca gcggctgcca ctgctggagt gcacccctca gtcccagtct   2280
gagagcaaga agaacagaag gggcggcaga gaggacatcc tggagaagtg gatcaccaca   2340
cgcagaaaag ctgaagaact ggaaaaggac ctgaggaagg cccgcaaaac aatcaagaag   2400
ctggaggatg aaaatccatg gctgggaaac atcatcggca tcatcaggaa gggcaaggac   2460
ggggaaggcg caccacctgc aaagcggcct agaacagatc agatggaaat cgattctggc   2520
accggcaaga ggccacacaa gagcggcttc accgacaagg agcgcgagga tcacagaagg   2580
cgcaaggccc tggagaacaa gaagaagcaa ttaagcagcg gcggcaagaa tctgtccaga   2640
gaagaagagg aggagctggg ccgcctgacc gtggaggacg aggagcggag aaggcgcgtg   2700
gcaggaccac gcacaggcga tgtgaacctg tccggaggag gaccaagggg agcacctgga   2760
ggcggcttcg tgcctagaat ggagggagtg cctgagtccc ccttcacccg caccggagag   2820
ggcctggaca tcagaggcaa tcagggattc ccatgggtga ggcccagccc accacagcag   2880
cgcctgccac tgctggagtg taccccccag ggcacaaacc tgtccacctc taatcccctg   2940
ggcttctttc ctgatcatca gctggaccca gccttcaggg ccaactccgc caatccagat   3000
tgggacttca acccgaataa ggatacttgg ccagatgcaa acaaggtcgg aggacagaac   3060
ctgagcacat ccaaccctct gggcttcttt cctgaccatc agctggatcc cgcctttcgc   3120
gccaataccg ccaaccctga ttgggacttc aaccctaata aggatacttg gcctgatgct   3180
aataaggtcg gg                                                        3192
```

<210> SEQ ID NO 13
<211> LENGTH: 3221
<212> TYPE: DNA
<213> ORGANISM: Artificial Sequence
<220> FEATURE:
<223> OTHER INFORMATION: Delta 1 optimized with restriction sites
(HindIII and EcoRI)

<400> SEQUENCE: 13

```
aagcttgcac catggccagc agaagtgaat caaaaaagaa tcggggaggg cgggaagaaa     60
tcctggaaca gtgggtcgga gcacggaaga aactggaaga actggagagg gacctgcgca    120
agatcaagaa gaagatcaag aagctggagg aggagaaccc ctggctgggc aatatcaagg    180
gcatcctggg caagaaggat cgggagggag agggagcacc acctgcaaag agggccagag    240
ccgaccagat ggaggtggat agcggaccaa ggaagcgccc tttcagagga gagtttaccg    300
acaaggagcg gagagatcac aggcgccgga aggccctgga gaacaagagg aagcagctga    360
gctccggcgg caagtccctg tctaaggagg aggaggagga gctgcgcaag ctgacagagg    420
aggacgagag aagggagagg agggtggcag gacctagggt gggaggcgtg aacccactgg    480
agggaggaac cagaggagca cctggaggag gattcgtgcc atccatgcag ggagtgcccg    540
agtctccttt tgcccggaca ggcgagggcc tggatgtgag aggcaatcag ggcttcccct    600
gggacatcct gtttcctgcc gatccaccct tctctcctca gagctgccgg ccacagagca    660
gatccgagtc taagaagaac aggggaggaa gagaggaggt gctggagcag tgggtgaatg    720
gccggaagaa gctggaggag ctggagcggg agctgagaag ggccagaaag aagatcaaga    780
agctggaaga cgataatcct tggctgggca atgtgaaagg catcctgggc aagaaggaca    840
aggatggaga gggagcacct ccagcaaaga gggcaagaac cgaccagatg gagatcgatt    900
ctggaccaag gaagcgcccc ctgagaggag gcttcacaga ccgggagaga caggatcacc    960
gccggagaaa ggccctgaag aacaagaaga agcagctgtc cgccggaggc aagagcctgt   1020
ccaaagaaga ggaagaggag ctgaagaggc tgacccgcga ggacgaggag aggaagaagg   1080
aggagcacgg accaagcagg ctgggagtga atccttccga gggaggacct aggggagcac   1140
caggaggagg cttcgtgcca tctatgcagg gcatccccga gagccggttt accagaacag   1200
gagagggcct ggacgtgagg ggctcccgcg gctttcctca ggacatcctg ttcccatctg   1260
atcccccttt ttcccccag tcttgtaggc ctcagggcac caacctgtct acaagcaatc   1320
cactgggctt ctttcccgac caccagctgg atcctgcctt ccgcgccaac agcgccaatc   1380
ccgactggga cttcaaccca aataaggaca cctggccaga tgccaacaag gtcggcggcc   1440
agaacctgtc cacatctaat cctctgggct tctttccaga ccaccagctg gatccagcct   1500
tccgggccaa cacagctaac cctgactggg acttcaaccc caataaggat acttggcccg   1560
acgccaacaa ggtcggcgga agcggagcta ctaacttcag cctgctgaag caggctggag   1620
acgtggagga gaaccctgga cctatgagcc agtccgagac aaggaggggc cggagaggaa   1680
ccagggagga gacactggag aagtggatca cagcccgcaa gaaggccgag gagctggaga   1740
aggacctgcg gaagaccaga aagacaatca agaagctgga agaagagaac ccatggctgg   1800
gcaatatcgt gggcatcatc agaaagggca aggacggcga gggagcacca ccagcaaaga   1860
ggcccaggac tgatcagatg gaagtcgata gcggaccagg caagcggcct cacaagtccg   1920
gcttcacaga caaggagaga gaggaccata ggcgccggaa ggccctggaa aacaagaaga   1980
agcaattatc cgccggcggc aagatcctgt ccaaagagga agaagaggag ctgagaaggc   2040
```

```
tgaccgacga ggatgaggag aggaaaagaa gggtggcagg accaagggtg ggcgacgtga   2100

atcccagcag gggaggacca agaggcgccc ctggcggcgg cttcgtgcca cagatggcag   2160

gagtgccaga gagcccettt tccaggacag gagagggcct ggatatcaga ggcacccagg   2220

gctttccttg ggtgtctcca agccctccac agcagcggct gccactgctg gagtgcaccc   2280

ctcagtccca gtctgagagc aagaagaaca gaaggggcgg cagagaggac atcctggaga   2340

agtggatcac cacacgcaga aaagctgaag aactggaaaa ggacctgagg aaggcccgca   2400

aaacaatcaa gaagctggag gatgaaaatc catggctggg aaacatcatc ggcatcatca   2460

ggaagggcaa ggacggggaa ggcgcaccac ctgcaaagcg gcctagaaca gatcagatgg   2520

aaatcgattc tggcaccggc aagaggccac acaagagcgg cttcaccgac aaggagcgcg   2580

aggatcacag aaggcgcaag gccctggaga acaagaagaa gcaattaagc agcggcggca   2640

agaatctgtc cagagaagaa gaggaggagc tgggccgcct gaccgtggag gacgaggagc   2700

ggagaaggcg cgtggcagga ccacgcacag gcgatgtgaa cctgtccgga ggaggaccaa   2760

ggggagcacc tggaggcggc ttcgtgccta gaatggaggg agtgcctgag tccccccttca   2820

cccgcaccgg agagggcctg gacatcagag gcaatcaggg attcccatgg gtgaggccca   2880

gcccaccaca gcagcgcctg ccactgctgg agtgtacccc ccagggcaca aacctgtcca   2940

cctctaatcc cctgggcttc tttcctgatc atcagctgga cccagccttc agggccaact   3000

ccgccaatcc agattgggac ttcaacccga ataaggatac ttggccagat gcaaacaagg   3060

tcggaggaca gaacctgagc acatccaacc ctctgggctt ctttcctgac catcagctgg   3120

atcccgcctt tcgcgccaat accgccaacc ctgattggga cttcaaccct aataaggata   3180

cttggcctga tgctaataag gtcgggtgat gagaattccg t                        3221
```

<210> SEQ ID NO 14
<211> LENGTH: 1065
<212> TYPE: PRT
<213> ORGANISM: Artificial Sequence
<220> FEATURE:
<223> OTHER INFORMATION: Delta 1 protein

<400> SEQUENCE: 14

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Gly Val Asn Pro Leu Glu Gly Gly Thr
```

-continued

```
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Ser Arg Ser Glu Ser Lys Lys Asn Arg
    210                 215                 220

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
                245                 250                 255

Lys Leu Glu Asp Asp Asn Pro Trp Leu Gly Asn Val Lys Gly Ile Leu
            260                 265                 270

Gly Lys Lys Asp Lys Asp Gly Glu Gly Ala Pro Pro Ala Lys Arg Ala
        275                 280                 285

Arg Thr Asp Gln Met Glu Ile Asp Ser Gly Pro Arg Lys Arg Pro Leu
    290                 295                 300

Arg Gly Gly Phe Thr Asp Arg Glu Arg Gln Asp His Arg Arg Arg Lys
305                 310                 315                 320

Ala Leu Lys Asn Lys Lys Lys Gln Leu Ser Ala Gly Gly Lys Ser Leu
                325                 330                 335

Ser Lys Glu Glu Glu Glu Glu Leu Lys Arg Leu Thr Arg Glu Asp Glu
            340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Gly Phe Val Pro Ser
    370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
                405                 410                 415

Asp Pro Pro Phe Ser Pro Gln Ser Cys Arg Pro Gln Gly Thr Asn Leu
            420                 425                 430

Ser Thr Ser Asn Pro Leu Gly Phe Phe Pro Asp His Gln Leu Asp Pro
        435                 440                 445

Ala Phe Arg Ala Asn Ser Ala Asn Pro Asp Trp Asp Phe Asn Pro Asn
    450                 455                 460

Lys Asp Thr Trp Pro Asp Ala Asn Lys Val Gly Gly Gln Asn Leu Ser
465                 470                 475                 480

Thr Ser Asn Pro Leu Gly Phe Phe Pro Asp His Gln Leu Asp Pro Ala
                485                 490                 495

Phe Arg Ala Asn Thr Ala Asn Pro Asp Trp Asp Phe Asn Pro Asn Lys
            500                 505                 510

Asp Thr Trp Pro Asp Ala Asn Lys Val Gly Gly Ser Gly Ala Thr Asn
        515                 520                 525

Phe Ser Leu Leu Lys Gln Ala Gly Asp Val Glu Glu Asn Pro Gly Pro
    530                 535                 540

Met Ser Gln Ser Glu Thr Arg Arg Gly Arg Arg Gly Thr Arg Glu Glu
545                 550                 555                 560

Thr Leu Glu Lys Trp Ile Thr Ala Arg Lys Lys Ala Glu Glu Leu Glu
                565                 570                 575
```

```
Lys Asp Leu Arg Lys Thr Arg Lys Thr Ile Lys Lys Leu Glu Glu Glu
            580                 585                 590

Asn Pro Trp Leu Gly Asn Ile Val Gly Ile Ile Arg Lys Gly Lys Asp
        595                 600                 605

Gly Glu Gly Ala Pro Pro Ala Lys Arg Pro Arg Thr Asp Gln Met Glu
    610                 615                 620

Val Asp Ser Gly Pro Gly Lys Arg Pro His Lys Ser Gly Phe Thr Asp
625                 630                 635                 640

Lys Glu Arg Glu Asp His Arg Arg Arg Lys Ala Leu Glu Asn Lys Lys
                645                 650                 655

Lys Gln Leu Ser Ala Gly Gly Lys Ile Leu Ser Lys Glu Glu Glu Glu
            660                 665                 670

Glu Leu Arg Arg Leu Thr Asp Glu Asp Glu Glu Arg Lys Arg Arg Val
        675                 680                 685

Ala Gly Pro Arg Val Gly Asp Val Asn Pro Ser Arg Gly Gly Pro Arg
    690                 695                 700

Gly Ala Pro Gly Gly Gly Phe Val Pro Gln Met Ala Gly Val Pro Glu
705                 710                 715                 720

Ser Pro Phe Ser Arg Thr Gly Glu Gly Leu Asp Ile Arg Gly Thr Gln
                725                 730                 735

Gly Phe Pro Trp Val Ser Pro Ser Pro Pro Gln Gln Arg Leu Pro Leu
            740                 745                 750

Leu Glu Cys Thr Pro Gln Ser Gln Ser Glu Ser Lys Lys Asn Arg Arg
        755                 760                 765

Gly Gly Arg Glu Asp Ile Leu Glu Lys Trp Ile Thr Thr Arg Arg Lys
    770                 775                 780

Ala Glu Glu Leu Glu Lys Asp Leu Arg Lys Ala Arg Lys Thr Ile Lys
785                 790                 795                 800

Lys Leu Glu Asp Glu Asn Pro Trp Leu Gly Asn Ile Ile Gly Ile Ile
                805                 810                 815

Arg Lys Gly Lys Asp Gly Glu Gly Ala Pro Pro Ala Lys Arg Pro Arg
            820                 825                 830

Thr Asp Gln Met Glu Ile Asp Ser Gly Thr Gly Lys Arg Pro His Lys
        835                 840                 845

Ser Gly Phe Thr Asp Lys Glu Arg Glu Asp His Arg Arg Arg Lys Ala
    850                 855                 860

Leu Glu Asn Lys Lys Lys Gln Leu Ser Ser Gly Gly Lys Asn Leu Ser
865                 870                 875                 880

Arg Glu Glu Glu Glu Glu Leu Gly Arg Leu Thr Val Glu Asp Glu Glu
                885                 890                 895

Arg Arg Arg Arg Val Ala Gly Pro Arg Thr Gly Asp Val Asn Leu Ser
            900                 905                 910

Gly Gly Gly Pro Arg Gly Ala Pro Gly Gly Gly Phe Val Pro Arg Met
        915                 920                 925

Glu Gly Val Pro Glu Ser Pro Phe Thr Arg Thr Gly Glu Gly Leu Asp
    930                 935                 940

Ile Arg Gly Asn Gln Gly Phe Pro Trp Val Arg Pro Ser Pro Pro Gln
945                 950                 955                 960

Gln Arg Leu Pro Leu Leu Glu Cys Thr Pro Gln Gly Thr Asn Leu Ser
                965                 970                 975

Thr Ser Asn Pro Leu Gly Phe Phe Pro Asp His Gln Leu Asp Pro Ala
            980                 985                 990
```

-continued

```
Phe Arg Ala Asn Ser Ala Asn Pro Asp Trp Asp Phe Asn Pro Asn Lys
        995                 1000                1005

Asp Thr Trp Pro Asp Ala Asn Lys Val Gly Gly Gln Asn Leu Ser Thr
    1010                1015                1020

Ser Asn Pro Leu Gly Phe Phe Pro Asp His Gln Leu Asp Pro Ala Phe
1025                1030                1035                1040

Arg Ala Asn Thr Ala Asn Pro Asp Trp Asp Phe Asn Pro Asn Lys Asp
                1045                1050                1055

Thr Trp Pro Asp Ala Asn Lys Val Gly
            1060                1065


<210> SEQ ID NO 15
<211> LENGTH: 3189
<212> TYPE: DNA
<213> ORGANISM: Artificial Sequence
<220> FEATURE:
<223> OTHER INFORMATION: Delta 2 sequence wt

<400> SEQUENCE: 15

ggcaccaacc tgagcaccag caacccgctg ggctttttc cggatcatca gctggatccg      60

gcgtttcgcg cgaacagcgc gaacccggat tgggatttta acccgaacaa agatacctgg    120

ccggatgcga acaaagtggg cggccagaac ctgagcacca gcaacccgct gggctttttt    180

ccggatcatc agctggatcc ggcgtttcgc gcgaacaccg cgaacccgga ttgggatttt    240

aacccgaaca aagatacctg gccggatgcg aacaaagtgg gcagccgcag cgaaagcaaa    300

aaaaaccgcg gcggccgcga agaaattctg gaacagtggg tgggcgcgcg caaaaaactg    360

gaagaactgg aacgcgatct gcgcaaaatt aaaaaaaaaa ttaaaaaact ggaagaagaa    420

aacccgtggc tgggcaacat taaaggcatt ctgggcaaaa aagatcgcga aggcgaaggc    480

gcgccgccgg cgaaacgcgc gcgcgcggat cagatggaag tggatagcgg cccgcgcaaa    540

cgcccgtttc gcggcgaatt taccgataaa gaacgccgcg atcatcgccg ccgcaaagcg    600

ctggaaaaca aacgcaaaca gctgagcagc ggcggcaaaa gcctgagcaa agaagaagaa    660

gaagaactgc gcaaactgac cgaagaagat gaacgccgcg aacgccgcgt ggcgggcccg    720

cgcgtgggcg gcgtgaaccc gctggaaggc ggcacccgcg gcgcgccggg cggcggcttt    780

gtgccgagca tgcagggcgt gccggaaagc ccgtttgcgc gcaccggcga aggcctggat    840

gtgcgcggca accagggctt tccgtgggat attctgtttc cggcggatcc gccgtttagc    900

ccgcagagct gccgcccgca gagccgcagc gaaagcaaaa aaaaccgcgg cggccgcgaa    960

gaagtgctgg aacagtgggt gaacggccgc aaaaaactgg aagaactgga acgcgaactg   1020

cgccgcgcgc gcaaaaaaat taaaaaactg gaagatgata acccgtggct gggcaacgtg   1080

aaaggcattc tgggcaaaaa agataaagat ggcgaaggcg cgccgccggc gaaacgcgcg   1140

cgcaccgatc agatggaaat tgatagcggc ccgcgcaaac gcccgctgcg cggcggcttt   1200

accgatcgcg aacgccagga tcatcgccgc cgcaaagcgc tgaaaaacaa aaaaaaacag   1260

ctgagcgcgg gcggcaaaag cctgagcaaa gaagaagaag aagaactgaa acgcctgacc   1320

cgcgaagatg aagaacgcaa aaaagaagaa catggcccga gccgcctggg cgtgaacccg   1380

agcgaaggcg gcccgcgcgg cgcgccgggc ggcggctttg tgccgagcat gcagggcatt   1440

ccggaaagcc gctttacccg caccggcgaa ggcctggatg tgcgcggcag ccgcggcttt   1500

ccgcaggata ttctgtttcc gagcgatccg ccgtttagcc cgcagagctg ccgcccgcag   1560

ggaagcggag ctactaactt cagcctgctg aagcaggctg gagacgtgga ggagaaccct   1620
```

-continued

```
ggacctatgg gcaccaacct gagcaccagc aacccgctgg gctttttttcc ggatcatcag   1680

ctggatccgg cgtttcgcgc gaacagcgcg aacccggatt gggattttaa cccgaacaaa   1740

gatacctggc cggatgcgaa caaagtgggc ggccagaacc tgagcaccag caacccgctg   1800

ggcttttttc cggatcatca gctggatccg gcgtttcgcg cgaacaccgc gaacccggat   1860

tgggatttta acccgaacaa agatacctgg ccggatgcga acaaagtggg cagccagagc   1920

gaaacccgcc gcggccgccg cggcacccgc gaagaaaccc tggaaaaatg gattaccgcg   1980

cgcaaaaaag cggaagaact ggaaaaagat ctgcgcaaaa cccgcaaaac cattaaaaaa   2040

ctggaagaag aaaacccgtg gctgggcaac attgtgggca ttattcgcaa aggcaaagat   2100

ggcgaaggcg cgccgccggc gaaacgcccg cgcaccgatc agatggaagt ggatagcggc   2160

ccgggcaaac gcccgcataa aagcggcttt accgataaag aacgcgaaga tcatcgccgc   2220

cgcaaagcgc tggaaaacaa aaaaaaacag ctgagcgcgg gcggcaaaat tctgagcaaa   2280

gaagaagaag aagaactgcg ccgcctgacc gatgaagatg aagaacgcaa acgccgcgtg   2340

gcgggcccgc gcgtgggcga tgtgaacccg agccgcggcg gcccgcgcgg cgcgccgggc   2400

ggcggctttg tgccgcagat ggcgggcgtg ccggaaagcc cgtttagccg caccggcgaa   2460

ggcctggata ttcgcggcac ccagggcttt ccgtgggtga gcccgagccc gccgcagcag   2520

cgcctgccgc tgctggaatg caccccgcag agccagagcg aaagcaaaaa aaaccgccgc   2580

ggcggccgcg aagatattct ggaaaaatgg attaccaccc gccgcaaagc ggaagaactg   2640

gaaaaagatc tgcgcaaagc gcgcaaaacc attaaaaaac tggaagatga aaacccgtgg   2700

ctgggcaaca ttattggcat tattcgcaaa ggcaaagatg gcgaaggcgc gccgccggcg   2760

aaacgcccgc gcaccgatca gatggaaatt gatagcggca ccggcaaacg cccgcataaa   2820

agcggcttta ccgataaaga acgcgaagat catcgccgcc gcaaagcgct ggaaaacaaa   2880

aaaaaacagc tgagcagcgg cggcaaaaac ctgagccgcg aagaagaaga agaactgggc   2940

cgcctgaccg tggaagatga agaacgccgc cgccgcgtgg cgggcccgcg caccggcgat   3000

gtgaacctga gcggcggcgg cccgcgcggc gcgccgggcg gcggctttgt gccgcgcatg   3060

gaaggcgtgc cggaaagccc gtttacccgc accggcgaag gcctggatat tcgcggcaac   3120

cagggctttc cgtgggtgcg cccgagcccg ccgcagcagc gcctgccgct gctggaatgc   3180

accccgcag                                                              3189
```

<210> SEQ ID NO 16
<211> LENGTH: 3221
<212> TYPE: DNA
<213> ORGANISM: Artificial Sequence
<220> FEATURE:
<223> OTHER INFORMATION: Delta 2 wt with restriction sites (HindIII /EcoRI)

<400> SEQUENCE: 16

```
aagcttgcac catggccggc accaacctga gcaccagcaa cccgctgggc tttttttccgg     60

atcatcagct ggatccggcg tttcgcgcga acagcgcgaa cccggattgg gattttaacc    120

cgaacaaaga tacctggccg gatgcgaaca aagtgggcgg ccagaacctg agcaccagca    180

acccgctggg ctttttttccg gatcatcagc tggatccggc gtttcgcgcg aacaccgcga    240

acccggattg ggattttaac ccgaacaaag atacctggcc ggatgcgaac aaagtgggca    300

gccgcagcga aagcaaaaaa aaccgcggcg gccgcgaaga aattctggaa cagtgggtgg    360

gcgcgcgcaa aaaactggaa gaactggaac gcgatctgcg caaaattaaa aaaaaaatta    420
```

-continued

```
aaaaactgga agaagaaaac ccgtggctgg gcaacattaa aggcattctg ggcaaaaaag    480
atcgcgaagg cgaaggcgcg ccgccggcga aacgcgcgcg cgcggatcag atggaagtgg    540
atagcggccc gcgcaaacgc ccgtttcgcg gcgaatttac cgataaagaa cgccgcgatc    600
atcgccgccg caaagcgctg gaaaacaaac gcaaacagct gagcagcggc ggcaaaagcc    660
tgagcaaaga agaagaagaa gaactgcgca aactgaccga agaagatgaa cgccgcgaac    720
gccgcgtggc gggcccgcgc gtgggcggcg tgaacccgct ggaaggcggc acccgcggcg    780
cgccgggcgg cggctttgtg ccgagcatgc agggcgtgcc ggaaagcccg tttgcgcgca    840
ccggcgaagg cctggatgtg cgcggcaacc agggctttcc gtgggatatt ctgtttccgg    900
cggatccgcc gtttagcccg cagagctgcc gcccgcagag ccgcagcgaa agcaaaaaaa    960
accgcggcgg ccgcgaagaa gtgctggaac agtgggtgaa cggccgcaaa aaactggaag   1020
aactggaacg cgaactgcgc cgcgcgcgca aaaaaattaa aaaactggaa gatgataacc   1080
cgtggctggg caacgtgaaa ggcattctgg gcaaaaaaga taaagatggc gaaggcgcgc   1140
cgccggcgaa acgcgcgcgc accgatcaga tggaaattga tagcggcccg cgcaaacgcc   1200
cgctgcgcgg cggctttacc gatcgcgaac gccaggatca tcgccgccgc aaagcgctga   1260
aaaacaaaaa aaaacagctg agcgcgggcg gcaaaagcct gagcaaagaa gaagaagaag   1320
aactgaaacg cctgacccgc gaagatgaag aacgcaaaaa agaagaacat ggcccgagcc   1380
gcctgggcgt gaacccgagc gaaggcggcc cgcgcggcgc gccgggcggc ggctttgtgc   1440
cgagcatgca gggcattccg gaaagccgct ttacccgcac cggcgaaggc ctggatgtgc   1500
gcggcagccg cggctttccg caggatattc tgtttccgag cgatccgccg tttagcccgc   1560
agagctgccg cccgcaggga agcggagcta ctaacttcag cctgctgaag caggctggag   1620
acgtggagga gaaccctgga cctatgggca ccaacctgag caccagcaac ccgctgggct   1680
tttttccgga tcatcagctg gatccggcgt ttcgcgcgaa cagcgcgaac ccggattggg   1740
attttaaccc gaacaaagat acctggccgg atgcgaacaa agtgggcggc cagaacctga   1800
gcaccagcaa cccgctgggc ttttttccgg atcatcagct ggatccggcg tttcgcgcga   1860
acaccgcgaa cccggattgg gattttaacc cgaacaaaga tacctggccg gatgcgaaca   1920
aagtgggcag ccagagcgaa acccgccgcg gccgccgcgg cacccgcgaa gaaaccctgg   1980
aaaaatggat taccgcgcgc aaaaaagcgg aagaactgga aaaagatctg cgcaaaaccc   2040
gcaaaaccat taaaaaactg gaagaagaaa acccgtggct gggcaacatt gtgggcatta   2100
ttcgcaaagg caaagatggc gaaggcgcgc cgccggcgaa acgcccgcgc accgatcaga   2160
tggaagtgga tagcggcccg ggcaaacgcc cgcataaaag cggctttacc gataaagaac   2220
gcgaagatca tcgccgccgc aaagcgctgg aaaacaaaaa aaaacagctg agcgcgggcg   2280
gcaaaattct gagcaaagaa gaagaagaag aactgcgccg cctgaccgat gaagatgaag   2340
aacgcaaacg ccgcgtggcg ggcccgcgcg tgggcgatgt gaacccgagc cgcggcggcc   2400
cgcgcggcgc gccgggcggc ggctttgtgc cgcagatggc gggcgtgccg gaaagcccgt   2460
ttagccgcac cggcgaaggc ctggatattc gcggcaccca gggctttccg tgggtgagcc   2520
cgagcccgcc gcagcagcgc ctgccgctgc tggaatgcac cccgcagagc cagagcgaaa   2580
gcaaaaaaaa ccgccgcggc ggccgcgaag atattctgga aaaatggatt accacccgcc   2640
gcaaagcgga agaactggaa aaagatctgc gcaaagcgcg caaaaccatt aaaaaactgg   2700
aagatgaaaa cccgtggctg ggcaacatta ttggcattat tcgcaaaggc aaagatggcg   2760
aaggcgcgcc gccggcgaaa cgcccgcgca ccgatcagat ggaaattgat agcggcaccg   2820
```

```
gcaaacgccc gcataaaagc ggctttaccg ataaagaacg cgaagatcat cgccgccgca   2880

aagcgctgga aaacaaaaaa aaacagctga gcagcggcgg caaaaacctg agccgcgaag   2940

aagaagaaga actgggccgc ctgaccgtgg aagatgaaga acgccgccgc cgcgtggcgg   3000

gcccgcgcac cggcgatgtg aacctgagcg gcggcggccc gcgcggcgcg ccgggcggcg   3060

gctttgtgcc gcgcatggaa ggcgtgccgg aaagcccgtt tacccgcacc ggcgaaggcc   3120

tggatattcg cggcaaccag ggctttccgt gggtgcgccc gagcccgccg cagcagcgcc   3180

tgccgctgct ggaatgcacc ccgcagtgat gagaattccg t                       3221


<210> SEQ ID NO 17
<211> LENGTH: 3192
<212> TYPE: DNA
<213> ORGANISM: Artificial Sequence
<220> FEATURE:
<223> OTHER INFORMATION: Delta 2 optimized

<400> SEQUENCE: 17

gccggcacta acctgtctac atcaaaccct ctgggatttt tccccgatca tcagctggac     60

cccgcatttc gcgctaactc tgctaaccct gactgggatt tcaaccctaa taaggacaca    120

tggccagatg ccaacaaggt cggcggccag aacctgtcca cctctaatcc cctgggcttc    180

tttcctgacc accagctgga tcctgccttc agggccaaca ccgccaatcc cgactgggac    240

ttcaacccaa ataaggatac ctggcctgac gctaacaagg tcggcagccg gtccgagtct    300

aagaagaata ggggaggaag ggaggagatc ctggagcagt gggtgggcgc cagaaagaag    360

ctggaggagc tggagcggga cctgagaaag atcaagaaga agatcaagaa gctggaggag    420

gagaacccct ggctgggcaa tatcaagggc atcctgggca agaaggatcg ggagggagag    480

ggagcaccac ctgcaaagag ggccagagcc gaccagatgg aggtggattc cggccctagg    540

aagcgcccat tcagaggcga gtttacagac aaggagcgga gagatcacag gcgccggaag    600

gccctggaga acaagaggaa gcagctgagc tccggcggca agagcctgtc caaggaggag    660

gaggaggagc tgcgcaagct gaccgaggag gacgagagaa gggagaggag ggtggcagga    720

cctagggtgg gaggcgtgaa cccactggag ggaggaacaa gaggagcacc cggaggaggc    780

ttcgtgcctt ctatgcaggg cgtgcctgag agcccatttg ccaggaccgg agagggcctg    840

gacgtgagag gcaatcaggg cttcccatgg gacatcctgt ttcccgccga tccacccttc    900

agcccacagt cctgcaggcc ccagtctcgc agcgagtcca agaagaacag aggcggaagg    960

gaggaggtgc tggagcagtg ggtgaatggc aggaagaagc tggaagaact ggagagggag   1020

ctgagaaggg cccgcaagaa gatcaagaag ctggaagacg ataatccttg gctgggcaat   1080

gtgaaaggca tcctgggcaa gaaggacaag gatggagagg gagcacctcc agcaaagagg   1140

gcaagaacag accagatgga gatcgattcc ggaccaagga agcgccctct gaggggaggc   1200

ttcaccgacc gggagagaca ggatcaccgc cggagaaagg ccctgaagaa caagaagaag   1260

cagctgagcg ccggcggcaa gtctctgagt aaagaagaag aggaggagct gaagcggctg   1320

acaagagagg acgaggagag gaagaaggag gagcacggac catccaggct gggagtgaat   1380

ccttctgagg gaggaccaag ggcgcccct ggcggaggct tcgtgcctag catgcagggc     1440

atcccagagt ccaggtttac caggacaggc gaaggcctgg acgtgcgggg ctctagaggc   1500

tttccccagg acatcctgtt ccctagcgat cccccttttt ctcctcagag ctgtagacca   1560

cagggaagcg gagctactaa cttcagcctg ctgaagcagg ctggagacgt ggaggagaac   1620
```

```
cctggaccta tgggcaccaa cctgtccaca tctaaccctc tgggcttctt tccagatcat   1680

cagctggacc cagccttcag ggccaacagc gccaatccag actgggactt caaccccaat   1740

aaggacacat ggcctgacgc aaacaaggtc ggaggacaga acctgagcac ctccaatcca   1800

ctgggcttct ttcccgacca ccagctggat ccagccttcc gcgccaacac tgctaaccct   1860

gattgggact tcaaccctaa taaggataca tggcctgatg ccaataaggt cggctctcag   1920

agcgagacaa ggaggggccg gagaggaacc agggaggaga cactggagaa gtggatcacc   1980

gcccgcaaga aggccgagga gctggagaag gacctgagga agacccgcaa gacaatcaag   2040

aagctggaag aagagaaccc atggctgggc aatatcgtgg gcatcatcag aaagggcaag   2100

gacggcgagg gagcaccacc agcaaagagg ccccgcacag atcagatgga agtggattcc   2160

ggacctggca agcggccaca caagtctggc ttcaccgaca aggagagaga ggaccatagg   2220

cgccggaagg ccctggaaaa caagaagaag caattatctg ccggcggcaa gatcctgagt   2280

aaagaagagg aagaggagct gagaaggctg accgacgagg atgaggagag gaagcgccgg   2340

gtggccggcc cacgcgtggg cgacgtgaat ccctccaggg gaggaccaag aggagcacct   2400

ggaggcggct tcgtgcccca gatggccggc gtgcccgagt ccccttttc tcggaccggc   2460

gagggcctgg atatcagagg cacacagggc tttccatggg tgtcccccctc tcctccacag   2520

cagaggctgc cactgctgga gtgcacaccc cagagccaga gcgaatctaa gaagaacaga   2580

aggggaggcc gcgaggacat cctggaaaaa tggatcacca cacgcagaaa agctgaagaa   2640

ctggaaaagg acctgcggaa ggccagaaag accatcaaga agctggagga tgaaaatcca   2700

tggctgggaa acatcatcgg catcatccgg aagggcaagg acggggaagg cgcaccacct   2760

gcaaagcggc ctagaaccga tcagatggaa atcgatagcg gcacaggcaa gaggccacac   2820

aagtccggct tcaccgataa agagcgcgag gatcacagaa ggcgcaaggc cctggagaac   2880

aagaagaagc aattaagcag cggcggcaag aatctgtcca gagaagagga ggaagagctg   2940

ggccgcctga cagtggagga cgaggagcgg agaaggcgcg tggcaggacc cagaaccggc   3000

gatgtgaacc tgtccggagg aggacctagg ggagcaccag gaggcggctt cgtgcctaga   3060

atggagggcg tgccagagtc tcccttttacc cggacaggcg agggcctgga catcagaggc   3120

aatcagggct ttccctgggt ccgcccctcc ccccctcagc agagactgcc actgctggaa   3180

tgcacaccac ag                                                     3192
```

<210> SEQ ID NO 18
<211> LENGTH: 3221
<212> TYPE: DNA
<213> ORGANISM: Artificial Sequence
<220> FEATURE:
<223> OTHER INFORMATION: Delta 2 codon optimized + Restriction sites

<400> SEQUENCE: 18

```
aagcttgcac catggccggc actaacctgt ctacatcaaa ccctctggga tttttccccg     60

atcatcagct ggaccccgca tttcgcgcta actctgctaa ccctgactgg gatttcaacc    120

ctaataagga cacatggcca gatgccaaca aggtcggcgg ccagaacctg tccacctcta    180

atcccctggg cttctttcct gaccaccagc tggatcctgc cttcagggcc aacaccgcca    240

atcccgactg ggacttcaac ccaaataagg atacctggcc tgacgctaac aaggtcggca    300

gccggtccga gtctaagaag aataggggag gaagggagga gatcctggag cagtgggtgg    360

gcgccagaaa gaagctggag gagctggagc gggacctgag aaagatcaag aagaagatca    420

agaagctgga ggaggagaac ccctggctgg gcaatatcaa gggcatcctg ggcaagaagg    480
```

```
atcgggaggg agagggagca ccacctgcaa agagggccag agccgaccag atggaggtgg    540
attccggccc taggaagcgc ccattcagag gcgagtttac agacaaggag cggagagatc    600
acaggcgccg gaaggccctg gagaacaaga ggaagcagct gagctccggc ggcaagagcc    660
tgtccaagga ggaggaggag gagctgcgca agctgaccga ggaggacgag agaagggaga    720
ggagggtggc aggacctagg gtgggaggcg tgaacccact ggagggagga acaagaggag    780
cacccggagg aggcttcgtg ccttctatgc agggcgtgcc tgagagccca tttgccagga    840
ccggagaggg cctggacgtg agaggcaatc agggcttccc atgggacatc ctgtttcccg    900
ccgatccacc cttcagccca cagtcctgca ggcccccagtc tcgcagcgag tccaagaaga    960
acagaggcgg aagggaggag gtgctggagc agtgggtgaa tggcaggaag aagctggaag   1020
aactggagag ggagctgaga agggcccgca agaagatcaa gaagctggaa gacgataatc   1080
cttggctggg caatgtgaaa ggcatcctgg gcaagaagga caaggatgga gagggagcac   1140
ctccagcaaa gagggcaaga acagaccaga tggagatcga ttccggacca aggaagcgcc   1200
ctctgagggg aggcttcacc gaccgggaga gacaggatca ccgccggaga aaggccctga   1260
agaacaagaa gaagcagctg agcgccggcg gcaagtctct gagtaaagaa gaagaggagg   1320
agctgaagcg gctgacaaga gaggacgagg agaggaagaa ggaggagcac ggaccatcca   1380
ggctgggagt gaatccttct gagggaggac caaggggcgc ccctggcgga ggcttcgtgc   1440
ctagcatgca gggcatccca gagtccaggt ttaccaggac aggcgaaggc ctggacgtgc   1500
ggggctctag aggctttccc caggacatcc tgttccctag cgatcccccct ttttctcctc   1560
agagctgtag accacaggga agcggagcta ctaacttcag cctgctgaag caggctggag   1620
acgtggagga gaaccctgga cctatgggca ccaacctgtc cacatctaac cctctgggct   1680
tctttccaga tcatcagctg gacccagcct tcagggccaa cagcgccaat ccagactggg   1740
acttcaaccc caataaggac acatggcctg acgcaaacaa ggtcggagga cagaacctga   1800
gcacctccaa tccactgggc ttctttcccg accaccagct ggatccagcc ttccgcgcca   1860
acactgctaa ccctgattgg gacttcaacc ctaataagga tacatggcct gatgccaata   1920
aggtcggctc tcagagcgag acaaggaggg gccggagagg aaccagggag gagacactgg   1980
agaagtggat caccgcccgc aagaaggccg aggagctgga gaaggacctg aggaagaccc   2040
gcaagacaat caagaagctg gaagaagaga acccatggct gggcaatatc gtgggcatca   2100
tcagaaaggg caaggacggc gagggagcac caccagcaaa gaggccccgc acagatcaga   2160
tggaagtgga ttccggacct ggcaagcggc cacacaagtc tggcttcacc gacaaggaga   2220
gagaggacca taggcgccgg aaggccctgg aaaacaagaa gaagcaatta tctgccggcg   2280
gcaagatcct gagtaaagaa gaggaagagg agctgagaag gctgaccgac gaggatgagg   2340
agaggaagcg ccgggtggcc ggcccacgcg tgggcgacgt gaatccctcc aggggaggac   2400
caagaggagc acctggaggc ggcttcgtgc cccagatggc cggcgtgccc gagtcccctt   2460
tttctcggac cggcgagggc ctggatatca gaggcacaca gggctttcca tgggtgtccc   2520
cctctcctcc acagcagagg ctgccactgc tggagtgcac accccagagc cagagcgaat   2580
ctaagaagaa cagaagggga ggccgcgagg acatcctgga aaaatggatc accacacgca   2640
gaaaagctga agaactggaa aaggacctgc ggaaggccag aaagaccatc aagaagctgg   2700
aggatgaaaa tccatggctg ggaaacatca tcggcatcat ccggaagggc aaggacgggg   2760
aaggcgcacc acctgcaaag cggcctagaa ccgatcagat ggaaatcgat agcggcacag   2820
```

```
gcaagaggcc acacaagtcc ggcttcaccg ataaagagcg cgaggatcac agaaggcgca   2880

aggccctgga gaacaagaag aagcaattaa gcagcggcgg caagaatctg tccagagaag   2940

aggaggaaga gctgggccgc ctgacagtgg aggacgagga gcggagaagg cgcgtggcag   3000

gacccagaac cggcgatgtg aacctgtccg gaggaggacc taggggagca ccaggaggcg   3060

gcttcgtgcc tagaatggag ggcgtgccag agtctccctt tacccggaca ggcgagggcc   3120

tggacatcag aggcaatcag ggctttccct gggtccgccc ctcccccccct cagcagagac   3180

tgccactgct ggaatgcaca ccacagtgat gagaattccg t                       3221


<210> SEQ ID NO 19
<211> LENGTH: 1065
<212> TYPE: PRT
<213> ORGANISM: Artificial Sequence
<220> FEATURE:
<223> OTHER INFORMATION: Delta 2 protein

<400> SEQUENCE: 19

Met Ala Gly Thr Asn Leu Ser Thr Ser Asn Pro Leu Gly Phe Phe Pro
1               5                   10                  15

Asp His Gln Leu Asp Pro Ala Phe Arg Ala Asn Ser Ala Asn Pro Asp
            20                  25                  30

Trp Asp Phe Asn Pro Asn Lys Asp Thr Trp Pro Asp Ala Asn Lys Val
        35                  40                  45

Gly Gly Gln Asn Leu Ser Thr Ser Asn Pro Leu Gly Phe Phe Pro Asp
    50                  55                  60

His Gln Leu Asp Pro Ala Phe Arg Ala Asn Thr Ala Asn Pro Asp Trp
65                  70                  75                  80

Asp Phe Asn Pro Asn Lys Asp Thr Trp Pro Asp Ala Asn Lys Val Gly
                85                  90                  95

Ser Arg Ser Glu Ser Lys Lys Asn Arg Gly Gly Arg Glu Glu Ile Leu
            100                 105                 110

Glu Gln Trp Val Gly Ala Arg Lys Lys Leu Glu Glu Leu Glu Arg Asp
        115                 120                 125

Leu Arg Lys Ile Lys Lys Lys Ile Lys Lys Leu Glu Glu Glu Asn Pro
    130                 135                 140

Trp Leu Gly Asn Ile Lys Gly Ile Leu Gly Lys Lys Asp Arg Glu Gly
145                 150                 155                 160

Glu Gly Ala Pro Pro Ala Lys Arg Ala Arg Ala Asp Gln Met Glu Val
                165                 170                 175

Asp Ser Gly Pro Arg Lys Arg Pro Phe Arg Gly Glu Phe Thr Asp Lys
            180                 185                 190

Glu Arg Arg Asp His Arg Arg Arg Lys Ala Leu Glu Asn Lys Arg Lys
        195                 200                 205

Gln Leu Ser Ser Gly Gly Lys Ser Leu Ser Lys Glu Glu Glu Glu Glu
    210                 215                 220

Leu Arg Lys Leu Thr Glu Glu Asp Glu Arg Arg Glu Arg Arg Val Ala
225                 230                 235                 240

Gly Pro Arg Val Gly Gly Val Asn Pro Leu Glu Gly Gly Thr Arg Gly
                245                 250                 255

Ala Pro Gly Gly Gly Phe Val Pro Ser Met Gln Gly Val Pro Glu Ser
            260                 265                 270

Pro Phe Ala Arg Thr Gly Glu Gly Leu Asp Val Arg Gly Asn Gln Gly
        275                 280                 285

Phe Pro Trp Asp Ile Leu Phe Pro Ala Asp Pro Pro Phe Ser Pro Gln
```

```
    290                 295                 300

Ser Cys Arg Pro Gln Ser Arg Ser Glu Ser Lys Lys Asn Arg Gly Gly
305                 310                 315                 320

Arg Glu Glu Val Leu Glu Gln Trp Val Asn Gly Arg Lys Lys Leu Glu
                325                 330                 335

Glu Leu Glu Arg Glu Leu Arg Arg Ala Arg Lys Lys Ile Lys Lys Leu
            340                 345                 350

Glu Asp Asp Asn Pro Trp Leu Gly Asn Val Lys Gly Ile Leu Gly Lys
        355                 360                 365

Lys Asp Lys Asp Gly Glu Gly Ala Pro Pro Ala Lys Arg Ala Arg Thr
    370                 375                 380

Asp Gln Met Glu Ile Asp Ser Gly Pro Arg Lys Arg Pro Leu Arg Gly
385                 390                 395                 400

Gly Phe Thr Asp Arg Glu Arg Gln Asp His Arg Arg Arg Lys Ala Leu
                405                 410                 415

Lys Asn Lys Lys Lys Gln Leu Ser Ala Gly Gly Lys Ser Leu Ser Lys
            420                 425                 430

Glu Glu Glu Glu Glu Leu Lys Arg Leu Thr Arg Glu Asp Glu Glu Arg
        435                 440                 445

Lys Lys Glu Glu His Gly Pro Ser Arg Leu Gly Val Asn Pro Ser Glu
    450                 455                 460

Gly Gly Pro Arg Gly Ala Pro Gly Gly Gly Phe Val Pro Ser Met Gln
465                 470                 475                 480

Gly Ile Pro Glu Ser Arg Phe Thr Arg Thr Gly Glu Gly Leu Asp Val
                485                 490                 495

Arg Gly Ser Arg Gly Phe Pro Gln Asp Ile Leu Phe Pro Ser Asp Pro
            500                 505                 510

Pro Phe Ser Pro Gln Ser Cys Arg Pro Gln Gly Ser Gly Ala Thr Asn
        515                 520                 525

Phe Ser Leu Leu Lys Gln Ala Gly Asp Val Glu Glu Asn Pro Gly Pro
    530                 535                 540

Met Gly Thr Asn Leu Ser Thr Ser Asn Pro Leu Gly Phe Phe Pro Asp
545                 550                 555                 560

His Gln Leu Asp Pro Ala Phe Arg Ala Asn Ser Ala Asn Pro Asp Trp
                565                 570                 575

Asp Phe Asn Pro Asn Lys Asp Thr Trp Pro Asp Ala Asn Lys Val Gly
            580                 585                 590

Gly Gln Asn Leu Ser Thr Ser Asn Pro Leu Gly Phe Phe Pro Asp His
        595                 600                 605

Gln Leu Asp Pro Ala Phe Arg Ala Asn Thr Ala Asn Pro Asp Trp Asp
    610                 615                 620

Phe Asn Pro Asn Lys Asp Thr Trp Pro Asp Ala Asn Lys Val Gly Ser
625                 630                 635                 640

Gln Ser Glu Thr Arg Arg Gly Arg Arg Gly Thr Arg Glu Glu Thr Leu
                645                 650                 655

Glu Lys Trp Ile Thr Ala Arg Lys Lys Ala Glu Glu Leu Glu Lys Asp
            660                 665                 670

Leu Arg Lys Thr Arg Lys Thr Ile Lys Lys Leu Glu Glu Glu Asn Pro
        675                 680                 685

Trp Leu Gly Asn Ile Val Gly Ile Ile Arg Lys Gly Lys Asp Gly Glu
    690                 695                 700

Gly Ala Pro Pro Ala Lys Arg Pro Arg Thr Asp Gln Met Glu Val Asp
705                 710                 715                 720
```

```
Ser Gly Pro Gly Lys Arg Pro His Lys Ser Gly Phe Thr Asp Lys Glu
                725                 730                 735

Arg Glu Asp His Arg Arg Arg Lys Ala Leu Glu Asn Lys Lys Lys Gln
            740                 745                 750

Leu Ser Ala Gly Gly Lys Ile Leu Ser Lys Glu Glu Glu Glu Glu Leu
        755                 760                 765

Arg Arg Leu Thr Asp Glu Asp Glu Glu Arg Lys Arg Arg Val Ala Gly
    770                 775                 780

Pro Arg Val Gly Asp Val Asn Pro Ser Arg Gly Gly Pro Arg Gly Ala
785                 790                 795                 800

Pro Gly Gly Gly Phe Val Pro Gln Met Ala Gly Val Pro Glu Ser Pro
                805                 810                 815

Phe Ser Arg Thr Gly Glu Gly Leu Asp Ile Arg Gly Thr Gln Gly Phe
            820                 825                 830

Pro Trp Val Ser Pro Ser Pro Pro Gln Gln Arg Leu Pro Leu Leu Glu
        835                 840                 845

Cys Thr Pro Gln Ser Gln Ser Glu Ser Lys Lys Asn Arg Arg Gly Gly
    850                 855                 860

Arg Glu Asp Ile Leu Glu Lys Trp Ile Thr Thr Arg Arg Lys Ala Glu
865                 870                 875                 880

Glu Leu Glu Lys Asp Leu Arg Lys Ala Arg Lys Thr Ile Lys Lys Leu
                885                 890                 895

Glu Asp Glu Asn Pro Trp Leu Gly Asn Ile Ile Gly Ile Ile Arg Lys
            900                 905                 910

Gly Lys Asp Gly Glu Gly Ala Pro Pro Ala Lys Arg Pro Arg Thr Asp
        915                 920                 925

Gln Met Glu Ile Asp Ser Gly Thr Gly Lys Arg Pro His Lys Ser Gly
    930                 935                 940

Phe Thr Asp Lys Glu Arg Glu Asp His Arg Arg Arg Lys Ala Leu Glu
945                 950                 955                 960

Asn Lys Lys Lys Gln Leu Ser Ser Gly Gly Lys Asn Leu Ser Arg Glu
                965                 970                 975

Glu Glu Glu Glu Leu Gly Arg Leu Thr Val Glu Asp Glu Glu Arg Arg
            980                 985                 990

Arg Arg Val Ala Gly Pro Arg Thr Gly Asp Val Asn Leu Ser Gly Gly
        995                 1000                1005

Gly Pro Arg Gly Ala Pro Gly Gly Gly Phe Val Pro Arg Met Glu Gly
    1010                1015                1020

Val Pro Glu Ser Pro Phe Thr Arg Thr Gly Glu Gly Leu Asp Ile Arg
1025                1030                1035                1040

Gly Asn Gln Gly Phe Pro Trp Val Arg Pro Ser Pro Pro Gln Gln Arg
                1045                1050                1055

Leu Pro Leu Leu Glu Cys Thr Pro Gln
            1060                1065
```

<210> SEQ ID NO 20
<211> LENGTH: 3753
<212> TYPE: DNA
<213> ORGANISM: Artificial Sequence
<220> FEATURE:
<223> OTHER INFORMATION: Delta 3 wt

<400> SEQUENCE: 20
ggcaccaacc tgagcaccag caacccgctg ggcttttttc cggatcatca gctggatccg 60

-continued

```
gcgtttcgcg cgaacagcgc gaacccggat tgggatttta acccgaacaa agatacctgg    120
ccggatgcga acaaagtggg cggccagaac ctgagcacca gcaacccgct gggctttttt    180
ccggatcatc agctggatcc ggcgtttcgc gcgaacaccg cgaacccgga ttgggatttt    240
aacccgaaca aagatacctg gccggatgcg aacaaagtgg gcagccgcag cgaaagcaaa    300
aaaaaccgcg gcggccgcga agaaattctg gaacagtggg tgggcgcgcg caaaaaactg    360
gaagaactgg aacgcgatct gcgcaaaatt aaaaaaaaaa ttaaaaaact ggaagaagaa    420
aacccgtggc tgggcaacat taaaggcatt ctgggcaaaa aagatcgcga aggcgaaggc    480
gcgccgccgg cgaaacgcgc gcgcgcggat cagatggaag tggatagcgg cccgcgcaaa    540
cgcccgtttc gcggcgaatt taccgataaa gaacgccgcg atcatcgccg ccgcaaagcg    600
ctggaaaaca aacgcaaaca gctgagcagc ggcggcaaaa gcctgagcaa agaagaagaa    660
gaagaactgc gcaaactgac cgaagaagat gaacgccgcg aacgccgcgt ggcgggcccg    720
cgcgtgggcg gcgtgaaccc gctggaaggc ggcacccgcg gcgcgccggg cggcggcttt    780
gtgccgagca tgcagggcgt gccggaaagc ccgtttgcgc gcaccggcga aggcctggat    840
gtgcgcggca accagggctt tccgtgggat attctgtttc cggcggatcc gccgtttagc    900
ccgcagagct gccgcccgca gagccgcagc gaaagcaaaa aaaaccgcgg cggccgcgaa    960
gaagtgctgg aacagtgggt gaacggccgc aaaaaactgg aagaactgga acgcgaactg   1020
cgccgcgcgc gcaaaaaaat taaaaaactg gaagatgata acccgtggct gggcaacgtg   1080
aaaggcattc tgggcaaaaa agataaagat ggcgaaggcg cgccgccggc gaaacgcgcg   1140
cgcaccgatc agatggaaat tgatagcggc ccgcgcaaac gcccgctgcg cggcggcttt   1200
accgatcgcg aacgccagga tcatcgccgc cgcaaagcgc tgaaaaacaa aaaaaaacag   1260
ctgagcgcgg gcggcaaaag cctgagcaaa gaagaagaag aagaactgaa acgcctgacc   1320
cgcgaagatg aagaacgcaa aaaagaagaa catggcccga gccgcctggg cgtgaacccg   1380
agcgaaggcg gcccgcgcgg cgcgccgggc ggcggctttg tgccgagcat gcagggcatt   1440
ccggaaagcc gctttacccg caccggcgaa ggcctggatg tgcgcggcag ccgcggcttt   1500
ccgcaggata ttctgtttcc gagcgatccg ccgtttagcc cgcagagctg ccgcccgcag   1560
ggcaccaacc tgagcaccag caacccgctg ggctttttcc ggatcatca gctggatccg    1620
gcgtttcgcg cgaacagcgc gaacccggat tgggatttta acccgaacaa agatacctgg   1680
ccggatgcga acaaagtggg cggccagaac ctgagcacca gcaacccgct gggctttttt   1740
ccggatcatc agctggatcc ggcgtttcgc gcgaacaccg cgaacccgga ttgggatttt   1800
aacccgaaca aagatacctg gccggatgcg aacaaagtgg gcggaagcgg agctactaac   1860
ttcagcctgc tgaagcaggc tggagacgtg gaggagaacc ctggacctat gggcaccaac   1920
ctgagcacca gcaacccgct gggctttttt ccggatcatc agctggatcc ggcgtttcgc   1980
gcgaacagcg cgaacccgga ttgggatttt aacccgaaca aagatacctg gccggatgcg   2040
aacaaagtgg gcggccagaa cctgagcacc agcaacccgc tgggcttttt tccggatcat   2100
cagctggatc cggcgtttcg cgcgaacacc gcgaacccgg attgggattt taacccgaac   2160
aaagatacct ggccggatgc gaacaaagtg ggcagccaga gcgaaacccg ccgcggccgc   2220
cgcggcaccc gcgaagaaac cctggaaaaa tggattaccg cgcgcaaaaa agcggaagaa   2280
ctggaaaaag atctgcgcaa aacccgcaaa accattaaaa aactggaaga agaaaacccg   2340
tggctgggca acattgtggg cattattcgc aaaggcaaag atggcgaagg cgcgccgccg   2400
gcgaaacgcc cgcgcaccga tcagatggaa gtggatagcg gcccgggcaa acgcccgcat   2460
```

aaaagcggct ttaccgataa agaacgcgaa gatcatcgcc gccgcaaagc gctggaaaac 2520
aaaaaaaaac agctgagcgc gggcggcaaa attctgagca aagaagaaga agaagaactg 2580
cgccgcctga ccgatgaaga tgaagaacgc aaacgccgcg tggcgggccc gcgcgtgggc 2640
gatgtgaacc cgagccgcgg cggcccgcgc ggcgcgccgg gcggcggctt tgtgccgcag 2700
atggcgggcg tgccggaaag cccgtttagc cgcaccggcg aaggcctgga tattcgcggc 2760
acccagggct ttccgtgggt gagcccgagc ccgccgcagc agcgcctgcc gctgctggaa 2820
tgcaccccgc agagccagag cgaaagcaaa aaaaaccgcc gcggcggccg cgaagatatt 2880
ctggaaaaat ggattaccac ccgccgcaaa gcggaagaac tggaaaaaga tctgcgcaaa 2940
gcgcgcaaaa ccattaaaaa actggaagat gaaaacccgt ggctgggcaa cattattggc 3000
attattcgca aaggcaaaga tggcgaaggc gcgccgccgg cgaaacgccc gcgcaccgat 3060
cagatggaaa ttgatagcgg caccggcaaa cgcccgcata aaagcggctt taccgataaa 3120
gaacgcgaag atcatcgccg ccgcaaagcg ctggaaaaca aaaaaaaaca gctgagcagc 3180
ggcggcaaaa acctgagccg cgaagaagaa gaagaactgg gccgcctgac cgtggaagat 3240
gaagaacgcc gccgccgcgt ggcgggcccg cgcaccggcg atgtgaacct gagcggcggc 3300
ggcccgcgcg gcgcgccggg cggcggcttt gtgccgcgca tggaaggcgt gccggaaagc 3360
ccgtttaccc gcaccggcga aggcctggat attcgcggca accagggctt tccgtgggtg 3420
cgcccgagcc cgccgcagca gcgcctgccg ctgctggaat gcaccccgca gggcaccaac 3480
ctgagcacca gcaacccgct gggctttttt ccggatcatc agctggatcc ggcgtttcgc 3540
gcgaacagcg cgaacccgga ttgggatttt aacccgaaca aagatacctg gccggatgcg 3600
aacaaagtgg gcggccagaa cctgagcacc agcaacccgc tgggcttttt tccggatcat 3660
cagctggatc cggcgtttcg cgcgaacacc gcgaacccgg attgggattt taacccgaac 3720
aaagatacct ggccggatgc gaacaaagtg ggc 3753

<210> SEQ ID NO 21
<211> LENGTH: 3785
<212> TYPE: DNA
<213> ORGANISM: Artificial Sequence
<220> FEATURE:
<223> OTHER INFORMATION: Delta 3 wt + with restriction sites (HindIII /EcoRI)

<400> SEQUENCE: 21
aagcttgcac catggccggc accaacctga gcaccagcaa cccgctgggc ttttttccgg 60
atcatcagct ggatccggcg tttcgcgcga acagcgcgaa cccggattgg gattttaacc 120
cgaacaaaga tacctggccg gatgcgaaca aagtgggcgg ccagaacctg agcaccagca 180
acccgctggg ctttttccg gatcatcagc tggatccggc gtttcgcgcg aacaccgcga 240
acccggattg ggattttaac ccgaacaaag atacctggcc ggatgcgaac aaagtgggca 300
gccgcagcga aagcaaaaaa aaccgcggcg gccgcgaaga aattctggaa cagtgggtgg 360
gcgcgcgcaa aaaactggaa gaactggaac gcgatctgcg caaaattaaa aaaaaaatta 420
aaaaactgga agaagaaaac ccgtggctgg gcaacattaa aggcattctg ggcaaaaaag 480
atcgcgaagg cgaaggcgcg ccgccggcga aacgcgcgcg cgcggatcag atggaagtgg 540
atagcggccc gcgcaaacgc ccgtttcgcg gcgaatttac cgataaagaa cgccgcgatc 600
atcgccgccg caaagcgctg gaaaacaaac gcaaacagct gagcagcggc ggcaaaagcc 660
tgagcaaaga agaagaagaa gaactgcgca aactgaccga agaagatgaa cgccgcgaac 720

-continued

```
gccgcgtggc gggcccgcgc gtgggcggcg tgaacccgct ggaaggcggc acccgcggcg    780
cgccgggcgg cggctttgtg ccgagcatgc agggcgtgcc ggaaagcccg tttgcgcgca    840
ccggcgaagg cctggatgtg cgcggcaacc agggctttcc gtgggatatt ctgtttccgg    900
cggatccgcc gtttagcccg cagagctgcc gcccgcagag ccgcagcgaa agcaaaaaaa    960
accgcggcgg ccgcgaagaa gtgctggaac agtgggtgaa cggccgcaaa aaactggaag   1020
aactggaacg cgaactgcgc cgcgcgcgca aaaaaattaa aaaactggaa gatgataacc   1080
cgtggctggg caacgtgaaa ggcattctgg gcaaaaaaga taaagatggc gaaggcgcgc   1140
cgccggcgaa acgcgcgcgc accgatcaga tggaaattga tagcggcccg cgcaaacgcc   1200
cgctgcgcgg cggctttacc gatcgcgaac gccaggatca tcgccgccgc aaagcgctga   1260
aaaacaaaaa aaaacagctg agcgcgggcg gcaaaagcct gagcaaagaa gaagaagaag   1320
aactgaaacg cctgacccgc gaagatgaag aacgcaaaaa agaagaacat ggcccgagcc   1380
gcctgggcgt gaacccgagc gaaggcggcc cgcgcggcgc gccgggcggc ggctttgtgc   1440
cgagcatgca gggcattccg gaaagccgct ttacccgcac cggcgaaggc ctggatgtgc   1500
gcggcagccg cggctttccg caggatattc tgtttccgag cgatccgccg tttagcccgc   1560
agagctgccg cccgcagggc accaacctga gcaccagcaa cccgctgggc ttttttccgg   1620
atcatcagct ggatccggcg tttcgcgcga acagcgcgaa cccggattgg gattttaacc   1680
cgaacaaaga tacctggccg gatgcgaaca aagtgggcgg ccagaacctg agcaccagca   1740
acccgctggg ctttttttccg gatcatcagc tggatccggc gtttcgcgcg aacaccgcga   1800
acccggattg ggattttaac ccgaacaaag atacctggcc ggatgcgaac aaagtgggcg   1860
gaagcggagc tactaacttc agcctgctga agcaggctgg agacgtggag gagaaccctg   1920
gacctatggg caccaacctg agcaccagca acccgctggg ctttttttccg gatcatcagc   1980
tggatccggc gtttcgcgcg aacagcgcga acccggattg ggattttaac ccgaacaaag   2040
atacctggcc ggatgcgaac aaagtgggcg gccagaacct gagcaccagc aacccgctgg   2100
gctttttttcc ggatcatcag ctggatccgg cgtttcgcgc gaacaccgcg aacccggatt   2160
gggattttaa cccgaacaaa gatacctggc cggatgcgaa caaagtgggc agccagagcg   2220
aaacccgccg cggccgccgc ggcacccgcg aagaaaccct ggaaaaatgg attaccgcgc   2280
gcaaaaaagc ggaagaactg gaaaaagatc tgcgcaaaac ccgcaaaacc attaaaaaac   2340
tggaagaaga aaacccgtgg ctgggcaaca ttgtgggcat tattcgcaaa ggcaaagatg   2400
gcgaaggcgc gccgccggcg aaacgcccgc gcaccgatca gatggaagtg gatagcggcc   2460
cgggcaaacg cccgcataaa agcggcttta ccgataaaga acgcgaagat catcgccgcc   2520
gcaaagcgct ggaaaacaaa aaaaaacagc tgagcgcggg cggcaaaatt ctgagcaaag   2580
aagaagaaga agaactgcgc cgcctgaccg atgaagatga agaacgcaaa cgccgcgtgg   2640
cgggcccgcg cgtgggcgat gtgaacccga gccgcggcgg cccgcgcggc gcgccgggcg   2700
gcggctttgt gccgcagatg gcgggcgtgc cggaaagccc gtttagccgc accggcgaag   2760
gcctggatat tcgcggcacc cagggctttc cgtgggtgag cccgagcccg ccgcagcagc   2820
gcctgccgct gctggaatgc accccgcaga gccagagcga aagcaaaaaa aaccgccgcg   2880
gcggccgcga agatattctg gaaaaatgga ttaccacccg ccgcaaagcg gaagaactgg   2940
aaaaagatct gcgcaaagcg cgcaaaacca ttaaaaaact ggaagatgaa aacccgtggc   3000
tgggcaacat tattggcatt attcgcaaag gcaaagatgg cgaaggcgcg ccgccggcga   3060
```

-continued

```
aacgcccgcg caccgatcag atggaaattg atagcggcac cggcaaacgc ccgcataaaa   3120

gcggctttac cgataaagaa cgcgaagatc atcgccgccg caaagcgctg gaaaacaaaa   3180

aaaaacagct gagcagcggc ggcaaaaacc tgagccgcga agaagaagaa gaactgggcc   3240

gcctgaccgt ggaagatgaa gaacgccgcc gccgcgtggc gggcccgcgc accggcgatg   3300

tgaacctgag cggcggcggc ccgcgcggcg cgccgggcgg cggctttgtg ccgcgcatgg   3360

aaggcgtgcc ggaaagcccg tttacccgca ccggcgaagg cctggatatt cgcggcaacc   3420

agggctttcc gtgggtgcgc ccgagcccgc cgcagcagcg cctgccgctg ctggaatgca   3480

ccccgcaggg caccaacctg agcaccagca acccgctggg ctttttttccg gatcatcagc   3540

tggatccggc gtttcgcgcg aacagcgcga acccggattg ggattttaac ccgaacaaag   3600

atacctggcc ggatgcgaac aaagtgggcg gccagaacct gagcaccagc aacccgctgg   3660

gcttttttcc ggatcatcag ctggatccgg cgtttcgcgc gaacaccgcg aacccggatt   3720

gggattttaa cccgaacaaa gatacctggc cggatgcgaa caaagtgggc tgatgagaat   3780

tccgt                                                               3785
```

<210> SEQ ID NO 22
<211> LENGTH: 3756
<212> TYPE: DNA
<213> ORGANISM: Artificial Sequence
<220> FEATURE:
<223> OTHER INFORMATION: Delta 3 optimized

<400> SEQUENCE: 22

```
gccggcacca atctgtctac ctcaaatccc ctgggcttct tccccgatca tcagctggac     60

cctgccttcc gagcaaattc cgctaatcct gattgggatt tcaacccaaa taaggacaca    120

tggccagatg ccaacaaggt cggcggccag aacctgtcca cctctaatcc tctgggcttc    180

tttccagacc accagctgga tcccgccttc agggccaaca cagccaatcc cgactgggac    240

ttcaacccta ataaggacac ctggcctgac gccaacaagg tcggcagcag gtccgagtct    300

aagaagaata ggggaggaag ggaggagatc ctggagcagt gggtgggagc acgcaagaag    360

ctggaggagc tggagcggga cctgagaaag atcaagaaga agatcaagaa gctggaggag    420

gagaacccct ggctgggcaa tatcaagggc atcctgggca agaaggatcg ggagggagag    480

ggagcaccac ctgcaaagag ggccagagcc gaccagatgg aggtggattc cggaccaagg    540

aagcgccctt tcagaggaga gtttacagac aaggagcgga gagatcacag gcgccggaag    600

gccctggaga acaagcggaa gcagctgagc tccggcggca agagcctgtc caaggaggag    660

gaggaggagc tgagaaagct gaccgaggag gacgagagaa gggagaggag ggtggccggc    720

cccagggtgg gcggcgtgaa ccctctggag ggaggaacaa ggggagcacc aggaggaggc    780

ttcgtgcctt ccatgcaggg cgtgcccgag tctccttttg ccaggaccgg agagggcctg    840

gacgtgcgcg gcaatcaggg cttcccatgg gacatcctgt ttcccgccga tccacccttc    900

tctccccaga gctgcaggcc tcagtctcgc agcgagtcca agaagaacag aggcggaagg    960

gaggaggtgc tggagcagtg ggtgaatggc aggaagaagc tggaagaact ggagagggag   1020

ctgagaaggg cccgcaagaa gatcaagaag ctggaagacg ataatccttg gctgggcaat   1080

gtgaaaggca tcctgggcaa gaaggacaag gatggagagg gagcacctcc agcaaagagg   1140

gcaagaacag accagatgga gatcgattct ggaccaagga agcgccccct gaggggaggc   1200

ttcaccgacc gggagagaca ggatcaccgc cggagaaagg ccctgaagaa caagaagaag   1260

cagctgagcg ccggcggcaa gtctctgagt aaagaagaag aggaggagct gaagcggctg   1320
```

-continued accagagagg acgaggagcg gaagaaggag gagcacggcc caagcagact gggagtgaat 1380
ccatccgagg gaggacctag aggcgcccct ggcggcggct tcgtgccttc tatgcagggc 1440
atcccagaga gcaggtttac caggacaggc gaaggcctgg acgtgcgggg ctccagaggc 1500
tttccccagg acatcctgtt cccttctgat ccccctttt ccccacagtc ttgtaggccc 1560
cagggcacca acctgtccac atctaaccca ctgggcttct ttcctgatca ccagctggat 1620
ccagccttcc gcgccaactc cgccaatcca gactgggact tcaaccccaa taaggacaca 1680
tggcctgatg ctaacaaggt cggaggccag aacctgagca cctccaatcc cctgggcttc 1740
tttcctgacc accagctgga tcctgccttc cgcgccaaca cagctaaccc tgattgggac 1800
ttcaacccaa ataaggatac ctggcctgat gcaaacaagg tcggaggaag cggagctact 1860
aacttcagcc tgctgaagca ggctggagac gtggaggaga accctggacc tatgggcacc 1920
aacctgtcta caagcaatcc actgggcttc tttcccgacc atcagctgga cccagccttc 1980
agggccaaca gcgccaaccc tgactgggac ttcaacccaa ataaggacac gtggcctgat 2040
gccaacaagg tcggaggaca aaacctgtcc acctctaacc ccctgggctt ctttcccgat 2100
catcaattag acccagcctt ccgcgctaac actgctaacc ctgactggga cttcaacccg 2160
aataaggata cttggcctga tgccaataag gtcggcagcc agtccgagac aaggaggggc 2220
cggagaggaa ccagggagga gacactggag aagtggatca ccgccagaaa gaaggccgag 2280
gagctggaga aggacctgag gaagacccgc aagacaatca agaagctgga agaagagaac 2340
ccttggctgg gcaatatcgt gggcatcatc agaaagggca aggacggcga gggagcacca 2400
ccagccaaga ggccacgcac agatcagatg gaagtggata gcggaccagg caagaggcct 2460
cacaagtccg gcttcaccga caaggagagg gaggaccata ggcgccggaa ggccctggaa 2520
aacaagaaga agcaattatc cgccggcggc aagatcctgt ctaaagaaga ggaagaagag 2580
ctgagaaggc tgaccgacga ggatgaggag aggaagagga gggtggcagg acctagagtg 2640
ggcgacgtga atccatccag gggaggacca agaggagcac caggaggcgg cttcgtgcca 2700
cagatggcag gagtgccaga gagccccttt tccaggacag gagagggcct ggatatcagg 2760
ggaacccagg gctttccttg ggtgtctcca agccctccac agcagcggct gccactgctg 2820
gagtgcacac cccagtccca gtctgagagc aagaagaaca gaaggggcgg cagagaggac 2880
atcctggaaa aatggatcac cacacgcaga aaagctgaag aactggaaaa ggacctgcgg 2940
aaggccagaa agaccatcaa gaagctggag gatgaaaatc catggctggg aaatatcatc 3000
ggcatcatcc ggaagggcaa ggacggggaa ggcgcaccac ctgcaaagcg gcccaggacc 3060
gatcagatgg aaatcgattc tggaaccggc aagcggcctc acaagagtgg cttcaccgat 3120
aaggagagag aggatcacag aaggcgcaag gccctggaga acaagaagaa gcaattaagc 3180
agcggcggca agaatctgtc cagagaagag gaagaggagc tgggcagact gacagtggag 3240
gacgaggagc ggagaaggcg cgtggcagga ccaagaaccg gcgatgtgaa cctgtccgga 3300
ggaggaccaa ggggagcacc tgggggaggc ttcgtgccaa ggatggaggg agtgcctgag 3360
tccccttca ccagaaccgg cgaaggcctg gacatcaggg gcaatcaggg attcccatgg 3420
gtgcggccct ccccacccca gcagagactg cctctgctgg agtgtacccc acagggcact 3480
aacctgtcca cctctaaccc gttaggcttc tttcctgacc atcaattaga tcccgccttc 3540
cgggccaaca gcgccaatcc tgattgggac ttcaacccga ataaggacac ctggcccgac 3600
gcaaacaagg tcggagggca aaacctgagc acctccaacc ctttaggctt ctttccagat 3660

```
catcagctgg atccagcctt tagagccaat accgccaacc ctgactggga tttcaaccct   3720

aacaaagata cctggcccga cgctaacaaa gtggga                             3756


<210> SEQ ID NO 23
<211> LENGTH: 3785
<212> TYPE: DNA
<213> ORGANISM: Artificial Sequence
<220> FEATURE:
<223> OTHER INFORMATION: Delta 3 codon optimized with restriction sites
      (HindIII/EcoR1)

<400> SEQUENCE: 23

aagcttgcac catggccggc accaatctgt ctacctcaaa tcccctgggc ttcttccccg     60

atcatcagct ggaccctgcc ttccgagcaa attccgctaa tcctgattgg gatttcaacc    120

caaataagga cacatggcca gatgccaaca aggtcggcgg ccagaacctg tccacctcta    180

atcctctggg cttctttcca gaccaccagc tggatcccgc cttcagggcc aacacagcca    240

atcccgactg ggacttcaac cctaataagg acacctggcc tgacgccaac aaggtcggca    300

gcaggtccga gtctaagaag aataggggag gaagggagga gatcctggag cagtgggtgg    360

gagcacgcaa gaagctggag gagctggagc gggacctgag aaagatcaag aagaagatca    420

agaagctgga ggaggagaac cctggctgg gcaatatcaa gggcatcctg ggcaagaagg    480

atcgggaggg agagggagca ccacctgcaa agagggccag agccgaccag atggaggtgg    540

attccggacc aaggaagcgc cctttcagag gagagtttac agacaaggag cggagagatc    600

acaggcgccg gaaggccctg gagaacaagc ggaagcagct gagctccggc ggcaagagcc    660

tgtccaagga ggaggaggag gagctgagaa agctgaccga ggaggacgag agaagggaga    720

ggagggtggc cggccccagg gtgggcggcg tgaaccctct ggagggagga acaaggggag    780

caccaggagg aggcttcgtg ccttccatgc agggcgtgcc cgagtctcct tttgccagga    840

ccggagaggg cctggacgtg cgcggcaatc agggcttccc atgggacatc ctgtttcccg    900

ccgatccacc cttctctccc cagagctgca ggcctcagtc tcgcagcgag tccaagaaga    960

acagaggcgg aagggaggag gtgctggagc agtgggtgaa tggcaggaag aagctggaag   1020

aactggagag ggagctgaga agggcccgca agaagatcaa gaagctggaa gacgataatc   1080

cttggctggg caatgtgaaa ggcatcctgg gcaagaagga caaggatgga gagggagcac   1140

ctccagcaaa gagggcaaga acagaccaga tggagatcga ttctggacca aggaagcgcc   1200

ccctgagggg aggcttcacc gaccgggaga gacaggatca ccgccggaga aaggccctga   1260

agaacaagaa gaagcagctg agcgccggcg gcaagtctct gagtaaagaa gaagaggagg   1320

agctgaagcg gctgaccaga gaggacgagg agcggaagaa ggaggagcac ggcccaagca   1380

gactgggagt gaatccatcc gagggaggac ctagaggcgc ccctggcggc ggcttcgtgc   1440

cttctatgca gggcatccca gagagcaggt ttaccaggac aggcgaaggc ctggacgtgc   1500

ggggctccag aggctttccc caggacatcc tgttcccttc tgatcccccct ttttccccac   1560

agtcttgtag gccccagggc accaacctgt ccacatctaa cccactgggc ttctttcctg   1620

atcaccagct ggatccagcc ttccgcgcca actccgccaa tccagactgg gacttcaacc   1680

ccaataagga cacatggcct gatgctaaca aggtcggagg ccagaacctg agcacctcca   1740

atcccctggg cttctttcct gaccaccagc tggatcctgc cttccgcgcc aacacagcta   1800

accctgattg ggacttcaac ccaaataagg atacctggcc tgatgcaaac aaggtcggag   1860

gaagcggagc tactaacttc agcctgctga agcaggctgg agacgtggag gagaaccctg   1920
```

-continued

```
gacctatggg caccaacctg tctacaagca atccactggg cttctttccc gaccatcagc   1980

tggacccagc cttcagggcc aacagcgcca accctgactg ggacttcaac ccaaataagg   2040

acacgtggcc tgatgccaac aaggtcggag gacaaaacct gtccacctct aaccccctgg   2100

gcttctttcc cgatcatcaa ttagacccag ccttccgcgc taacactgct aaccctgact   2160

gggacttcaa cccgaataag gatacttggc ctgatgccaa taaggtcggc agccagtccg   2220

agacaaggag gggccggaga ggaaccaggg aggagacact ggagaagtgg atcaccgcca   2280

gaaagaaggc cgaggagctg gagaaggacc tgaggaagac ccgcaagaca atcaagaagc   2340

tggaagaaga gaacccttgg ctgggcaata tcgtgggcat catcagaaag ggcaaggacg   2400

gcgagggagc accaccagcc aagaggccac gcacagatca gatggaagtg gatagcggac   2460

caggcaagag gcctcacaag tccggcttca ccgacaagga gagggaggac cataggcgcc   2520

ggaaggccct ggaaaacaag aagaagcaat tatccgccgg cggcaagatc ctgtctaaag   2580

aagaggaaga agagctgaga aggctgaccg acgaggatga ggagaggaag aggagggtgg   2640

caggacctag agtgggcgac gtgaatccat ccaggggagg accaagagga gcaccaggag   2700

gcggcttcgt gccacagatg gcaggagtgc cagagagccc cttttccagg acaggagagg   2760

gcctggatat caggggaacc cagggctttc cttgggtgtc tccaagccct ccacagcagc   2820

ggctgccact gctggagtgc acaccccagt cccagtctga gagcaagaag aacagaaggg   2880

gcggcagaga ggacatcctg gaaaaatgga tcaccacacg cagaaaagct gaagaactgg   2940

aaaaggacct gcggaaggcc agaaagacca tcaagaagct ggaggatgaa aatccatggc   3000

tgggaaatat catcggcatc atccggaagg gcaaggacgg ggaaggcgca ccacctgcaa   3060

agcggcccag gaccgatcag atggaaatcg attctggaac cggcaagcgg cctcacaaga   3120

gtggcttcac cgataaggag agagaggatc acagaaggcg caaggccctg gagaacaaga   3180

agaagcaatt aagcagcggc ggcaagaatc tgtccagaga agaggaagag gagctgggca   3240

gactgacagt ggaggacgag gagcggagaa ggcgcgtggc aggaccaaga accggcgatg   3300

tgaacctgtc cggaggagga ccaaggggag cacctggggg aggcttcgtg ccaaggatgg   3360

agggagtgcc tgagtccccc ttcaccagaa ccggcgaagg cctggacatc aggggcaatc   3420

agggattccc atgggtgcgg ccctccccac cccagcagag actgcctctg ctggagtgta   3480

ccccacaggg cactaacctg tccacctcta acccgttagg cttctttcct gaccatcaat   3540

tagatcccgc cttccgggcc aacagcgcca atcctgattg ggacttcaac ccgaataagg   3600

acacctggcc cgacgcaaac aaggtcggag ggcaaaacct gagcacctcc aaccctttag   3660

gcttctttcc agatcatcag ctggatccag cctttagagc caataccgcc aaccctgact   3720

gggatttcaa ccctaacaaa gatacctggc ccgacgctaa caaagtggga tgatgagaat   3780

tccgt                                                               3785
```

<210> SEQ ID NO 24
<211> LENGTH: 1253
<212> TYPE: PRT
<213> ORGANISM: Artificial Sequence
<220> FEATURE:
<223> OTHER INFORMATION: Delta 3 protein

<400> SEQUENCE: 24

```
Met Ala Gly Thr Asn Leu Ser Thr Ser Asn Pro Leu Gly Phe Phe Pro
1               5                   10                  15

Asp His Gln Leu Asp Pro Ala Phe Arg Ala Asn Ser Ala Asn Pro Asp
            20                  25                  30
```

```
Trp Asp Phe Asn Pro Asn Lys Asp Thr Trp Pro Asp Ala Asn Lys Val
        35                  40                  45

Gly Gly Gln Asn Leu Ser Thr Ser Asn Pro Leu Gly Phe Phe Pro Asp
    50                  55                  60

His Gln Leu Asp Pro Ala Phe Arg Ala Asn Thr Ala Asn Pro Asp Trp
65                  70                  75                  80

Asp Phe Asn Pro Asn Lys Asp Thr Trp Pro Asp Ala Asn Lys Val Gly
                85                  90                  95

Ser Arg Ser Glu Ser Lys Lys Asn Arg Gly Gly Arg Glu Glu Ile Leu
            100                 105                 110

Glu Gln Trp Val Gly Ala Arg Lys Lys Leu Glu Glu Leu Glu Arg Asp
        115                 120                 125

Leu Arg Lys Ile Lys Lys Lys Ile Lys Lys Leu Glu Glu Glu Asn Pro
    130                 135                 140

Trp Leu Gly Asn Ile Lys Gly Ile Leu Gly Lys Lys Asp Arg Glu Gly
145                 150                 155                 160

Glu Gly Ala Pro Pro Ala Lys Arg Ala Arg Ala Asp Gln Met Glu Val
                165                 170                 175

Asp Ser Gly Pro Arg Lys Arg Pro Phe Arg Gly Glu Phe Thr Asp Lys
            180                 185                 190

Glu Arg Arg Asp His Arg Arg Arg Lys Ala Leu Glu Asn Lys Arg Lys
        195                 200                 205

Gln Leu Ser Ser Gly Gly Lys Ser Leu Ser Lys Glu Glu Glu Glu Glu
    210                 215                 220

Leu Arg Lys Leu Thr Glu Glu Asp Glu Arg Arg Glu Arg Arg Val Ala
225                 230                 235                 240

Gly Pro Arg Val Gly Gly Val Asn Pro Leu Glu Gly Gly Thr Arg Gly
                245                 250                 255

Ala Pro Gly Gly Gly Phe Val Pro Ser Met Gln Gly Val Pro Glu Ser
            260                 265                 270

Pro Phe Ala Arg Thr Gly Glu Gly Leu Asp Val Arg Gly Asn Gln Gly
        275                 280                 285

Phe Pro Trp Asp Ile Leu Phe Pro Ala Asp Pro Pro Phe Ser Pro Gln
    290                 295                 300

Ser Cys Arg Pro Gln Ser Arg Ser Glu Ser Lys Lys Asn Arg Gly Gly
305                 310                 315                 320

Arg Glu Glu Val Leu Glu Gln Trp Val Asn Gly Arg Lys Lys Leu Glu
                325                 330                 335

Glu Leu Glu Arg Glu Leu Arg Arg Ala Arg Lys Lys Ile Lys Lys Leu
            340                 345                 350

Glu Asp Asp Asn Pro Trp Leu Gly Asn Val Lys Gly Ile Leu Gly Lys
        355                 360                 365

Lys Asp Lys Asp Gly Glu Gly Ala Pro Pro Ala Lys Arg Ala Arg Thr
    370                 375                 380

Asp Gln Met Glu Ile Asp Ser Gly Pro Arg Lys Arg Pro Leu Arg Gly
385                 390                 395                 400

Gly Phe Thr Asp Arg Glu Arg Gln Asp His Arg Arg Arg Lys Ala Leu
                405                 410                 415

Lys Asn Lys Lys Lys Gln Leu Ser Ala Gly Gly Lys Ser Leu Ser Lys
            420                 425                 430

Glu Glu Glu Glu Glu Leu Lys Arg Leu Thr Arg Glu Asp Glu Glu Arg
        435                 440                 445
```

```
Lys Lys Glu Glu His Gly Pro Ser Arg Leu Gly Val Asn Pro Ser Glu
    450                 455                 460

Gly Gly Pro Arg Gly Ala Pro Gly Gly Gly Phe Val Pro Ser Met Gln
465                 470                 475                 480

Gly Ile Pro Glu Ser Arg Phe Thr Arg Thr Gly Glu Gly Leu Asp Val
                485                 490                 495

Arg Gly Ser Arg Gly Phe Pro Gln Asp Ile Leu Phe Pro Ser Asp Pro
            500                 505                 510

Pro Phe Ser Pro Gln Ser Cys Arg Pro Gln Gly Thr Asn Leu Ser Thr
        515                 520                 525

Ser Asn Pro Leu Gly Phe Phe Pro Asp His Gln Leu Asp Pro Ala Phe
    530                 535                 540

Arg Ala Asn Ser Ala Asn Pro Asp Trp Asp Phe Asn Pro Asn Lys Asp
545                 550                 555                 560

Thr Trp Pro Asp Ala Asn Lys Val Gly Gly Gln Asn Leu Ser Thr Ser
                565                 570                 575

Asn Pro Leu Gly Phe Phe Pro Asp His Gln Leu Asp Pro Ala Phe Arg
            580                 585                 590

Ala Asn Thr Ala Asn Pro Asp Trp Asp Phe Asn Pro Asn Lys Asp Thr
        595                 600                 605

Trp Pro Asp Ala Asn Lys Val Gly Gly Ser Gly Ala Thr Asn Phe Ser
    610                 615                 620

Leu Leu Lys Gln Ala Gly Asp Val Glu Glu Asn Pro Gly Pro Met Gly
625                 630                 635                 640

Thr Asn Leu Ser Thr Ser Asn Pro Leu Gly Phe Phe Pro Asp His Gln
                645                 650                 655

Leu Asp Pro Ala Phe Arg Ala Asn Ser Ala Asn Pro Asp Trp Asp Phe
            660                 665                 670

Asn Pro Asn Lys Asp Thr Trp Pro Asp Ala Asn Lys Val Gly Gly Gln
        675                 680                 685

Asn Leu Ser Thr Ser Asn Pro Leu Gly Phe Phe Pro Asp His Gln Leu
    690                 695                 700

Asp Pro Ala Phe Arg Ala Asn Thr Ala Asn Pro Asp Trp Asp Phe Asn
705                 710                 715                 720

Pro Asn Lys Asp Thr Trp Pro Asp Ala Asn Lys Val Gly Ser Gln Ser
                725                 730                 735

Glu Thr Arg Arg Gly Arg Arg Gly Thr Arg Glu Glu Thr Leu Glu Lys
            740                 745                 750

Trp Ile Thr Ala Arg Lys Lys Ala Glu Glu Leu Glu Lys Asp Leu Arg
        755                 760                 765

Lys Thr Arg Lys Thr Ile Lys Lys Leu Glu Glu Glu Asn Pro Trp Leu
    770                 775                 780

Gly Asn Ile Val Gly Ile Ile Arg Lys Gly Lys Asp Gly Glu Gly Ala
785                 790                 795                 800

Pro Pro Ala Lys Arg Pro Arg Thr Asp Gln Met Glu Val Asp Ser Gly
                805                 810                 815

Pro Gly Lys Arg Pro His Lys Ser Gly Phe Thr Asp Lys Glu Arg Glu
            820                 825                 830

Asp His Arg Arg Arg Lys Ala Leu Glu Asn Lys Lys Lys Gln Leu Ser
        835                 840                 845

Ala Gly Gly Lys Ile Leu Ser Lys Glu Glu Glu Glu Glu Leu Arg Arg
    850                 855                 860

Leu Thr Asp Glu Asp Glu Glu Arg Lys Arg Arg Val Ala Gly Pro Arg
```

865 870 875 880

Val Gly Asp Val Asn Pro Ser Arg Gly Gly Pro Arg Gly Ala Pro Gly
885 890 895

Gly Gly Phe Val Pro Gln Met Ala Gly Val Pro Glu Ser Pro Phe Ser
900 905 910

Arg Thr Gly Glu Gly Leu Asp Ile Arg Gly Thr Gln Gly Phe Pro Trp
915 920 925

Val Ser Pro Ser Pro Pro Gln Gln Arg Leu Pro Leu Leu Glu Cys Thr
930 935 940

Pro Gln Ser Gln Ser Glu Ser Lys Lys Asn Arg Arg Gly Gly Arg Glu
945 950 955 960

Asp Ile Leu Glu Lys Trp Ile Thr Thr Arg Arg Lys Ala Glu Glu Leu
965 970 975

Glu Lys Asp Leu Arg Lys Ala Arg Lys Thr Ile Lys Lys Leu Glu Asp
980 985 990

Glu Asn Pro Trp Leu Gly Asn Ile Ile Gly Ile Ile Arg Lys Gly Lys
995 1000 1005

Asp Gly Glu Gly Ala Pro Pro Ala Lys Arg Pro Arg Thr Asp Gln Met
1010 1015 1020

Glu Ile Asp Ser Gly Thr Gly Lys Arg Pro His Lys Ser Gly Phe Thr
1025 1030 1035 1040

Asp Lys Glu Arg Glu Asp His Arg Arg Arg Lys Ala Leu Glu Asn Lys
1045 1050 1055

Lys Lys Gln Leu Ser Ser Gly Gly Lys Asn Leu Ser Arg Glu Glu Glu
1060 1065 1070

Glu Glu Leu Gly Arg Leu Thr Val Glu Asp Glu Glu Arg Arg Arg Arg
1075 1080 1085

Val Ala Gly Pro Arg Thr Gly Asp Val Asn Leu Ser Gly Gly Gly Pro
1090 1095 1100

Arg Gly Ala Pro Gly Gly Gly Phe Val Pro Arg Met Glu Gly Val Pro
1105 1110 1115 1120

Glu Ser Pro Phe Thr Arg Thr Gly Glu Gly Leu Asp Ile Arg Gly Asn
1125 1130 1135

Gln Gly Phe Pro Trp Val Arg Pro Ser Pro Pro Gln Gln Arg Leu Pro
1140 1145 1150

Leu Leu Glu Cys Thr Pro Gln Gly Thr Asn Leu Ser Thr Ser Asn Pro
1155 1160 1165

Leu Gly Phe Phe Pro Asp His Gln Leu Asp Pro Ala Phe Arg Ala Asn
1170 1175 1180

Ser Ala Asn Pro Asp Trp Asp Phe Asn Pro Asn Lys Asp Thr Trp Pro
1185 1190 1195 1200

Asp Ala Asn Lys Val Gly Gly Gln Asn Leu Ser Thr Ser Asn Pro Leu
1205 1210 1215

Gly Phe Phe Pro Asp His Gln Leu Asp Pro Ala Phe Arg Ala Asn Thr
1220 1225 1230

Ala Asn Pro Asp Trp Asp Phe Asn Pro Asn Lys Asp Thr Trp Pro Asp
1235 1240 1245

Ala Asn Lys Val Gly
1250

<210> SEQ ID NO 25
<211> LENGTH: 3891
<212> TYPE: DNA
<213> ORGANISM: Artificial Sequence
<220> FEATURE:
<223> OTHER INFORMATION: Delta 4 wt

<400> SEQUENCE: 25

```
agccgcagcg aaagcaaaaa aaaccgcggc ggccgcgaag aaattctgga acagtgggtg     60
ggcgcgcgca aaaaactgga agaactggaa cgcgatctgc gcaaaattaa aaaaaaaatt    120
aaaaaactgg aagaagaaaa cccgtggctg ggcaacatta aaggcattct gggcaaaaaa    180
gatcgcgaag gcgaaggcgc gccgccggcg aaacgcgcgc gcgcggatca gatggaagtg    240
gatagcggcc cgcgcaaacg cccgtttcgc ggcgaattta ccgataaaga acgccgcgat    300
catcgccgcc gcaaagcgct ggaaaacaaa cgcaaacagc tgagcagcgg cggcaaaagc    360
ctgagcaaag aagaagaaga agaactgcgc aaactgaccg aagaagatga acgccgcgaa    420
cgccgcgtgg cgggcccgcg cgtgggcggc gtgaacccgc tggaaggcgg cacccgcggc    480
gcgccgggcg gcggctttgt gccgagcatg cagggcgtgc cggaaagccc gtttgcgcgc    540
accggcgaag gcctggatgt gcgcggcaac cagggctttc cgtgggatat tctgtttccg    600
gcggatccgc cgtttagccc gcagagctgc cgcccgcagg gcaccaacct gagcaccagc    660
aacccgctgg gctttttttcc ggatcatcag ctggatccgg cgtttcgcgc gaacagcgcg    720
aacccggatt gggattttaa cccgaacaaa gatacctggc cggatgcgaa caaagtgggc    780
ggccagaacc tgagcaccag caacccgctg ggcttttttc cggatcatca gctggatccg    840
gcgtttcgcg cgaacaccgc gaacccggat tgggatttta acccgaacaa agatacctgg    900
ccggatgcga acaaagtggg cggaagcgga gctactaact tcagcctgct gaagcaggct    960
ggagacgtgg aggagaaccc tggacctatg agccgcagcg aaagcaaaaa aaaccgcggc   1020
ggccgcgaag aagtgctgga acagtgggtg aacggccgca aaaaactgga agaactggaa   1080
cgcgaactgc gccgcgcgcg caaaaaaatt aaaaaactgg aagatgataa cccgtggctg   1140
ggcaacgtga aaggcattct gggcaaaaaa gataaagatg gcgaaggcgc gccgccggcg   1200
aaacgcgcgc gcaccgatca gatggaaatt gatagcggcc cgcgcaaacg cccgctgcgc   1260
ggcggcttta ccgatcgcga acgccaggat catcgccgcc gcaaagcgct gaaaaacaaa   1320
aaaaaacagc tgagcgcggg cggcaaaagc ctgagcaaag aagaagaaga agaactgaaa   1380
cgcctgaccc gcgaagatga agaacgcaaa aaagaagaac atggcccgag ccgcctgggc   1440
gtgaacccga gcgaaggcgg cccgcgcggc gcgccgggcg gcggctttgt gccgagcatg   1500
cagggcattc cggaaagccg ctttacccgc accggcgaag gcctggatgt gcgcggcagc   1560
cgcggctttc cgcaggatat tctgtttccg agcgatccgc cgtttagccc gcagagctgc   1620
cgcccgcagg gcaccaacct gagcaccagc aacccgctgg gctttttttcc ggatcatcag   1680
ctggatccgg cgtttcgcgc gaacagcgcg aacccggatt gggattttaa cccgaacaaa   1740
gatacctggc cggatgcgaa caaagtgggc ggccagaacc tgagcaccag caacccgctg   1800
ggcttttttc cggatcatca gctggatccg gcgtttcgcg cgaacaccgc gaacccggat   1860
tgggatttta acccgaacaa agatacctgg ccggatgcga acaaagtggg cggaagcgga   1920
gctactaact tcagcctgct gaagcaggct ggagacgtgg aggagaaccc tggacctatg   1980
agccagagcg aaacccgccg cggccgccgc ggcacccgcg aagaaaccct ggaaaaatgg   2040
attaccgcgc gcaaaaaagc ggaagaactg gaaaaagatc tgcgcaaaac ccgcaaaacc   2100
attaaaaaac tggaagaaga aaacccgtgg ctgggcaaca ttgtgggcat tattcgcaaa   2160
ggcaaagatg gcgaaggcgc gccgccggcg aaacgcccgc gcaccgatca gatggaagtg   2220
```

gatagcggcc cgggcaaacg cccgcataaa agcggcttta ccgataaaga acgcgaagat 2280
catcgccgcc gcaaagcgct ggaaaacaaa aaaaaacagc tgagcgcggg cggcaaaatt 2340
ctgagcaaag aagaagaaga agaactgcgc cgcctgaccg atgaagatga agaacgcaaa 2400
cgccgcgtgg cgggcccgcg cgtgggcgat gtgaacccga gccgcggcgg cccgcgcggc 2460
gcgccgggcg gcggctttgt gccgcagatg gcgggcgtgc cggaaagccc gtttagccgc 2520
accggcgaag gcctggatat tcgcggcacc cagggctttc cgtgggtgag cccgagcccg 2580
ccgcagcagc gcctgccgct gctggaatgc accccgcagg gcaccaacct gagcaccagc 2640
aacccgctgg gctttttcc ggatcatcag ctggatccgg cgtttcgcgc gaacagcgcg 2700
aacccggatt gggattttaa cccgaacaaa gatacctggc cggatgcgaa caaagtgggc 2760
ggccagaacc tgagcaccag caacccgctg ggcttttttc cggatcatca gctggatccg 2820
gcgtttcgcg cgaacaccgc gaacccggat tgggatttta acccgaacaa agatacctgg 2880
ccggatgcga acaaagtggg cggaagcgga gctactaact tcagcctgct gaagcaggct 2940
ggagacgtgg aggagaaccc tggacctatg agccagagcg aaagcaaaaa aaaccgccgc 3000
ggcggccgcg aagatattct ggaaaaatgg attaccaccc gccgcaaagc ggaagaactg 3060
gaaaaagatc tgcgcaaagc gcgcaaaacc attaaaaaac tggaagatga aaacccgtgg 3120
ctgggcaaca ttattggcat tattcgcaaa ggcaaagatg gcgaaggcgc gccgccggcg 3180
aaacgcccgc gcaccgatca gatggaaatt gatagcggca ccggcaaacg cccgcataaa 3240
agcggcttta ccgataaaga acgcgaagat catcgccgcc gcaaagcgct ggaaaacaaa 3300
aaaaaacagc tgagcagcgg cggcaaaaac ctgagccgcg aagaagaaga agaactgggc 3360
cgcctgaccg tggaagatga agaacgccgc cgccgcgtgg cgggcccgcg caccggcgat 3420
gtgaacctga gcggcggcgg cccgcgcggc gcgccgggcg gcggctttgt gccgcgcatg 3480
gaaggcgtgc cggaaagccc gtttacccgc accggcgaag gcctggatat tcgcggcaac 3540
cagggctttc cgtgggtgcg cccgagcccg ccgcagcagc gcctgccgct gctggaatgc 3600
accccgcagg gcaccaacct gagcaccagc aacccgctgg gctttttcc ggatcatcag 3660 ctggatccgg cgtttcgcgc gaacagcgcg aacccggatt gggattttaa cccgaacaaa 3720
gatacctggc cggatgcgaa caaagtgggc ggccagaacc tgagcaccag caacccgctg 3780
ggcttttttc cggatcatca gctggatccg gcgtttcgcg cgaacaccgc gaacccggat 3840
tgggatttta acccgaacaa agatacctgg ccggatgcga acaaagtggg c 3891

<210> SEQ ID NO 26
<211> LENGTH: 3923
<212> TYPE: DNA
<213> ORGANISM: Artificial Sequence
<220> FEATURE:
<223> OTHER INFORMATION: Delta 4 wt with restriction sites
      (HindIII/EcoR1)

<400> SEQUENCE: 26
aagcttgcac catggccagc cgcagcgaaa gcaaaaaaaa ccgcggcggc cgcgaagaaa 60
ttctggaaca gtgggtgggc gcgcgcaaaa aactggaaga actggaacgc gatctgcgca 120
aaattaaaaa aaaaattaaa aaactggaag aagaaaaccc gtggctgggc aacattaaag 180
gcattctggg caaaaaagat cgcgaaggcg aaggcgcgcc gccggcgaaa cgcgcgcgcg 240
cggatcagat ggaagtggat agcggcccgc gcaaacgccc gtttcgcggc gaatttaccg 300
ataaagaacg ccgcgatcat cgccgccgca aagcgctgga aaacaaacgc aaacagctga 360

-continued

```
gcagcggcgg caaaagcctg agcaaagaag aagaagaaga actgcgcaaa ctgaccgaag    420
aagatgaacg ccgcgaacgc cgcgtggcgg gcccgcgcgt gggcggcgtg aacccgctgg    480
aaggcggcac ccgcggcgcg ccgggcggcg gctttgtgcc gagcatgcag ggcgtgccgg    540
aaagcccgtt tgcgcgcacc ggcgaaggcc tggatgtgcg cggcaaccag ggctttccgt    600
gggatattct gtttccggcg gatccgccgt ttagcccgca gagctgccgc ccgcagggca    660
ccaacctgag caccagcaac ccgctgggct tttttccgga tcatcagctg gatccggcgt    720
ttcgcgcgaa cagcgcgaac ccggattggg attttaaccc gaacaaagat acctggccgg    780
atgcgaacaa agtgggcggc cagaacctga gcaccagcaa cccgctgggc tttttttccgg   840
atcatcagct ggatccggcg tttcgcgcga acaccgcgaa cccggattgg gattttaacc    900
cgaacaaaga tacctggccg gatgcgaaca aagtgggcgg aagcggagct actaacttca    960
gcctgctgaa gcaggctgga gacgtggagg agaaccctgg acctatgagc cgcagcgaaa   1020
gcaaaaaaaa ccgcggcggc cgcgaagaag tgctggaaca gtgggtgaac ggccgcaaaa   1080
aactggaaga actggaacgc gaactgcgcc gcgcgcgcaa aaaaattaaa aaactggaag   1140
atgataaccc gtggctgggc aacgtgaaag gcattctggg caaaaaagat aaagatggcg   1200
aaggcgcgcc gccggcgaaa cgcgcgcgca ccgatcagat ggaaattgat agcggcccgc   1260
gcaaacgccc gctgcgcggc ggctttaccg atcgcgaacg ccaggatcat cgccgccgca   1320
aagcgctgaa aaacaaaaaa aaacagctga gcgcgggcgg caaaagcctg agcaaagaag   1380
aagaagaaga actgaaacgc ctgacccgcg aagatgaaga acgcaaaaaa gaagaacatg   1440
gcccgagccg cctgggcgtg aacccgagcg aaggcggccc gcgcggcgcg ccgggcggcg   1500
gctttgtgcc gagcatgcag ggcattccgg aaagccgctt tacccgcacc ggcgaaggcc   1560
tggatgtgcg cggcagccgc ggctttccgc aggatattct gtttccgagc gatccgccgt   1620
ttagcccgca gagctgccgc ccgcagggca ccaacctgag caccagcaac ccgctgggct   1680
tttttccgga tcatcagctg gatccggcgt ttcgcgcgaa cagcgcgaac ccggattggg   1740
attttaaccc gaacaaagat acctggccgg atgcgaacaa agtgggcggc cagaacctga   1800
gcaccagcaa cccgctgggc tttttttccgg atcatcagct ggatccggcg tttcgcgcga  1860
acaccgcgaa cccggattgg gattttaacc cgaacaaaga tacctggccg gatgcgaaca   1920
aagtgggcgg aagcggagct actaacttca gcctgctgaa gcaggctgga gacgtggagg   1980
agaaccctgg acctatgagc cagagcgaaa cccgccgcgg ccgccgcggc acccgcgaag   2040
aaaccctgga aaaatggatt accgcgcgca aaaaagcgga agaactggaa aaagatctgc   2100
gcaaaacccg caaaaccatt aaaaaactgg aagaagaaaa cccgtggctg ggcaacattg   2160
tgggcattat tcgcaaaggc aaagatggcg aaggcgcgcc gccggcgaaa cgcccgcgca   2220
ccgatcagat ggaagtggat agcggcccgg gcaaacgccc gcataaaagc ggctttaccg   2280
ataaagaacg cgaagatcat cgccgccgca aagcgctgga aaacaaaaaa aaacagctga   2340
gcgcgggcgg caaaattctg agcaaagaag aagaagaaga actgcgccgc ctgaccgatg   2400
aagatgaaga acgcaaacgc cgcgtggcgg gcccgcgcgt gggcgatgtg aacccgagcc   2460
gcggcggccc gcgcggcgcg ccgggcggcg gctttgtgcc gcagatggcg ggcgtgccgg   2520
aaagcccgtt tagccgcacc ggcgaaggcc tggatattcg cggcacccag ggctttccgt   2580
gggtgagccc gagcccgccg cagcagcgcc tgccgctgct ggaatgcacc ccgcagggca   2640
ccaacctgag caccagcaac ccgctgggct tttttccgga tcatcagctg gatccggcgt   2700
ttcgcgcgaa cagcgcgaac ccggattggg attttaaccc gaacaaagat acctggccgg   2760
```

atgcgaacaa agtgggcggc cagaacctga gcaccagcaa cccgctgggc ttttttccgg 2820
atcatcagct ggatccggcg tttcgcgcga acaccgcgaa cccggattgg gattttaacc 2880
cgaacaaaga tacctggccg gatgcgaaca aagtgggcgg aagcggagct actaacttca 2940
gcctgctgaa gcaggctgga gacgtggagg agaaccctgg acctatgagc cagagcgaaa 3000
gcaaaaaaaa ccgccgcggc ggccgcgaag atattctgga aaaatggatt accacccgcc 3060
gcaaagcgga agaactggaa aaagatctgc gcaaagcgcg caaaaccatt aaaaaactgg 3120
aagatgaaaa cccgtggctg ggcaacatta ttggcattat tcgcaaaggc aaagatggcg 3180
aaggcgcgcc gccggcgaaa cgcccgcgca ccgatcagat ggaaattgat agcggcaccg 3240
gcaaacgccc gcataaaagc ggctttaccg ataaagaacg cgaagatcat cgccgccgca 3300
aagcgctgga aaacaaaaaa aaacagctga gcagcggcgg caaaaacctg agccgcgaag 3360
aagaagaaga actgggccgc ctgaccgtgg aagatgaaga acgccgccgc cgcgtggcgg 3420
gcccgcgcac cggcgatgtg aacctgagcg gcggcggccc gcgcggcgcg ccgggcggcg 3480
gctttgtgcc gcgcatggaa ggcgtgccgg aaagcccgtt tacccgcacc ggcgaaggcc 3540
tggatattcg cggcaaccag ggctttccgt gggtgcgccc gagcccgccg cagcagcgcc 3600
tgccgctgct ggaatgcacc ccgcagggca ccaacctgag caccagcaac ccgctgggct 3660
tttttccgga tcatcagctg gatccggcgt ttcgcgcgaa cagcgcgaac ccggattggg 3720
attttaaccc gaacaaagat acctggccgg atgcgaacaa agtgggcggc cagaacctga 3780
gcaccagcaa cccgctgggc ttttttccgg atcatcagct ggatccggcg tttcgcgcga 3840
acaccgcgaa cccggattgg gattttaacc cgaacaaaga tacctggccg gatgcgaaca 3900
aagtgggctg atgagaattc cgt 3923

<210> SEQ ID NO 27
<211> LENGTH: 3894
<212> TYPE: DNA
<213> ORGANISM: Artificial Sequence
<220> FEATURE:
<223> OTHER INFORMATION: Delta 4 codon optimized

<400> SEQUENCE: 27
gccagtcgga gcgaatcaaa gaaaaatagg ggagggcggg aagaaatcct ggagcagtgg 60
gtcggagcac gaaagaaact ggaagaactg gagagggacc tgcgcaagat caagaagaag 120
atcaagaagc tggaggagga gaacccctgg ctgggcaata tcaagggcat cctgggcaag 180
aaggatcggg agggagaggg agcaccacct gcaaagaggg ccagagccga ccagatggag 240
gtggatagcg gccctaggaa gcgcccattc agaggcgagt ttacagacaa ggagcggaga 300
gatcacaggc gccggaaggc cctggagaac aagcggaagc agctgagctc cggcggcaag 360
tccctgtcta aggaggagga ggaggagctg agaaagctga ccgaggagga cgagagaagg 420
gagaggaggg tggcaggacc tagggtggga ggcgtgaacc cactggaggg aggaacaagg 480
ggagcacctg gaggaggatt cgtgccatcc atgcagggag tgcctgagtc tccatttgcc 540
aggaccggag agggcctgga tgtgcgcgga aatcagggct tcccctggga catcctgttt 600
cctgccgatc caccttctc cccacagtct tgcaggccac agggaaccaa cctgagcaca 660
tccaatcctc tgggcttctt tccagaccac cagctggatc ctgccttcag agccaactcc 720
gccaatccag actgggactt caaccccaat aaggacacat ggcctgatgc caacaaggtc 780
ggcggccaga acctgtctac cagcaatccc ctgggcttct ttcctgacca ccagctggat 840

-continued

```
ccagccttcc gggccaacac tgctaaccct gattgggact tcaaccctaa taaggatacc    900
tggccagacg ccaacaaggt cggcggaagc ggagctacta acttcagcct gctgaagcag    960
gctggagacg tggaggagaa ccctggacct atgtccaggt ctgagagcaa gaagaatagg   1020
ggaggaagag aggaggtgct ggagcagtgg gtgaacggcc gcaagaagct ggaggagctg   1080
gagagggagc tgagaagggc ccgcaagaag atcaagaagc tggaagacga taatccttgg   1140
ctgggcaatg tgaaaggcat cctgggcaag aaggacaagg atggagaggg agcacctcca   1200
gcaaagaggg caagaacaga ccagatggag atcgattctg gaccaaggaa gcgccctctg   1260
aggggaggct tcaccgaccg ggagagacag gatcaccgcc ggagaaaggc cctgaagaac   1320
aagaagaagc agctgtccgc cggcggcaag tccctgagca aagaagagga agaggagctg   1380
aagaggctga cccgcgagga cgaggagcgg aagaaggagg agcacggacc aagcagactg   1440
ggagtgaatc cttccgaggg aggaccaaga ggagcacccg gaggaggctt cgtgccatct   1500
atgcagggca tccccgagag ccggtttacc agaacaggag agggcctgga cgtgaggggc   1560
tcccgcggct ttcctcagga catcctgttc ccatctgatc cccctttag  cccacagtcc   1620
tgtaggcccc agggcactaa cctgagcaca tccaacccac tgggcttctt tcctgatcat   1680
cagctggacc cagccttccg cgccaacagc gccaaccctg actgggactt caacccaaat   1740
aaggacacat ggccagatgc taacaaggtc ggaggacaaa acctgtctac cagcaaccct   1800
ctgggcttct ttcccgatca tcagctggac cccgccttca gggccaacac agccaatccc   1860
gactgggact tcaacccgaa taaggacacc tggccagatg caaacaaggt cggaggaagc   1920
ggagctacta acttcagcct gctgaagcag gctggagacg tggaggagaa ccctggacct   1980
atgagccagt ctgagacaag gaggggccgg agaggaacca gggaggagac actggagaag   2040
tggatcaccg ccagaaagaa ggccgaggag ctggagaagg acctgcggaa gaccagaaag   2100
acaatcaaga agctggaaga agagaaccca tggctgggca atatcgtggg catcatccgc   2160
aagggcaagg acggcgaggg agcaccacca gcaaagaggc cccgcacaga tcagatggaa   2220
gtggatagcg gccctggcaa gaggccacac aagtccggct tcaccgacaa ggagagggag   2280
gaccataggc gccggaaggc cctggaaaac aagaagaagc aattatccgc cggcggcaag   2340
atcctgtcca aagaggaaga agaggagctg agaaggctga ccgacgagga tgaggagagg   2400
aaaagaaggg tggcaggacc aagagtgggc gacgtgaatc ccagcagagg cggaccaaga   2460
ggagcacctg gaggcggctt cgtgccccag atggccggcg tgcccgagtc tccttttagc   2520
agaactggag agggcctgga tatcagggga acacagggct ttccatgggt gagcccatcc   2580
cctccacagc agaggctgcc actgctggag tgcacccctc agggaaccaa cctgtctacc   2640
agcaacccgc tgggcttctt tcccgaccat cagctggacc ctgccttccg cgccaactcc   2700
gccaaccctg attgggactt caacccgaat aaggatacct ggcccgacgc taacaaggtc   2760
ggaggccaga acctgtccac ctctaacccc ttaggcttct ttcccgatca ccagctggat   2820
cccgccttca gagccaacac tgctaacccc gattgggact tcaacccgaa taaggacacg   2880
tggccagacg ctaacaaggt cgggggaagc ggagctacta acttcagcct gctgaagcag   2940
gctggagacg tggaggagaa ccctggacct atgtcgcagt ccgagtctaa gaagaataga   3000
aggggcggcc gggaggatat cctggaaaaa tggatcacca cacgcagaaa agctgaagaa   3060
ctggaaaagg acctgaggaa ggcccgcaag accatcaaga agctggagga tgaaaatcca   3120
tggctgggaa acatcatcgg catcatcaga aagggcaagg acggggaagg cgccccacct   3180
gcaaagcggc ctagaaccga tcagatggaa atcgattctg gcacaggcaa gcggccacac   3240
```

aagagtggct tcaccgataa ggagagagag gatcacagaa ggcgcaaggc cctggagaac 3300
aagaagaagc aattaagcag cggcggcaag aatctgtcca gagaagaaga ggaggagctg 3360
ggcagactga cagtggagga cgaggagcgg agaaggcgcg tggcaggacc aaggaccggc 3420
gatgtgaacc tgagcggagg aggacctagg ggagcaccag gaggcggctt cgtgcctagg 3480
atggagggag tgccagagtc cccctttacc aggactggcg agggcctgga catcagggga 3540
aatcagggat tcccatgggt gcggcctagc ccaccacagc agagactgcc actgctggag 3600
tgtacacccc agggcacaaa cctgagcaca tccaatccgc tgggcttctt tccagatcat 3660
caattagatc cagccttcag ggccaactcc gccaatccgg attgggactt caacccgaat 3720
aaggacactt ggcccgacgc aaacaaggtc ggagggcaaa acctgtctac cagcaatcca 3780
cttggcttct ttcctgacca tcagctggat cccgcctttc gcgccaatac cgccaatcct 3840
gactgggact tcaatcctaa caaagacacc tggcccgacg caaacaaagt ggga 3894

<210> SEQ ID NO 28
<211> LENGTH: 3923
<212> TYPE: DNA
<213> ORGANISM: Artificial Sequence
<220> FEATURE:
<223> OTHER INFORMATION: Delta 4 optimized with restriction sites (HindIII /EcoRI)

<400> SEQUENCE: 28
aagcttgcac catggccagt cggagcgaat caaagaaaaa taggggaggg cgggaagaaa 60
tcctggagca gtgggtcgga gcacgaaaga aactggaaga actggagagg gacctgcgca 120
agatcaagaa gaagatcaag aagctggagg aggagaaccc ctggctgggc aatatcaagg 180
gcatcctggg caagaaggat cgggagggag agggagcacc acctgcaaag agggccagag 240
ccgaccagat ggaggtggat agcggcccta ggaagcgccc attcagaggc gagtttacag 300
acaaggagcg gagagatcac aggcgccgga aggccctgga gaacaagcgg aagcagctga 360
gctccggcgg caagtccctg tctaaggagg aggaggagga gctgagaaag ctgaccgagg 420
aggacgagag aagggagagg agggtggcag gacctagggt gggaggcgtg aacccactgg 480
agggaggaac aaggggagca cctggaggag gattcgtgcc atccatgcag ggagtgcctg 540
agtctccatt tgccaggacc ggagagggcc tggatgtgcg cggaaatcag ggcttcccct 600
gggacatcct gtttcctgcc gatccaccct tctccccaca gtcttgcagg ccacagggaa 660
ccaacctgag cacatccaat cctctgggct tctttccaga ccaccagctg gatcctgcct 720
tcagagccaa ctccgccaat ccagactggg acttcaaccc caataaggac acatggcctg 780
atgccaacaa ggtcggcggc cagaacctgt ctaccagcaa tcccctgggc ttctttcctg 840
accaccagct ggatccagcc ttccgggcca acactgctaa ccctgattgg gacttcaacc 900
ctaataagga tacctggcca gacgccaaca aggtcggcgg aagcggagct actaacttca 960
gcctgctgaa gcaggctgga gacgtggagg agaaccctgg acctatgtcc aggtctgaga 1020
gcaagaagaa taggggagga agagaggagg tgctggagca gtgggtgaac ggccgcaaga 1080
agctggagga gctggagagg gagctgagaa gggcccgcaa gaagatcaag aagctggaag 1140
acgataatcc ttggctgggc aatgtgaaag gcatcctggg caagaaggac aaggatggag 1200
agggagcacc tccagcaaag agggcaagaa cagaccagat ggagatcgat tctggaccaa 1260
ggaagcgccc tctgagggga ggcttcaccg accgggagag acaggatcac cgccggagaa 1320
aggccctgaa gaacaagaag aagcagctgt ccgccggcgg caagtccctg agcaaagaag 1380

-continued

```
aggaagagga gctgaagagg ctgacccgcg aggacgagga gcggaagaag gaggagcacg   1440
gaccaagcag actgggagtg aatccttccg agggaggacc aagaggagca cccggaggag   1500
gcttcgtgcc atctatgcag ggcatccccg agagccggtt taccagaaca ggagagggcc   1560
tggacgtgag ggctcccgc ggctttcctc aggacatcct gttcccatct gatcccccctt   1620
ttagcccaca gtcctgtagg ccccagggca ctaacctgag cacatccaac ccactgggct   1680
tctttcctga tcatcagctg gacccagcct tccgcgccaa cagcgccaac cctgactggg   1740
acttcaaccc aaataaggac acatggccag atgctaacaa ggtcggagga caaaacctgt   1800
ctaccagcaa ccctctgggc ttctttcccg atcatcagct ggacccgcc ttcagggcca   1860
acacagccaa tcccgactgg gacttcaacc cgaataagga cacctggcca gatgcaaaca   1920
aggtcggagg aagcggagct actaacttca gcctgctgaa gcaggctgga gacgtggagg   1980
agaaccctgg acctatgagc cagtctgaga caaggagggg ccggagagga accagggagg   2040
agacactgga gaagtggatc accgccagaa agaaggccga ggagctggag aaggacctgc   2100
ggaagaccag aaagacaatc aagaagctgg aagaagagaa cccatggctg ggcaatatcg   2160
tgggcatcat ccgcaagggc aaggacggcg agggagcacc accagcaaag aggccccgca   2220
cagatcagat ggaagtggat agcggccctg gcaagaggcc acacaagtcc ggcttcaccg   2280
acaaggagag ggaggaccat aggcgccgga aggccctgga aaacaagaag aagcaattat   2340
ccgccggcgg caagatcctg tccaaagagg aagaagagga gctgagaagg ctgaccgacg   2400
aggatgagga gaggaaaaga agggtggcag gaccaagagt gggcgacgtg aatcccagca   2460
gaggcggacc aagaggagca cctggaggcg gcttcgtgcc ccagatggcc ggcgtgcccg   2520
agtctccttt tagcagaact ggagagggcc tggatatcag gggaacacag ggctttccat   2580
gggtgagccc atcccctcca cagcagaggc tgccactgct ggagtgcacc cctcagggaa   2640
ccaacctgtc taccagcaac ccgctgggct tctttcccga ccatcagctg gaccctgcct   2700
tccgcgccaa ctccgccaac cctgattggg acttcaaccc gaataaggat acctggcccg   2760
acgctaacaa ggtcggaggc cagaacctgt ccacctctaa cccccttaggc ttctttcccg   2820
atcaccagct ggatcccgcc ttcagagcca acactgctaa ccccgattgg gacttcaacc   2880
cgaataagga cacgtggcca gacgctaaca aggtcggggg aagcggagct actaacttca   2940
gcctgctgaa gcaggctgga gacgtggagg agaaccctgg acctatgtcg cagtccgagt   3000
ctaagaagaa tagaaggggc ggccgggagg atatcctgga aaaatggatc accacacgca   3060
gaaaagctga agaactggaa aaggacctga ggaaggcccg caagaccatc aagaagctgg   3120
aggatgaaaa tccatggctg ggaaacatca tcggcatcat cagaaagggc aaggacgggg   3180
aaggcgcccc acctgcaaag cggcctagaa ccgatcagat ggaaatcgat tctggcacag   3240
gcaagcggcc acacaagagt ggcttcaccg ataaggagag agaggatcac agaaggcgca   3300
aggccctgga gaacaagaag aagcaattaa gcagcggcgg caagaatctg tccagagaag   3360
aagaggagga gctgggcaga ctgacagtgg aggacgagga gcggagaagg cgcgtggcag   3420
gaccaaggac cggcgatgtg aacctgagcg gaggaggacc taggggagca ccaggaggcg   3480
gcttcgtgcc taggatggag ggagtgccag agtccccctt taccaggact ggcgagggcc   3540
tggacatcag gggaaatcag ggattcccat gggtgcggcc tagcccacca cagcagagac   3600
tgccactgct ggagtgtaca ccccagggca caaacctgag cacatccaat ccgctgggct   3660
tctttccaga tcatcaatta gatccagcct tcagggccaa ctccgccaat ccggattggg   3720
```

```
acttcaaccc gaataaggac acttggcccg acgcaaacaa ggtcggaggg caaaacctgt   3780

ctaccagcaa tccacttggc ttctttcctg accatcagct ggatcccgcc tttcgcgcca   3840

ataccgccaa tcctgactgg gacttcaatc ctaacaaaga cacctggccc gacgcaaaca   3900

aagtgggatg atgagaattc cgt                                           3923


<210> SEQ ID NO 29
<211> LENGTH: 1299
<212> TYPE: PRT
<213> ORGANISM: Artificial Sequence
<220> FEATURE:
<223> OTHER INFORMATION: Delta 4 protein

<400> SEQUENCE: 29

Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Gly Thr Asn Leu Ser Thr Ser Asn Pro
    210                 215                 220

Leu Gly Phe Phe Pro Asp His Gln Leu Asp Pro Ala Phe Arg Ala Asn
225                 230                 235                 240

Ser Ala Asn Pro Asp Trp Asp Phe Asn Pro Asn Lys Asp Thr Trp Pro
                245                 250                 255

Asp Ala Asn Lys Val Gly Gly Gln Asn Leu Ser Thr Ser Asn Pro Leu
            260                 265                 270

Gly Phe Phe Pro Asp His Gln Leu Asp Pro Ala Phe Arg Ala Asn Thr
        275                 280                 285

Ala Asn Pro Asp Trp Asp Phe Asn Pro Asn Lys Asp Thr Trp Pro Asp
    290                 295                 300

Ala Asn Lys Val Gly Gly Ser Gly Ala Thr Asn Phe Ser Leu Leu Lys
305                 310                 315                 320

Gln Ala Gly Asp Val Glu Glu Asn Pro Gly Pro Met Ser Arg Ser Glu
```

```
                325                 330                 335

Ser Lys Lys Asn Arg Gly Gly Arg Glu Glu Val Leu Glu Gln Trp Val
            340                 345                 350

Asn Gly Arg Lys Lys Leu Glu Glu Leu Glu Arg Glu Leu Arg Arg Ala
        355                 360                 365

Arg Lys Lys Ile Lys Lys Leu Glu Asp Asp Asn Pro Trp Leu Gly Asn
    370                 375                 380

Val Lys Gly Ile Leu Gly Lys Lys Asp Lys Asp Gly Glu Gly Ala Pro
385                 390                 395                 400

Pro Ala Lys Arg Ala Arg Thr Asp Gln Met Glu Ile Asp Ser Gly Pro
                405                 410                 415

Arg Lys Arg Pro Leu Arg Gly Gly Phe Thr Asp Arg Glu Arg Gln Asp
            420                 425                 430

His Arg Arg Arg Lys Ala Leu Lys Asn Lys Lys Lys Gln Leu Ser Ala
        435                 440                 445

Gly Gly Lys Ser Leu Ser Lys Glu Glu Glu Glu Glu Leu Lys Arg Leu
    450                 455                 460

Thr Arg Glu Asp Glu Glu Arg Lys Lys Glu Glu His Gly Pro Ser Arg
465                 470                 475                 480

Leu Gly Val Asn Pro Ser Glu Gly Gly Pro Arg Gly Ala Pro Gly Gly
                485                 490                 495

Gly Phe Val Pro Ser Met Gln Gly Ile Pro Glu Ser Arg Phe Thr Arg
            500                 505                 510

Thr Gly Glu Gly Leu Asp Val Arg Gly Ser Arg Gly Phe Pro Gln Asp
        515                 520                 525

Ile Leu Phe Pro Ser Asp Pro Pro Phe Ser Pro Gln Ser Cys Arg Pro
    530                 535                 540

Gln Gly Thr Asn Leu Ser Thr Ser Asn Pro Leu Gly Phe Phe Pro Asp
545                 550                 555                 560

His Gln Leu Asp Pro Ala Phe Arg Ala Asn Ser Ala Asn Pro Asp Trp
                565                 570                 575

Asp Phe Asn Pro Asn Lys Asp Thr Trp Pro Asp Ala Asn Lys Val Gly
            580                 585                 590

Gly Gln Asn Leu Ser Thr Ser Asn Pro Leu Gly Phe Phe Pro Asp His
        595                 600                 605

Gln Leu Asp Pro Ala Phe Arg Ala Asn Thr Ala Asn Pro Asp Trp Asp
    610                 615                 620

Phe Asn Pro Asn Lys Asp Thr Trp Pro Asp Ala Asn Lys Val Gly Gly
625                 630                 635                 640

Ser Gly Ala Thr Asn Phe Ser Leu Leu Lys Gln Ala Gly Asp Val Glu
                645                 650                 655

Glu Asn Pro Gly Pro Met Ser Gln Ser Glu Thr Arg Arg Gly Arg Arg
            660                 665                 670

Gly Thr Arg Glu Glu Thr Leu Glu Lys Trp Ile Thr Ala Arg Lys Lys
        675                 680                 685

Ala Glu Glu Leu Glu Lys Asp Leu Arg Lys Thr Arg Lys Thr Ile Lys
    690                 695                 700

Lys Leu Glu Glu Glu Asn Pro Trp Leu Gly Asn Ile Val Gly Ile Ile
705                 710                 715                 720

Arg Lys Gly Lys Asp Gly Glu Gly Ala Pro Pro Ala Lys Arg Pro Arg
                725                 730                 735

Thr Asp Gln Met Glu Val Asp Ser Gly Pro Gly Lys Arg Pro His Lys
            740                 745                 750
```

Ser Gly Phe Thr Asp Lys Glu Arg Glu Asp His Arg Arg Arg Lys Ala
755 760 765

Leu Glu Asn Lys Lys Lys Gln Leu Ser Ala Gly Gly Lys Ile Leu Ser
770 775 780

Lys Glu Glu Glu Glu Glu Leu Arg Arg Leu Thr Asp Glu Asp Glu Glu
785 790 795 800

Arg Lys Arg Arg Val Ala Gly Pro Arg Val Gly Asp Val Asn Pro Ser
805 810 815

Arg Gly Gly Pro Arg Gly Ala Pro Gly Gly Gly Phe Val Pro Gln Met
820 825 830

Ala Gly Val Pro Glu Ser Pro Phe Ser Arg Thr Gly Glu Gly Leu Asp
835 840 845

Ile Arg Gly Thr Gln Gly Phe Pro Trp Val Ser Pro Ser Pro Pro Gln
850 855 860

Gln Arg Leu Pro Leu Leu Glu Cys Thr Pro Gln Gly Thr Asn Leu Ser
865 870 875 880

Thr Ser Asn Pro Leu Gly Phe Phe Pro Asp His Gln Leu Asp Pro Ala
885 890 895

Phe Arg Ala Asn Ser Ala Asn Pro Asp Trp Asp Phe Asn Pro Asn Lys
900 905 910

Asp Thr Trp Pro Asp Ala Asn Lys Val Gly Gly Gln Asn Leu Ser Thr
915 920 925

Ser Asn Pro Leu Gly Phe Phe Pro Asp His Gln Leu Asp Pro Ala Phe
930 935 940

Arg Ala Asn Thr Ala Asn Pro Asp Trp Asp Phe Asn Pro Asn Lys Asp
945 950 955 960

Thr Trp Pro Asp Ala Asn Lys Val Gly Gly Ser Gly Ala Thr Asn Phe
965 970 975

Ser Leu Leu Lys Gln Ala Gly Asp Val Glu Glu Asn Pro Gly Pro Met
980 985 990

Ser Gln Ser Glu Ser Lys Lys Asn Arg Arg Gly Gly Arg Glu Asp Ile
995 1000 1005

Leu Glu Lys Trp Ile Thr Thr Arg Arg Lys Ala Glu Glu Leu Glu Lys
1010 1015 1020

Asp Leu Arg Lys Ala Arg Lys Thr Ile Lys Lys Leu Glu Asp Glu Asn
1025 1030 1035 1040

Pro Trp Leu Gly Asn Ile Ile Gly Ile Ile Arg Lys Gly Lys Asp Gly
1045 1050 1055

Glu Gly Ala Pro Pro Ala Lys Arg Pro Arg Thr Asp Gln Met Glu Ile
1060 1065 1070

Asp Ser Gly Thr Gly Lys Arg Pro His Lys Ser Gly Phe Thr Asp Lys
1075 1080 1085

Glu Arg Glu Asp His Arg Arg Arg Lys Ala Leu Glu Asn Lys Lys Lys
1090 1095 1100

Gln Leu Ser Ser Gly Gly Lys Asn Leu Ser Arg Glu Glu Glu Glu Glu
1105 1110 1115 1120

Leu Gly Arg Leu Thr Val Glu Asp Glu Glu Arg Arg Arg Arg Val Ala
1125 1130 1135

Gly Pro Arg Thr Gly Asp Val Asn Leu Ser Gly Gly Gly Pro Arg Gly
1140 1145 1150

Ala Pro Gly Gly Gly Phe Val Pro Arg Met Glu Gly Val Pro Glu Ser
1155 1160 1165

Pro Phe Thr Arg Thr Gly Glu Gly Leu Asp Ile Arg Gly Asn Gln Gly
    1170                1175                1180

Phe Pro Trp Val Arg Pro Ser Pro Pro Gln Gln Arg Leu Pro Leu Leu
1185                1190                1195                1200

Glu Cys Thr Pro Gln Gly Thr Asn Leu Ser Thr Ser Asn Pro Leu Gly
                1205                1210                1215

Phe Phe Pro Asp His Gln Leu Asp Pro Ala Phe Arg Ala Asn Ser Ala
            1220                1225                1230

Asn Pro Asp Trp Asp Phe Asn Pro Asn Lys Asp Thr Trp Pro Asp Ala
        1235                1240                1245

Asn Lys Val Gly Gly Gln Asn Leu Ser Thr Ser Asn Pro Leu Gly Phe
    1250                1255                1260

Phe Pro Asp His Gln Leu Asp Pro Ala Phe Arg Ala Asn Thr Ala Asn
1265                1270                1275                1280

Pro Asp Trp Asp Phe Asn Pro Asn Lys Asp Thr Trp Pro Asp Ala Asn
                1285                1290                1295

Lys Val Gly

<210> SEQ ID NO 30
<211> LENGTH: 2625
<212> TYPE: DNA
<213> ORGANISM: Artificial Sequence
<220> FEATURE:
<223> OTHER INFORMATION: Delta 5 wt

<400> SEQUENCE: 30
agccgcagcg aaagcaaaaa aaaccgcggc ggccgcgaag aaattctgga acagtgggtg 60
ggcgcgcgca aaaaactgga agaactggaa cgcgatctgc gcaaaattaa aaaaaaaatt 120
aaaaaactgg aagaagaaaa cccgtggctg ggcaacatta aaggcattct gggcaaaaaa 180
gatcgcgaag gcgaaggcgc gccgccggcg aaacgcgcgc gcgcggatca gatggaagtg 240
gatagcggcc cgcgcaaacg cccgtttcgc ggcgaattta ccgataaaga acgccgcgat 300
catcgccgcc gcaaagcgct ggaaaacaaa cgcaaacagc tgagcagcgg cggcaaaagc 360
ctgagcaaag aagaagaaga agaactgcgc aaactgaccg aagaagatga acgccgcgaa 420
cgccgcgtgg cgggcccgcg cgtgggcggc gtgaacccgc tggaaggcgg cacccgcggc 480
gcgccgggcg gcggctttgt gccgagcatg cagggcgtgc cggaaagccc gtttgcgcgc 540
accggcgaag gcctggatgt gcgcggcaac cagggctttc cgtgggatat tctgtttccg 600
gcggatccgc cgtttagccc gcagagctgc cgcccgcaga gccgcagcga aagcaaaaaa 660
aaccgcggcg gccgcgaaga agtgctggaa cagtgggtga acggccgcaa aaaactggaa 720
gaactggaac gcgaactgcg ccgcgcgcgc aaaaaaatta aaaaactgga agatgataac 780
ccgtggctgg gcaacgtgaa aggcattctg ggcaaaaaag ataaagatgg cgaaggcgcg 840
ccgccggcga aacgcgcgcg caccgatcag atggaaattg atagcggccc gcgcaaacgc 900
ccgctgcgcg gcggctttac cgatcgcgaa cgccaggatc atcgccgccg caaagcgctg 960
aaaaacaaaa aaaaacagct gagcgcgggc ggcaaaagcc tgagcaaaga agaagaagaa 1020
gaactgaaac gcctgacccg cgaagatgaa gaacgcaaaa aagaagaaca tggcccgagc 1080
cgcctgggcg tgaacccgag cgaaggcggc ccgcgcggcg cgccgggcgg cggctttgtg 1140
ccgagcatgc agggcattcc ggaaagccgc tttacccgca ccggcgaagg cctggatgtg 1200
cgcggcagcc gcggctttcc gcaggatatt ctgtttccga gcgatccgcc gtttagcccg 1260
cagagctgcc gcccgcaggg aagcggagct actaacttca gcctgctgaa gcaggctgga 1320
gacgtggagg agaaccctgg acctatgagc cagagcgaaa cccgccgcgg ccgccgcggc 1380
acccgcgaag aaaccctgga aaaatggatt accgcgcgca aaaaagcgga agaactggaa 1440
aaagatctgc gcaaaacccg caaaaccatt aaaaaactgg aagaagaaaa cccgtggctg 1500
ggcaacattg tgggcattat tcgcaaaggc aaagatggcg aaggcgcgcc gccggcgaaa 1560
cgcccgcgca ccgatcagat ggaagtggat agcggcccgg gcaaacgccc gcataaaagc 1620
ggctttaccg ataaagaacg cgaagatcat cgccgccgca aagcgctgga aaacaaaaaa 1680
aaacagctga gcgcgggcgg caaaattctg agcaaagaag aagaagaaga actgcgccgc 1740
ctgaccgatg aagatgaaga acgcaaacgc cgcgtggcgg gcccgcgcgt gggcgatgtg 1800
aacccgagcc gcggcggccc gcgcggcgcg ccgggcggcg gctttgtgcc gcagatggcg 1860
ggcgtgccgg aaagcccgtt tagccgcacc ggcgaaggcc tggatattcg cggcacccag 1920
ggctttccgt gggtgagccc gagcccgccg cagcagcgcc tgccgctgct ggaatgcacc 1980
ccgcagagcc agagcgaaag caaaaaaaac cgccgcggcg gccgcgaaga tattctggaa 2040
aaatggatta ccacccgccg caaagcggaa gaactggaaa aagatctgcg caaagcgcgc 2100
aaaaccatta aaaaactgga agatgaaaac ccgtggctgg gcaacattat tggcattatt 2160
cgcaaaggca aagatggcga aggcgcgccg ccggcgaaac gcccgcgcac cgatcagatg 2220
gaaattgata gcggcaccgg caaacgcccg cataaaagcg gctttaccga taaagaacgc 2280
gaagatcatc gccgccgcaa agcgctggaa aacaaaaaaa aacagctgag cagcggcggc 2340
aaaaacctga gccgcgaaga agaagaagaa ctgggccgcc tgaccgtgga agatgaagaa 2400
cgccgccgcc gcgtggcggg cccgcgcacc ggcgatgtga acctgagcgg cggcggcccg 2460
cgcggcgcgc cgggcggcgg ctttgtgccg cgcatggaag gcgtgccgga aagcccgttt 2520
acccgcaccg gcgaaggcct ggatattcgc ggcaaccagg gctttccgtg ggtgcgcccg 2580
agcccgccgc agcagcgcct gccgctgctg gaatgcaccc cgcag 2625

<210> SEQ ID NO 31
<211> LENGTH: 2657
<212> TYPE: DNA
<213> ORGANISM: Artificial Sequence
<220> FEATURE:
<223> OTHER INFORMATION: Delta 5 wt with restriction sites (HindIII /EcoRI)

<400> SEQUENCE: 31
aagcttgcac catggccagc cgcagcgaaa gcaaaaaaaa ccgcggcggc cgcgaagaaa 60
ttctggaaca gtgggtgggc gcgcgcaaaa aactggaaga actggaacgc gatctgcgca 120
aaattaaaaa aaaaattaaa aaactggaag aagaaaaccc gtggctgggc aacattaaag 180
gcattctggg caaaaaagat cgcgaaggcg aaggcgcgcc gccggcgaaa cgcgcgcgcg 240
cggatcagat ggaagtggat agcggcccgc gcaaacgccc gtttcgcggc gaatttaccg 300
ataaagaacg ccgcgatcat cgccgccgca aagcgctgga aaacaaacgc aaacagctga 360
gcagcggcgg caaaagcctg agcaaagaag aagaagaaga actgcgcaaa ctgaccgaag 420
aagatgaacg ccgcgaacgc cgcgtggcgg gcccgcgcgt gggcggcgtg aacccgctgg 480
aaggcggcac ccgcggcgcg ccgggcggcg gctttgtgcc gagcatgcag ggcgtgccgg 540
aaagcccgtt tgcgcgcacc ggcgaaggcc tggatgtgcg cggcaaccag ggctttccgt 600
gggatattct gtttccggcg gatccgccgt ttagcccgca gagctgccgc ccgcagagcc 660
gcagcgaaag caaaaaaaac cgcggcggcc gcgaagaagt gctggaacag tgggtgaacg 720

```
gccgcaaaaa actggaagaa ctggaacgcg aactgcgccg cgcgcgcaaa aaaattaaaa    780
aactggaaga tgataacccg tggctgggca acgtgaaagg cattctgggc aaaaaagata    840
aagatggcga aggcgcgccg ccggcgaaac gcgcgcgcac cgatcagatg gaaattgata    900
gcggcccgcg caaacgcccg ctgcgcggcg gctttaccga tcgcgaacgc caggatcatc    960
gccgccgcaa agcgctgaaa aacaaaaaaa aacagctgag cgcgggcggc aaaagcctga   1020
gcaaagaaga agaagaagaa ctgaaacgcc tgacccgcga agatgaagaa cgcaaaaaag   1080
aagaacatgg cccgagccgc ctgggcgtga acccgagcga aggcggcccg cgcggcgcgc   1140
cgggcggcgg ctttgtgccg agcatgcagg gcattccgga aagccgcttt acccgcaccg   1200
gcgaaggcct ggatgtgcgc ggcagccgcg gctttccgca ggatattctg tttccgagcg   1260
atccgccgtt tagcccgcag agctgccgcc cgcagggaag cggagctact aacttcagcc   1320
tgctgaagca ggctggagac gtggaggaga accctggacc tatgagccag agcgaaaccc   1380
gccgcggccg ccgcggcacc cgcgaagaaa ccctggaaaa atggattacc gcgcgcaaaa   1440
aagcggaaga actggaaaaa gatctgcgca aaacccgcaa aaccattaaa aaactggaag   1500
aagaaaaccc gtggctgggc aacattgtgg gcattattcg caaaggcaaa gatggcgaag   1560
gcgcgccgcc ggcgaaacgc ccgcgcaccg atcagatgga agtggatagc ggcccgggca   1620
aacgcccgca taaaagcggc tttaccgata aagaacgcga agatcatcgc cgccgcaaag   1680
cgctggaaaa caaaaaaaaa cagctgagcg cgggcggcaa aattctgagc aaagaagaag   1740
aagaagaact gcgccgcctg accgatgaag atgaagaacg caaacgccgc gtggcgggcc   1800
cgcgcgtggg cgatgtgaac ccgagccgcg gcggcccgcg cggcgcgccg ggcggcggct   1860
ttgtgccgca gatggcgggc gtgccggaaa gcccgtttag ccgcaccggc gaaggcctgg   1920
atattcgcgg cacccagggc tttccgtggg tgagcccgag cccgccgcag cagcgcctgc   1980
cgctgctgga atgcaccccg cagagccaga gcgaaagcaa aaaaaaccgc cgcggcggcc   2040
gcgaagatat tctggaaaaa tggattacca cccgccgcaa agcggaagaa ctggaaaaag   2100
atctgcgcaa agcgcgcaaa accattaaaa aactggaaga tgaaaacccg tggctgggca   2160
acattattgg cattattcgc aaaggcaaag atggcgaagg cgcgccgccg gcgaaacgcc   2220
cgcgcaccga tcagatggaa attgatagcg gcaccggcaa acgcccgcat aaaagcggct   2280
ttaccgataa agaacgcgaa gatcatcgcc gccgcaaagc gctggaaaac aaaaaaaaac   2340
agctgagcag cggcggcaaa aacctgagcc gcgaagaaga agaagaactg ggccgcctga   2400
ccgtggaaga tgaagaacgc cgccgccgcg tggcgggccc gcgcaccggc gatgtgaacc   2460
tgagcggcgg cggcccgcgc ggcgcgccgg gcggcggctt tgtgccgcgc atggaaggcg   2520
tgccggaaag cccgtttacc cgcaccggcg aaggcctgga tattcgcggc aaccagggct   2580
ttccgtgggt gcgcccgagc ccgccgcagc agcgcctgcc gctgctggaa tgcaccccgc   2640
agtgatgaga attccgt                                                  2657
```

<210> SEQ ID NO 32
<211> LENGTH: 2628
<212> TYPE: DNA
<213> ORGANISM: Artificial Sequence
<220> FEATURE:
<223> OTHER INFORMATION: Delta 5 codon optimized

<400> SEQUENCE: 32

```
gcctcacggt cagagtcaaa gaaaaatagg ggggggcggg aagaaatcct ggaacagtgg     60
```

-continued

```
gtcggagcac ggaaaaaact ggaagagctg gagagggacc tgcgcaagat caagaagaag    120
atcaagaagc tggaggagga gaacccctgg ctgggcaata tcaagggcat cctgggcaag    180
aaggatcggg agggagaggg agcaccacct gcaaagaggg ccagagccga ccagatggag    240
gtggatagcg gccctaggaa gcgcccattc agaggcgagt ttaccgacaa ggagcggaga    300
gatcacaggc gccggaaggc cctggagaac aagcggaagc agctgagctc cggcggcaag    360
tccctgtcta aggaggagga ggaggagctg agaaagctga cagaggagga cgagagaagg    420
gagcgccggg tggccggccc aagggtgggc ggcgtgaacc ccctggaggg aggaaccagg    480
ggagcacctg gaggaggctt cgtgccatct atgcagggcg tgcctgagag cccatttgcc    540
aggacaggag agggcctgga tgtgcgcggc aatcagggct tcccctggga catcctgttt    600
cctgccgatc caccccttcag cccacagtcc tgcaggcctc agagcagatc cgagtctaag    660
aagaacaggg gaggaagaga ggaggtgctg gagcagtggg tgaatggccg gaagaagctg    720
gaggagctgg agcgggagct gagaagggcc agaaagaaga tcaagaagct ggaagacgat    780
aatccttggc tgggcaatgt gaaaggcatc ctgggcaaga aggacaagga tggagaggga    840
gcacctccag caaagagggc aagaaccgac cagatggaga tcgatagcgg accaaggaag    900
cgccctctga gaggaggctt cacagaccgg gagagacagg atcaccgccg gagaaaggcc    960
ctgaagaaca agaagaagca gctgtccgcc ggaggcaaga gcctgtccaa agaagaggaa   1020
gaggagctga agaggctgac ccgcgaggac gaggagcgga agaaggagga gcacggccct   1080
tccagactgg gcgtgaatcc atctgaggga ggaccaaggg gagcaccagg cggcggcttc   1140
gtgccaagca tgcagggcat ccccgagtcc cggtttacca gaacaggaga gggcctggac   1200
gtgaggggct ctcgcggctt tcctcaggac atcctgttcc caagcgatcc ccctttttct   1260
ccacagagct gtcgccccca gggaagcgga gctactaact tcagcctgct gaagcaggct   1320
ggagacgtgg aggagaaccc tggacctatg tctcagagcg agacaaggag ggggccggaga   1380
ggaaccaggg aggagacact ggagaagtgg atcacagcca gaaagaaggc cgaggagctg   1440
gagaaggacc tgcggaagac cagaaagaca atcaagaagc tggaagaaga aaatccatgg   1500
ctgggaaata tcgtgggcat catcaggaag ggcaaggacg gcgagggagc accaccagcc   1560
aagaggcctc gcactgatca gatggaggtg gattccggcc ctggcaagag gccacacaag   1620
tctggcttca cagacaagga gagggaggac cataggcgcc ggaaggccct ggaaaacaag   1680
aagaagcaat tatctgccgg cggcaagatc ctgagcaaag aggaagagga ggagctgaga   1740
aggctgaccg acgaggatga ggagaggaag aggagggtgg caggaccaag agtgggcgac   1800
gtgaatccta gcagaggcgg accaagaggc gccccaggcg gggcttcgt gccacagatg   1860
gcaggagtgc cagagtcccc tttttctagg accggagagg gcctggatat caggggaaca   1920
cagggctttc catgggtgtc cccatctcct ccacagcaga ggctgccact gctggagtgc   1980
accccctcaga gccagtccga gtctaagaag aatagaaggg gcggccgcga ggacatcctg   2040
gagaagtgga tcaccacacg cagaaaagct gaagaactgg aaaaggacct gaggaaggcc   2100
cgcaaaacaa tcaagaagct ggaggatgag aacccttggc tgggcaatat catcggaatt   2160
atcaggaagg gcaaggatgg cgaaggcgcc ccacctgcaa agcggccaag gactgatcag   2220
atggaaatcg atagcggaac aggcaagcgg ccccacaagt ccggcttcac cgacaaggag   2280
agagaggatc acagaaggcg caaggccctg gagaacaaga agaagcaatt aagcagcggc   2340
ggcaagaatc tgtccagaga agaagaggag gagctgggca gactgaccgt ggaggacgag   2400
gagcggagaa ggcgcgtggc aggacctcgc acaggcgatg tgaacctgtc cggaggagga   2460
```

```
cctaggggag caccaggagg cggcttcgtg ccacgcatgg agggcgtgcc agagtctccc   2520

tttacccgca ccggagaggg cctggacatc aggggcaatc agggctttcc ctgggtccgc   2580

ccctcccccc ctcagcagag actgcccctg ctggaatgca caccacag                2628


<210> SEQ ID NO 33
<211> LENGTH: 2657
<212> TYPE: DNA
<213> ORGANISM: Artificial Sequence
<220> FEATURE:
<223> OTHER INFORMATION: Delta 5 codon optimized with restriction sites
      (HindIII /EcoRI)

<400> SEQUENCE: 33

aagcttgcac catggcctca cggtcagagt caaagaaaaa tagggggggg cgggaagaaa     60

tcctggaaca gtgggtcgga gcacggaaaa aactggaaga gctggagagg gacctgcgca    120

agatcaagaa gaagatcaag aagctggagg aggagaaccc ctggctgggc aatatcaagg    180

gcatcctggg caagaaggat cgggagggag agggagcacc acctgcaaag agggccagag    240

ccgaccagat ggaggtggat agcggcccta ggaagcgccc attcagaggc gagtttaccg    300

acaaggagcg gagagatcac aggcgccgga aggccctgga gaacaagcgg aagcagctga    360

gctccggcgg caagtccctg tctaaggagg aggaggagga gctgagaaag ctgacagagg    420

aggacgagag aagggagcgc cgggtggccg gcccaagggt gggcggcgtg aaccccctgg    480

agggaggaac caggggagca cctggaggag gcttcgtgcc atctatgcag ggcgtgcctg    540

agagcccatt tgccaggaca ggagagggcc tggatgtgcg cggcaatcag ggcttcccct    600

gggacatcct gtttcctgcc gatccaccct tcagcccaca gtcctgcagg cctcagagca    660

gatccgagtc taagaagaac aggggaggaa gagaggaggt gctggagcag tgggtgaatg    720

gccggaagaa gctggaggag ctggagcggg agctgagaag ggccagaaag aagatcaaga    780

agctggaaga cgataatcct tggctgggca atgtgaaagg catcctgggc aagaaggaca    840

aggatggaga gggagcacct ccagcaaaga gggcaagaac cgaccagatg gagatcgata    900

gcggaccaag gaagcgccct ctgagaggag gcttcacaga ccgggagaga caggatcacc    960

gccggagaaa ggccctgaag aacaagaaga agcagctgtc cgccggaggc aagagcctgt   1020

ccaaagaaga ggaagaggag ctgaagaggc tgacccgcga ggacgaggag cggaagaagg   1080

aggagcacgg cccttccaga ctgggcgtga atccatctga gggaggacca aggggagcac   1140

caggcggcgg cttcgtgcca agcatgcagg gcatccccga gtcccggttt accagaacag   1200

gagagggcct ggacgtgagg ggctctcgcg gctttcctca ggacatcctg ttcccaagcg   1260

atcccccttt ttctccacag agctgtcgcc cccagggaag cggagctact aacttcagcc   1320

tgctgaagca ggctggagac gtggaggaga accctggacc tatgtctcag agcgagacaa   1380

ggaggggccg gagaggaacc agggaggaga cactggagaa gtggatcaca gccagaaaga   1440

aggccgagga gctggagaag gacctgcgga agaccagaaa gacaatcaag aagctggaag   1500

aagaaaatcc atggctggga aatatcgtgg gcatcatcag gaagggcaag gacggcgagg   1560

gagcaccacc agccaagagg cctcgcactg atcagatgga ggtggattcc ggccctggca   1620

agaggccaca caagtctggc ttcacagaca aggagaggga ggaccatagg cgccggaagg   1680

ccctggaaaa caagaagaag caattatctg ccggcggcaa gatcctgagc aaagaggaag   1740

aggaggagct gagaaggctg accgacgagg atgaggagag gaagaggagg gtggcaggac   1800

caagagtggg cgacgtgaat cctagcagag gcggaccaag aggcgcccca ggcgggggct   1860
```

```
tcgtgccaca gatggcagga gtgccagagt ccccttttc taggaccgga gagggcctgg   1920

atatcagggg aacacagggc tttccatggg tgtccccatc tcctccacag cagaggctgc   1980

cactgctgga gtgcacccct cagagccagt ccgagtctaa gaagaataga aggggcggcc   2040

gcgaggacat cctggagaag tggatcacca cacgcagaaa agctgaagaa ctggaaaagg   2100

acctgaggaa ggcccgcaaa acaatcaaga agctggagga tgagaaccct tggctgggca   2160

atatcatcgg aattatcagg aagggcaagg atggcgaagg cgccccacct gcaaagcggc   2220

caaggactga tcagatggaa atcgatagcg gaacaggcaa gcggccccac aagtccggct   2280

tcaccgacaa ggagagagag gatcacagaa ggcgcaaggc cctggagaac aagaagaagc   2340

aattaagcag cggcggcaag aatctgtcca gagaagaaga ggaggagctg ggcagactga   2400

ccgtggagga cgaggagcgg agaaggcgcg tggcaggacc tcgcacaggc gatgtgaacc   2460

tgtccggagg aggacctagg ggagcaccag gaggcggctt cgtgccacgc atggagggcg   2520

tgccagagtc tccctttacc cgcaccggag agggcctgga catcaggggc aatcagggct   2580

ttccctgggt ccgcccctcc ccccctcagc agagactgcc cctgctggaa tgcacaccac   2640

agtgatgaga attccgt                                                  2657


<210> SEQ ID NO 34
<211> LENGTH: 877
<212> TYPE: PRT
<213> ORGANISM: Artificial Sequence
<220> FEATURE:
<223> OTHER INFORMATION: Delta 5 protein

<400> SEQUENCE: 34

Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Ser Arg Ser Glu Ser Lys Lys Asn Arg
```

-continued

```
    210                 215                 220

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
                245                 250                 255

Lys Leu Glu Asp Asp Asn Pro Trp Leu Gly Asn Val Lys Gly Ile Leu
            260                 265                 270

Gly Lys Lys Asp Lys Asp Gly Glu Gly Ala Pro Pro Ala Lys Arg Ala
        275                 280                 285

Arg Thr Asp Gln Met Glu Ile Asp Ser Gly Pro Arg Lys Arg Pro Leu
    290                 295                 300

Arg Gly Gly Phe Thr Asp Arg Glu Arg Gln Asp His Arg Arg Arg Lys
305                 310                 315                 320

Ala Leu Lys Asn Lys Lys Lys Gln Leu Ser Ala Gly Gly Lys Ser Leu
                325                 330                 335

Ser Lys Glu Glu Glu Glu Glu Leu Lys Arg Leu Thr Arg Glu Asp Glu
            340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Gly Phe Val Pro Ser
    370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
                405                 410                 415

Asp Pro Pro Phe Ser Pro Gln Ser Cys Arg Pro Gln Gly Ser Gly Ala
            420                 425                 430

Thr Asn Phe Ser Leu Leu Lys Gln Ala Gly Asp Val Glu Glu Asn Pro
        435                 440                 445

Gly Pro Met Ser Gln Ser Glu Thr Arg Arg Gly Arg Arg Gly Thr Arg
    450                 455                 460

Glu Glu Thr Leu Glu Lys Trp Ile Thr Ala Arg Lys Lys Ala Glu Glu
465                 470                 475                 480

Leu Glu Lys Asp Leu Arg Lys Thr Arg Lys Thr Ile Lys Lys Leu Glu
                485                 490                 495

Glu Glu Asn Pro Trp Leu Gly Asn Ile Val Gly Ile Ile Arg Lys Gly
            500                 505                 510

Lys Asp Gly Glu Gly Ala Pro Pro Ala Lys Arg Pro Arg Thr Asp Gln
        515                 520                 525

Met Glu Val Asp Ser Gly Pro Gly Lys Arg Pro His Lys Ser Gly Phe
    530                 535                 540

Thr Asp Lys Glu Arg Glu Asp His Arg Arg Arg Lys Ala Leu Glu Asn
545                 550                 555                 560

Lys Lys Lys Gln Leu Ser Ala Gly Gly Lys Ile Leu Ser Lys Glu Glu
                565                 570                 575

Glu Glu Glu Leu Arg Arg Leu Thr Asp Glu Asp Glu Glu Arg Lys Arg
            580                 585                 590

Arg Val Ala Gly Pro Arg Val Gly Asp Val Asn Pro Ser Arg Gly Gly
        595                 600                 605

Pro Arg Gly Ala Pro Gly Gly Gly Phe Val Pro Gln Met Ala Gly Val
    610                 615                 620

Pro Glu Ser Pro Phe Ser Arg Thr Gly Glu Gly Leu Asp Ile Arg Gly
625                 630                 635                 640
```

```
Thr Gln Gly Phe Pro Trp Val Ser Pro Ser Pro Pro Gln Gln Arg Leu
                645                 650                 655

Pro Leu Leu Glu Cys Thr Pro Gln Ser Gln Ser Glu Ser Lys Lys Asn
            660                 665                 670

Arg Arg Gly Gly Arg Glu Asp Ile Leu Glu Lys Trp Ile Thr Thr Arg
        675                 680                 685

Arg Lys Ala Glu Glu Leu Glu Lys Asp Leu Arg Lys Ala Arg Lys Thr
    690                 695                 700

Ile Lys Lys Leu Glu Asp Glu Asn Pro Trp Leu Gly Asn Ile Ile Gly
705                 710                 715                 720

Ile Ile Arg Lys Gly Lys Asp Gly Glu Gly Ala Pro Pro Ala Lys Arg
                725                 730                 735

Pro Arg Thr Asp Gln Met Glu Ile Asp Ser Gly Thr Gly Lys Arg Pro
            740                 745                 750

His Lys Ser Gly Phe Thr Asp Lys Glu Arg Glu Asp His Arg Arg Arg
        755                 760                 765

Lys Ala Leu Glu Asn Lys Lys Lys Gln Leu Ser Ser Gly Gly Lys Asn
    770                 775                 780

Leu Ser Arg Glu Glu Glu Glu Glu Leu Gly Arg Leu Thr Val Glu Asp
785                 790                 795                 800

Glu Glu Arg Arg Arg Arg Val Ala Gly Pro Arg Thr Gly Asp Val Asn
                805                 810                 815

Leu Ser Gly Gly Gly Pro Arg Gly Ala Pro Gly Gly Gly Phe Val Pro
            820                 825                 830

Arg Met Glu Gly Val Pro Glu Ser Pro Phe Thr Arg Thr Gly Glu Gly
        835                 840                 845

Leu Asp Ile Arg Gly Asn Gln Gly Phe Pro Trp Val Arg Pro Ser Pro
    850                 855                 860

Pro Gln Gln Arg Leu Pro Leu Leu Glu Cys Thr Pro Gln
865                 870                 875
```

<210> SEQ ID NO 35
<211> LENGTH: 2763
<212> TYPE: DNA
<213> ORGANISM: Artificial Sequence
<220> FEATURE:
<223> OTHER INFORMATION: Delta 6 wt

<400> SEQUENCE: 35

```
agccgcagcg aaagcaaaaa aaaccgcggc ggccgcgaag aaattctgga acagtgggtg      60

ggcgcgcgca aaaaactgga agaactggaa cgcgatctgc gcaaaattaa aaaaaaaatt     120

aaaaaactgg aagaagaaaa cccgtggctg ggcaacatta aaggcattct gggcaaaaaa     180

gatcgcgaag gcgaaggcgc gccgccggcg aaacgcgcgc gcgcggatca gatggaagtg     240

gatagcggcc cgcgcaaacg cccgtttcgc ggcgaattta ccgataaaga acgccgcgat     300

catcgccgcc gcaaagcgct ggaaaacaaa cgcaaacagc tgagcagcgg cggcaaaagc     360

ctgagcaaag aagaagaaga agaactgcgc aaactgaccg aagaagatga acgccgcgaa     420

cgccgcgtgg cgggcccgcg cgtgggcggc gtgaacccgc tggaaggcgg cacccgcggc     480

gcgccgggcg gcggctttgt gccgagcatg cagggcgtgc cggaaagccc gtttgcgcgc     540

accggcgaag gcctggatgt gcgcggcaac cagggctttc cgtgggatat tctgtttccg     600

gcggatccgc cgtttagccc gcagagctgc cgcccgcagg gaagcggagc tactaacttc     660

agcctgctga agcaggctgg agacgtggag gagaaccctg gacctatgag ccgcagcgaa     720
```

```
agcaaaaaaa accgcggcgg ccgcgaagaa gtgctggaac agtgggtgaa cggccgcaaa    780
aaactggaag aactggaacg cgaactgcgc cgcgcgcgca aaaaaattaa aaaactggaa    840
gatgataacc cgtggctggg caacgtgaaa ggcattctgg gcaaaaaaga taaagatggc    900
gaaggcgcgc cgccggcgaa acgcgcgcgc accgatcaga tggaaattga tagcggcccg    960
cgcaaacgcc cgctgcgcgg cggctttacc gatcgcgaac gccaggatca tcgccgccgc   1020
aaagcgctga aaaacaaaaa aaaacagctg agcgcgggcg gcaaaagcct gagcaaagaa   1080
gaagaagaag aactgaaacg cctgacccgc gaagatgaag aacgcaaaaa agaagaacat   1140
ggcccgagcc gcctgggcgt gaacccgagc gaaggcggcc cgcgcggcgc gccgggcggc   1200
ggctttgtgc cgagcatgca gggcattccg gaaagccgct ttacccgcac cggcgaaggc   1260
ctggatgtgc gcggcagccg cggctttccg caggatattc tgtttccgag cgatccgccg   1320
tttagcccgc agagctgccg cccgcaggga agcggagcta ctaacttcag cctgctgaag   1380
caggctggag acgtggagga gaaccctgga cctatgagcc agagcgaaac ccgccgcggc   1440
cgccgcggca cccgcgaaga aaccctggaa aaatggatta ccgcgcgcaa aaaagcggaa   1500
gaactggaaa aagatctgcg caaaacccgc aaaaccatta aaaaactgga agaagaaaac   1560
ccgtggctgg gcaacattgt gggcattatt cgcaaaggca aagatggcga aggcgcgccg   1620
ccggcgaaac gcccgcgcac cgatcagatg gaagtggata gcggcccggg caaacgcccg   1680
cataaaagcg gctttaccga taaagaacgc gaagatcatc gccgccgcaa agcgctggaa   1740
aacaaaaaaa aacagctgag cgcgggcggc aaaattctga gcaaagaaga agaagaagaa   1800
ctgcgccgcc tgaccgatga agatgaagaa cgcaaacgcc gcgtggcggg cccgcgcgtg   1860
ggcgatgtga acccgagccg cggcggcccg cgcggcgcgc cgggcggcgg ctttgtgccg   1920
cagatggcgg gcgtgccgga aagcccgttt agccgcaccg gcgaaggcct ggatattcgc   1980
ggcacccagg gctttccgtg ggtgagcccg agcccgccgc agcagcgcct gccgctgctg   2040
gaatgcaccc cgcagggaag cggagctact aacttcagcc tgctgaagca ggctggagac   2100
gtggaggaga accctggacc tatgagccag agcgaaagca aaaaaaaccg ccgcggcggc   2160
cgcgaagata ttctggaaaa atggattacc acccgccgca aagcggaaga actggaaaaa   2220
gatctgcgca aagcgcgcaa aaccattaaa aaactggaag atgaaaaccc gtggctgggc   2280
aacattattg gcattattcg caaaggcaaa gatggcgaag gcgcgccgcc ggcgaaacgc   2340
ccgcgcaccg atcagatgga aattgatagc ggcaccggca aacgcccgca taaaagcggc   2400
tttaccgata aagaacgcga agatcatcgc cgccgcaaag cgctggaaaa caaaaaaaaa   2460
cagctgagca gcggcggcaa aaacctgagc cgcgaagaag aagaagaact gggccgcctg   2520
accgtggaag atgaagaacg ccgccgccgc gtggcgggcc cgcgcaccgg cgatgtgaac   2580
ctgagcggcg gcggcccgcg cggcgcgccg ggcggcggct ttgtgccgcg catggaaggc   2640
gtgccggaaa gcccgtttac ccgcaccggc gaaggcctgg atattcgcgg caaccagggc   2700
tttccgtggg tgcgcccgag cccgccgcag cagcgcctgc cgctgctgga atgcaccccg   2760
cag                                                                 2763
```

<210> SEQ ID NO 36
<211> LENGTH: 2795
<212> TYPE: DNA
<213> ORGANISM: Artificial Sequence
<220> FEATURE:
<223> OTHER INFORMATION: Delta 6 wt with restriction sites (HindIII /EcoRI)

<400> SEQUENCE: 36
aagcttgcac catggccagc cgcagcgaaa gcaaaaaaaa ccgcggcggc cgcgaagaaa 60
ttctggaaca gtgggtgggc gcgcgcaaaa aactggaaga actggaacgc gatctgcgca 120
aaattaaaaa aaaaattaaa aaactggaag aagaaaaccc gtggctgggc aacattaaag 180
gcattctggg caaaaaagat cgcgaaggcg aaggcgcgcc gccggcgaaa cgcgcgcgcg 240
cggatcagat ggaagtggat agcggcccgc gcaaacgccc gtttcgcggc gaatttaccg 300
ataaagaacg ccgcgatcat cgccgccgca aagcgctgga aaacaaacgc aaacagctga 360
gcagcggcgg caaaagcctg agcaaagaag aagaagaaga actgcgcaaa ctgaccgaag 420
aagatgaacg ccgcgaacgc cgcgtggcgg gcccgcgcgt gggcggcgtg aacccgctgg 480
aaggcggcac ccgcggcgcg ccgggcggcg gctttgtgcc gagcatgcag ggcgtgccgg 540
aaagcccgtt tgcgcgcacc ggcgaaggcc tggatgtgcg cggcaaccag ggctttccgt 600
gggatattct gtttccggcg gatccgccgt ttagcccgca gagctgccgc ccgcagggaa 660
gcggagctac taacttcagc ctgctgaagc aggctggaga cgtggaggag aaccctggac 720
ctatgagccg cagcgaaagc aaaaaaaacc gcggcggccg cgaagaagtg ctggaacagt 780
gggtgaacgg ccgcaaaaaa ctggaagaac tggaacgcga actgcgccgc gcgcgcaaaa 840
aaattaaaaa actggaagat gataacccgt ggctgggcaa cgtgaaaggc attctgggca 900
aaaaagataa agatggcgaa ggcgcgccgc cggcgaaacg cgcgcgcacc gatcagatgg 960
aaattgatag cggcccgcgc aaacgcccgc tgcgcggcgg ctttaccgat cgcgaacgcc 1020
aggatcatcg ccgccgcaaa gcgctgaaaa acaaaaaaaa acagctgagc gcgggcggca 1080
aaagcctgag caaagaagaa gaagaagaac tgaaacgcct gacccgcgaa gatgaagaac 1140
gcaaaaaaga agaacatggc ccgagccgcc tgggcgtgaa cccgagcgaa ggcggcccgc 1200
gcggcgcgcc gggcggcggc tttgtgccga gcatgcaggg cattccggaa agccgcttta 1260
cccgcaccgg cgaaggcctg gatgtgcgcg gcagccgcgg ctttccgcag gatattctgt 1320
ttccgagcga tccgccgttt agcccgcaga gctgccgccc gcagggaagc ggagctacta 1380
acttcagcct gctgaagcag gctggagacg tggaggagaa ccctggacct atgagccaga 1440
gcgaaacccg ccgcggccgc cgcggcaccc gcgaagaaac cctggaaaaa tggattaccg 1500
cgcgcaaaaa agcggaagaa ctggaaaaag atctgcgcaa aacccgcaaa accattaaaa 1560
aactggaaga agaaaacccg tggctgggca acattgtggg cattattcgc aaaggcaaag 1620
atggcgaagg cgcgccgccg gcgaaacgcc cgcgcaccga tcagatggaa gtggatagcg 1680
gcccgggcaa acgcccgcat aaaagcggct ttaccgataa agaacgcgaa gatcatcgcc 1740
gccgcaaagc gctggaaaac aaaaaaaaac agctgagcgc gggcggcaaa attctgagca 1800
aagaagaaga agaagaactg cgccgcctga ccgatgaaga tgaagaacgc aaacgccgcg 1860
tggcgggccc gcgcgtgggc gatgtgaacc cgagccgcgg cggcccgcgc ggcgcgccgg 1920
gcggcggctt tgtgccgcag atggcgggcg tgccggaaag cccgtttagc cgcaccggcg 1980
aaggcctgga tattcgcggc acccagggct ttccgtgggt gagcccgagc ccgccgcagc 2040
agcgcctgcc gctgctggaa tgcaccccgc agggaagcgg agctactaac ttcagcctgc 2100
tgaagcaggc tggagacgtg gaggagaacc ctggacctat gagccagagc gaaagcaaaa 2160
aaaaccgccg cggcggccgc gaagatattc tggaaaaatg gattaccacc cgccgcaaag 2220
cggaagaact ggaaaaagat ctgcgcaaag cgcgcaaaac cattaaaaaa ctggaagatg 2280

```
aaaacccgtg gctgggcaac attattggca ttattcgcaa aggcaaagat ggcgaaggcg   2340
cgccgccggc gaaacgcccg cgcaccgatc agatggaaat tgatagcggc accggcaaac   2400
gcccgcataa aagcggcttt accgataaag aacgcgaaga tcatcgccgc cgcaaagcgc   2460
tggaaaacaa aaaaaaacag ctgagcagcg gcggcaaaaa cctgagccgc gaagaagaag   2520
aagaactggg ccgcctgacc gtggaagatg aagaacgccg ccgccgcgtg gcgggcccgc   2580
gcaccggcga tgtgaacctg agcggcggcg gcccgcgcgg cgcgccgggc ggcggctttg   2640
tgccgcgcat ggaaggcgtg ccggaaagcc cgtttacccg caccggcgaa ggcctggata   2700
ttcgcggcaa ccagggcttt ccgtgggtgc gcccgagccc gccgcagcag cgcctgccgc   2760
tgctggaatg caccccgcag tgatgagaat tccgt                              2795
```

<210> SEQ ID NO 37
<211> LENGTH: 2766
<212> TYPE: DNA
<213> ORGANISM: Artificial Sequence
<220> FEATURE:
<223> OTHER INFORMATION: Delta 6 codon optimized

<400> SEQUENCE: 37

```
gcctcacggt cagagtcaaa gaagaacaga ggcggaagag aagaaatcct ggagcagtgg     60
gtcggagcac ggaaaaagct ggaagaactg gagagggacc tgcgcaagat caagaagaag    120
atcaagaagc tggaggagga gaacccctgg ctgggcaata tcaagggcat cctgggcaag    180
aaggataggg agggagaggg agcaccacct gcaaagaggg ccagagccga ccagatggag    240
gtggatagcg gaccaaggaa gcgccccttc cgcggagagt ttaccgacaa ggagcggaga    300
gatcacaggc gccggaaggc cctggagaac aagaggaagc agctgagctc cggcggcaag    360
tccctgtcta aggaggagga ggaggagctg cgcaagctga cagaggagga cgagagaagg    420
gagaggaggg tggcaggacc aagggtggga ggagtgaatc ctctggaggg aggaaccaga    480
ggagcaccag gaggaggctt cgtgccaagc atgcagggag tgccagagtc cccctttgcc    540
aggacaggag agggcctgga cgtgagaggc aaccagggct tcccttggga catcctgttt    600
ccagccgatc caccccttcag ccctcagtcc tgcaggccac agggaagcgg agctactaac    660
ttcagcctgc tgaagcaggc tggagacgtg gaggagaacc ctggacctat gagccggtcc    720
gagtctaaga agaatagggg aggaagagag gaggtgctgg agcagtgggt gaacggcaga    780
aagaagctgg aggagctgga gagggagctg agaagggccc gcaagaagat caagaagctg    840
gaagacgata atccttggct gggcaatgtg aaaggcatcc tgggcaagaa ggacaaggat    900
ggagagggag cacctccagc aaagagggca agaaccgacc agatggagat cgatagcgga    960
cctaggaagc gcccactgag gggaggcttt acagaccggg agagacagga tcaccgccgg   1020
agaaaggccc tgaagaacaa gaagaagcag ctgtccgccg gaggcaagag cctgtccaaa   1080
gaagaggaag aggagctgaa gaggctgacc cgcgaggacg aggagaggaa gaaggaggag   1140
cacggaccat ctaggctggg agtgaatccc agcgagggag gaccaagggg agcacctgga   1200
ggaggcttcg tgccctccat gcagggcatc cctgagtctc ggtttaccag aaccggcgag   1260
ggcctggacg tgaggggcag ccgcggcttt ccacaggaca tcctgttccc ctccgatccc   1320
ccttttctc cccagagctg tcgccctcaa ggaagcggag ctactaactt cagcctgctg   1380
aagcaggctg gagacgtgga ggagaaccct ggacctatgt ctcagagcga gacaaggagg   1440
ggccggagag gaaccaggga ggagacactg gagaagtgga tcacagcccg caagaaggcc   1500
gaggagctgg agaaggacct gcggaagacc agaaagacaa tcaagaagct ggaagaagag   1560
```

aacccttggc tgggcaatat cgtgggcatc atcaggaagg gcaaggacgg cgagggagca 1620
ccaccagcca agaggccacg cactgatcag atggaggtgg attctggacc aggcaagcgg 1680
ccccacaaga gcggcttcac agacaaggag agagaggacc ataggcgccg gaaggccctg 1740
gaaaacaaga agaagcaatt aagcgccggc ggcaagatcc tgtccaaaga ggaagaggag 1800
gagctgagaa ggctgaccga cgaggatgag gagaggaaaa gaagggtggc aggacctagg 1860
gtgggcgacg tgaatccaag caggggagga cctagaggag caccaggagg cggcttcgtg 1920
ccacagatgg caggagtgcc tgagtcccca ttttctcgga ccggcgaggg cctggatatc 1980
agaggcacac agggcttccc ctgggtgtcc ccttctcctc cacagcagcg gctgcctctg 2040
ctggagtgca cccctcaggg aagcggagct actaacttca gcctgctgaa gcaggctgga 2100
gacgtggagg agaaccctgg acctatgtcg cagagcgaat ctaagaagaa tagaaggggc 2160
ggcagagagg atatcctgga gaagtggatc accacacgca gaaaagctga agaactggaa 2220
aaggacctga ggaaggcccg caagaccatc aagaagctgg aggatgaaaa tccatggctg 2280
ggaaatatca tcggcatcat ccggaagggc aaggacgggg aaggcgcccc acctgcaaag 2340
cggcccagga ctgatcagat ggaaatcgat tccggcacag gcaagaggcc tcacaagtct 2400
ggcttcacag ataaagagcg cgaggatcac agaaggcgca aggccctgga gaacaagaag 2460
aagcaattat ctagcggcgg caagaatctg tccagagaag aagaggagga gctgggccgc 2520
ctgaccgtgg aggacgagga gcggagaagg cgcgtggcag gaccaagaac aggcgatgtg 2580
aacctgtctg gaggcggccc aaggggcgcc cccggcggag gcttcgtgcc aagaatggaa 2640
ggcgtgccag agtccccttt tacccggaca ggggaaggcc tggacattag aggcaatcag 2700
ggctttccct gggtgcgacc aagcccccct cagcagcgac tgcctctgct ggagtgtacc 2760
cctcag 2766

<210> SEQ ID NO 38
<211> LENGTH: 2795
<212> TYPE: DNA
<213> ORGANISM: Artificial Sequence
<220> FEATURE:
<223> OTHER INFORMATION: Delta 6 codon optimized with restriction sites
(HindIII /EcoRI)

<400> SEQUENCE: 38
aagcttgcac catggcctca cggtcagagt caaagaagaa cagaggcgga agagaagaaa 60
tcctggagca gtgggtcgga gcacggaaaa agctggaaga actggagagg gacctgcgca 120
agatcaagaa gaagatcaag aagctggagg aggagaaccc ctggctgggc aatatcaagg 180
gcatcctggg caagaaggat agggagggag agggagcacc acctgcaaag agggccagag 240
ccgaccagat ggaggtggat agcggaccaa ggaagcgccc cttccgcgga gagtttaccg 300
acaaggagcg gagagatcac aggcgccgga aggccctgga gaacaagagg aagcagctga 360
gctccggcgg caagtccctg tctaaggagg aggaggagga gctgcgcaag ctgacagagg 420
aggacgagag aagggagagg agggtggcag gaccaagggt gggaggagtg aatcctctgg 480
agggaggaac cagaggagca ccaggaggag gcttcgtgcc aagcatgcag ggagtgccag 540
agtccccctt tgccaggaca ggagagggcc tggacgtgag aggcaaccag ggcttccctt 600
gggacatcct gtttccagcc gatccaccct tcagccctca gtcctgcagg ccacagggaa 660
gcggagctac taacttcagc ctgctgaagc aggctggaga cgtggaggag aaccctggac 720
ctatgagccg gtccgagtct aagaagaata ggggaggaag agaggaggtg ctggagcagt 780

-continued

```
gggtgaacgg cagaaagaag ctggaggagc tggagaggga gctgagaagg gcccgcaaga    840
agatcaagaa gctggaagac gataatcctt ggctgggcaa tgtgaaaggc atcctgggca    900
agaaggacaa ggatggagag ggagcacctc cagcaaagag ggcaagaacc gaccagatgg    960
agatcgatag cggacctagg aagcgcccac tgaggggagg ctttacagac cgggagagac   1020
aggatcaccg ccggagaaag gccctgaaga acaagaagaa gcagctgtcc gccggaggca   1080
agagcctgtc caaagaagag gaagaggagc tgaagaggct gacccgcgag gacgaggaga   1140
ggaagaagga ggagcacgga ccatctaggc tgggagtgaa tcccagcgag ggaggaccaa   1200
ggggagcacc tggaggaggc ttcgtgccct ccatgcaggg catccctgag tctcggttta   1260
ccagaaccgg cgagggcctg gacgtgaggg gcagccgcgg ctttccacag gacatcctgt   1320
tcccctccga tccccctttt tctccccaga gctgtcgccc tcaaggaagc ggagctacta   1380
acttcagcct gctgaagcag gctggagacg tggaggagaa ccctggacct atgtctcaga   1440
gcgagacaag gaggggccgg agaggaacca gggaggagac actggagaag tggatcacag   1500
cccgcaagaa ggccgaggag ctggagaagg acctgcggaa gaccagaaag acaatcaaga   1560
agctggaaga agagaaccct tggctgggca atatcgtggg catcatcagg aagggcaagg   1620
acggcgaggg agcaccacca gccaagaggc cacgcactga tcagatggag gtggattctg   1680
gaccaggcaa gcggccccac aagagcggct tcacagacaa ggagagagag gaccataggc   1740
gccggaaggc cctggaaaac aagaagaagc aattaagcgc cggcggcaag atcctgtcca   1800
aagaggaaga ggaggagctg agaaggctga ccgacgagga tgaggagagg aaaagaaggg   1860
tggcaggacc tagggtgggc gacgtgaatc caagcagggg aggacctaga ggagcaccag   1920
gaggcggctt cgtgccacag atggcaggag tgcctgagtc ccccattttct cggaccggcg   1980
agggcctgga tatcagaggc acacagggct tcccctgggt gtccccttct cctccacagc   2040
agcggctgcc tctgctggag tgcacccctc agggaagcgg agctactaac ttcagcctgc   2100
tgaagcaggc tggagacgtg gaggagaacc ctggacctat gtcgcagagc gaatctaaga   2160
agaatagaag gggcggcaga gaggatatcc tggagaagtg gatcaccaca cgcagaaaag   2220
ctgaagaact ggaaaaggac ctgaggaagg cccgcaagac catcaagaag ctggaggatg   2280
aaaatccatg gctgggaaat atcatcggca tcatccggaa gggcaaggac ggggaaggcg   2340
ccccacctgc aaagcggccc aggactgatc agatggaaat cgattccggc acaggcaaga   2400
ggcctcacaa gtctggcttc acagataaag agcgcgagga tcacagaagg cgcaaggccc   2460
tggagaacaa gaagaagcaa ttatctagcg gcggcaagaa tctgtccaga gaagaagagg   2520
aggagctggg ccgcctgacc gtggaggacg aggagcggag aaggcgcgtg gcaggaccaa   2580
gaacaggcga tgtgaacctg tctggaggcg gcccaagggg cgcccccggc ggaggcttcg   2640
tgccaagaat ggaaggcgtg ccagagtccc cttttacccg gacaggggaa ggcctggaca   2700
ttagaggcaa tcagggcttt ccctgggtgc gaccaagccc ccctcagcag cgactgcctc   2760
tgctggagtg tacccctcag tgatgagaat tccgt                              2795
```

<210> SEQ ID NO 39
<211> LENGTH: 923
<212> TYPE: PRT
<213> ORGANISM: Artificial Sequence
<220> FEATURE:
<223> OTHER INFORMATION: Delta 6 protein

<400> SEQUENCE: 39

-continued

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Gly Ser Gly Ala Thr Asn Phe Ser Leu
    210                 215                 220

Leu Lys Gln Ala Gly Asp Val Glu Glu Asn Pro Gly Pro Met Ser Arg
225                 230                 235                 240

Ser Glu Ser Lys Lys Asn Arg Gly Gly Arg Glu Glu Val Leu Glu Gln
                245                 250                 255

Trp Val Asn Gly Arg Lys Lys Leu Glu Glu Leu Glu Arg Glu Leu Arg
            260                 265                 270

Arg Ala Arg Lys Lys Ile Lys Lys Leu Glu Asp Asp Asn Pro Trp Leu
        275                 280                 285

Gly Asn Val Lys Gly Ile Leu Gly Lys Lys Asp Lys Asp Gly Glu Gly
    290                 295                 300

Ala Pro Pro Ala Lys Arg Ala Arg Thr Asp Gln Met Glu Ile Asp Ser
305                 310                 315                 320

Gly Pro Arg Lys Arg Pro Leu Arg Gly Gly Phe Thr Asp Arg Glu Arg
                325                 330                 335

Gln Asp His Arg Arg Arg Lys Ala Leu Lys Asn Lys Lys Lys Gln Leu
            340                 345                 350

Ser Ala Gly Gly Lys Ser Leu Ser Lys Glu Glu Glu Glu Glu Leu Lys
        355                 360                 365

Arg Leu Thr Arg Glu Asp Glu Glu Arg Lys Lys Glu Glu His Gly Pro
    370                 375                 380

Ser Arg Leu Gly Val Asn Pro Ser Glu Gly Gly Pro Arg Gly Ala Pro
385                 390                 395                 400

Gly Gly Gly Phe Val Pro Ser Met Gln Gly Ile Pro Glu Ser Arg Phe
                405                 410                 415

Thr Arg Thr Gly Glu Gly Leu Asp Val Arg Gly Ser Arg Gly Phe Pro
```

-continued

```
            420                 425                 430

Gln Asp Ile Leu Phe Pro Ser Asp Pro Pro Phe Ser Pro Gln Ser Cys
        435                 440                 445

Arg Pro Gln Gly Ser Gly Ala Thr Asn Phe Ser Leu Leu Lys Gln Ala
    450                 455                 460

Gly Asp Val Glu Glu Asn Pro Gly Pro Met Ser Gln Ser Glu Thr Arg
465                 470                 475                 480

Arg Gly Arg Arg Gly Thr Arg Glu Glu Thr Leu Glu Lys Trp Ile Thr
                485                 490                 495

Ala Arg Lys Lys Ala Glu Glu Leu Glu Lys Asp Leu Arg Lys Thr Arg
            500                 505                 510

Lys Thr Ile Lys Lys Leu Glu Glu Glu Asn Pro Trp Leu Gly Asn Ile
        515                 520                 525

Val Gly Ile Ile Arg Lys Gly Lys Asp Gly Glu Gly Ala Pro Pro Ala
    530                 535                 540

Lys Arg Pro Arg Thr Asp Gln Met Glu Val Asp Ser Gly Pro Gly Lys
545                 550                 555                 560

Arg Pro His Lys Ser Gly Phe Thr Asp Lys Glu Arg Glu Asp His Arg
                565                 570                 575

Arg Arg Lys Ala Leu Glu Asn Lys Lys Lys Gln Leu Ser Ala Gly Gly
            580                 585                 590

Lys Ile Leu Ser Lys Glu Glu Glu Glu Glu Leu Arg Arg Leu Thr Asp
        595                 600                 605

Glu Asp Glu Glu Arg Lys Arg Arg Val Ala Gly Pro Arg Val Gly Asp
    610                 615                 620

Val Asn Pro Ser Arg Gly Gly Pro Arg Gly Ala Pro Gly Gly Gly Phe
625                 630                 635                 640

Val Pro Gln Met Ala Gly Val Pro Glu Ser Pro Phe Ser Arg Thr Gly
                645                 650                 655

Glu Gly Leu Asp Ile Arg Gly Thr Gln Gly Phe Pro Trp Val Ser Pro
            660                 665                 670

Ser Pro Pro Gln Gln Arg Leu Pro Leu Leu Glu Cys Thr Pro Gln Gly
        675                 680                 685

Ser Gly Ala Thr Asn Phe Ser Leu Leu Lys Gln Ala Gly Asp Val Glu
    690                 695                 700

Glu Asn Pro Gly Pro Met Ser Gln Ser Glu Ser Lys Lys Asn Arg Arg
705                 710                 715                 720

Gly Gly Arg Glu Asp Ile Leu Glu Lys Trp Ile Thr Thr Arg Arg Lys
                725                 730                 735

Ala Glu Glu Leu Glu Lys Asp Leu Arg Lys Ala Arg Lys Thr Ile Lys
            740                 745                 750

Lys Leu Glu Asp Glu Asn Pro Trp Leu Gly Asn Ile Ile Gly Ile Ile
        755                 760                 765

Arg Lys Gly Lys Asp Gly Glu Gly Ala Pro Pro Ala Lys Arg Pro Arg
    770                 775                 780

Thr Asp Gln Met Glu Ile Asp Ser Gly Thr Gly Lys Arg Pro His Lys
785                 790                 795                 800

Ser Gly Phe Thr Asp Lys Glu Arg Glu Asp His Arg Arg Arg Lys Ala
                805                 810                 815

Leu Glu Asn Lys Lys Lys Gln Leu Ser Ser Gly Gly Lys Asn Leu Ser
            820                 825                 830

Arg Glu Glu Glu Glu Glu Leu Gly Arg Leu Thr Val Glu Asp Glu Glu
        835                 840                 845
```

```
Arg Arg Arg Arg Val Ala Gly Pro Arg Thr Gly Asp Val Asn Leu Ser
    850                 855                 860

Gly Gly Gly Pro Arg Gly Ala Pro Gly Gly Gly Phe Val Pro Arg Met
865                 870                 875                 880

Glu Gly Val Pro Glu Ser Pro Phe Thr Arg Thr Gly Glu Gly Leu Asp
                885                 890                 895

Ile Arg Gly Asn Gln Gly Phe Pro Trp Val Arg Pro Ser Pro Pro Gln
            900                 905                 910

Gln Arg Leu Pro Leu Leu Glu Cys Thr Pro Gln
        915                 920


<210> SEQ ID NO 40
<211> LENGTH: 1560
<212> TYPE: DNA
<213> ORGANISM: Artificial Sequence
<220> FEATURE:
<223> OTHER INFORMATION: Delta 7 wt

<400> SEQUENCE: 40

agccgcagcg aaagcaaaaa aaaccgcggc ggccgcgaag aaattctgga acagtgggtg      60

ggcgcgcgca aaaaactgga agaactggaa cgcgatctgc gcaaaattaa aaaaaaaatt     120

aaaaaactgg aagaagaaaa cccgtggctg ggcaacatta aaggcattct gggcaaaaaa     180

gatcgcgaag gcgaaggcgc gccgccggcg aaacgcgcgc gcgcggatca gatggaagtg     240

gatagcggcc cgcgcaaacg cccgtttcgc ggcgaattta ccgataaaga acgccgcgat     300

catcgccgcc gcaaagcgct ggaaaacaaa cgcaaacagc tgagcagcgg cggcaaaagc     360

ctgagcaaag aagaagaaga agaactgcgc aaactgaccg aagaagatga acgccgcgaa     420

cgccgcgtgg cgggcccgcg cgtgggcggc gtgaacccgc tggaaggcgg cacccgcggc     480

gcgccgggcg gcggctttgt gccgagcatg cagggcgtgc cggaaagccc gtttgcgcgc     540

accggcgaag gcctggatgt gcgcggcaac cagggctttc cgtgggatat tctgtttccg     600

gcggatccgc cgtttagccc gcagagctgc cgcccgcaga gccgcagcga aagcaaaaaa     660

aaccgcggcg gccgcgaaga agtgctggaa cagtgggtga acggccgcaa aaaactggaa     720

gaactggaac gcgaactgcg ccgcgcgcgc aaaaaaatta aaaaactgga agatgataac     780

ccgtggctgg gcaacgtgaa aggcattctg ggcaaaaaag ataaagatgg cgaaggcgcg     840

ccgccggcga aacgcgcgcg caccgatcag atggaaattg atagcggccc gcgcaaacgc     900

ccgctgcgcg gcggctttac cgatcgcgaa cgccaggatc atcgccgccg caaagcgctg     960

aaaaacaaaa aaaaacagct gagcgcgggc ggcaaaagcc tgagcaaaga agaagaagaa    1020

gaactgaaac gcctgacccg cgaagatgaa gaacgcaaaa aagaagaaca tggcccgagc    1080

cgcctgggcg tgaacccgag cgaaggcggc ccgcgcggcg cgccgggcgg cggctttgtg    1140

ccgagcatgc agggcattcc ggaaagccgc tttacccgca ccggcgaagg cctggatgtg    1200

cgcggcagcc gcggctttcc gcaggatatt ctgtttccga gcgatccgcc gtttagcccg    1260

cagagctgcc gcccgcaggg caccaacctg agcaccagca acccgctggg ctttttttccg    1320

gatcatcagc tggatccggc gtttcgcgcg aacagcgcga acccggattg ggattttaac    1380

ccgaacaaag atacctggcc ggatgcgaac aaagtgggcg gccagaacct gagcaccagc    1440

aacccgctgg gctttttttcc ggatcatcag ctggatccgg cgtttcgcgc gaacaccgcg    1500

aacccggatt gggattttaa cccgaacaaa gatacctggc cggatgcgaa caaagtgggc    1560
```

<210> SEQ ID NO 41
<211> LENGTH: 1592
<212> TYPE: DNA
<213> ORGANISM: Artificial Sequence
<220> FEATURE:
<223> OTHER INFORMATION: Delta 7 wt with restriction sites (HindIII /EcoRI)

<400> SEQUENCE: 41
aagcttgcac catggccagc cgcagcgaaa gcaaaaaaaa ccgcggcggc cgcgaagaaa 60
ttctggaaca gtgggtgggc gcgcgcaaaa aactggaaga actggaacgc gatctgcgca 120
aaattaaaaa aaaaattaaa aaactggaag aagaaaaccc gtggctgggc aacattaaag 180
gcattctggg caaaaaagat cgcgaaggcg aaggcgcgcc gccggcgaaa cgcgcgcgcg 240
cggatcagat ggaagtggat agcggcccgc gcaaacgccc gtttcgcggc gaatttaccg 300
ataaagaacg ccgcgatcat cgccgccgca aagcgctgga aaacaaacgc aaacagctga 360
gcagcggcgg caaaagcctg agcaaagaag aagaagaaga actgcgcaaa ctgaccgaag 420
aagatgaacg ccgcgaacgc cgcgtggcgg gcccgcgcgt gggcggcgtg aacccgctgg 480
aaggcggcac ccgcggcgcg ccgggcggcg gctttgtgcc gagcatgcag ggcgtgccgg 540
aaagcccgtt tgcgcgcacc ggcgaaggcc tggatgtgcg cggcaaccag ggctttccgt 600
gggatattct gtttccggcg gatccgccgt ttagcccgca gagctgccgc ccgcagagcc 660
gcagcgaaag caaaaaaaac cgcggcggcc gcgaagaagt gctggaacag tgggtgaacg 720
gccgcaaaaa actggaagaa ctggaacgcg aactgcgccg cgcgcgcaaa aaaattaaaa 780
aactggaaga tgataacccg tggctgggca acgtgaaagg cattctgggc aaaaaagata 840
aagatggcga aggcgcgccg ccggcgaaac gcgcgcgcac cgatcagatg gaaattgata 900
gcggcccgcg caaacgcccg ctgcgcggcg gctttaccga tcgcgaacgc caggatcatc 960
gccgccgcaa agcgctgaaa aacaaaaaaa aacagctgag cgcgggcggc aaaagcctga 1020
gcaaagaaga agaagaagaa ctgaaacgcc tgacccgcga agatgaagaa cgcaaaaaag 1080
aagaacatgg cccgagccgc ctgggcgtga acccgagcga aggcggcccg cgcggcgcgc 1140
cgggcggcgg ctttgtgccg agcatgcagg gcattccgga aagccgcttt acccgcaccg 1200
gcgaaggcct ggatgtgcgc ggcagccgcg gctttccgca ggatattctg tttccgagcg 1260
atccgccgtt tagcccgcag agctgccgcc cgcagggcac caacctgagc accagcaacc 1320
cgctgggctt ttttccggat catcagctgg atccggcgtt tcgcgcgaac agcgcgaacc 1380
cggattggga ttttaacccg aacaaagata cctggccgga tgcgaacaaa gtgggcggcc 1440
agaacctgag caccagcaac ccgctgggct tttttccgga tcatcagctg gatccggcgt 1500
ttcgcgcgaa caccgcgaac ccggattggg attttaaccc gaacaaagat acctggccgg 1560
atgcgaacaa agtgggctga tgagaattcc gt 1592

<210> SEQ ID NO 42
<211> LENGTH: 1563
<212> TYPE: DNA
<213> ORGANISM: Artificial Sequence
<220> FEATURE:
<223> OTHER INFORMATION: Delta 7 codon optimized

<400> SEQUENCE: 42
gcctcacggt ctgagtcaaa gaagaatcgg gggggaagag aagaaatcct ggaacagtgg 60
gtcggcgcac ggaaaaaact ggaagaactg gagcgggacc tgagaaagat caagaagaag 120
atcaagaagc tggaggaaga gaacccctgg ctgggcaata tcaagggcat cctgggcaag 180
aaggatcggg agggcgaggg agcaccacct gcaaagaggg caagggcaga ccagatggag 240
gtggattccg gacctaggaa gcggcccttc cggggagagt ttaccgacaa ggagcggaga 300
gatcacaggc gccggaaggc cctggagaac aagcggaagc agctgagctc cggcggcaag 360
tctctgagca aggaggagga ggaggagctg agaaagctga cagaggagga cgagagaagg 420
gagcgccggg tggccggccc aagggtgggc ggcgtgaacc ccctggaggg aggaaccagg 480
ggagcaccag gaggaggctt cgtgccttct atgcagggcg tgccagagag ccccttttgcc 540 aggacaggag agggcctgga tgtgcgcggc aatcagggct tcccatggga catcctgttt 600
cccgccgatc caccccttctc ccctcagtct tgcaggccac agtcccgctc tgagagcaag 660
aagaacaggg gaggaaggga ggaggtgctg gagcagtggg tgaatggcag gaagaagctg 720
gaggagctgg agcgggagct gagaagggcc agaaagaaga tcaagaagct ggaagacgat 780
aatccttggc tgggcaatgt gaaaggcatc ctgggcaaga aggacaagga tggagaggga 840
gcacctccag caaagagggc acgcaccgac cagatggaga tcgattccgg accaaggaag 900
cggcccctga ggggaggctt cacagacagg gagcgccagg atcaccgccg gagaaaggcc 960
ctgaagaaca agaagaagca gctgtctgcc ggcggcaagt ccctgtctaa agaagaggag 1020
gaggagctga agcggctgac cagagaggac gaggagcgga agaaggagga gcacggccct 1080
tccagactgg gcgtgaatcc atctgaggga ggaccaagag gcgcccctgg cggaggcttc 1140
gtgcctagca tgcagggcat cccagagtcc aggtttacca gaaccggaga gggcctggac 1200
gtgcggggct ctagaggctt tccccaggac atcctgttcc ctagcgatcc cccttttagc 1260
ccccagtcct gtaggcctca gggcaccaac ctgagcacat ccaatccact gggcttcttt 1320
ccagaccacc agctggatcc agccttccgc gccaacagcg ccaatccaga ctgggacttc 1380
aaccccaata aggacacctg gcctgatgcc aacaaggtcg gcggccagaa cctgtctaca 1440
agcaatcctc tgggcttctt tcctgatcac cagctggatc ctgcctttcg ggccaataca 1500
gccaaccctg actgggactt caatcctaac aaagacactt ggcccgatgc taataaggtc 1560
ggc 1563

<210> SEQ ID NO 43
<211> LENGTH: 1592
<212> TYPE: DNA
<213> ORGANISM: Artificial Sequence
<220> FEATURE:
<223> OTHER INFORMATION: Delta 7 codon optimized with restriction sites
(HindIII /EcoRI)

<400> SEQUENCE: 43
aagcttgcac catggcctca cggtctgagt caaagaagaa tcgggggga agagaagaaa 60 tcctggaaca gtgggtcggc gcacggaaaa aactggaaga actggagcgg gacctgagaa 120
agatcaagaa gaagatcaag aagctggagg aagagaaccc ctggctgggc aatatcaagg 180
gcatcctggg caagaaggat cgggagggcg agggagcacc acctgcaaag agggcaaggg 240
cagaccagat ggaggtggat tccggaccta ggaagcggcc cttccgggga gagtttaccg 300
acaaggagcg gagagatcac aggcgccgga aggccctgga gaacaagcgg aagcagctga 360
gctccggcgg caagtctctg agcaaggagg aggaggagga gctgagaaag ctgacagagg 420
aggacgagag aagggagcgc cgggtggccg gcccaagggt gggcggcgtg aacccccctgg 480 agggaggaac caggggagca ccaggaggag gcttcgtgcc ttctatgcag ggcgtgccag 540
agagcccctt tgccaggaca ggagagggcc tggatgtgcg cggcaatcag ggcttcccat 600

```
gggacatcct gtttcccgcc gatccaccct tctcccctca gtcttgcagg ccacagtccc    660

gctctgagag caagaagaac aggggaggaa gggaggaggt gctggagcag tgggtgaatg    720

gcaggaagaa gctggaggag ctggagcggg agctgagaag ggccagaaag aagatcaaga    780

agctggaaga cgataatcct tggctgggca atgtgaaagg catcctgggc aagaaggaca    840

aggatggaga gggagcacct ccagcaaaga gggcacgcac cgaccagatg gagatcgatt    900

ccggaccaag gaagcggccc ctgaggggag gcttcacaga cagggagcgc caggatcacc    960

gccggagaaa ggccctgaag aacaagaaga agcagctgtc tgccggcggc aagtccctgt   1020

ctaaagaaga ggaggaggag ctgaagcggc tgaccagaga ggacgaggag cggaagaagg   1080

aggagcacgg cccttccaga ctgggcgtga atccatctga gggaggacca agaggcgccc   1140

ctggcggagg cttcgtgcct agcatgcagg gcatcccaga gtccaggttt accagaaccg   1200

gagagggcct ggacgtgcgg ggctctagag gctttcccca ggacatcctg ttccctagcg   1260

atccccccttt tagcccccag tcctgtaggc ctcagggcac caacctgagc acatccaatc   1320

cactgggctt ctttccagac caccagctgg atccagcctt ccgcgccaac agcgccaatc   1380

cagactggga cttcaacccc aataaggaca cctggcctga tgccaacaag gtcggcggcc   1440

agaacctgtc tacaagcaat cctctgggct tctttcctga tcaccagctg gatcctgcct   1500

ttcgggccaa tacagccaac cctgactggg acttcaatcc taacaaagac acttggcccg   1560

atgctaataa ggtcggctga tgagaattcc gt                                 1592
```

<210> SEQ ID NO 44
<211> LENGTH: 522
<212> TYPE: PRT
<213> ORGANISM: Artificial Sequence
<220> FEATURE:
<223> OTHER INFORMATION: Delta 7 protein

<400> SEQUENCE: 44

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
```

```
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Ser Arg Ser Glu Ser Lys Lys Asn Arg
    210                 215                 220

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
                245                 250                 255

Lys Leu Glu Asp Asp Asn Pro Trp Leu Gly Asn Val Lys Gly Ile Leu
            260                 265                 270

Gly Lys Lys Asp Lys Asp Gly Glu Gly Ala Pro Pro Ala Lys Arg Ala
        275                 280                 285

Arg Thr Asp Gln Met Glu Ile Asp Ser Gly Pro Arg Lys Arg Pro Leu
    290                 295                 300

Arg Gly Gly Phe Thr Asp Arg Glu Arg Gln Asp His Arg Arg Arg Lys
305                 310                 315                 320

Ala Leu Lys Asn Lys Lys Lys Gln Leu Ser Ala Gly Gly Lys Ser Leu
                325                 330                 335

Ser Lys Glu Glu Glu Glu Glu Leu Lys Arg Leu Thr Arg Glu Asp Glu
            340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Gly Phe Val Pro Ser
    370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
                405                 410                 415

Asp Pro Pro Phe Ser Pro Gln Ser Cys Arg Pro Gln Gly Thr Asn Leu
            420                 425                 430

Ser Thr Ser Asn Pro Leu Gly Phe Phe Pro Asp His Gln Leu Asp Pro
        435                 440                 445

Ala Phe Arg Ala Asn Ser Ala Asn Pro Asp Trp Asp Phe Asn Pro Asn
    450                 455                 460

Lys Asp Thr Trp Pro Asp Ala Asn Lys Val Gly Gly Gln Asn Leu Ser
465                 470                 475                 480

Thr Ser Asn Pro Leu Gly Phe Phe Pro Asp His Gln Leu Asp Pro Ala
                485                 490                 495

Phe Arg Ala Asn Thr Ala Asn Pro Asp Trp Asp Phe Asn Pro Asn Lys
            500                 505                 510

Asp Thr Trp Pro Asp Ala Asn Lys Val Gly
        515                 520
```

<210> SEQ ID NO 45
<211> LENGTH: 1560
<212> TYPE: DNA
<213> ORGANISM: Artificial Sequence
<220> FEATURE:
<223> OTHER INFORMATION: Delta 8 wt

<400> SEQUENCE: 45

```
agccagagcg aaacccgccg cggccgccgc ggcacccgcg aagaaaccct ggaaaaatgg     60

attaccgcgc gcaaaaaagc ggaagaactg gaaaaagatc tgcgcaaaac ccgcaaaacc    120
```

-continued attaaaaaac tggaagaaga aaacccgtgg ctgggcaaca ttgtgggcat tattcgcaaa 180
ggcaaagatg gcgaaggcgc gccgccggcg aaacgcccgc gcaccgatca gatggaagtg 240
gatagcggcc cgggcaaacg cccgcataaa agcggcttta ccgataaaga acgcgaagat 300
catcgccgcc gcaaagcgct ggaaaacaaa aaaaaacagc tgagcgcggg cggcaaaatt 360
ctgagcaaag aagaagaaga agaactgcgc cgcctgaccg atgaagatga agaacgcaaa 420
cgccgcgtgg cgggcccgcg cgtgggcgat gtgaacccga gccgcggcgg cccgcgcggc 480
gcgccgggcg gcggctttgt gccgcagatg gcgggcgtgc cggaaagccc gtttagccgc 540
accggcgaag gcctggatat tcgcggcacc cagggctttc cgtgggtgag cccgagcccg 600
ccgcagcagc gcctgccgct gctggaatgc accccgcaga gccagagcga aagcaaaaaa 660
aaccgccgcg gcggccgcga agatattctg gaaaaatgga ttaccacccg ccgcaaagcg 720
gaagaactgg aaaaagatct gcgcaaagcg cgcaaaacca ttaaaaaact ggaagatgaa 780
aacccgtggc tgggcaacat tattggcatt attcgcaaag gcaaagatgg cgaaggcgcg 840
ccgccggcga aacgcccgcg caccgatcag atggaaattg atagcggcac cggcaaacgc 900
ccgcataaaa gcggctttac cgataaagaa cgcgaagatc atcgccgccg caaagcgctg 960
gaaaacaaaa aaaaacagct gagcagcggc ggcaaaaacc tgagccgcga agaagaagaa 1020
gaactgggcc gcctgaccgt ggaagatgaa gaacgccgcc gccgcgtggc gggcccgcgc 1080
accggcgatg tgaacctgag cggcggcggc ccgcgcggcg cgccgggcgg cggctttgtg 1140
ccgcgcatgg aaggcgtgcc ggaaagcccg tttacccgca ccggcgaagg cctggatatt 1200
cgcggcaacc agggctttcc gtgggtgcgc ccgagcccgc cgcagcagcg cctgccgctg 1260
ctggaatgca ccccgcaggg caccaacctg agcaccagca acccgctggg ctttttttccg 1320 gatcatcagc tggatccggc gtttcgcgcg aacagcgcga acccggattg ggattttaac 1380
ccgaacaaag atacctggcc ggatgcgaac aaagtgggcg gccagaacct gagcaccagc 1440
aacccgctgg gctttttttcc ggatcatcag ctggatccgg cgtttcgcgc gaacaccgcg 1500
aacccggatt gggattttaa cccgaacaaa gatacctggc cggatgcgaa caaagtgggc 1560

<210> SEQ ID NO 46
<211> LENGTH: 1592
<212> TYPE: DNA
<213> ORGANISM: Artificial Sequence
<220> FEATURE:
<223> OTHER INFORMATION: Delta 8 wt with restriction sites (HindIII /EcoRI)

<400> SEQUENCE: 46
aagcttgcac catggccagc cagagcgaaa cccgccgcgg ccgccgcggc acccgcgaag 60
aaaccctgga aaaatggatt accgcgcgca aaaaagcgga agaactggaa aaagatctgc 120
gcaaaacccg caaaaccatt aaaaaactgg aagaagaaaa cccgtggctg ggcaacattg 180
tgggcattat tcgcaaaggc aaagatggcg aaggcgcgcc gccggcgaaa cgcccgcgca 240
ccgatcagat ggaagtggat agcggcccgg gcaaacgccc gcataaaagc ggctttaccg 300
ataaagaacg cgaagatcat cgccgccgca aagcgctgga aaacaaaaaa aaacagctga 360
gcgcgggcgg caaaattctg agcaaagaag aagaagaaga actgcgccgc ctgaccgatg 420
aagatgaaga acgcaaacgc cgcgtggcgg gcccgcgcgt gggcgatgtg aacccgagcc 480
gcggcggccc gcgcggcgcg ccgggcggcg gctttgtgcc gcagatggcg ggcgtgccgg 540
aaagcccgtt tagccgcacc ggcgaaggcc tggatattcg cggcacccag ggctttccgt 600

-continued

```
gggtgagccc gagcccgccg cagcagcgcc tgccgctgct ggaatgcacc ccgcagagcc    660

agagcgaaag caaaaaaaac cgccgcggcg gccgcgaaga tattctggaa aaatggatta    720

ccacccgccg caaagcggaa gaactggaaa aagatctgcg caaagcgcgc aaaaccatta    780

aaaaactgga agatgaaaac ccgtggctgg gcaacattat tggcattatt cgcaaaggca    840

aagatggcga aggcgcgccg ccggcgaaac gcccgcgcac cgatcagatg gaaattgata    900

gcggcaccgg caaacgcccg cataaaagcg gctttaccga taaagaacgc gaagatcatc    960

gccgccgcaa agcgctggaa aacaaaaaaa aacagctgag cagcggcggc aaaaacctga   1020

gccgcgaaga agaagaagaa ctgggccgcc tgaccgtgga agatgaagaa cgccgccgcc   1080

gcgtggcggg cccgcgcacc ggcgatgtga acctgagcgg cggcggcccg cgcggcgcgc   1140

cgggcggcgg ctttgtgccg cgcatggaag gcgtgccgga aagcccgttt acccgcaccg   1200

gcgaaggcct ggatattcgc ggcaaccagg gctttccgtg ggtgcgcccg agcccgccgc   1260

agcagcgcct gccgctgctg gaatgcaccc cgcagggcac caacctgagc accagcaacc   1320

cgctgggctt ttttccggat catcagctgg atccggcgtt tcgcgcgaac agcgcgaacc   1380

cggattggga ttttaacccg aacaaagata cctggccgga tgcgaacaaa gtgggcggcc   1440

agaacctgag caccagcaac ccgctgggct tttttccgga tcatcagctg gatccggcgt   1500

ttcgcgcgaa caccgcgaac ccggattggg attttaaccc gaacaaagat acctggccgg   1560

atgcgaacaa agtgggctga tgagaattcc gt                                 1592
```

<210> SEQ ID NO 47
<211> LENGTH: 1563
<212> TYPE: DNA
<213> ORGANISM: Artificial Sequence
<220> FEATURE:
<223> OTHER INFORMATION: Delta 8 optimized

<400> SEQUENCE: 47

```
gccagtcaga gcgagacccg cagaggacgg agaggaacac gagaagagac actggagaaa     60

tggattacag cacggaagaa ggcagaagag ctggagaagg acctgaggaa gacccgcaag    120

acaatcaaga agctggagga ggagaacccc tggctgggca atatcgtggg catcatcagg    180

aagggcaagg atggagaggg agcaccacct gccaagaggc ctcgcacaga ccagatggag    240

gtggatagcg gaccaggcaa gcggcctcac aagtccggct tcaccgacaa ggagagagag    300

gatcaccgga gaaggaaggc cctggagaac aagaagaagc agctgtccgc cggcggcaag    360

atcctgtcta aggaggagga ggaggagctg cgccggctga cagacgagga tgaggagagg    420

aagagaaggg tggcaggacc aagggtgggc gacgtgaatc cttctagggg aggaccaagg    480

ggagcaccag gaggaggctt cgtgcctcag atggccggcg tgccagagtc tccctttagc    540

cggacaggcg agggcctgga tatcagaggc acccagggct ttccttgggt gtctccaagc    600

ccaccacagc agcggctgcc actgctggag tgcacacccc agtcccagtc tgagagcaag    660

aagaacagga ggggaggaag agaggacatc ctggagaagt ggatcaccac aagaaggaag    720

gccgaggagc tggagaagga cctgcggaag gccagaaaga ccatcaagaa gctggaggat    780

gaaaatcctt ggctgggaaa tatcatcgga attattagaa aaggcaagga cggagaggga    840

gcacctccag caaagcggcc aagaacagac cagatggaga tcgattctgg aaccggcaag    900

aggccccaca agagtggctt caccgataag gagcgcgagg atcaccgccg gagaaaggcc    960

ctggaaaaca agaagaagca attaagctcc ggcggcaaga atctgagcag agaagaagag   1020

gaggagctgg gccgcctgac agtggaggac gaggagaggc gccggagagt ggcaggacct   1080
```

```
agaaccggcg atgtgaacct gtccggaggc ggcccaaggg gagcacctgg aggcggcttc   1140

gtgccacgca tggagggcgt gcctgagtct ccccttcacca ggacaggaga gggcctggac   1200

atcagaggca atcagggatt cccatgggtg cggcccagcc cacctcagca gagactgcct   1260

ctgctggagt gtaccccaca gggcacaaac ctgtccacct ctaatcctct gggcttcttt   1320

ccagaccacc agctggatcc agccttcagg gccaactccg ccaaccctga ctgggacttc   1380

aaccctaata aggacacatg gccagatgcc aacaaggtcg gcggccagaa cctgagcacc   1440

tccaatcccc tgggcttctt tcctgaccac cagctggatc ccgcctttcg cgccaatacc   1500

gccaatcccg actgggactt caatccaaat aaggacacct ggcccgatgc taacaaagtg   1560

gga                                                                 1563
```

<210> SEQ ID NO 48
<211> LENGTH: 1592
<212> TYPE: DNA
<213> ORGANISM: Artificial Sequence
<220> FEATURE:
<223> OTHER INFORMATION: Delta 8 codon optimized with restriction sites (HindIII /EcoRI)

<400> SEQUENCE: 48

```
aagcttgcac catggccagt cagagcgaga cccgcagagg acggagagga acacgagaag     60

agacactgga gaaatggatt acagcacgga agaaggcaga agagctggag aaggacctga    120

ggaagacccg caagacaatc aagaagctgg aggaggagaa cccctggctg ggcaatatcg    180

tgggcatcat caggaagggc aaggatggag agggagcacc acctgccaag aggcctcgca    240

cagaccagat ggaggtggat agcggaccag gcaagcggcc tcacaagtcc ggcttcaccg    300

acaaggagag agaggatcac cggagaagga aggccctgga gaacaagaag aagcagctgt    360

ccgccggcgg caagatcctg tctaaggagg aggaggagga gctgcgccgg ctgacagacg    420

aggatgagga gaggaagaga agggtggcag gaccaagggt gggcgacgtg aatccttcta    480

ggggaggacc aaggggagca ccaggaggag gcttcgtgcc tcagatggcc ggcgtgccag    540

agtctcccctt tagccggaca ggcgagggcc tggatatcag aggcacccag ggctttcctt    600

gggtgtctcc aagcccacca cagcagcggc tgccactgct ggagtgcaca ccccagtccc    660

agtctgagag caagaagaac aggaggggag gaagagagga catcctggag aagtggatca    720

ccacaagaag gaaggccgag gagctggaga aggacctgcg gaaggccaga aagaccatca    780

agaagctgga ggatgaaaat ccttggctgg gaaatatcat cggaattatt agaaaaggca    840

aggacggaga gggagcacct ccagcaaagc ggccaagaac agaccagatg gagatcgatt    900

ctggaaccgg caagaggccc cacaagagtg gcttcaccga taaggagcgc gaggatcacc    960

gccggagaaa ggccctggaa aacaagaaga agcaattaag ctccggcggc aagaatctga   1020

gcagagaaga agaggaggag ctgggccgcc tgacagtgga ggacgaggag aggcgccgga   1080

gagtggcagg acctagaacc ggcgatgtga acctgtccgg aggcggccca aggggagcac   1140

ctggaggcgg cttcgtgcca cgcatggagg gcgtgcctga gtctcccttc accaggacag   1200

gagagggcct ggacatcaga ggcaatcagg gattcccatg ggtgcggccc agcccacctc   1260

agcagagact gcctctgctg gagtgtaccc cacagggcac aaacctgtcc acctctaatc   1320

ctctgggctt ctttccagac caccagctgg atccagcctt cagggccaac tccgccaacc   1380

ctgactggga cttcaaccct aataaggaca catggccaga tgccaacaag gtcggcggcc   1440

agaacctgag cacctccaat cccctgggct tctttcctga ccaccagctg gatcccgcct   1500
```

ttcgcgccaa taccgccaat cccgactggg acttcaatcc aaataaggac acctggcccg 1560
atgctaacaa agtgggatga tgagaattcc gt 1592

<210> SEQ ID NO 49
<211> LENGTH: 522
<212> TYPE: PRT
<213> ORGANISM: Artificial Sequence
<220> FEATURE:
<223> OTHER INFORMATION: Delta 8 protein

<400> SEQUENCE: 49

Met Ala Ser Gln Ser Glu Thr Arg Arg Gly Arg Arg Gly Thr Arg Glu
1 5 10 15

Glu Thr Leu Glu Lys Trp Ile Thr Ala Arg Lys Lys Ala Glu Glu Leu
20 25 30

Glu Lys Asp Leu Arg Lys Thr Arg Lys Thr Ile Lys Lys Leu Glu Glu
35 40 45

Glu Asn Pro Trp Leu Gly Asn Ile Val Gly Ile Ile Arg Lys Gly Lys
50 55 60

Asp Gly Glu Gly Ala Pro Pro Ala Lys Arg Pro Arg Thr Asp Gln Met
65 70 75 80

Glu Val Asp Ser Gly Pro Gly Lys Arg Pro His Lys Ser Gly Phe Thr
85 90 95

Asp Lys Glu Arg Glu Asp His Arg Arg Arg Lys Ala Leu Glu Asn Lys
100 105 110

Lys Lys Gln Leu Ser Ala Gly Gly Lys Ile Leu Ser Lys Glu Glu Glu
115 120 125

Glu Glu Leu Arg Arg Leu Thr Asp Glu Asp Glu Glu Arg Lys Arg Arg
130 135 140

Val Ala Gly Pro Arg Val Gly Asp Val Asn Pro Ser Arg Gly Gly Pro
145 150 155 160

Arg Gly Ala Pro Gly Gly Gly Phe Val Pro Gln Met Ala Gly Val Pro
165 170 175

Glu Ser Pro Phe Ser Arg Thr Gly Glu Gly Leu Asp Ile Arg Gly Thr
180 185 190

Gln Gly Phe Pro Trp Val Ser Pro Ser Pro Pro Gln Gln Arg Leu Pro
195 200 205

Leu Leu Glu Cys Thr Pro Gln Ser Gln Ser Glu Ser Lys Lys Asn Arg
210 215 220

Arg Gly Gly Arg Glu Asp Ile Leu Glu Lys Trp Ile Thr Thr Arg Arg
225 230 235 240

Lys Ala Glu Glu Leu Glu Lys Asp Leu Arg Lys Ala Arg Lys Thr Ile
245 250 255

Lys Lys Leu Glu Asp Glu Asn Pro Trp Leu Gly Asn Ile Ile Gly Ile
260 265 270

Ile Arg Lys Gly Lys Asp Gly Glu Gly Ala Pro Pro Ala Lys Arg Pro
275 280 285

Arg Thr Asp Gln Met Glu Ile Asp Ser Gly Thr Gly Lys Arg Pro His
290 295 300

Lys Ser Gly Phe Thr Asp Lys Glu Arg Glu Asp His Arg Arg Arg Lys
305 310 315 320

Ala Leu Glu Asn Lys Lys Lys Gln Leu Ser Ser Gly Gly Lys Asn Leu
325 330 335

Ser Arg Glu Glu Glu Glu Glu Leu Gly Arg Leu Thr Val Glu Asp Glu

```
            340                 345                 350

Glu Arg Arg Arg Arg Val Ala Gly Pro Arg Thr Gly Asp Val Asn Leu
        355                 360                 365

Ser Gly Gly Gly Pro Arg Gly Ala Pro Gly Gly Gly Phe Val Pro Arg
    370                 375                 380

Met Glu Gly Val Pro Glu Ser Pro Phe Thr Arg Thr Gly Glu Gly Leu
385                 390                 395                 400

Asp Ile Arg Gly Asn Gln Gly Phe Pro Trp Val Arg Pro Ser Pro Pro
                405                 410                 415

Gln Gln Arg Leu Pro Leu Leu Glu Cys Thr Pro Gln Gly Thr Asn Leu
            420                 425                 430

Ser Thr Ser Asn Pro Leu Gly Phe Phe Pro Asp His Gln Leu Asp Pro
        435                 440                 445

Ala Phe Arg Ala Asn Ser Ala Asn Pro Asp Trp Asp Phe Asn Pro Asn
    450                 455                 460

Lys Asp Thr Trp Pro Asp Ala Asn Lys Val Gly Gly Gln Asn Leu Ser
465                 470                 475                 480

Thr Ser Asn Pro Leu Gly Phe Phe Pro Asp His Gln Leu Asp Pro Ala
                485                 490                 495

Phe Arg Ala Asn Thr Ala Asn Pro Asp Trp Asp Phe Asn Pro Asn Lys
            500                 505                 510

Asp Thr Trp Pro Asp Ala Asn Lys Val Gly
        515                 520
```

<210> SEQ ID NO 50
<211> LENGTH: 1278
<212> TYPE: DNA
<213> ORGANISM: Artificial Sequence
<220> FEATURE:
<223> OTHER INFORMATION: Delta 9 wt

<400> SEQUENCE: 50

```
agccgcagcg aaagcaaaaa aaaccgcggc ggccgcgaag aaattctgga acagtgggtg     60

ggcgcgcgca aaaaactgga agaactggaa cgcgatctgc gcaaaattaa aaaaaaaatt    120

aaaaaactgg aagaagaaaa cccgtggctg ggcaacatta aaggcattct gggcaaaaaa    180

gatcgcgaag gcgaaggcgc gccgccggcg aaacgcgcgc gcgcggatca gatggaagtg    240

gatagcggcc cgcgcaaacg cccgtttcgc ggcgaattta ccgataaaga acgccgcgat    300

catcgccgcc gcaaagcgct ggaaaacaaa cgcaaacagc tgagcagcgg cggcaaaagc    360

ctgagcaaag aagaagaaga agaactgcgc aaactgaccg aagaagatga acgccgcgaa    420

cgccgcgtgg cgggcccgcg cgtgggcggc gtgaacccgc tggaaggcgg cacccgcggc    480

gcgccgggcg gcggctttgt gccgagcatg cagggcgtgc cggaaagccc gtttgcgcgc    540

accggcgaag gcctggatgt gcgcggcaac cagggctttc cgtgggatat tctgtttccg    600

gcggatccgc cgtttagccc gcagagctgc cgcccgcaga gccgcagcga aagcaaaaaa    660

aaccgcggcg gccgcgaaga agtgctggaa cagtgggtga acggccgcaa aaaactggaa    720

gaactggaac gcgaactgcg ccgcgcgcgc aaaaaaatta aaaaactgga agatgataac    780

ccgtggctgg gcaacgtgaa aggcattctg ggcaaaaaag ataaagatgg cgaaggcgcg    840

ccgccggcga aacgcgcgcg caccgatcag atggaaattg atagcggccc gcgcaaacgc    900

ccgctgcgcg gcggctttac cgatcgcgaa cgccaggatc atcgccgccg caaagcgctg    960

aaaaacaaaa aaaaacagct gagcgcgggc ggcaaaagcc tgagcaaaga agaagaagaa   1020
```

```
gaactgaaac gcctgacccg cgaagatgaa gaacgcaaaa aagaagaaca tggccccgagc   1080

cgcctgggcg tgaacccgag cgaaggcggc ccgcgcggcg cgccgggcgg cggctttgtg   1140

ccgagcatgc agggcattcc ggaaagccgc tttacccgca ccggcgaagg cctggatgtg   1200

cgcggcagcc gcggctttcc gcaggatatt ctgtttccga gcgatccgcc gtttagcccg   1260

cagagctgcc gcccgcag                                                  1278
```

```
<210> SEQ ID NO 51
<211> LENGTH: 1310
<212> TYPE: DNA
<213> ORGANISM: Artificial Sequence
<220> FEATURE:
<223> OTHER INFORMATION: Delta 9 wt with restriction sites (HindIII
      /EcoRI)

<400> SEQUENCE: 51

aagcttgcac catggccagc cgcagcgaaa gcaaaaaaaa ccgcggcggc cgcgaagaaa     60

ttctggaaca gtgggtgggc gcgcgcaaaa aactggaaga actggaacgc gatctgcgca    120

aaattaaaaa aaaaattaaa aaactggaag aagaaaaccc gtggctgggc aacattaaag    180

gcattctggg caaaaaagat cgcgaaggcg aaggcgcgcc gccggcgaaa cgcgcgcgcg    240

cggatcagat ggaagtggat agcggcccgc gcaaacgccc gtttcgcggc gaatttaccg    300

ataaagaacg ccgcgatcat cgccgccgca aagcgctgga aaacaaacgc aaacagctga    360

gcagcggcgg caaaagcctg agcaaagaag aagaagaaga actgcgcaaa ctgaccgaag    420

aagatgaacg ccgcgaacgc cgcgtggcgg gcccgcgcgt gggcggcgtg aacccgctgg    480

aaggcggcac ccgcggcgcg ccgggcggcg gctttgtgcc gagcatgcag ggcgtgccgg    540

aaagcccgtt tgcgcgcacc ggcgaaggcc tggatgtgcg cggcaaccag ggctttccgt    600

gggatattct gtttccggcg gatccgccgt ttagcccgca gagctgccgc ccgcagagcc    660

gcagcgaaag caaaaaaaac cgcggcggcc gcgaagaagt gctggaacag tgggtgaacg    720

gccgcaaaaa actggaagaa ctggaacgcg aactgcgccg cgcgcgcaaa aaaattaaaa    780

aactggaaga tgataacccg tggctgggca acgtgaaagg cattctgggc aaaaaagata    840

aagatggcga aggcgcgccg ccggcgaaac gcgcgcgcac cgatcagatg gaaattgata    900

gcggcccgcg caaacgcccg ctgcgcggcg gctttaccga tcgcgaacgc caggatcatc    960

gccgccgcaa agcgctgaaa aacaaaaaaa aacagctgag cgcgggcggc aaaagcctga   1020

gcaaagaaga agaagaagaa ctgaaacgcc tgacccgcga agatgaagaa cgcaaaaaag   1080

aagaacatgg cccgagccgc ctgggcgtga acccgagcga aggcggcccg cgcggcgcgc   1140

cgggcggcgg ctttgtgccg agcatgcagg gcattccgga aagccgcttt acccgcaccg   1200

gcgaaggcct ggatgtgcgc ggcagccgcg gctttccgca ggatattctg tttccgagcg   1260

atccgccgtt tagcccgcag agctgccgcc cgcagtgatg agaattccgt              1310
```

```
<210> SEQ ID NO 52
<211> LENGTH: 1281
<212> TYPE: DNA
<213> ORGANISM: Artificial Sequence
<220> FEATURE:
<223> OTHER INFORMATION: Delta 9 codon optimized

<400> SEQUENCE: 52

gccagtcgga gcgaatcaaa gaaaaataga gggggaagag aagaaatcct ggagcagtgg     60

gtcggggcac ggaaaaaact ggaagaactg gagcgggacc tgagaaagat caagaagaag    120
```

```
atcaagaagc tggaggaaga gaacccctgg ctgggcaata tcaagggcat cctgggcaag    180

aaggataggg agggcgaggg agcaccacct gcaaagaggg caagggcaga ccagatggag    240

gtggattccg gaccaaggaa gcggcccttc cggggagagt ttaccgacaa ggagcggaga    300

gatcacaggc gccggaaggc cctggagaac aagcggaagc agctgagctc cggcggcaag    360

tctctgagca aggaggagga ggaggagctg agaaagctga cagaggagga cgagagaagg    420

gagaggaggg tggcaggacc tagggtggga ggcgtgaacc cactggaggg aggaaccagg    480

ggagcacctg gaggaggctt tgtgccatct atgcagggag tgccagagag ccctttcgcc    540

aggacaggag agggcctgga tgtgcgcggc aatcagggct tcccctggga catcctgttt    600

cctgccgatc cacccttcag cccacagtcc tgcaggccac agtcccgctc tgagagcaag    660

aagaacaggg gaggaaggga ggaggtgctg gagcagtggg tgaatggccg gaagaagctg    720

gaggagctgg agcgggagct gagaagggcc agaaagaaga tcaagaagct ggaagacgat    780

aatccttggc tgggcaatgt gaaaggcatc ctgggcaaga aggacaagga tggagaggga    840

gcacctccag caaagagggc acgcaccgac cagatggaga tcgattctgg acctaggaag    900

cggcccctga gaggaggctt tacagacagg gagcgccagg atcaccgccg gagaaaggcc    960

ctgaagaaca agaagaagca gctgagcgcc ggcggcaagt ccctgtctaa agaagaggag   1020

gaggagctga agcggctgac cagagaggac gaggagcgga agaaggagga gcacggacca   1080

tccagactgg gagtgaatcc ttctgaggga ggaccaagag gcgccccagg cggcggcttt   1140

gtgccaagca tgcagggcat ccccgagtcc aggttcacca gaaccggcga aggcctggat   1200

gtgcggggca gcagaggctt cccccaggat attctgtttc cctccgaccc cccctcagt    1260

ccccagtctt gccgacctca g                                             1281
```

<210> SEQ ID NO 53
<211> LENGTH: 1310
<212> TYPE: DNA
<213> ORGANISM: Artificial Sequence
<220> FEATURE:
<223> OTHER INFORMATION: Delta 9 codon optimized with restriction sites (HindIII /EcoRI)

<400> SEQUENCE: 53

```
aagcttgcac catggccagt cggagcgaat caaagaaaaa tagaggggga agagaagaaa     60

tcctggagca gtgggtcggg gcacggaaaa aactggaaga actggagcgg gacctgagaa    120

agatcaagaa gaagatcaag aagctggagg aagagaaccc ctggctgggc aatatcaagg    180

gcatcctggg caagaaggat agggagggcg agggagcacc acctgcaaag agggcaaggg    240

cagaccagat ggaggtggat tccggaccaa ggaagcggcc cttccgggga gagtttaccg    300

acaaggagcg gagagatcac aggcgccgga aggccctgga gaacaagcgg aagcagctga    360

gctccggcgg caagtctctg agcaaggagg aggaggagga gctgagaaag ctgacagagg    420

aggacgagag aagggagagg agggtggcag gacctagggt gggaggcgtg aacccactgg    480

agggaggaac caggggagca cctggaggag gctttgtgcc atctatgcag ggagtgccag    540

agagcccttt cgccaggaca ggagagggcc tggatgtgcg cggcaatcag ggcttcccct    600

gggacatcct gtttcctgcc gatccaccct tcagcccaca gtcctgcagg ccacagtccc    660

gctctgagag caagaagaac aggggaggaa gggaggaggt gctggagcag tgggtgaatg    720

gccggaagaa gctggaggag ctggagcggg agctgagaag ggccagaaag aagatcaaga    780

agctggaaga cgataatcct tggctgggca atgtgaaagg catcctgggc aagaaggaca    840
```

-continued

```
aggatggaga gggagcacct ccagcaaaga gggcacgcac cgaccagatg gagatcgatt    900

ctggacctag gaagcggccc ctgagaggag gctttacaga cagggagcgc caggatcacc    960

gccggagaaa ggccctgaag aacaagaaga agcagctgag cgccggcggc aagtccctgt   1020

ctaaagaaga ggaggaggag ctgaagcggc tgaccagaga ggacgaggag cggaagaagg   1080

aggagcacgg accatccaga ctgggagtga atccttctga gggaggacca agaggcgccc   1140

caggcggcgg ctttgtgcca agcatgcagg gcatccccga gtccaggttc accagaaccg   1200

gcgaaggcct ggatgtgcgg ggcagcagag gcttccccca ggatattctg tttccctccg   1260

accccccctt cagtccccag tcttgccgac ctcagtgatg agaattccgt              1310
```

<210> SEQ ID NO 54
<211> LENGTH: 428
<212> TYPE: PRT
<213> ORGANISM: Artificial Sequence
<220> FEATURE:
<223> OTHER INFORMATION: Delta 9 protein

<400> SEQUENCE: 54

```
Met Ala Ser Arg Ser Glu Ser Lys Lys Asn Arg Gly Gly Arg Glu Glu
1               5                   10                  15

Ile Leu Glu Gln Trp Val Gly Ala Arg Lys Lys Leu Glu Glu Leu Glu
            20                  25                  30

Arg Asp Leu Arg Lys Ile Lys Lys Lys Ile Lys Lys Leu Glu Glu Glu
        35                  40                  45

Asn Pro Trp Leu Gly Asn Ile Lys Gly Ile Leu Gly Lys Lys Asp Arg
    50                  55                  60

Glu Gly Glu Gly Ala Pro Pro Ala Lys Arg Ala Arg Ala Asp Gln Met
65                  70                  75                  80

Glu Val Asp Ser Gly Pro Arg Lys Arg Pro Phe Arg Gly Glu Phe Thr
                85                  90                  95

Asp Lys Glu Arg Arg Asp His Arg Arg Arg Lys Ala Leu Glu Asn Lys
            100                 105                 110

Arg Lys Gln Leu Ser Ser Gly Gly Lys Ser Leu Ser Lys Glu Glu Glu
        115                 120                 125

Glu Glu Leu Arg Lys Leu Thr Glu Glu Asp Glu Arg Arg Glu Arg Arg
    130                 135                 140

Val Ala Gly Pro Arg Val Gly Gly Val Asn Pro Leu Glu Gly Gly Thr
145                 150                 155                 160

Arg Gly Ala Pro Gly Gly Gly Phe Val Pro Ser Met Gln Gly Val Pro
                165                 170                 175

Glu Ser Pro Phe Ala Arg Thr Gly Glu Gly Leu Asp Val Arg Gly Asn
            180                 185                 190

Gln Gly Phe Pro Trp Asp Ile Leu Phe Pro Ala Asp Pro Pro Phe Ser
        195                 200                 205

Pro Gln Ser Cys Arg Pro Gln Ser Arg Ser Glu Ser Lys Lys Asn Arg
    210                 215                 220

Gly Gly Arg Glu Glu Val Leu Glu Gln Trp Val Asn Gly Arg Lys Lys
225                 230                 235                 240

Leu Glu Glu Leu Glu Arg Glu Leu Arg Arg Ala Arg Lys Lys Ile Lys
                245                 250                 255

Lys Leu Glu Asp Asp Asn Pro Trp Leu Gly Asn Val Lys Gly Ile Leu
            260                 265                 270

Gly Lys Lys Asp Lys Asp Gly Glu Gly Ala Pro Pro Ala Lys Arg Ala
        275                 280                 285
```

```
Arg Thr Asp Gln Met Glu Ile Asp Ser Gly Pro Arg Lys Arg Pro Leu
    290                 295                 300

Arg Gly Gly Phe Thr Asp Arg Glu Arg Gln Asp His Arg Arg Arg Lys
305                 310                 315                 320

Ala Leu Lys Asn Lys Lys Lys Gln Leu Ser Ala Gly Gly Lys Ser Leu
                325                 330                 335

Ser Lys Glu Glu Glu Glu Glu Leu Lys Arg Leu Thr Arg Glu Asp Glu
            340                 345                 350

Glu Arg Lys Lys Glu Glu His Gly Pro Ser Arg Leu Gly Val Asn Pro
        355                 360                 365

Ser Glu Gly Gly Pro Arg Gly Ala Pro Gly Gly Gly Phe Val Pro Ser
    370                 375                 380

Met Gln Gly Ile Pro Glu Ser Arg Phe Thr Arg Thr Gly Glu Gly Leu
385                 390                 395                 400

Asp Val Arg Gly Ser Arg Gly Phe Pro Gln Asp Ile Leu Phe Pro Ser
                405                 410                 415

Asp Pro Pro Phe Ser Pro Gln Ser Cys Arg Pro Gln
            420                 425


<210> SEQ ID NO 55
<211> LENGTH: 1278
<212> TYPE: DNA
<213> ORGANISM: Artificial Sequence
<220> FEATURE:
<223> OTHER INFORMATION: Delta 10 wt

<400> SEQUENCE: 55

agccagagcg aaacccgccg cggccgccgc ggcacccgcg aagaaaccct ggaaaaatgg     60

attaccgcgc gcaaaaaagc ggaagaactg gaaaaagatc tgcgcaaaac ccgcaaaacc    120

attaaaaaac tggaagaaga aaacccgtgg ctgggcaaca ttgtgggcat tattcgcaaa    180

ggcaaagatg gcgaaggcgc gccgccggcg aaacgcccgc gcaccgatca gatggaagtg    240

gatagcggcc cgggcaaacg cccgcataaa agcggcttta ccgataaaga acgcgaagat    300

catcgccgcc gcaaagcgct ggaaaacaaa aaaaaacagc tgagcgcggg cggcaaaatt    360

ctgagcaaag aagaagaaga agaactgcgc cgcctgaccg atgaagatga agaacgcaaa    420

cgccgcgtgg cgggcccgcg cgtgggcgat gtgaacccga gccgcggcgg cccgcgcggc    480

gcgccgggcg gcggctttgt gccgcagatg gcgggcgtgc cggaaagccc gtttagccgc    540

accggcgaag gcctggatat tcgcggcacc cagggctttc cgtgggtgag cccgagcccg    600

ccgcagcagc gcctgccgct gctggaatgc accccgcaga gccagagcga aagcaaaaaa    660

aaccgccgcg gcggccgcga agatattctg gaaaaatgga ttaccacccg ccgcaaagcg    720

gaagaactgg aaaaagatct gcgcaaagcg cgcaaaacca ttaaaaaact ggaagatgaa    780

aacccgtggc tgggcaacat tattggcatt attcgcaaag gcaaagatgg cgaaggcgcg    840

ccgccggcga aacgcccgcg caccgatcag atggaaattg atagcggcac cggcaaacgc    900

ccgcataaaa gcggctttac cgataaagaa cgcgaagatc atcgccgccg caaagcgctg    960

gaaaacaaaa aaaaacagct gagcagcggc ggcaaaaacc tgagccgcga agaagaagaa   1020

gaactgggcc gcctgaccgt ggaagatgaa gaacgccgcc gccgcgtggc gggcccgcgc   1080

accggcgatg tgaacctgag cggcggcggc ccgcgcggcg cgccgggcgg cggctttgtg   1140

ccgcgcatgg aaggcgtgcc ggaaagcccg tttacccgca ccggcgaagg cctggatatt   1200

cgcggcaacc agggctttcc gtgggtgcgc ccgagcccgc cgcagcagcg cctgccgctg   1260
```

ctggaatgca ccccgcag 1278

<210> SEQ ID NO 56
<211> LENGTH: 1310
<212> TYPE: DNA
<213> ORGANISM: Artificial Sequence
<220> FEATURE:
<223> OTHER INFORMATION: Delta 10 wt with restriction sites (HindIII /EcoRI)

<400> SEQUENCE: 56
aagcttgcac catggccagc cagagcgaaa cccgccgcgg ccgccgcggc acccgcgaag 60
aaaccctgga aaaatggatt accgcgcgca aaaaagcgga agaactggaa aaagatctgc 120
gcaaaacccg caaaaccatt aaaaaactgg aagaagaaaa cccgtggctg ggcaacattg 180
tgggcattat tcgcaaaggc aaagatggcg aaggcgcgcc gccggcgaaa cgcccgcgca 240
ccgatcagat ggaagtggat agcggcccgg gcaaacgccc gcataaaagc ggctttaccg 300
ataaagaacg cgaagatcat cgccgccgca aagcgctgga aacaaaaaa aaacagctga 360 gcgcgggcgg caaaattctg agcaaagaag aagaagaaga actgcgccgc ctgaccgatg 420
aagatgaaga acgcaaacgc cgcgtggcgg gcccgcgcgt gggcgatgtg aacccgagcc 480
gcggcggccc gcgcggcgcg ccgggcggcg gctttgtgcc gcagatggcg ggcgtgccgg 540
aaagcccgtt tagccgcacc ggcgaaggcc tggatattcg cggcacccag ggctttccgt 600
gggtgagccc gagcccgccg cagcagcgcc tgccgctgct ggaatgcacc ccgcagagcc 660
agagcgaaag caaaaaaaac cgcccgcggcg gccgcgaaga tattctggaa aaatggatta 720
ccacccgccg caaagcggaa gaactggaaa aagatctgcg caaagcgcgc aaaaccatta 780
aaaaactgga agatgaaaac ccgtggctgg gcaacattat tggcattatt cgcaaaggca 840
aagatggcga aggcgcgccg ccggcgaaac gcccgcgcac cgatcagatg gaaattgata 900
gcggcaccgg caaacgcccg cataaaagcg gctttaccga taaagaacgc gaagatcatc 960
gccgccgcaa agcgctggaa aacaaaaaaa aacagctgag cagcggcggc aaaaacctga 1020
gccgcgaaga agaagaagaa ctgggccgcc tgaccgtgga agatgaagaa cgccgccgcc 1080
gcgtggcggg cccgcgcacc ggcgatgtga acctgagcgg cggcggcccg cgcggcgcgc 1140
cgggcggcgg ctttgtgccg cgcatggaag gcgtgccgga aagcccgttt acccgcaccg 1200
gcgaaggcct ggatattcgc ggcaaccagg gctttccgtg ggtgcgcccg agcccgccgc 1260
agcagcgcct gccgctgctg gaatgcaccc cgcagtgatg agaattccgt 1310

<210> SEQ ID NO 57
<211> LENGTH: 1281
<212> TYPE: DNA
<213> ORGANISM: Artificial Sequence
<220> FEATURE:
<223> OTHER INFORMATION: Delta 10 codon optimized

<400> SEQUENCE: 57
gcctcacaga gcgaaacacg gcgggggcgg aggggaacta gagaggaaac actggaaaaa 60
tggattacag cacggaaaaa ggcagaggaa ctggagaagg acctgaggaa gacccgcaag 120
acaatcaaga agctggagga ggagaaccca tggctgggca atatcgtggg catcatccgg 180
aagggcaagg atggagaggg agcaccacct gcaaagaggc cccgcaccga ccagatggag 240
gtggattctg gccctggcaa gaggccacac aagagcggct tcacagacaa ggagcgcgag 300
gatcaccgga gaaggaaggc cctggagaac aagaagaagc agctgagcgc cggcggcaag 360

```
atcctgtcca aggaggagga ggaggagctg cgccggctga ccgacgagga tgaggagcgg    420

aagagaaggg tggcaggacc aagagtgggc gacgtgaatc cctctagggg aggaccaagg    480

ggagcacctg gaggaggctt cgtgcctcag atggcaggag tgccagagtc cccttttttct   540

aggaccggag agggcctgga tatcagggga acacagggct ttccatgggt gtctccaagc    600

ccaccacagc agaggctgcc actgctggag tgcacccctc agtcccagtc tgagagcaag    660

aagaacagga ggggaggaag ggaggacatc ctggagaagt ggatcaccac aagaaggaag    720

gccgaggagc tggagaagga cctgcggaag gccagaaaaa caatcaagaa gctggaagat    780

gagaacccct ggctgggcaa tatcatcggc atcatcagaa aaggcaagga cggcgaggga    840

gcacctccag caaagcggcc tagaaccgac cagatggaga tcgattccgg cacaggcaag    900

cggccacaca agtctggctt caccgacaag gagagagagg atcaccgccg gagaaaggcc    960

ctggaaaaca agaagaagca attaagctcc ggcggcaaga atctgagcag agaagaagag   1020

gaggagctgg gcagactgac cgtggaggac gaggagaggc gccggagagt ggcaggaccc   1080

agaacaggcg atgtgaacct gagcggagga ggacctaggg gagcaccagg aggcggcttc   1140

gtgcctagaa tggagggcgt gccagagtcc cccttttacca ggacaggaga gggcctggac  1200

atcaggggca atcagggctt tccctgggtc cgcccttcac caccacagca gagactgccc   1260

ctgctggaat gcacaccaca g                                             1281
```

<210> SEQ ID NO 58
<211> LENGTH: 1310
<212> TYPE: DNA
<213> ORGANISM: Artificial Sequence
<220> FEATURE:
<223> OTHER INFORMATION: Delta 10 codon optimized with restriction sites (HindIII /EcoRI)

<400> SEQUENCE: 58

```
aagcttgcac catggcctca cagagcgaaa cacggcgggg gcggagggga actagagagg     60

aaacactgga aaaatggatt acagcacgga aaaaggcaga ggaactggag aaggacctga    120

ggaagacccg caagacaatc aagaagctgg aggaggagaa cccatggctg ggcaatatcg    180

tgggcatcat ccggaagggc aaggatggag agggagcacc acctgcaaag aggccccgca    240

ccgaccagat ggaggtggat tctggccctg gcaagaggcc acacaagagc ggcttcacag    300

acaaggagcg cgaggatcac cggagaagga aggccctgga gaacaagaag aagcagctga    360

gcgccggcgg caagatcctg tccaaggagg aggaggagga gctgcgccgg ctgaccgacg    420

aggatgagga gcggaagaga agggtggcag gaccaagagt gggcgacgtg aatccctcta    480

ggggaggacc aaggggagca cctggaggag gcttcgtgcc tcagatggca ggagtgccag    540

agtcccccttt ttctaggacc ggagagggcc tggatatcag gggaacacag ggctttccat   600

gggtgtctcc aagcccacca cagcagaggc tgccactgct ggagtgcacc cctcagtccc    660

agtctgagag caagaagaac aggaggggag gaagggagga catcctggag aagtggatca    720

ccacaagaag gaaggccgag gagctggaga aggacctgcg gaaggccaga aaaacaatca    780

agaagctgga agatgagaac ccctggctgg gcaatatcat cggcatcatc agaaaaggca    840

aggacggcga gggagcacct ccagcaaagc ggcctagaac cgaccagatg gagatcgatt    900

ccggcacagg caagcggcca cacaagtctg gcttcaccga caaggagaga gaggatcacc    960

gccggagaaa ggccctggaa aacaagaaga agcaattaag ctccggcggc aagaatctga   1020

gcagagaaga agaggaggag ctgggcagac tgaccgtgga ggacgaggag aggcgccgga   1080
```

```
gagtggcagg acccagaaca ggcgatgtga acctgagcgg aggaggacct aggggagcac   1140

caggaggcgg cttcgtgcct agaatggagg gcgtgccaga gtccccccttt accaggacag  1200

gagagggcct ggacatcagg ggcaatcagg gctttccctg ggtccgccct tcaccaccac   1260

agcagagact gcccctgctg gaatgcacac cacagtgatg agaattccgt              1310
```

```
<210> SEQ ID NO 59
<211> LENGTH: 428
<212> TYPE: PRT
<213> ORGANISM: Artificial Sequence
<220> FEATURE:
<223> OTHER INFORMATION: Delta 10 protein

<400> SEQUENCE: 59

Met Ala Ser Gln Ser Glu Thr Arg Arg Gly Arg Arg Gly Thr Arg Glu
1               5                   10                  15

Glu Thr Leu Glu Lys Trp Ile Thr Ala Arg Lys Lys Ala Glu Glu Leu
            20                  25                  30

Glu Lys Asp Leu Arg Lys Thr Arg Lys Thr Ile Lys Lys Leu Glu Glu
        35                  40                  45

Glu Asn Pro Trp Leu Gly Asn Ile Val Gly Ile Ile Arg Lys Gly Lys
    50                  55                  60

Asp Gly Glu Gly Ala Pro Pro Ala Lys Arg Pro Arg Thr Asp Gln Met
65                  70                  75                  80

Glu Val Asp Ser Gly Pro Gly Lys Arg Pro His Lys Ser Gly Phe Thr
                85                  90                  95

Asp Lys Glu Arg Glu Asp His Arg Arg Arg Lys Ala Leu Glu Asn Lys
            100                 105                 110

Lys Lys Gln Leu Ser Ala Gly Gly Lys Ile Leu Ser Lys Glu Glu Glu
        115                 120                 125

Glu Glu Leu Arg Arg Leu Thr Asp Glu Asp Glu Glu Arg Lys Arg Arg
    130                 135                 140

Val Ala Gly Pro Arg Val Gly Asp Val Asn Pro Ser Arg Gly Gly Pro
145                 150                 155                 160

Arg Gly Ala Pro Gly Gly Gly Phe Val Pro Gln Met Ala Gly Val Pro
                165                 170                 175

Glu Ser Pro Phe Ser Arg Thr Gly Glu Gly Leu Asp Ile Arg Gly Thr
            180                 185                 190

Gln Gly Phe Pro Trp Val Ser Pro Ser Pro Pro Gln Gln Arg Leu Pro
        195                 200                 205

Leu Leu Glu Cys Thr Pro Gln Ser Gln Ser Glu Ser Lys Lys Asn Arg
    210                 215                 220

Arg Gly Gly Arg Glu Asp Ile Leu Glu Lys Trp Ile Thr Thr Arg Arg
225                 230                 235                 240

Lys Ala Glu Glu Leu Glu Lys Asp Leu Arg Lys Ala Arg Lys Thr Ile
                245                 250                 255

Lys Lys Leu Glu Asp Glu Asn Pro Trp Leu Gly Asn Ile Ile Gly Ile
            260                 265                 270

Ile Arg Lys Gly Lys Asp Gly Glu Gly Ala Pro Pro Ala Lys Arg Pro
        275                 280                 285

Arg Thr Asp Gln Met Glu Ile Asp Ser Gly Thr Gly Lys Arg Pro His
    290                 295                 300

Lys Ser Gly Phe Thr Asp Lys Glu Arg Glu Asp His Arg Arg Arg Lys
305                 310                 315                 320
```

```
Ala Leu Glu Asn Lys Lys Lys Gln Leu Ser Ser Gly Gly Lys Asn Leu
                325                 330                 335

Ser Arg Glu Glu Glu Glu Glu Leu Gly Arg Leu Thr Val Glu Asp Glu
            340                 345                 350

Glu Arg Arg Arg Arg Val Ala Gly Pro Arg Thr Gly Asp Val Asn Leu
        355                 360                 365

Ser Gly Gly Gly Pro Arg Gly Ala Pro Gly Gly Gly Phe Val Pro Arg
    370                 375                 380

Met Glu Gly Val Pro Glu Ser Pro Phe Thr Arg Thr Gly Glu Gly Leu
385                 390                 395                 400

Asp Ile Arg Gly Asn Gln Gly Phe Pro Trp Val Arg Pro Ser Pro Pro
                405                 410                 415

Gln Gln Arg Leu Pro Leu Leu Glu Cys Thr Pro Gln
            420                 425


<210> SEQ ID NO 60
<211> LENGTH: 546
<212> TYPE: DNA
<213> ORGANISM: Artificial Sequence
<220> FEATURE:
<223> OTHER INFORMATION: Core 1 wt (C-gt-H)

<400> SEQUENCE: 60

gatattgatc cgtataaaga atttggcgcg agcgtggaac tgctgagctt tctgccgagc      60

gatttttttc cgagcgtgcg cgatctgctg gataccgcga gcgcgctgta tcgcgatgcg     120

ctggaaagcc cggaacattg caccccgaac cataccgcgc tgcgccaggc gattctgtgc     180

tggggcgaac tgatgaccct ggcgagctgg gtgggcaaca acctggaaga tccggcggcg     240

cgcgatctgg tggtgaacta tgtgaacacc aacatgggcc tgaaaattcg ccagctgctg     300

tggtttcata ttagctgcct gacctttggc cgcgaaaccg tgctggaata tctggtgagc     360

tttggcgtgt ggattcgcac cccgccggcg tatcgcccgc cgaacgcgcc gattctgagc     420

accctgccgg aaaccaccgt ggtgcgccag cgcggccgcg cgccgcgccg ccgcaccccg     480

agcccgcgcc gccgccgcag ccagagcccg cgccgccgcc gcagccagag cccggcgagc     540

cagtgc                                                                546


<210> SEQ ID NO 61
<211> LENGTH: 575
<212> TYPE: DNA
<213> ORGANISM: Artificial Sequence
<220> FEATURE:
<223> OTHER INFORMATION: Core 1 wt with restriction sites (HindIII
      /EcoRI)

<400> SEQUENCE: 61

aagcttgcac catggatatt gatccgtata aagaatttgg cgcgagcgtg gaactgctga      60

gctttctgcc gagcgatttt tttccgagcg tgcgcgatct gctggatacc gcgagcgcgc     120

tgtatcgcga tgcgctggaa agcccggaac attgcacccc gaaccatacc gcgctgcgcc     180

aggcgattct gtgctggggc gaactgatga ccctggcgag ctgggtgggc aacaacctgg     240

aagatccggc ggcgcgcgat ctggtggtga actatgtgaa caccaacatg ggcctgaaaa     300

ttcgccagct gctgtggttt catattagct gcctgacctt tggccgcgaa accgtgctgg     360

aatatctggt gagctttggc gtgtggattc gcaccccgcc ggcgtatcgc ccgccgaacg     420

cgccgattct gagcaccctg ccggaaacca ccgtggtgcg ccagcgcggc cgcgcgccgc     480

gccgccgcac cccgagcccg cgccgccgcc gcagccagag cccgcgccgc cgccgcagcc     540
```

agagcccggc gagccagtgc tgatgagaat tccgt 575

<210> SEQ ID NO 62
<211> LENGTH: 546
<212> TYPE: DNA
<213> ORGANISM: Artificial Sequence
<220> FEATURE:
<223> OTHER INFORMATION: Core 1 codon optimized

<400> SEQUENCE: 62
gatattgatc cctataagga gtttggagcc tctgtggagc tgctgagttt tctgccatcc 60
gatttctttc ccagtgtccg agacctgctg gacaccgcaa gcgccctgta cagggatgca 120
ctggagtccc cagagcactg cacccctaac cacacagccc tgaggcaggc aatcctgtgc 180
tggggagagc tgatgaccct ggcaagctgg gtgggcaaca atctggagga ccctgcagca 240
cgggatctgg tggtgaatta tgtgaacaca aatatgggcc tgaagatccg gcagctgctg 300
tggttccaca tctcttgcct gacctttggc agagagacag tgctggagta cctggtgagc 360
ttcggcgtgt ggatcaggac ccccacctgca tataggccac caaacgcacc aatcctgtcc 420
acactgccag agacaacagt ggtgcgccag aggggaagag caccacggag aaggacacct 480
tctccaagac gaaggcgaag ccagagcccc aggcgaagac gaagccagtc cccagcaagc 540
cagtgc 546

<210> SEQ ID NO 63
<211> LENGTH: 575
<212> TYPE: DNA
<213> ORGANISM: Artificial Sequence
<220> FEATURE:
<223> OTHER INFORMATION: Core 1 codon optimized with restriction sites (HindIII /EcoRI)

<400> SEQUENCE: 63
aagcttgcac catggatatt gatccctata aggagtttgg agcctctgtg gagctgctga 60
gttttctgcc atccgatttc tttcccagtg tccgagacct gctggacacc gcaagcgccc 120
tgtacaggga tgcactggag tccccagagc actgcacccc taaccacaca gccctgaggc 180
aggcaatcct gtgctgggga gagctgatga ccctggcaag ctgggtgggc aacaatctgg 240
aggaccctgc agcacgggat ctggtggtga attatgtgaa cacaaatatg ggcctgaaga 300
tccggcagct gctgtggttc cacatctctt gcctgacctt tggcagagag acagtgctgg 360
agtacctggt gagcttcggc gtgtggatca ggaccccacc tgcatatagg ccaccaaacg 420
caccaatcct gtccacactg ccagagacaa cagtggtgcg ccagagggga agagcaccac 480
ggagaaggac accttctcca agacgaaggc gaagccagag ccccaggcga agacgaagcc 540
agtccccagc aagccagtgc tgatgagaat tccgt 575

<210> SEQ ID NO 64
<211> LENGTH: 183
<212> TYPE: PRT
<213> ORGANISM: Artificial Sequence
<220> FEATURE:
<223> OTHER INFORMATION: Core 1 protein

<400> SEQUENCE: 64

Met Asp Ile Asp Pro Tyr Lys Glu Phe Gly Ala Ser Val Glu Leu Leu
1 5 10 15

Ser Phe Leu Pro Ser Asp Phe Phe Pro Ser Val Arg Asp Leu Leu Asp
20 25 30

-continued

Thr Ala Ser Ala Leu Tyr Arg Asp Ala Leu Glu Ser Pro Glu His Cys
35 40 45

Thr Pro Asn His Thr Ala Leu Arg Gln Ala Ile Leu Cys Trp Gly Glu
50 55 60

Leu Met Thr Leu Ala Ser Trp Val Gly Asn Asn Leu Glu Asp Pro Ala
65 70 75 80

Ala Arg Asp Leu Val Val Asn Tyr Val Asn Thr Asn Met Gly Leu Lys
85 90 95

Ile Arg Gln Leu Leu Trp Phe His Ile Ser Cys Leu Thr Phe Gly Arg
100 105 110

Glu Thr Val Leu Glu Tyr Leu Val Ser Phe Gly Val Trp Ile Arg Thr
115 120 125

Pro Pro Ala Tyr Arg Pro Pro Asn Ala Pro Ile Leu Ser Thr Leu Pro
130 135 140

Glu Thr Thr Val Val Arg Gln Arg Gly Arg Ala Pro Arg Arg Arg Thr
145 150 155 160

Pro Ser Pro Arg Arg Arg Arg Ser Gln Ser Pro Arg Arg Arg Arg Ser
165 170 175

Gln Ser Pro Ala Ser Gln Cys
180

<210> SEQ ID NO 65
<211> LENGTH: 633
<212> TYPE: DNA
<213> ORGANISM: Artificial Sequence
<220> FEATURE:
<223> OTHER INFORMATION: Pre-C-gt-H wt

<400> SEQUENCE: 65
cagctgtttc atctgtgcct gattattttt tgcagctgcc cgaccgtgca ggcgagcaaa 60
ctgtgcctgg gctggctgtg gggcatggat attgatccgt ataaagaatt tggcgcgagc 120
gtggaactgc tgagctttct gccgagcgat ttttttccga gcgtgcgcga tctgctggat 180
accgcgagcg cgctgtatcg cgatgcgctg gaaagcccgg aacattgcac cccgaaccat 240
accgcgctgc gccaggcgat tctgtgctgg ggcgaactga tgaccctggc gagctgggtg 300
ggcaacaacc tggaagatcc ggcggcgcgc gatctggtgg tgaactatgt gaacaccaac 360
atgggcctga aaattcgcca gctgctgtgg tttcatatta gctgcctgac ctttggccgc 420
gaaaccgtgc tggaatatct ggtgagcttt ggcgtgtgga ttcgcacccc gccggcgtat 480
cgcccgccga acgcgccgat tctgagcacc ctgccggaaa ccaccgtggt gcgccagcgc 540
ggccgcgcgc cgcgccgccg caccccgagc ccgcgccgcc gccgcagcca gagcccgcgc 600
cgccgccgca gccagagccc ggcgagccag tgc 633

<210> SEQ ID NO 66
<211> LENGTH: 665
<212> TYPE: DNA
<213> ORGANISM: Artificial Sequence
<220> FEATURE:
<223> OTHER INFORMATION: Pre-C-gt-H wt with restriction sites (HindIII /EcoRI)

<400> SEQUENCE: 66
aagcttgcac catggcccag ctgtttcatc tgtgcctgat tatttttgc agctgcccga 60 ccgtgcaggc gagcaaactg tgcctgggct ggctgtgggg catggatatt gatccgtata 120
aagaatttgg cgcgagcgtg gaactgctga gctttctgcc gagcgatttt tttccgagcg 180

-continued tgcgcgatct gctggatacc gcgagcgcgc tgtatcgcga tgcgctggaa agcccggaac 240
attgcacccc gaaccatacc gcgctgcgcc aggcgattct gtgctggggc gaactgatga 300
ccctggcgag ctgggtgggc aacaacctgg aagatccggc ggcgcgcgat ctggtggtga 360
actatgtgaa caccaacatg ggcctgaaaa ttcgccagct gctgtggttt catattagct 420
gcctgacctt tggccgcgaa accgtgctgg aatatctggt gagctttggc gtgtggattc 480
gcaccccgcc ggcgtatcgc ccgccgaacg cgccgattct gagcaccctg ccggaaacca 540
ccgtggtgcg ccagcgcggc cgcgcgccgc gccgccgcac cccgagcccg cgccgccgcc 600
gcagccagag cccgcgccgc cgccgcagcc agagcccggc gagccagtgc tgatgagaat 660
tccgt 665

<210> SEQ ID NO 67
<211> LENGTH: 636
<212> TYPE: DNA
<213> ORGANISM: Artificial Sequence
<220> FEATURE:
<223> OTHER INFORMATION: Pre-C-gt-H codon optimized

<400> SEQUENCE: 67
gcccagctgt ttcatctgtg cctgattatt ttctgttcat gccctaccgt ccaggcttct 60
aaactgtgcc tggggtggct gtggggaatg gacatcgatc cctacaagga gttcggcgcc 120
agcgtggagc tgctgagctt tctgccctcc gacttctttc cttctgtgcg ggacctgctg 180
gataccgcaa gcgccctgta tagagatgca ctggagtccc cagagcactg caccccaaac 240
cacacagccc tgaggcaggc aatcctgtgc tggggagagc tgatgaccct ggcatcctgg 300
gtgggcaaca atctggagga ccctgccgcc agagatctgg tggtgaatta cgtgaacaca 360
aatatgggcc tgaagatcag gcagctgctg tggttccaca tctcttgcct gacctttggc 420
cgcgagacag tgctggagta cctggtgagc ttcggcgtgt ggatcaggac cccacctgca 480
tataggccac caaacgcacc tatcctgtcc acactgccag agacaacagt ggtgcgccag 540
aggggaagag caccacggag aaggacacct tctccaagga ggagaagaag ccagtcccca 600
cgaagaagac gaagccagag cccagccagc cagtgt 636

<210> SEQ ID NO 68
<211> LENGTH: 665
<212> TYPE: DNA
<213> ORGANISM: Artificial Sequence
<220> FEATURE:
<223> OTHER INFORMATION: Pre-C-gt-H codon optimized with restriction
sites (HindIII /EcoRI)

<400> SEQUENCE: 68
aagcttgcac catggcccag ctgtttcatc tgtgcctgat tattttctgt tcatgcccta 60
ccgtccaggc ttctaaactg tgcctggggt ggctgtgggg aatggacatc gatccctaca 120
aggagttcgg cgccagcgtg gagctgctga gctttctgcc ctccgacttc tttccttctg 180
tgcgggacct gctggatacc gcaagcgccc tgtatagaga tgcactggag tccccagagc 240
actgcacccc aaaccacaca gccctgaggc aggcaatcct gtgctgggga gagctgatga 300
ccctggcatc ctgggtgggc aacaatctgg aggaccctgc cgccagagat ctggtggtga 360
attacgtgaa cacaaatatg ggcctgaaga tcaggcagct gctgtggttc cacatctctt 420
gcctgacctt tggccgcgag acagtgctgg agtacctggt gagcttcggc gtgtggatca 480
ggaccccacc tgcatatagg ccaccaaacg cacctatcct gtccacactg ccagagacaa 540

```
cagtggtgcg ccagagggga agagcaccac ggagaaggac accttctcca aggaggagaa    600

gaagccagtc cccacgaaga agacgaagcc agagcccagc cagccagtgt tgatgagaat    660

tccgt                                                                665


<210> SEQ ID NO 69
<211> LENGTH: 213
<212> TYPE: PRT
<213> ORGANISM: Artificial Sequence
<220> FEATURE:
<223> OTHER INFORMATION: Pre-C-gt-H protein

<400> SEQUENCE: 69

Met Ala Gln Leu Phe His Leu Cys Leu Ile Ile Phe Cys Ser Cys Pro
1               5                   10                  15

Thr Val Gln Ala Ser Lys Leu Cys Leu Gly Trp Leu Trp Gly Met Asp
            20                  25                  30

Ile Asp Pro Tyr Lys Glu Phe Gly Ala Ser Val Glu Leu Leu Ser Phe
        35                  40                  45

Leu Pro Ser Asp Phe Phe Pro Ser Val Arg Asp Leu Leu Asp Thr Ala
    50                  55                  60

Ser Ala Leu Tyr Arg Asp Ala Leu Glu Ser Pro Glu His Cys Thr Pro
65                  70                  75                  80

Asn His Thr Ala Leu Arg Gln Ala Ile Leu Cys Trp Gly Glu Leu Met
                85                  90                  95

Thr Leu Ala Ser Trp Val Gly Asn Asn Leu Glu Asp Pro Ala Ala Arg
            100                 105                 110

Asp Leu Val Val Asn Tyr Val Asn Thr Asn Met Gly Leu Lys Ile Arg
        115                 120                 125

Gln Leu Leu Trp Phe His Ile Ser Cys Leu Thr Phe Gly Arg Glu Thr
    130                 135                 140

Val Leu Glu Tyr Leu Val Ser Phe Gly Val Trp Ile Arg Thr Pro Pro
145                 150                 155                 160

Ala Tyr Arg Pro Pro Asn Ala Pro Ile Leu Ser Thr Leu Pro Glu Thr
                165                 170                 175

Thr Val Val Arg Gln Arg Gly Arg Ala Pro Arg Arg Arg Thr Pro Ser
            180                 185                 190

Pro Arg Arg Arg Arg Ser Gln Ser Pro Arg Arg Arg Arg Ser Gln Ser
        195                 200                 205

Pro Ala Ser Gln Cys
    210


<210> SEQ ID NO 70
<211> LENGTH: 633
<212> TYPE: DNA
<213> ORGANISM: Artificial Sequence
<220> FEATURE:
<223> OTHER INFORMATION: PreC-C-Mut-gt-H wt

<400> SEQUENCE: 70

cagctgtttc atctgtgcct gattattttt tgcagctgcc cgacctttca gtttccgaaa     60

ctgtgcctgg gctggctgtg gggcatggat attgatccgt ataaagaatt tggcgcgagc    120

gtggaactgc tgagctttct gccgagcgat ttttttccga gcgtgcgcga tctgctggat    180

accgcgagcg cgctgtatcg cgatgcgctg gaaagcccgg aacattgcac cccgaaccat    240

accgcgctgc gccaggcgat tctgtgctgg ggcgaactga tgaccctggc gagctgggtg    300
```

ggcaacaacc tggaagatcc ggcggcgcgc gatctggtgg tgaactatgt gaacaccaac 360
atgggcctga aaattcgcca gctgctgtgg tttcatatta gctgcctgac ctttggccgc 420
gaaaccgtgc tggaatatct ggtgagcttt ggcgtgtgga ttcgcacccc gccggcgtat 480
cgcccgccga acgcgccgat tctgagcacc ctgccggaaa ccaccgtggt gcgccagcgc 540
ggccgcgcgc cgcgccgccg caccccgagc ccgcgccgcc gccgcagcca gagcccgcgc 600
cgccgccgca gccagagccc ggcgagccag tgc 633

<210> SEQ ID NO 71
<211> LENGTH: 665
<212> TYPE: DNA
<213> ORGANISM: Artificial Sequence
<220> FEATURE:
<223> OTHER INFORMATION: PreC-C-Mut-gt-H wt with restriction sites (HindIII /EcoRI)

<400> SEQUENCE: 71
aagcttgcac catggcccag ctgtttcatc tgtgcctgat tatttttgc agctgcccga 60 cctttcagtt tccgaaactg tgcctgggct ggctgtgggg catggatatt gatccgtata 120
aagaatttgg cgcgagcgtg gaactgctga gctttctgcc gagcgatttt tttccgagcg 180
tgcgcgatct gctggatacc gcgagcgcgc tgtatcgcga tgcgctggaa agcccggaac 240
attgcacccc gaaccatacc gcgctgcgcc aggcgattct gtgctggggc gaactgatga 300
ccctggcgag ctgggtgggc aacaacctgg aagatccggc ggcgcgcgat ctggtggtga 360
actatgtgaa caccaacatg ggcctgaaaa ttcgccagct gctgtggttt catattagct 420
gcctgacctt tggccgcgaa accgtgctgg aatatctggt gagctttggc gtgtggattc 480
gcaccccgcc ggcgtatcgc ccgccgaacg cgccgattct gagcaccctg ccggaaacca 540
ccgtggtgcg ccagcgcggc cgcgcgccgc gccgccgcac cccgagcccg cgccgccgcc 600
gcagccagag cccgcgccgc cgccgcagcc agagcccggc gagccagtgc tgatgagaat 660
tccgt 665

<210> SEQ ID NO 72
<211> LENGTH: 636
<212> TYPE: DNA
<213> ORGANISM: Artificial Sequence
<220> FEATURE:
<223> OTHER INFORMATION: PreC-C-Mut-gt-H codon optimized

<400> SEQUENCE: 72
gcccagctgt ttcatctgtg cctgattatt ttctgttcat gccctacctt ccagttcccc 60
aaactgtgcc tggggtggct gtggggaatg gacatcgatc cctacaagga gttcggcgcc 120
agcgtggagc tgctgagctt tctgccctcc gacttctttc cttctgtgcg ggacctgctg 180
gataccgcaa gcgccctgta tagagatgca ctggagtccc cagagcactg caccccaaac 240
cacacagccc tgaggcaggc aatcctgtgc tggggagagc tgatgaccct ggcatcctgg 300
gtgggcaaca atctggagga ccctgccgcc agagatctgg tggtgaatta cgtgaacaca 360
aatatgggcc tgaagatcag gcagctgctg tggttccaca tctcttgcct gacctttggc 420
cgcgagacag tgctggagta cctggtgagc ttcggcgtgt ggatcaggac cccacctgca 480
tataggccac caaacgcacc tatcctgtcc acactgccag agacaacagt ggtgcgccag 540
aggggaagag caccacggag aaggacacct tctccaagga ggagaagaag ccagtcccca 600
cgaagaagac gaagccagag cccagccagc cagtgt 636

<210> SEQ ID NO 73
<211> LENGTH: 665
<212> TYPE: DNA
<213> ORGANISM: Artificial Sequence
<220> FEATURE:
<223> OTHER INFORMATION: PreC-C-Mut-gt-H codon optimized with restriction sites (HindIII /EcoRI)

<400> SEQUENCE: 73
aagcttgcac catggcccag ctgtttcatc tgtgcctgat tattttctgt tcatgcccta 60
ccttccagtt ccccaaactg tgcctggggt ggctgtgggg aatggacatc gatccctaca 120
aggagttcgg cgccagcgtg gagctgctga gctttctgcc ctccgacttc tttccttctg 180
tgcgggacct gctggatacc gcaagcgccc tgtatagaga tgcactggag tccccagagc 240
actgcacccc aaaccacaca gccctgaggc aggcaatcct gtgctgggga gagctgatga 300
ccctggcatc ctgggtgggc aacaatctgg aggaccctgc cgccagagat ctggtggtga 360
attacgtgaa cacaaatatg ggcctgaaga tcaggcagct gctgtggttc cacatctctt 420
gcctgacctt tggccgcgag acagtgctgg agtacctggt gagcttcggc gtgtggatca 480
ggaccccacc tgcatatagg ccaccaaacg cacctatcct gtccacactg ccagagacaa 540
cagtggtgcg ccagagggga agagcaccac ggagaaggac accttctcca aggaggagaa 600
gaagccagtc cccacgaaga agacgaagcc agagcccagc cagccagtgt tgatgagaat 660
tccgt 665

<210> SEQ ID NO 74
<211> LENGTH: 213
<212> TYPE: PRT
<213> ORGANISM: Artificial Sequence
<220> FEATURE:
<223> OTHER INFORMATION: PreC-C-Mut-gt-H protein

<400> SEQUENCE: 74

Met Ala Gln Leu Phe His Leu Cys Leu Ile Ile Phe Cys Ser Cys Pro
1 5 10 15

Thr Phe Gln Phe Pro Lys Leu Cys Leu Gly Trp Leu Trp Gly Met Asp
20 25 30

Ile Asp Pro Tyr Lys Glu Phe Gly Ala Ser Val Glu Leu Leu Ser Phe
35 40 45

Leu Pro Ser Asp Phe Phe Pro Ser Val Arg Asp Leu Leu Asp Thr Ala
50 55 60

Ser Ala Leu Tyr Arg Asp Ala Leu Glu Ser Pro Glu His Cys Thr Pro
65 70 75 80

Asn His Thr Ala Leu Arg Gln Ala Ile Leu Cys Trp Gly Glu Leu Met
85 90 95

Thr Leu Ala Ser Trp Val Gly Asn Asn Leu Glu Asp Pro Ala Ala Arg
100 105 110

Asp Leu Val Val Asn Tyr Val Asn Thr Asn Met Gly Leu Lys Ile Arg
115 120 125

Gln Leu Leu Trp Phe His Ile Ser Cys Leu Thr Phe Gly Arg Glu Thr
130 135 140

Val Leu Glu Tyr Leu Val Ser Phe Gly Val Trp Ile Arg Thr Pro Pro
145 150 155 160

Ala Tyr Arg Pro Pro Asn Ala Pro Ile Leu Ser Thr Leu Pro Glu Thr
165 170 175

Thr Val Val Arg Gln Arg Gly Arg Ala Pro Arg Arg Arg Thr Pro Ser

```
            180                 185                 190

Pro Arg Arg Arg Arg Ser Gln Ser Pro Arg Arg Arg Arg Ser Gln Ser
        195                 200                 205

Pro Ala Ser Gln Cys
    210


<210> SEQ ID NO 75
<211> LENGTH: 20
<212> TYPE: PRT
<213> ORGANISM: Artificial Sequence
<220> FEATURE:
<223> OTHER INFORMATION: L-HDAg-gt1-#1

<400> SEQUENCE: 75

Met Gly Arg Ser Glu Ser Lys Arg Asn Arg Asp Gly Arg Glu Gly Ile
1               5                   10                  15

Leu Glu Gln Trp
            20


<210> SEQ ID NO 76
<211> LENGTH: 20
<212> TYPE: PRT
<213> ORGANISM: Artificial Sequence
<220> FEATURE:
<223> OTHER INFORMATION: L-HDAg-gt1-#2

<400> SEQUENCE: 76

Asp Gly Arg Glu Gly Ile Leu Glu Gln Trp Val Asn Gly Arg Lys Lys
1               5                   10                  15

Leu Glu Asp Leu
            20


<210> SEQ ID NO 77
<211> LENGTH: 20
<212> TYPE: PRT
<213> ORGANISM: Artificial Sequence
<220> FEATURE:
<223> OTHER INFORMATION: L-HDAg-gt1-#3

<400> SEQUENCE: 77

Val Asn Gly Arg Lys Lys Leu Glu Asp Leu Glu Arg Glu Ala Arg Lys
1               5                   10                  15

Ile Lys Lys Lys
            20


<210> SEQ ID NO 78
<211> LENGTH: 20
<212> TYPE: PRT
<213> ORGANISM: Artificial Sequence
<220> FEATURE:
<223> OTHER INFORMATION: L-HDAg-gt1-#4

<400> SEQUENCE: 78

Glu Arg Glu Ala Arg Lys Ile Lys Lys Lys Ile Lys Lys Leu Glu Asp
1               5                   10                  15

Glu Asn Pro Trp
            20


<210> SEQ ID NO 79
<211> LENGTH: 20
<212> TYPE: PRT
<213> ORGANISM: Artificial Sequence
<220> FEATURE:
<223> OTHER INFORMATION: L-HDAg-gt1-#5
```

<400> SEQUENCE: 79

Ile Lys Lys Leu Glu Asp Glu Asn Pro Trp Leu Gly Asn Ile Lys Gly
1 5 10 15

Ile Leu Gly Lys
20

<210> SEQ ID NO 80
<211> LENGTH: 20
<212> TYPE: PRT
<213> ORGANISM: Artificial Sequence
<220> FEATURE:
<223> OTHER INFORMATION: L-HDAg-gt1-#6

<400> SEQUENCE: 80

Leu Gly Asn Ile Lys Gly Ile Leu Gly Lys Arg Asp Lys Asp Gly Glu
1 5 10 15

Gly Ala Pro Pro
20

<210> SEQ ID NO 81
<211> LENGTH: 20
<212> TYPE: PRT
<213> ORGANISM: Artificial Sequence
<220> FEATURE:
<223> OTHER INFORMATION: L-HDAg-gt1-#7

<400> SEQUENCE: 81

Arg Asp Lys Asp Gly Glu Gly Ala Pro Pro Ala Lys Arg Ala Arg Thr
1 5 10 15

Asp Gln Met Glu
20

<210> SEQ ID NO 82
<211> LENGTH: 20
<212> TYPE: PRT
<213> ORGANISM: Artificial Sequence
<220> FEATURE:
<223> OTHER INFORMATION: L-HDAg-gt1-#8

<400> SEQUENCE: 82

Ala Lys Arg Ala Arg Thr Asp Gln Met Glu Ile Asp Ser Gly Pro Gly
1 5 10 15

Lys Arg Pro Leu
20

<210> SEQ ID NO 83
<211> LENGTH: 20
<212> TYPE: PRT
<213> ORGANISM: Artificial Sequence
<220> FEATURE:
<223> OTHER INFORMATION: L-HDAg-gt1-#9

<400> SEQUENCE: 83

Ile Asp Ser Gly Pro Gly Lys Arg Pro Leu Arg Gly Gly Phe Ser Asp
1 5 10 15

Lys Glu Arg Gln
20

<210> SEQ ID NO 84
<211> LENGTH: 20
<212> TYPE: PRT
<213> ORGANISM: Artificial Sequence
<220> FEATURE:

<223> OTHER INFORMATION: L-HDAg-gt1-#10

<400> SEQUENCE: 84

Arg Gly Gly Phe Ser Asp Lys Glu Arg Gln Asp His Arg Arg Arg Lys
1 5 10 15

Ala Leu Glu Asn
20

<210> SEQ ID NO 85
<211> LENGTH: 20
<212> TYPE: PRT
<213> ORGANISM: Artificial Sequence
<220> FEATURE:
<223> OTHER INFORMATION: L-HDAg-gt1-#11

<400> SEQUENCE: 85

Asp His Arg Arg Arg Lys Ala Leu Glu Asn Lys Arg Lys Gln Leu Ala
1 5 10 15

Ala Gly Gly Lys
20

<210> SEQ ID NO 86
<211> LENGTH: 20
<212> TYPE: PRT
<213> ORGANISM: Artificial Sequence
<220> FEATURE:
<223> OTHER INFORMATION: L-HDAg-gt1-#12

<400> SEQUENCE: 86

Lys Arg Lys Gln Leu Ala Ala Gly Gly Lys His Leu Ser Lys Glu Glu
1 5 10 15

Glu Glu Glu Leu
20

<210> SEQ ID NO 87
<211> LENGTH: 20
<212> TYPE: PRT
<213> ORGANISM: Artificial Sequence
<220> FEATURE:
<223> OTHER INFORMATION: L-HDAg-gt1-#13

<400> SEQUENCE: 87

His Leu Ser Lys Glu Glu Glu Glu Glu Leu Lys Arg Leu Thr Glu Glu
1 5 10 15

Asp Glu Arg Arg
20

<210> SEQ ID NO 88
<211> LENGTH: 20
<212> TYPE: PRT
<213> ORGANISM: Artificial Sequence
<220> FEATURE:
<223> OTHER INFORMATION: L-HDAg-gt1-#14

<400> SEQUENCE: 88

Lys Arg Leu Thr Glu Glu Asp Glu Arg Arg Glu Arg Arg Thr Ala Gly
1 5 10 15

Pro Ser Val Gly
20

<210> SEQ ID NO 89
<211> LENGTH: 20
<212> TYPE: PRT
<213> ORGANISM: Artificial Sequence
<220> FEATURE:
<223> OTHER INFORMATION: L-HDAg-gt1-#15

<400> SEQUENCE: 89

Glu Arg Arg Thr Ala Gly Pro Ser Val Gly Gly Val Asn Pro Leu Glu
1 5 10 15

Gly Gly Ser Arg
20

<210> SEQ ID NO 90
<211> LENGTH: 20
<212> TYPE: PRT
<213> ORGANISM: Artificial Sequence
<220> FEATURE:
<223> OTHER INFORMATION: L-HDAg-gt1-#16

<400> SEQUENCE: 90

Gly Val Asn Pro Leu Glu Gly Gly Ser Arg Gly Ala Pro Gly Gly Gly
1 5 10 15

Phe Val Pro Asn
20

<210> SEQ ID NO 91
<211> LENGTH: 20
<212> TYPE: PRT
<213> ORGANISM: Artificial Sequence
<220> FEATURE:
<223> OTHER INFORMATION: L-HDAg-gt1-#17

<400> SEQUENCE: 91

Gly Ala Pro Gly Gly Gly Phe Val Pro Asn Met Leu Ser Val Pro Glu
1 5 10 15

Ser Pro Phe Ser
20

<210> SEQ ID NO 92
<211> LENGTH: 20
<212> TYPE: PRT
<213> ORGANISM: Artificial Sequence
<220> FEATURE:
<223> OTHER INFORMATION: L-HDAg-gt1-#18

<400> SEQUENCE: 92

Met Leu Ser Val Pro Glu Ser Pro Phe Ser Arg Thr Gly Glu Gly Leu
1 5 10 15

Asp Val Arg Gly
20

<210> SEQ ID NO 93
<211> LENGTH: 20
<212> TYPE: PRT
<213> ORGANISM: Artificial Sequence
<220> FEATURE:
<223> OTHER INFORMATION: L-HDAg-gt1-#19

<400> SEQUENCE: 93

Arg Thr Gly Glu Gly Leu Asp Val Arg Gly Asn Gln Gly Phe Pro Trp
1 5 10 15

Asp Ile Leu Phe
20

<210> SEQ ID NO 94
<211> LENGTH: 20
<212> TYPE: PRT

<213> ORGANISM: Artificial Sequence
<220> FEATURE:
<223> OTHER INFORMATION: L-HDAg-gt1-#20

<400> SEQUENCE: 94

Asn Gln Gly Phe Pro Trp Asp Ile Leu Phe Pro Ala Asp Pro Pro Phe
1 5 10 15

Ser Pro Gln Ser
20

<210> SEQ ID NO 95
<211> LENGTH: 14
<212> TYPE: PRT
<213> ORGANISM: Artificial Sequence
<220> FEATURE:
<223> OTHER INFORMATION: L-HDAg-gt1-#21

<400> SEQUENCE: 95

Pro Ala Asp Pro Pro Phe Ser Pro Gln Ser Cys Arg Pro Gln
1 5 10

<210> SEQ ID NO 96
<211> LENGTH: 20
<212> TYPE: PRT
<213> ORGANISM: Artificial Sequence
<220> FEATURE:
<223> OTHER INFORMATION: L-HDAg-gt2-#1

<400> SEQUENCE: 96

Met Gly Gln Pro Asp Ser Arg Arg Pro Arg Arg Gly Arg Glu Glu Ser
1 5 10 15

Leu Gly Lys Trp
20

<210> SEQ ID NO 97
<211> LENGTH: 20
<212> TYPE: PRT
<213> ORGANISM: Artificial Sequence
<220> FEATURE:
<223> OTHER INFORMATION: L-HDAg-gt2-#2

<400> SEQUENCE: 97

Arg Gly Arg Glu Glu Ser Leu Gly Lys Trp Ile Asp Ala Arg Arg Arg
1 5 10 15

Lys Glu Glu Leu
20

<210> SEQ ID NO 98
<211> LENGTH: 20
<212> TYPE: PRT
<213> ORGANISM: Artificial Sequence
<220> FEATURE:
<223> OTHER INFORMATION: L-HDAg-gt2-#3

<400> SEQUENCE: 98

Ile Asp Ala Arg Arg Arg Lys Glu Glu Leu Glu Arg Asp Leu Arg Lys
1 5 10 15

Val Asn Lys Thr
20

<210> SEQ ID NO 99
<211> LENGTH: 20
<212> TYPE: PRT
<213> ORGANISM: Artificial Sequence
<220> FEATURE:

```
<223> OTHER INFORMATION: L-HDAg-gt2-#4

<400> SEQUENCE: 99

Glu Arg Asp Leu Arg Lys Val Asn Lys Thr Ile Lys Arg Leu Glu Glu
1               5                   10                  15

Asp Asn Pro Trp
            20


<210> SEQ ID NO 100
<211> LENGTH: 20
<212> TYPE: PRT
<213> ORGANISM: Artificial Sequence
<220> FEATURE:
<223> OTHER INFORMATION: L-HDAg-gt2-#5

<400> SEQUENCE: 100

Ile Lys Arg Leu Glu Glu Asp Asn Pro Trp Leu Gly Asn Ile Arg Gly
1               5                   10                  15

Ile Ile Gly Arg
            20


<210> SEQ ID NO 101
<211> LENGTH: 20
<212> TYPE: PRT
<213> ORGANISM: Artificial Sequence
<220> FEATURE:
<223> OTHER INFORMATION: L-HDAg-gt2-#6

<400> SEQUENCE: 101

Leu Gly Asn Ile Arg Gly Ile Ile Gly Arg Lys Asp Lys Asp Gly Glu
1               5                   10                  15

Gly Ala Pro Pro
            20


<210> SEQ ID NO 102
<211> LENGTH: 20
<212> TYPE: PRT
<213> ORGANISM: Artificial Sequence
<220> FEATURE:
<223> OTHER INFORMATION: L-HDAg-gt2-#7

<400> SEQUENCE: 102

Lys Asp Lys Asp Gly Glu Gly Ala Pro Pro Ala Lys Arg Ala Arg Thr
1               5                   10                  15

Asp Gln Met Glu
            20


<210> SEQ ID NO 103
<211> LENGTH: 20
<212> TYPE: PRT
<213> ORGANISM: Artificial Sequence
<220> FEATURE:
<223> OTHER INFORMATION: L-HDAg-gt2-#8

<400> SEQUENCE: 103

Ala Lys Arg Ala Arg Thr Asp Gln Met Glu Val Asp Ser Gly Pro Arg
1               5                   10                  15

Lys Arg Lys His
            20


<210> SEQ ID NO 104
<211> LENGTH: 20
<212> TYPE: PRT
<213> ORGANISM: Artificial Sequence
```

<220> FEATURE:
<223> OTHER INFORMATION: L-HDAg-gt2-#9

<400> SEQUENCE: 104

Val Asp Ser Gly Pro Arg Lys Arg Lys His Pro Gly Gly Phe Thr Glu
1 5 10 15

Gln Glu Arg Arg
20

<210> SEQ ID NO 105
<211> LENGTH: 20
<212> TYPE: PRT
<213> ORGANISM: Artificial Sequence
<220> FEATURE:
<223> OTHER INFORMATION: L-HDAg-gt2-#10

<400> SEQUENCE: 105

Pro Gly Gly Phe Thr Glu Gln Glu Arg Arg Asp His Arg Arg Arg Lys
1 5 10 15

Ala Leu Glu Asn
20

<210> SEQ ID NO 106
<211> LENGTH: 20
<212> TYPE: PRT
<213> ORGANISM: Artificial Sequence
<220> FEATURE:
<223> OTHER INFORMATION: L-HDAg-gt2-#11

<400> SEQUENCE: 106

Asp His Arg Arg Arg Lys Ala Leu Glu Asn Lys Lys Lys Gln Leu Ser
1 5 10 15

Ser Gly Gly Lys
20

<210> SEQ ID NO 107
<211> LENGTH: 20
<212> TYPE: PRT
<213> ORGANISM: Artificial Sequence
<220> FEATURE:
<223> OTHER INFORMATION: L-HDAg-gt2-#12

<400> SEQUENCE: 107

Lys Lys Lys Gln Leu Ser Ser Gly Gly Lys Asp Leu Ser Arg Glu Glu
1 5 10 15

Glu Glu Glu Leu
20

<210> SEQ ID NO 108
<211> LENGTH: 20
<212> TYPE: PRT
<213> ORGANISM: Artificial Sequence
<220> FEATURE:
<223> OTHER INFORMATION: L-HDAg-gt2-#13

<400> SEQUENCE: 108

Asp Leu Ser Arg Glu Glu Glu Glu Glu Leu Arg Arg Leu Thr Glu Glu
1 5 10 15

Asp Glu Arg Arg
20

<210> SEQ ID NO 109
<211> LENGTH: 20
<212> TYPE: PRT

<213> ORGANISM: Artificial Sequence
<220> FEATURE:
<223> OTHER INFORMATION: L-HDAg-gt2-#14

<400> SEQUENCE: 109

Arg Arg Leu Thr Glu Glu Asp Glu Arg Arg Glu Arg Arg Val Ala Gly
1 5 10 15

Pro Arg Val Gly
20

<210> SEQ ID NO 110
<211> LENGTH: 20
<212> TYPE: PRT
<213> ORGANISM: Artificial Sequence
<220> FEATURE:
<223> OTHER INFORMATION: L-HDAg-gt2-#15

<400> SEQUENCE: 110

Glu Arg Arg Val Ala Gly Pro Arg Val Gly Asp Val Asn Pro Leu Asp
1 5 10 15

Gly Gly Pro Arg
20

<210> SEQ ID NO 111
<211> LENGTH: 20
<212> TYPE: PRT
<213> ORGANISM: Artificial Sequence
<220> FEATURE:
<223> OTHER INFORMATION: L-HDAg-gt2-#16

<400> SEQUENCE: 111

Asp Val Asn Pro Leu Asp Gly Gly Pro Arg Gly Ala Pro Gly Gly Gly
1 5 10 15

Phe Val Pro Ser
20

<210> SEQ ID NO 112
<211> LENGTH: 20
<212> TYPE: PRT
<213> ORGANISM: Artificial Sequence
<220> FEATURE:
<223> OTHER INFORMATION: L-HDAg-gt2-#17

<400> SEQUENCE: 112

Gly Ala Pro Gly Gly Gly Phe Val Pro Ser Met Gln Gly Ile Pro Glu
1 5 10 15

Ser Pro Phe Thr
20

<210> SEQ ID NO 113
<211> LENGTH: 20
<212> TYPE: PRT
<213> ORGANISM: Artificial Sequence
<220> FEATURE:
<223> OTHER INFORMATION: L-HDAg-gt2-#18

<400> SEQUENCE: 113

Met Gln Gly Ile Pro Glu Ser Pro Phe Thr Arg Arg Gly Asp Gly Leu
1 5 10 15

Asp Thr Arg Gly
20

<210> SEQ ID NO 114
<211> LENGTH: 20

-continued

```
<212> TYPE: PRT
<213> ORGANISM: Artificial Sequence
<220> FEATURE:
<223> OTHER INFORMATION: L-HDAg-gt2-#19

<400> SEQUENCE: 114

Arg Arg Gly Asp Gly Leu Asp Thr Arg Gly Thr Gln Glu Phe Pro Trp
1               5                   10                  15

Val Asn Pro Gln
            20


<210> SEQ ID NO 115
<211> LENGTH: 20
<212> TYPE: PRT
<213> ORGANISM: Artificial Sequence
<220> FEATURE:
<223> OTHER INFORMATION: L-HDAg-gt2-#20

<400> SEQUENCE: 115

Thr Gln Glu Phe Pro Trp Val Asn Pro Gln Pro Pro Pro Pro Arg Leu
1               5                   10                  15

Pro Leu Leu Glu
            20


<210> SEQ ID NO 116
<211> LENGTH: 14
<212> TYPE: PRT
<213> ORGANISM: Artificial Sequence
<220> FEATURE:
<223> OTHER INFORMATION: L-HDAg-gt2-#21

<400> SEQUENCE: 116

Pro Pro Pro Pro Arg Leu Pro Leu Leu Glu Cys Thr Pro Gln
1               5                   10
```